US010004765B2

(12) United States Patent
Lawrence et al.

(10) Patent No.: US 10,004,765 B2
(45) Date of Patent: *Jun. 26, 2018

(54) DOSAGE COMPENSATING TRANSGENES AND CELLS

(71) Applicant: University of Massachusetts, Boston, MA (US)

(72) Inventors: Jeanne B. Lawrence, Mapleville, RI (US); Jun Jiang, Shrewsbury, MA (US); Lisa L. Hall, Framingham, MA (US)

(73) Assignee: University of Massachusetts, Boston, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/776,672

(22) PCT Filed: Mar. 14, 2014

(86) PCT No.: PCT/US2014/027525

§ 371 (c)(1),
(2) Date: Sep. 14, 2015

(87) PCT Pub. No.: WO2014/152607

PCT Pub. Date: Sep. 25, 2014

(65) Prior Publication Data

US 2016/0143951 A1 May 26, 2016

Related U.S. Application Data

(60) Provisional application No. 61/790,917, filed on Mar. 15, 2013, provisional application No. 61/785,481, filed on Mar. 14, 2013.

(51) Int. Cl.

| | |
|---|---|
| ***C12N 15/113*** | (2010.01) |
| ***C12N 15/63*** | (2006.01) |
| ***A61K 35/28*** | (2015.01) |
| ***A01K 67/027*** | (2006.01) |
| ***C12N 9/12*** | (2006.01) |
| ***C12N 15/85*** | (2006.01) |
| ***C12N 15/90*** | (2006.01) |
| ***C12N 15/11*** | (2006.01) |
| *A61K 48/00* | (2006.01) |
| *A61K 35/12* | (2015.01) |

(52) U.S. Cl.

CPC .......... *A61K 35/28* (2013.01); *A01K 67/0271* (2013.01); *A01K 67/0275* (2013.01); *C12N 9/12* (2013.01); *C12N 15/111* (2013.01); *C12N 15/1137* (2013.01); *C12N 15/85* (2013.01); *C12N 15/8509* (2013.01); *C12N 15/907* (2013.01); *C12Y 207/12001* (2013.01); *A01K 2207/12* (2013.01); *A01K 2217/072* (2013.01); *A01K 2217/15* (2013.01); *A01K 2217/203* (2013.01); *A01K 2227/105* (2013.01); *A01K 2267/0318* (2013.01); *A01K 2267/0356* (2013.01); *A61K 48/005* (2013.01); *A61K 48/0075* (2013.01); *A61K 2035/124* (2013.01); *C12N 2310/111* (2013.01); *C12N 2310/113* (2013.01); *C12N 2310/14* (2013.01); *C12N 2330/51* (2013.01); *C12N 2800/40* (2013.01); *C12N 2810/10* (2013.01); *C12N 2830/003* (2013.01); *C12N 2830/32* (2013.01); *C12N 2999/005* (2013.01)

(58) Field of Classification Search

None

See application file for complete search history.

(56) References Cited

U.S. PATENT DOCUMENTS

| | | | |
|---|---|---|---|
| 9,297,023 | B2 | 3/2016 | Lawrence et al. |
| 2010/0160417 | A1 | 6/2010 | Lawrence et al. |
| 2012/0142758 | A1 | 6/2012 | Collard et al. |
| 2012/0252123 | A1 | 10/2012 | Lawrence et al. |
| 2016/0264994 | A1 | 9/2016 | Lawrence et al. |

OTHER PUBLICATIONS

Hall et al. Overview: Generation of Gene Knockout Mice. Current Protocols in Cell Biology, 2009. Supplement 44. 19.12.1-19.12.17.*
Fish & Richardson P.C., Preliminary Amendment in Response to Restriction Requirement dated Jan. 23, 2015 in U.S. Appl. No. 14/045,057, filed Mar. 20, 2015, 6 pages.
Fish & Richardson P.C., Preliminary Amendment in U.S. Appl. No. 13/483,240, filed Nov. 16, 2012 (3 pages).
Fish & Richardson P.C., Response to Final Office Action in U.S. Appl. No. 13/483,240, filed Jun. 24, 2013, 6 pages.
Fish & Richardson P.C., Response to Final Office Action in U.S. Appl. No. 14/045,057, filed Oct. 21, 2015, 4 pages.
Fish & Richardson P.C., Response to Office Action in U.S. Appl. No. 13/483,240, filed Mar. 26, 2013, 8 pages.
Fish & Richardson P.C., Response to Office Action in U.S. Appl. No. 14/045,057, filed Aug. 27, 2015, 8 pages.
Fish & Richardson P.C., Response to Office Action in U.S. Appl. No. 12/512,964, filed Jan. 23, 2012.
Fish & Richardson P.C., Response to Restriction Requirement in U.S. Appl. No. 12/512,964, filed Jul. 6, 2011 (8 pages).
Fish & Richardson P.C., Response to Restriction Requirement in U.S. Appl. No. 13/483,240, filed Nov. 7, 2012 (6 pages).
International Preliminary Report on Patentability (IPRP) mailed in Application No. PCT/US2014/027525 dated Sep. 15, 2015, 10 pages.
International Search Report and Written Opinion for PCT/US2014/027525, dated Sep. 12, 2014 (13 pages).
U.S. Patent and Trademark Office Notice of Allowability in U.S. Appl. No. 12/512,964, dated Apr. 24, 2012 (5 pages).

(Continued)

*Primary Examiner* — Christopher M Babic
*Assistant Examiner* — Kimberly A Aron
(74) *Attorney, Agent, or Firm* — Fish & Richardson P.C.

(57) ABSTRACT

Methods and compositions for reducing expression of genes on Chromosome 21 ("Chr 21") by targeting an XIST transgene to the Dual specificity tyrosine-phosphorylation-regulated kinase 1A (DYRK1A) gene or a Regulator of calcineurin 1 (RCAN1) gene, and cells and transgenic animals comprising an XIST transgene inserted into a DYRK1A or RCAN1 allele, e.g., cells and animals trisomic for human Chr 21 and mouse Chr 16.

15 Claims, 50 Drawing Sheets

(56) References Cited

OTHER PUBLICATIONS

U.S. Patent and Trademark Office Notice of Allowance in U.S. Appl. No. 12/512,964, dated Mar. 5, 2012 (9 pages).
U.S. Patent and Trademark Office, Final Office Action in U.S. Appl. No. 13/483,240, dated May 28, 2013, 6 pages.
U.S. Patent and Trademark Office, Final Office Action in U.S. Appl. No. 14/045,057, dated Sep. 15, 2015, 6 pages.
U.S. Patent and Trademark Office, Non Final Office Action in U.S. Appl. No. 12/512,964, dated Sep. 21, 2011 (12 pages).
U.S. Patent and Trademark Office, Office Action in U.S. Appl. No. 14/045,057, dated Apr. 27, 2015, 11 pages.
U.S. Patent and Trademark Office, Office Action in U.S. Appl. No. 13/483,240, dated Jan. 9, 2013 (9 pages).
U.S. Patent and Trademark Office, Restriction Requirement in U.S. Appl. No. 14/045,057, dated Jan. 23, 2015, 9 pages.
U.S. Patent and Trademark Office, Restriction Requirement in U.S. Appl. No. 12/512,964, dated Apr. 6, 2011 (9 pages).
U.S. Patent and Trademark Office, Restriction Requirement in U.S. Appl. No. 13/483,240, dated Oct. 11, 2012 (9 pages).
U.S. Patent and Trademark Office, Notice of Allowance in U.S. Appl. No. 13/483,240, dated Jul. 3, 2013, 6 pages.
U.S. Patent and Trademark Office, Notice of Allowance in U.S. Appl. No. 14/045,057, dated Nov. 19, 2015, 5 pages.
Antonarakis et al., "The challenge of Down syndrome", Trends Mol Med., vol. 12:473-479 (2006).
Bailey et al., "Molecular evidence for a relationship between LINE-1 elements and X chromosome inactivation: The Lyon repeat hypothesis", PNAS, vol. 97:6634-6639 (2000).
Biancotti et al., "Human Embryonic Stem Cells as Models for Aneuploid Chromosomal Syndromes", Stem Cells, vol. 28:1530-1540 (2010).
Brockdorff et al., "X Chromosome Inactivation and the Xist Gene", Cell. Mol. Life Sci., 1998, vol. 54, pp. 104-112.
Brockdorff, N, "Chromosome silencing mechanisms in X-chromosome inactivation: unknown unknowns", Development, vol. 138:5057-5065 (2011).
Brown et al., "Expression of genes from the human active and inactive X chromosomes", Am J Hum Genet, vol. 60:1333-1343 (1997).
Brown, C. J. et al. The human XIST gene: analysis of a 17 kb inactive X-specific RNA that contains conserved repeats and is highly localized within the nucleus, Cell 71:527-542 (1992).
Carrel et al., "X-inactivation profile reveals extensive variability in X-linked gene expression in females", Nature, vol. 434:400-404 (2005).
Cathomen et al., "Zinc-finger Nucleases: The Next Generation Emerges", Molecular Therapy, vol. 16:1200-1207 (2008).
Chow et al., "Characterization of expression at the human XIST locus in somatic, embryonal carcinoma, and transgenic cell lines", Genomics, vol. 82:309-322 (2003).
Chow et al., "Inducible XIST-dependent X-chromosome inactivation in human somatic cells is reversible", Proc. Natl. Acad. Sci. USA, vol. 104:10104-10109 (2007).
Clemson et al., "The X chromosome is organized into a gene-rich outer rim and an internal core containing silenced nongenic sequences", Proc Natl Acad Sci USA 103, 7688-7693 (2006).
Clemson et al., "XIST RNA Paints the Inactive X Chromosome at Interphase: Evidence for a Novel RNA Involved in Nuclear/Chromosome Structure", J. Cell Biol., vol. 132:259-275 (1996).
Cotton et al., "Chromosome-wide DNA methylation analysis predicts human tissue-specific X inactivation", Human Genetics, vol. 130:187-201 (2011).
Csankovszki et al., "Synergism of XIST RNA, DNA Methylation, and Histone Hypoacetylation in Maintaining X Chromosome Inactivation", J. of Cell Biol., vol. 153:773-783 (2001).
Debrand et al., "Functional Analysis of the DXPas34 Locus, a 3' Regulator of Xist Expression", Mol. Cell. Bio., vol. 19:8513-8525 (1999).
DeKelver et al., "Functional genomics, proteomics, and regulatory DNA analysis in isogenic settings using zinc finger nuclease-driven transgenesis into a safe harbor locus in the human genome", Genome Research, vol. 20:1133-1142 (2010).
Douillard-Guilloux et al., "Partial phenotypic correction and immune tolerance induction to enzyme replacement therapy after hematopoietic stem cell gene transfer of alpha—glucosidase in Pompe disease", J Gene Med., vol. 11:279-287 (2009).
Gardiner, "Molecular basis of pharmacotherapies for cognition in Down syndrome", Trends Pharmacol Sci., vol. 31:66-73 (2010).
Goodrich et al. "From bacteria to humans, chromatin to elongation, and activation to repression: The expanding roles of nonconding RNAs in regulating transcription", Crit. Rev. Biochem. Mol. Biol., vol. 44:3-15 (2009).
Greene et al., "The Human Xist Gene Promoter Prevents Silencing of an Integrated Reporter Gene", Blood, vol. 104(11), Abstract #2114 (2004).
Guidi, et al., "Widespread Proliferation Impairment and Hypocellularity in the Cerebellum of Fetuses with Down Syndrome", Brain Pathol., vol. 21:361-373 (2011).
Hall et al., "An ectopic human XIST gene can induce chromosome inactivation in postdifferentiation human HT-1080 cells", Proc. Natl. Acad. Sci. USA, vol. 99:8677-8682 (2002).
Hall et al., "Unbalanced X;autosome translocations provide evidence for sequence specificity in the association of XIST RNA with chromatin", Hum Mol Genet., vol. 11:3157-3165 (2002).
Hall et al., "The cell biology of a novel chromosomal RNA: chromosome painting by XIST/Xist RNA initiates a remodeling cascade", Semin Cell Dev Biol, vol. 14:369-378 (2003).
Haydar et al., "Trisomy and early brain development", Trends Neurosci, vol. 35:81-91 (2012).
Heard, "Delving into the diversity of facultative heterochromatin: the epigenetics of the inactive X chromosome", Curr Opin Genet Dev., vol. 15:482-489 (2005).
Hockemeyer et al., "Efficient targeting of expressed and silent genes in human ESCs and iPSCs using zinc-finger nucleases", Nat Biotechnol, vol. 27:851-857 (2009).
Khalil et al., "Many human large intergenic noncoding RNAs associate with chromatin-modifying complexes and affect gene expression", PNAS, vol. 106:11667-11672 (2009).
Lau et al., "Skewed X-Chromosome Inactivation Is Common in Fetuses or Newborns Associated with Confined Placental Mosaicism", Am. J. Hum. Genet., vol. 61:1353-1361 (1997).
Lavon et al., "Derivation of Euploid Human Embryonic Stem Cells from Aneuploid Embryos", Stem Cells, vol. 26:1874-1882 (2008).
Lee et al., "A 450 kb Transgene Displays Properties of the Mammalian X-Inactivation Center", Cell, vol. 86:83-94 (1996).
Lee, "Gracefully ageing at 50, X-chromosome inactivation becomes a paradigm for RNA and chromatin control", Nat Rev Mol Cell Bioll, vol. 12:815-826 (2011).
Li et al., "Trisomy correction in down syndrome induced pluripotent stem cells", Cell Stem Cell, vol. 11:615-619 (2012).
Liu et al., "Mouse Models for Down Syndrome-Associated Developmental Cognitive Disabilities", Dev Neurosci, vol. 33:404-413 (2011).
Lockstone et al., "Gene expression profiling in the adult Down syndrome brain", Genomics, vol. 90:647-660 (2007).
Lyon, "Gene Action in the X-chromosome of the Mouse (*Mus musculus* L.)," Nature, vol. 190:372-373 (1961).
McNeil et al., "Word frequency analysis reveals enrichment of dinucleotide repeats on the human X chromosome and $[GATA]_n$ in the X escape region", Genome Research, vol. 16:477-484 (2006).
Megarbane, et al., "The 50th anniversary of the discovery of trisomy 21: The past, present, and future of research and treatment of Down syndrome", Genetics in medicine: official journal of the American College of Medical Genetics, vol. 11:611-616 (2009).
Migeon et al., "X Inactivation in Triploidy and Trisomy: The Search for Autosomal Transfactors That Choose the Active X", European Journal of Human Genetics, published on-line Oct. 31, 2007, vol. 16:153-162 (2008).
Miller et al., "An improved zinc-finger nuclease architecture for highly specific genome editing", Nat Biotechnol, vol. 25:778-785 (2007).

(56) References Cited

OTHER PUBLICATIONS

Moehle et al., "Targeted gene addition into a specified location in the human genome using designed zinc finger nucleases", Proc. Natl. Acad. Sci. USA, vol. 104:3055-3060 (2007).
O'Doherty et al., "An Aneuploid Mouse Strain Carrying Human Chromosome 21 with Down Syndrome Phenotypes", Science, vol. 309:2033-2037 (2005).
Park et al., "Function and regulation of Dyrk1A: towards understanding Down syndrome", Cellular and molecular life sciences: CMLS, vol. 66:3235-3240 (2009).
Porteus, "Mammalian Gene Targeting with Designed Zinc Finger Nucleases", Molecular Therapy, 2006, vol. 13(2), pp. 438-446.
Prandini et al., "Natural Gene-Expression Variation in Down Syndrome Modulates the Outcome of Gene-Dosage Imbalance", Am J Hum Genet., vol. 81:252-263 (2007).
Reeves, "Down syndrome mouse models are looking up", Trends Mol Med., vol. 12:237-240 (2006).
Savarese et al., "Hematopoietic Precursor Cells Transiently Reestablish Permissiveness for X Inactivation", Molecular and Cellular Biology, 2006, vol. 26(19), pp. 7167-7177.
Sharp et al., "DNA methylation profiles of human active and inactive X chromosomes", Genome research, vol. 21:1592-1600 (2011).
Tam et al., "The 4q subtelomere harboring the FSHD locus is specifically anchored with peripheral heterochromatic unlike most human telomeres",. Journal of Cell Biology, vol. 167:269-279 (2004).
Tanzi et al., "Twenty Years of the Alzheimer's Disease Amyloid Hypothesis: A Genetic Perspective", Cell, vol. 120:545-555 (2005).
Urnov et al., Genome editing with engineered zinc finger nucleases, Nat Rev Genet., vol. 11:636-646 (2010).
Webb et al., "β-Secretases, Alzheimer's Disease, and Down Syndrome", Curr Gerontol Geriatr Res, vol. 2012, Article ID 362839, 8 pp. (2012).
Wutz et al., "A shift from reversible to irreversible X inactivation is triggered during ES cell differentiation", Mol Cell, vol. 5:695-705 (2000).
Wutz et al., "Chromosomal silencing and localization are mediated by different domains of Xist RNA", Nat. Genetics, vol. 30:167-174 (2002).
Wutz et al., "Xinactivation Xplained", Curr. Opin. Genet Dev., vol. 17:387-393 (2007).
Wutz, "Gene silencing in X-chromosome inactivation: advances in understanding facultative heterochromatin formation", Nat Rev Genet, vol. 12:542-553 (2011).
Yabut et al., "Dyrk1A Overexpression Inhibits Proliferation and Induces Premature Neuronal Differentiation of Neural Progenitor Cells", J Neurosci, vol. 30:4004-4014 (2010).
Yahya-Graison et al., "Classification of Human Chromosome 21 Gene-Expression Variations in Down Syndrome: Impact on Disease Phenotypes", Am J Hum Genet, vol. 81:475-491 (2007).
International Preliminary Report on Patentability (IPRP) mailed in Application No. PCT/US2009/052318 dated Feb. 1, 2011, enclosing Written Opinion dated Apr. 30, 2010.
International Search Report and Written Opinion for PCT/US2009/052318, dated Apr. 30, 2010 (17 pages).
Copenheaver, Brian R., "Notification of Transmittal of the International Search Report and the Written Opinion of the International Searching Authority, or the Declaration", International Application No. PCT/US2010/027525, dated Sep. 12, 2014, 17 pages.
Lepagnol-Bestel, Aude-Marie et al., "DYRK1A interacts with the REST/NRSF-SWI/SNF chromatin remodeling complex to deregulate gene clusters involved in the neuronal phenotypic traits of Down syndrome", Human Molecular Genetics, vol. 18(8):1405-1414, 2009.
Canzonetta et al., DYRK1A-Dosage Imbalance Perturbs NRSF/REST Levels, Deregulating Pluripotency and Embryonic Stem Cell Fate in Down Syndrome, The American Journal of Human Genetics, vol. 83:388-400, 2008.
Jiang, Jun et al., "Translating dosage compensation to trisomy 21", Nature, vol. 500:296-300, 2013.

* cited by examiner

FIG. 10A - CONSTRUCT 1 (3G/FL/hXIST/DYRK1A):

```
LOCUS       pTRE3G/DYRK1A LA &#38; RA/BglII/KpnI linker/FL XIST 18515 bp     DNA     SYN
       29-Nov-2012
DEFINITION  pTRE3G/DYRK1A LA &#38; RA/BglII/KpnI linker/FL XIST
ACCESSION
KEYWORDS
SOURCE
  ORGANISM  other sequences; artificial sequences; vectors.
FEATURES             Location/Qualifiers
     source          1..18515
                     /organism="pTRE3G/DYRK1A LA &#38; RA/BglII/KpnI linker/FL XIST"
                     /mol_type="other DNA"
     promoter        7..382
                     /label="pTRE3G promoter"
     misc_feature    289..308
                     /label="pCEP_fwd_primer"
     misc_feature    291..315
                     /label="LNCX_primer"
     misc_feature    454..14183
                     /label="human FL XIST"
     misc_feature    14460..14475
                     /label="SV40_int"
     misc_feature    14481..14528
                     /label="SV40_3_splice"
     misc_feature    14385..15182
                     /label="SV40 pA"
     terminator      15104..15223
                     /label="SV40_PA_terminator"
     misc_feature    15192..15211
                     /label="EBV_rev_primer"
     misc_feature    15423..16112
                     /label="DYRK1A left arm"
     rep_origin      complement(16158..16777)
                     /label="pBR322_origin"
     CDS             complement(16932..17792)
                     /label="Ampicillin"
                     /gene="Ampicillin"
                     /note="ORF frame 3"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"                                   (SEQ ID NO:25)
     gene            complement(16932..17792)
                     /label="Ampicillin"
                     /gene="Ampicillin"
     promoter        complement(17834..17862)
                     /label="AmpR_promoter"
     misc_feature    18003..18510
                     /label="DYRK1A right arm"
```

FIG. 10B - CONSTRUCT 2 (puro/rtTA/AAVS1)

```
LOCUS       AAVS1/ PEF1α-Tet3G/hPGK-PuroR-pA      9789 bpDNA    SYN    14-Mar-2013
DEFINITION  AAVS1/ PEF1α-Tet3G/hPGK-PuroR-pA
ACCESSION
KEYWORDS
SOURCE
  ORGANISM  other sequences; artificial sequences; vectors.
FEATURES             Location/Qualifiers
     source          1..9789
                     /organism="AAVS1/ PEF1α-Tet3G/hPGK-PuroR-pA"
                     /mol_type="other DNA"
     promoter        143..172
                     /label="lac_promoter"
     misc_feature    186..208
                     /label="M13_pUC_rev_primer"
     misc_feature    207..225
                     /label="M13_reverse_primer"
     promoter        242..261
                     /label="T3_promoter"
     misc_feature    295..1095
                     /label="Left arm"
     misc_feature    1120..1562
                     /label="SV40 pA signal"
     terminator      1444..1575
                     /label="SV40_PA_terminator"
     misc_feature    1532..1551
                     /label="EBV_rev_primer"
     CDS             complement(1585..2331)
                     /label="ORF frame 1"
                     /translation="MSRLDKSKVINSALELLNGVGIEGLTTRKLAQKLGVEQPTLYWH
                     VKNKRALLDALPIEMLDRHHTHSCPLEGESWQDFLRNNAKSYRCALLSHRDGAKVHLG
                     TRPTEKQYETLENQLAFLCQQGFSLENALYALSAVGHFTLGCVLEEQEHQVAKEERET
                     PTTDSMPPLLKQAIELFDRQGAEPAFLFGLELIICGLEKQLKCESGGPTDALDDFDLD
                     MLPADALDDFDLDMLPADALDDFDLDMLPG*"      (SEQ ID NO:26)
     misc_feature    1585..2331
                     /label="Tet3G"
     misc_feature    complement(2413..2437)
                     /label="LNCX_primer"
     misc_feature    complement(2469..2489)
                     /label="EF1a_fwd_primer"
     CDS             2697..3344
                     /label="ORF frame 3"
                     /translation="MKRRLRTERPFSFVWVTHPPALPSAASSILSSLQQGREAAIFPL
                     TQLVPTGPALPPRAGRYTAARGQAPEQAGQLETTPVRFSVAALAGPASPNMCAGTHGP
                     RRRPRPQKPKYQCADLGPHLQDYLARKKASQQVIKNFKWLETYRKQRDRREGATRFAR
                     GGPSAQARPQLKHEAKGLLKRKASNSPTHFQPEARDQESRTAARGVEVIQGTQGP*"
                               (SEQ ID NO:27)
     promoter        complement(2437..3624)
                     /label="EF1a_promoter"
     promoter        2437..3771
                     /label="EF1x promoter"
     misc_feature    3913..4419
                     /label="hPGK"
     CDS             4201..5040
                     /label="puro(variant)"
                     /gene="puro(variant)"
                     /note="ORF frame 1"
                     /translation="MAARRPRWAVANSGCSAGRAESSGREGAVREAGCGAVVWALFLP
                     ARCSAPCKPPERTSAVGSLVDRITDLSPQGDPPELTMTEYKPTVRLATRDDVPRAVRT
                     LAAAFADYPATRHTVDPDRHIERVTELQELFLTRVGLDIGKVWVADDGAAVAVWTTPE
                     SVEAGAVFAEIGPRMAELSGSRLAAQQQMEGLLAPHRPKEPAWFLATVGVSPDHQGKG
                     LGSAVVLPGVEAAERAGVPAFLETSAPRNLPFYERLGFTVTADVEVPEGPRTWCMTRK
                     PGA*"             (SEQ ID NO:28)
     gene            4441..5040
                     /label="puro(variant)"
                     /gene="puro(variant)"
     misc_feature    4441..5040
                     /label="Puro"
     misc_feature    5047..5271
```

FIG. 10B, Cont'd - CONSTRUCT 2 (puro/rtTA/AAVS1)

```
                     /label="BGH pA"
terminator           5056..5271
                     /label="bGH_PA_terminator"
misc_feature         5287..6126
                     /label="Right arm"
promoter             complement(6162..6180)
                     /label="T7_promoter"
misc_feature         complement(6187..6203)
                     /label="M13_forward20_primer"
misc_feature         complement(6196..6218)
                     /label="M13_pUC_fwd_primer"
misc_feature         6184..6327
                     /label="lacZ_a"
misc_feature         6350..6643
                     /label="ccdB"
promoter             6854..6903
                     /label="NEOKAN_promoter"
CDS                  6992..7786
                     /label="NeoR/KanR"
                     /gene="NeoR/KanR"
                     /note="ORF frame 2"
                     /translation="MIEQDGLHAGSPAAWVERLFGYDWAQQTIGCSDAAVFRLSAQGR
                     PVLFVKTDLSGALNELQDEAARLSWLATTGVPCAAVLDVVTEAGRDWLLLGEVPGQDL
                     LSSHLAPAEKVSIMADAMRRLHTLDPATCPFDHQAKHRIERARTRMEAGLVDQDDLDE
                     EHQGLAPAELFARLKASMPDGEDLVVTHGDACLPNIMVENGRFSGFIDCGRLGVADRY
                     QDIALATRDIAEELGGEWADRFLVLYGIAAPDSQRIAFYRLLDEFF*"  (SEQ ID NO:29)
gene                 6995..7783
                     /label="NeoR/KanR"
                     /gene="NeoR/KanR"
promoter             7919..7942
                     /label="AmpR_promoter"
CDS                  complement(8036..8896)
                     /label="Ampicillin"
                     /gene="Ampicillin"
                     /note="ORF frame 2"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"   (SEQ ID NO:25)
gene                 complement(8036..8896)
                     /label="Ampicillin"
                     /gene="Ampicillin"
rep_origin           9004..9623
                     /label="pBR322_origin"
```

FIG. 10C - CONSTRUCT 3 (FL/hXIST/RCAN1)

```
LOCUS       pcDNA5/TO/RCAN1 LA &#38; RA/FL human XIST    21055 bp      DNA     SYN     29-
Nov-2012
DEFINITION  pcDNA5/TO/RCAN1 LA &#38; RA/FL human XIST
ACCESSION
KEYWORDS
SOURCE
  ORGANISM  other sequences; artificial sequences; vectors.
FEATURES             Location/Qualifiers
     source          1..21055
                     /organism="pcDNA5/TO/RCAN1 LA &#38; RA/FL human XIST"
                     /mol_type="other DNA"
     misc_feature    209..966
                     /label="RCAN1 right arm"
     misc_feature    1073..1360
                     /label="CAG_enhancer"
     promoter        994..1570
                     /label="CMV_immearly_promoter"
     misc_feature    1527..1547
                     /label="CMV_fwd_primer"
     promoter        1528..1651
                     /label="CMV_promoter"
     misc_feature    1578..1617
                     /label="tetO"
     promoter        1540..1713
                     /label="CMV2_promoter"
     misc_feature    1627..1651
                     /label="LNCX_primer"
     misc_feature    1790..15520
                     /label="Full length juman XIST"
     misc_feature    complement(15719..15736)
                     /label="BGH_rev_primer"
     terminator      15722..15949
                     /label="bGH_PA_terminator"
     rep_origin      16012..16318
                     /label="f1_origin"
     misc_feature    complement(16432..16452)
                     /label="pBABE_3_primer"
     misc_feature    complement(16438..16653)
                     /label="SV40_enhancer"
     promoter        16450..16718
                     /label="SV40_promoter"
     rep_origin      16617..16694
                     /label="SV40_origin"
     misc_feature    16679..16698
                     /label="SV40pro_F_primer"
     CDS             complement(16752..17573)
                     /label="ORF frame 3"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHPRNRERGRCKVPINITIFVETIGAAIYPQDISTPSYIEAES
                     TRFFALRELHQVGDAVELFDQKLLDRRRGEFRLFHHVLIRSENGYTSSRELFAKA*"
                                 (SEQ ID NO:30)
     CDS             16815..17840
                     /label="hygroB"
                     /gene="hygroB"
                     /note="ORF frame 3"
                     /translation="MEKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"                  (SEQ ID NO:31)
     gene            16830..17837
                     /label="hygroB"
                     /gene="hygroB"
     terminator      17973..18092
```

FIG. 10C, Cont'd - CONSTRUCT 3 (FL/hXIST/RCAN1)

```
                  /label="SV40_PA_terminator"
misc_feature      18061..18080
                  /label="EBV_rev_primer"
misc_feature      18102..18860
                  /label="RCAN1 left arm"
misc_feature      complement(18894..18912)
                  /label="M13_reverse_primer"
misc_feature      complement(18911..18933)
                  /label="M13_pUC_rev_primer"
promoter          complement(18947..18976)
                  /label="lac_promoter"
rep_origin        complement(19285..19904)
                  /label="pBR322_origin"
CDS               complement(20059..20919)
                  /label="Ampicillin"
                  /gene="Ampicillin"
                  /note="ORF frame 1"
                  /translation="MSIQHFRVALIPFFAAFCLPVFAHPETLVKVKDAEDQLGARVGY
                  IELDLNSGKILESFRPEERFPMMSTFKVLLCGAVLSRIDAGQEQLGRRIHYSQNDLVE
                  YSPVTEKHLTDGMTVRELCSAAITMSDNTAANLLLTTIGGPKELTAFLHNMGDHVTRL
                  DRWEPELNEAIPNDERDTTMPVAMATTLRKLLTGELLTLASRQQLIDWMEADKVAGPL
                  LRSALPAGWFIADKSGAGERGSRGIIAALGPDGKPSRIVVIYTTGSQATMDERNRQIA
                  EIGASLIKHW*"     (SEQ ID NO:25)
gene              complement(20059..20919)
                  /label="Ampicillin"
                  /gene="Ampicillin"
promoter          complement(20961..20989)
                  /label="AmpR_promoter"
```

FIG. 10D - CONSTRUCT 4 (FL/hXIST/DYRK1A)

```
LOCUS       pcDNA5/TO/DYRK1A LA &#38; RA/FL human XIST   20737 bp    DNA    SYN    29-
Nov-2012
DEFINITION  pcDNA5/TO/DYRK1A LA &#38; RA/FL human XIST
ACCESSION
KEYWORDS
SOURCE
  ORGANISM  other sequences; artificial sequences; vectors.
FEATURES             Location/Qualifiers
     source          1..20737
                     /organism="pcDNA5/TO/DYRK1A LA &#38; RA/FL human XIST"
                     /mol_type="other DNA"
     misc_feature    209..716
                     /label="DYRK1A right arm"
     misc_feature    823..1110
                     /label="CAG_enhancer"
     promoter        744..1320
                     /label="CMV_immearly_promoter"
     misc_feature    1277..1297
                     /label="CMV_fwd_primer"
     promoter        1278..1401
                     /label="CMV_promoter"
     misc_feature    1328..1367
                     /label="tetO"
     promoter        1290..1463
                     /label="CMV2_promoter"
     misc_feature    1377..1401
                     /label="LNCX_primer"
     misc_feature    1540..15270
                     /label="Full length human XIST"
     misc_feature    complement(15469..15486)
                     /label="BGH_rev_primer"
     terminator      15472..15699
                     /label="bGH_PA_terminator"
     rep_origin      15762..16068
                     /label="f1_origin"
     misc_feature    complement(16182..16202)
                     /label="pBABE_3_primer"
     misc_feature    complement(16188..16403)
                     /label="SV40_enhancer"
     promoter        16200..16468
                     /label="SV40_promoter"
     rep_origin      16367..16444
                     /label="SV40_origin"
     misc_feature    16429..16448
                     /label="SV40pro_F_primer"
     CDS             complement(16502..17323)
                     /label="ORF frame 2"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNPERGRCKVPINITIFVETIGAAIYPQDISTPSYIEAES
                     TRFFALRELHQVGDAVELFDQKLLDRRRGEFRLFHHVLIRSENGYTSSRELFAKA*"
                                  (SEQ ID NO:30)
     CDS             16565..17590
                     /label="hygroB"
                     /gene="hygroB"
                     /note="ORF frame 2"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE* (SEQ ID NO:31)
     gene            16580..17587
                     /label="hygroB"
                     /gene="hygroB"
     terminator      17723..17842
```

FIG. 10D, Cont'd - CONSTRUCT 4 (FL/hXIST/DYRK1A)

```
                     /label="SV40_PA_terminator"
     misc_feature    17811..17830
                     /label="EBV_rev_primer"
     misc_feature    17853..18542
                     /label="DYRK1A left arm"
     misc_feature    complement(18576..18594)
                     /label="M13_reverse_primer"
     misc_feature    complement(18593..18615)
                     /label="M13_pUC_rev_primer"
     promoter        complement(18629..18658)
                     /label="lac_promoter"
     rep_origin      complement(18967..19586)
                     /label="pBR322_origin"
     CDS             complement(19741..20601)
                     /label="Ampicillin"
                     /gene="Ampicillin"
                     /note="ORF frame 1"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"    (SEQ ID NO:25)
     gene            complement(19741..20601)
                     /label="Ampicillin"
                     /gene="Ampicillin"
     promoter        complement(20643..20671)
                     /label="AmpR_promoter"
//
```

FIG. 10E - CONSTRUCT 5 (6.8 kb/hXIST/RCAN1)

```
LOCUS       pcDNA5/TO/RCAN1 LA &#38; RA/6.8kb human XIST 14026 bp    DNA    SYN    29-
Nov-2012
DEFINITION  pcDNA5/TO/RCAN1 LA &#38; RA/6.8kb human XIST
ACCESSION
KEYWORDS
SOURCE
  ORGANISM  other sequences; artificial sequences; vectors.
FEATURES             Location/Qualifiers
     source          1..14026
                     /organism="pcDNA5/TO/RCAN1 LA &#38; RA/6.8kb human XIST"
                     /mol_type="other DNA"
     misc_feature    209..966
                     /label="RCAN1 right arm"
     misc_feature    1073..1360
                     /label="CAG_enhancer"
     promoter        994..1570
                     /label="CMV_immearly_promoter"
     misc_feature    1527..1547
                     /label="CMV_fwd_primer"
     promoter        1528..1651
                     /label="CMV_promoter"
     misc_feature    1578..1617
                     /label="tetO"
     promoter        1540..1713
                     /label="CMV2_promoter"
     misc_feature    1627..1651
                     /label="LNCX_primer"
     misc_feature    1790..8630
                     /label="6.8kb human XIST"
     misc_feature    complement(8641..8657)
                     /label="pBluescriptKS_primer"
     misc_feature    complement(8690..8707)
                     /label="BGH_rev_primer"
     terminator      8693..8920
                     /label="bGH_PA_terminator"
     rep_origin      8983..9289
                     /label="f1_origin"
     misc_feature    complement(9403..9423)
                     /label="pEABE_3_primer"
     misc_feature    complement(9409..9624)
                     /label="SV40_enhancer"
     promoter        9421..9689
                     /label="SV40_promoter"
     rep_origin      9588..9665
                     /label="SV40_origin"
     misc_feature    9650..9669
                     /label="SV40pro_F_primer"
     CDS             complement(9723..10544)
                     /label="ORF frame 3"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNREKGRCKVPINITIFVETIGAAIYPQDISTPSYIEAES
                     TRFFALRELHQVGDAVELFDQKLLDRRRGEFRLFHHVLIRSENGYTSSRELFAKA*"
                           (SEQ ID NO:30)
     CDS             9786..10811
                     /label="hygroB"
                     /gene="hygroB"
                     /note="ORF frame 3"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"                         (SEQ ID NO:31)
     gene            9801..10808
                     /label="hygroB"
```

FIG. 10E, Cont'd - CONSTRUCT 5 (6.8 kb/hXIST/RCAN1)

```
                     /gene="hygroB"
terminator           10944..11063
                     /label="SV40_PA_terminator"
misc_feature         11032..11051
                     /label="EBV_rev_primer"
misc_feature         11074..11831
                     /label="RCAN1 left arm"
misc_feature         complement(11865..11883)
                     /label="M13_reverse_primer"
misc_feature         complement(11882..11904)
                     /label="M13_pUC_rev_primer"
promoter             complement(11918..11947)
                     /label="lac_promoter"
rep_origin           complement(12256..12875)
                     /label="pBR322_origin"
CDS                  complement(13030..13890)
                     /label="Ampicillin"
                     /gene="Ampicillin"
                     /note="ORF frame 1"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"       (SEQ ID NO:25)
gene                 complement(13030..13890)
                     /label="Ampicillin"
                     /gene="Ampicillin"
promoter             complement(13932..13960)
                     /label="AmpR_promoter"
```

FIG. 10F - CONSTRUCT 6 (6.8 kb/hXIST/DYRK1A)

```
LOCUS       pcDNA5/TO/DYRK1A LA &#38; RA/6.8kb human XIST       13708 bp      DNA     SYN
       29-Nov-2012
DEFINITION  pcDNA5/TO/DYRK1A LA &#38; RA/6.8kb human XIST
ACCESSION
KEYWORDS
SOURCE
  ORGANISM  other sequences; artificial sequences; vectors.
FEATURES             Location/Qualifiers
     source          1..13708
                     /organism="pcDNA5/TO/DYRK1A LA &#38; RA/6.8kb human XIST"
                     /mol_type="other DNA"
     misc_feature    209..716
                     /label="DYRK1A right arm"
     misc_feature    823..1110
                     /label="CAG_enhancer"
     promoter        744..1320
                     /label="CMV_immearly_promoter"
     misc_feature    1277..1297
                     /label="CMV_fwd_primer"
     promoter        1278..1401
                     /label="CMV_promoter"
     misc_feature    1328..1367
                     /label="tetO"
     promoter        1290..1463
                     /label="CMV2_promoter"
     misc_feature    1377..1401
                     /label="LNCX_primer"
     misc_feature    1540..8403
                     /label="6.8kb human XIST"
     misc_feature    complement(8391..8407)
                     /label="pBluescriptKS_primer"
     misc_feature    complement(8440..8457)
                     /label="BGH_rev_primer"
     terminator      8443..8670
                     /label="bGH_PA_terminator"
     rep_origin      8733..9039
                     /label="f1_origin"
     misc_feature    complement(9153..9173)
                     /label="pBABE_3_primer"
     misc_feature    complement(9159..9374)
                     /label="SV40_enhancer"
     promoter        9171..9439
                     /label="SV40_promoter"
     rep_origin      9338..9415
                     /label="SV40_origin"
     misc_feature    9400..9419
                     /label="SV40pro_F_primer"
     CDS             complement(9473..10294)
                     /label="ORF frame 2"
                     /translation="MPPLEVARLLLHTSQPRPPEEDVGDLVLGIPEHPLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNPERGRCKVPINITIFVETIGAAIYPQDISTPSYIEAES
                     TRFFALRELHQVGDAVELFDQKLLDRRRGEFRLFHHVLIRSENGYTSSRELFAKA*"
                               (SEQ ID NO:30)
     CDS             9536..10561
                     /label="hygroB"
                     /gene="hygroB"
                     /note="ORF frame 2"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"                              (SEQ ID NO:31)
     gene            9551..10558
                     /label="hygroB"
```

FIG. 10F, Cont'd - CONSTRUCT 6 (6.8 kb/hXIST/DYRK1A)

```
                     /gene="hygroB"
terminator           10694..10813
                     /label="SV40_PA_terminator"
misc_feature         10782..10801
                     /label="EBV_rev_primer"
misc_feature         10824..11513
                     /label="DYRK1A left arm"
misc_feature         complement(11547..11565)
                     /label="M13_reverse_primer"
misc_feature         complement(11564..11586)
                     /label="M13_pUC_rev_primer"
promoter             complement(11600..11629)
                     /label="lac_promoter"
rep_origin           complement(11938..12557)
                     /label="pBR322_origin"
CDS                  complement(12712..13572)
                     /label="Ampicillin"
                     /gene="Ampicillin"
                     /note="ORF frame 1"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"                       (SEQ ID NO:25)
gene                 complement(12712..13572)
                     /label="Ampicillin"
                     /gene="Ampicillin"
promoter             complement(13614..13642)
                     /label="AmpR_promoter"
```

FIG. 10G - CONSTRUCT 7 (6.8 kb/hXIST/AAVS1)

```
LOCUS       AAVS1 HindIII/pcDNA5/TO/6.8kb human XIST     15721 bp      DNA     SYN     29-
Nov-2012
DEFINITION  AAVS1 HindIII/pcDNA5/TO/6.8kb human XIST
ACCESSION
KEYWORDS
SOURCE
  ORGANISM  other sequences; artificial sequences; vectors.
FEATURES             Location/Qualifiers
     source          1..15721
                     /organism="AAVS1 HindIII/pcDNA5/TO/6.8kb human XIST"
                     /mol_type="other DNA"
     promoter        143..172
                     /label="lac_promoter"
     misc_feature    186..208
                     /label="M13_pUC_rev_primer"
     misc_feature    207..225
                     /label="M13_reverse_primer"
     promoter        242..261
                     /label="T3_promoter"
     misc_feature    295..1095
                     /label="Left arm"
     misc_feature    complement(1126..1145)
                     /label="EBV_rev_primer"
     terminator      complement(1112..1231)
                     /label="SV40_PA_terminator"
     gene            complement(1369..2376)
                     /label="hygroB"
                     /gene="hygroB"
     CDS             complement(1366..2391)
                     /label="ORF frame 1"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"    (SEQ ID NO: 31)
     CDS             1633..2454
                     /label="ORF frame 1"
                     /translation="MPPLEVARLLLHTSQPRPPEEDVGDLVLGIPEHRLAFVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNRERGRCKVPINITIFVETIGAAIYPQDISTPSYIEAES
                     TRFFALRELHQVGDAVELFDQKLLDRPRGEFRLFHHVLIRSENGYTSSRELFAKA*"
                              (SEQ ID NO: 30)
     misc_feature    complement(2508..2527)
                     /label="SV40pro_F_primer"
     rep_origin      complement(2512..2589)
                     /label="SV40_origin"
     promoter        complement(2488..2756)
                     /label="SV40_promoter"
     misc_feature    2559..2774
                     /label="SV40_enhancer"
     misc_feature    2754..2774
                     /label="pBABE_3_primer"
     rep_origin      complement(2886..3194)
                     /label="f1_origin"
     terminator      complement(3257..3484)
                     /label="bGH_PA_terminator"
     misc_feature    3470..3487
                     /label="BGH_rev_primer"
     misc_feature    3520..3536
                     /label="pBluescriptKS_primer"
     misc_feature    complement(3524..10387)
                     /label="6.8kb human XIST"
     misc_feature    complement(10526..10550)
                     /label="LNCX_primer"
     promoter        complement(10464..10637)
```

FIG. 10G, Cont'd - CONSTRUCT 7 (6.8 kb/hXIST/AAVS1)

```
                /label="CMV2_promoter"
misc_feature    complement(10560..10599)
                /label="tetO"
promoter        complement(10526..10651)
                /label="CMV_promoter"
misc_feature    complement(10630..10650)
                /label="CMV_fwd_primer"
promoter        complement(10603..11183)
                /label="CMV_immearly_promoter"
misc_feature    complement(10816..11103)
                /label="CAG_enhancer"
misc_feature    11219..12058
                /label="Right arm"
promoter        complement(12094..12112)
                /label="T7_promoter"
misc_feature    complement(12119..12135)
                /label="M13_forward20_primer"
misc_feature    complement(12128..12150)
                /label="M13_pUC_fwd_primer"
misc_feature    12116..12259
                /label="lacZ_a"
misc_feature    12282..12575
                /label="ccdB"
promoter        12786..12835
                /label="NEOKAN_promoter"
CDS             12924..13718
                /label="NeoR/KanR"
                /gene="NeoR/KanR"
                /note="ORF frame 3"
                /translation="MIEQDGLHAGSPAAWVERLFGYDWAQQTIGCSDAAVFRLSAQGR
                PVLFVKTDLSGALNELQDEAARLSWLATTGVPCAAVLDVVTEAGRDWLLLGEVPGQDL
                LSSHLAPAEKVSIMADAMRRLHTLDPATCPFDHQAKHRIERARTRMEAGLVDQDDLDE
                EHQGLAPAELFARLKASMPDGEDLVVTHGDACLPNIMVENGRFSGFIDCGRLGVADRY
                QDIALATRDIAEELGGEWADRFLVLYGIAAPDSQRIAFYRLLDEFF*"  (SEQ ID NO: 29)
gene            12927..13715
                /label="NeoR/KanR"
                /gene="NeoR/KanR"
promoter        13851..13874
                /label="AmpR_promoter"
CDS             complement(13968..14828)
                /label="Ampicillin"
                /gene="Ampicillin"
                /note="ORF frame 3"
                /translation="MSIQHFRVALIPFFAAFCLPVFAHPETLVKVKDAEDQLGARVGY
                IELDLNSGKILESFRPEERFPMMSTFKVLLCGAVLSRIDAGQEQLGRRIHYSQNDLVE
                YSPVTEKHLTDGMTVRELCSAAITMSDNTAANLLLTTIGGPKELTAFLHNMGDHVTRL
                DRWEPELNEAIPNDERDTTMPVAMATTLRKLLTGELLTLASRQQLIDWMEADKVAGPL
                LRSALPAGWFIADKSGAGERGSRGIIAALGPDGKPSRIVVIYTTGSQATMDERNRQIA
                EIGASLIKHW*"                  (SEQ ID NO:25)
gene            complement(13968..14828)
                /label="Ampicillin"
                /gene="Ampicillin"
rep_origin      14936..15555
                /label="pBR322_origin"
```

FIG. 10H - CONSTRUCT 8 (6.3 kb/mXist/Runx1)

```
LOCUS       Runx1/pcDNA5/TO/6.3kb mouse Xist-right direction   20607 bp    DNA
      SYN   29-Nov-2012
DEFINITION  Runx1/pcDNA5/TO/6.3kb mouse Xist-right direction
ACCESSION
KEYWORDS
SOURCE
  ORGANISM  other sequences; artificial sequences; vectors.
FEATURES             Location/Qualifiers
     source          1..20607
                     /organism="Runx1/pcDNA5/TO/6.3kb mouse Xist-right
direction"
                     /mol_type="other DNA"
     misc_feature    49..4008
                     /label="Left arm"
     misc_feature    complement(4037..4056)
                     /label="EBV_rev_primer"
     terminator      complement(4023..4142)
                     /label="SV40_PA_terminator"
     gene            complement(4280..5287)
                     /label="hygroB"
                     /gene="hygroB"
     CDS             complement(4277..5302)
                     /label="ORF frame 2"
                     /translation="MKKPELTATSVEKFLIEKFDSVSDLMQLSEGEESRAFSFDVGGR
                     GYVLRVNSCADGFYKDRYVYRHFASAALPIPEVLDIGEFSESLTYCISRRAQGVTLQD
                     LPETELPAVLQPVAEAMDAIAAADLSQTSGFGPFGPQGIGQYTTWRDFICAIADPHVY
                     HWQTVMDDTVSASVAQALDELMLWAEDCPEVRHLVHADFGSNNVLTDNGRITAVIDWS
                     EAMFGDSQYEVANIFFWRPWLACMEQQTRYFERRHPELAGSPRLRAYMLRIGLDQLYQ
                     SLVDGNFDDAAWAQGRCDAIVRSGAGTVGRTQIARRSAAVWTDGCVEVLADSGNRRPS
                     TRPRAKE*"      (SEQ ID NO:31)
     CDS             4544..5365
                     /label="ORF frame 2"
                     /translation="MPPLEVARLLLHTSQPRPPEEDVGDLVLGIPEHRLAPVNDRCYA
                     AIVRQDIVGAEIRVHEVPDFGAVLGPKHQLIESLRDGRTDGVVHHSLPVIHMGISNRA
                     YEITPCSVLTDSLRSEWAEPARLAKIGRSDRIHGLRDRLQNSGQFGFRQVLQRDTLCT
                     AGDAIGQALAEFPNVKHFRNRERGRCKVPINITIFVETIGAAIYPQDISTPSYIEAES
                     TRFFALRELHQVGDAVELFDQKLLDRRRGEFRLFHHVLIRSENGYTSSRELFAKA*"
                                   (SEQ ID NO:30)
     misc_feature    complement(5419..5438)
                     /label="SV40pro_F_primer"
     rep_origin      complement(5423..5500)
                     /label="SV40_origin"
     promoter        complement(5399..5667)
                     /label="SV40_promoter"
     misc_feature    5470..5685
                     /label="SV40_enhancer"
     misc_feature    5665..5685
                     /label="pBABE_3_primer"
     rep_origin      complement(5799..6105)
                     /label="f1_origin"
     terminator      complement(6168..6395)
                     /label="bGH_PA_terminator"
     misc_feature    6381..6398
                     /label="BGH_rev_primer"
     misc_feature    complement(6637..12936)
                     /label="6.3kb mouse Xist"
     misc_feature    complement(13105..13129)
                     /label="LNCX_primer"
     promoter        complement(13043..13216)
                     /label="CMV2_promoter"
```

FIG. 10H, Cont'd - CONSTRUCT 8 (6.3 kb/mXist/Runx1)

```
misc_feature     complement(13139..13178)
                 /label="tetO"
promoter         complement(13105..13230)
                 /label="CMV_promoter"
misc_feature     complement(13209..13229)
                 /label="CMV_fwd_primer"
promoter         complement(13182..13762)
                 /label="CMV_immearly_promoter"
misc_feature     complement(13395..13682)
                 /label="CAG_enhancer"
CDS              13759..14364
                 /label="ORF frame 1"
                 /translation="MSTRISGPYIGPRGQEHSLCPTHPPTVGRGTLGNPVCPEPQHSG
                 SLGSLCLPDHTLMPSLPLPAHSGSGPDRLRRPTPVPYSAVHLRPAHALPRRLHLLAAR
                 HVGHRHRHVSHELGLSLPHRPAAALPRLITGAGRALPDRLALLPSILRRLGRFLPVLH
                 GGRREIAPAHPAALHQRIHRRRAAQPQPPQPERRGGDRGQP*"
                       (SEQ ID NO:32)
misc_feature     13796..17681
                 /label="Right arm"
misc_feature     complement(17733..17750)
                 /label="Sp6_primer"
misc_feature     complement(17764..17782)
                 /label="M13_reverse_primer"
misc_feature     complement(17781..17803)
                 /label="M13_pUC_rev_primer"
promoter         complement(17817..17846)
                 /label="lac_promoter"
rep_origin       complement(18155..18774)
                 /label="pBR322_origin"
CDS              complement(18929..19789)
                 /label="Ampicillin"
                 /gene="Ampicillin"
                 /note="ORF frame 2"
                 /translation="MSIQHFRVALIPFFAAFCLPVFAHPETLVKVKDAEDQLGARVGY
                 IELDLNSGKILESFRPEERFPMMSTFKVLLCGAVLSRIDAGQEQLGRRIHYSQNDLVE
                 YSPVTEKHLTDGMTVRELCSAAITMSDNTAANLLLTTIGGPKELTAFLHNMGDHVTRL
                 DRWEPELNEAIPNDERDTTMPVAMATTLRKLLTGELLTLASRQQLIDWMEADKVAGPL
                 LRSALPAGWFIADKSGAGERGSRGIIAALGPDGKPSRIVVIYTTGSQATMDERNRQIA
                 EIGASLIKHW*"        (SEQ ID NO:25)
gene             complement(18929..19789)
                 /label="Ampicillin"
                 /gene="Ampicillin"
promoter         complement(19831..19859)
                 /label="AmpR_promoter"
rep_origin       complement(20104..20410)
                 /label="f1_origin"
misc_feature     complement(20439..20587)
                 /label="lacZ_a"
misc_feature     20553..20575
                 /label="M13_pUC_fwd_primer"
misc_feature     20568..20584
                 /label="M13_forward20_primer"
promoter         20591..2
                 /label="T7_promoter"
```

FIG. 10I - CONSTRUCT 9 (pEF1α/hDYRK1A/FL mXist)

```
LOCUS       pEF1x/hDYRK1A/FL mouse Xist 20647 bp DNA  SYN    27-Sep-2013
DEFINITION  pEF1x/hDYRK1A/FL mouse Xist
ACCESSION
KEYWORDS
SOURCE
  ORGANISM  other sequences; artificial sequences; vectors.
FEATURES             Location/Qualifiers
     source          1..20647
                     /organism="pEF1x/hDYRK1A/FL mouse Xist blunt ligation"
                     /mol_type="other DNA"
     promoter        191..1378
                     /label="EF1a_promoter"
     CDS             complement(471..1118)
                     /label="ORF frame 3"
                     /translation="MKRRLRTERPFSFVWVTHPPALPSAASSILSSLQQGREAAIFPL
                     TQLVPTGPALPPRAGRYTAARGQAPEQAGQLETTPVRFSVAALAGPASPNMCAGTHGP
                     RRRPRPQKPKYQCADLGPHLQDYLARKKASQQVIKNFKWLETYRKQRDRREGATRFAR
                     GGPSAQARPQLKHEAKGLLKRKASNSPTHFQPEARDQESRTAARGVEVIQGTQGP*"
                              (SEQ ID NO:27)
     misc_feature    1326..1346
                     /label="EF1a_fwd_primer"
     misc_feature    1378..1402
                     /label="LNCX_primer"
     misc_feature    1545..16406
                     /label="mouse FL Xist"
     misc_feature    16592..16607
                     /label="SV40_int"
     misc_feature    16613..16660
                     /label="SV40_3_splice"
     terminator      17236..17355
                     /label="SV40_PA_terminator"
     misc_feature    17324..17343
                     /label="EBV_rev_primer"
     misc_feature    17555..18244
                     /label="Human DYRK1A left arm"
     rep_origin      complement(18290..18909)
                     /label="pBR322_origin"
     CDS             complement(19064..19924)
                     /label="Ampicillin"
                     /gene="Ampicillin"
                     /note="ORF frame 2"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"              (SEQ ID NO:25)
     gene            complement(19064..19924)
                     /label="Ampicillin"
                     /gene="Ampicillin"
     promoter        complement(19966..19994)
                     /label="AmpR_promoter"
     misc_feature    20135..20642
                     /label="Human DYRK1A right arm"
```

FIG. 10J - CONSTRUCT 10 (pEF1α/hDYRK1A/6.3kb mXist)

```
LOCUS       pEF1α/hDYRK1A/6.3kb mXist 12230 bp DNA    SYN    27-Sep-2013
DEFINITION  pEF1α/hDYRK1A/6.3kb mXist
ACCESSION
KEYWORDS
SOURCE
  ORGANISM  other sequences; artificial sequences; vectors.
FEATURES             Location/Qualifiers
     source          1..12230
                     /organism=" pEF1α/hDYRK1A/6.3kb mXist"
                     /mol_type="other DNA"
     promoter        44..1378
                     /label="pEF1x promoter"
     promoter        191..1378
                     /label="EF1a_promoter"
     CDS             complement(471..1118)
                     /label="ORF frame 3"
                     /translation="MKRRLRTERPFSFVWVTHPPALPSAASSILSSLQQGREAAIFPL
                     TQLVPTGPALPPRAGRYTAARGQAPEQAGQLETTPVRFSVAALAGPASPNMCAGTHGP
                     RPRPRPQKPKYQCADLGPHLQDYLARKKASQQVIKNFKWLETYRKQRDRREGATRFAR
                     GGPSAQARPQLKHEAKGLLKRKASNSPTHFQPEARDQESRTAARGVEVIQGTQGP*"
                              (SEQ ID NO:27)
     misc_feature    1326..1346
                     /label="EF1a_fwd_primer"
     misc_feature    1378..1402
                     /label="LNCX_primer"
     misc_feature    1579..7878
                     /label="6.3kb mouse Xist"
     misc_feature    8175..8190
                     /label="SV40_int"
     misc_feature    8196..8243
                     /label="SV40_3_splice"
     misc_feature    8100..8897
                     /label="SV40 pA"
     terminator      8819..8938
                     /label="SV40_PA_terminator"
     misc_feature    8907..8926
                     /label="EBV_rev_primer"
     misc_feature    9138..9827
                     /label="Human DYRK1A left arm"
     rep_origin      complement(9873..10492)
                     /label="pBR322_origin"
     CDS             complement(10647..11507)
                     /label="Ampicillin"
                     /gene="Ampicillin"
                     /note="ORF frame 3"
                     /translation="MSIQHFRVALIPFFAAFCLPVFAHPETLVKVKDAEDQLGARVGY
                     IELDLNSGKILESFRPEERFPMMSTFKVLLCGAVLSRIDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPVAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*"                  (SEQ ID NO:25)
     gene            complement(10647..11507)
                     /label="Ampicillin"
                     /gene="Ampicillin"
     promoter        complement(11549..11577)
                     /label="AmpR_promoter"
     misc_feature    11718..12225
                     /label="Human DYRK1A right arm"
```

FIG. 10K - CONSTRUCT 11 (Rosa26/pEF1x-Tet3G/hPGK-PuroR)

```
LOCUS       Rosa26/pEF1x-Tet3G/hPGK-PuroR   10391 bp    DNA    SYN    03-Oct-
2013
DEFINITION  Rosa26/pEF1x-Tet3G/hPGK-PuroR
ACCESSION
KEYWORDS
SOURCE
  ORGANISM  other sequences; artificial sequences; vectors.
FEATURES             Location/Qualifiers
     source          1..10391
                     /organism="Rosa26/pEF1x-Tet3G/hPGK-PuroR"
                     /mol_type="other DNA"
     rep_origin      complement(135..441)
                     /label="f1_origin"
     misc_feature    complement(459..614)
                     /label="lacZ_a"
     misc_feature    585..607
                     /label="M13_pUC_fwd_primer"
     misc_feature    600..616
                     /label="M13_forward20_primer"
     promoter        626..644
                     /label="T7_promoter"
     misc_feature    653..1452
                     /label="Rosa26 left arm"
     misc_feature    1497..2297
                     /label="AAVS1 left arm"
     misc_feature    2322..2764
                     /label="SV40 pA signal"
     terminator      2646..2777
                     /label="SV40_PA_terminator"
     misc_feature    2734..2753
                     /label="EBV_rev_primer"
     CDS             complement(2787..3533)
                     /label="ORF frame 3"
                     /translation="MSRLDKSKVINSALELLNGVGIEGLTTRKLAQKLGVEQPTLYWH
                     VKNKRALLDALPIEMLDRHHTHSCPLEGESWQDFLRNNAKSYRCALLSHRDGAKVHLG
                     TRPTEKQYETLENQLAFLCQQGFSLENALYALSAVGHFTLGCVLEEQEHQVAKEERET
                     PTTDSMPPLLKQAIELFDRQGAEPAFLFGLELIICGLEKQLKCESGGPTDALDDFDLD
                     MLPADALDDFDLDMLPADALDDFDLDMLPG*"    (SEQ ID NO:26)
     misc_feature    2787..3533
                     /label="Tet3G"
     misc_feature    complement(3615..3639)
                     /label="LNCX_primer"
     misc_feature    complement(3671..3691)
                     /label="EF1a_fwd_primer"
     CDS             3899..4546
                     /label="ORF frame 2"
                     /translation="MKRRLRTERPFSFVWVTHPPALPSAASSILSSLQQGREAAIFPL
                     TQLVPTGPALPPRAGRYTAARGQAPEQAGQLETTPVRFSVAALAGPASPNMCAGTHGP
                     RRRPRPQKPKYQCADLGPHLQDYLARKKASQQVIKNFKWLETYRKQRDRREGATRFAR
                     GGPSAQARPQLKHEAKGLLKRKASNSPTHFQPEARDQESRTAARGVEVIQGTQGP*"
                           (SEQ ID NO:27)
     promoter        complement(3639..4826)
                     /label="EF1a_promoter"
     promoter        3639..4973
                     /label="pEF1x promoter"
     misc_feature    5115..5621
                     /label="hPGK"
     CDS             5403..6242
                     /label="puro(variant)"
```

FIG. 10K, Cont'd - CONSTRUCT 11 (Rosa26/pEF1x-Tet3G/hPGK-PuroR)

```
                /gene="puro(variant)"
                /note="ORF frame 3"
                /translation="MAARRPRWAVANSGCSAGRAESSGREGAVREAGCGAVVWALFLP
                ARCSAFCKPPERTSAVGSLVDRITDLSPQGDPPELTMTEYKPTVRLATRDDVPRAVRT
                LAAAFADYPATRHTVDPDRHIERVTELQELFLTRVGLDIGKVWVADDGAAVAVWTTPE
                SVEAGAVFAEIGPRMAELSGSRLAAQQQMEGLLAPHRPKEPAWFLATVGVSPDHQGKG
                LGSAVVLPGVEAAERAGVPAFLETSAPRNLPFYERLGFTVTADVEVPEGPRTWCMTRK
                PGA*"                         (SEQ ID NO:28)
gene            5643..6242
                /label="puro(variant)"
                /gene="puro(variant)"
misc_feature    5643..6242
                /label="Puro"
misc_feature    6249..6473
                /label="BGH pA"
terminator      6258..6473
                /label="bGH_PA_terminator"
misc_feature    6489..7328
                /label="AAVS1 right arm"
misc_feature    7366..8176
                /label="Rosa26 right arm"
promoter        complement(8202..8221)
                /label="T3_promoter"
misc_feature    complement(8238..8256)
                /label="M13_reverse_primer"
misc_feature    complement(8255..8277)
                /label="M13_pUC_rev_primer"
promoter        complement(8291..8320)
                /label="lac_promoter"
rep_origin      complement(8629..9248)
                /label="pBR322_origin"
CDS             complement(9403..10263)
                /label="Ampicillin"
                /gene="Ampicillin"
                /note="ORF frame 1"
                /translation="MSIQHFRVALIPFFAAFCLPVFAHPETLVKVKDAEDQLGARVGY
                IELDLNSGKILESFRPEERFPMMSTFKVLLCGAVLSRIDAGQEQLGRRIHYSQNDLVE
                YSPVTEKHLTDGMTVRELCSAAITMSDNTAANLLLTTIGGPKELTAFLHNMGDHVTRL
                DRWEPELNEAIPNDERDTTMPVAMATTLRKLLTGELLTLASRQQLIDWMEADKVAGPL
                LRSALPAGWFIADKSGAGERGSRGIIAALGPDGKPSRIVVIYTTGSQATMDERNRQIA
                EIGASLIKHW*"                  (SEQ ID NO:25)
gene            complement(9403..10263)
                /label="Ampicillin"
                /gene="Ampicillin"
promoter        complement(10305..10333)
                /label="AmpR_promoter"
```

DOSAGE COMPENSATING TRANSGENES AND CELLS

CLAIM OF PRIORITY

This application is a national phase application under 35 U.S.C. § 371 of PCT International Application No. PCT/US2014/02752, filed Mar. 14, 2014, which claims the benefit of U.S. patent application Ser. Nos. 61/785,481, filed on Mar. 14, 2013, and 61/790,917, filed on Mar. 15, 2013. The entire contents of the foregoing are hereby incorporated by reference.

FEDERALLY SPONSORED RESEARCH OR DEVELOPMENT

This invention was made with Government support under Grant No. GM053234, GM085548 and GM096400 RC4 awarded by the National Institutes of Health. The Government has certain rights in the invention.

TECHNICAL FIELD

This invention relates to methods of effecting dosage compensation in cells trisomic for chromosome 21, and cells produced by said methods.

BACKGROUND

In the U.S., about 1 in 300 live births carry a trisomy, roughly half of which are trisomy for chromosome 21 (Chr21), which causes Down syndrome (DS). DS is the leading genetic cause of cognitive disability with increasing prevalence, and millions of patients worldwide experience congenital and progressive medical issues that impact multiple organ systems[1,2]. In addition to progressive intellectual impairment and early onset Alzheimer disease, there is greatly increased risk of myeloproliferative disorder, childhood leukemia, heart defects, and both immune and endocrine system dysfunction. DS researchers have sought to define the more "DS critical" genes on Chr21, but this has proven difficult due to high genetic complexity and phenotypic variability of DS, confounded by normal variation between any individuals[1-3]. Much progress has been made in developing DS mouse models[4-6], however there remains a critical need for better ways to understand the underlying cell and developmental pathology of human DS, so key to rationale design of therapeutics of any kind.

The last decade has seen great advances in strategies to correct single-gene defects of rare monogenic disorders, beginning with cells in vitro and in several cases advancing to in vivo and clinical trials. In contrast, genetic correction of the over-dose of genes across a whole extra chromosome in trisomic cells has remained outside the realm of possibility.

SUMMARY

At least in part, the present invention is based on the discovery that the imbalanced expression of hundreds of genes across an extra chromosome can be de facto corrected in DS patient stem cells, by the targeted addition of one gene, XIST, into a specified gene, e.g., the Dual specificity tyrosine-phosphorylation-regulated kinase 1A (DYRK1A) locus, or the Regulator of calcineurin 1 (RCAN1) locus, on Chromosome 21 ("Chr 21"). Using genome editing with zinc finger nucleases, addition of a large, inducible XIST transgene to a precise position in the Chr 21 DYRK1A or RCAN1 loci was achieved in DS iPSCs. This resulted in Chr 21 coating by the non-coding XIST RNA, heterochromatin modifications, chromosome-wide transcriptional silencing and DNA methylation to form a "Chr 21 Barr Body". Silencing became irreversible in differentiated cells. A model to study human chromosome silencing that avoids the selection against silencing of a disomic autosome was created by targeting a trisomic chromosome with an inducible XIST transgene. Such inducible correction of the trisomy provides a system to investigate genomic expression changes and the cellular pathology of trisomy 21, free from genetic and epigenetic noise. Remarkably, a proliferative deficit of DS cells in vitro was reversed upon induced silencing of one Chr 21. The present vectors may be useful in "chromosome therapy" for Down syndrome.

Accordingly, the present invention features nucleic acid constructs that include a silencing sequence encoding an XIST RNA or fragment thereof that silences a segment of a chromosome), driven by a regulatory sequence comprising a promoter; first and second sequences that direct insertion of the silencing sequence into or near the DYRK1A or RCAN1 genes on chromosome 21; and, optionally, a selectable marker. The first and second sequences that direct insertion of the silencing sequence into DYRK1A or RCAN1 may also be referred to herein as "first and second targeting elements." These sequences or elements can be readily selected and inserted into the nucleic acid constructs using methods well known in the art.

Thus, in one aspect, the invention provides silencing vectors comprising: a silencing element comprising a silencing sequence flanked by first and second targeting sequences, wherein each of the first and second targeting sequences are homologous to at least 50 bp (e.g., 50, 100, 200, or 500) of sequence in or near (e.g., within 1 MB, 0.5 MB, 0.1 MB, 0.05 MB, 10000 MB, 5000 MB, 1000 KB, 500 KB, 100 KB, 50 KB, 10 KB, 5 KB, or 1 KB) the dual specificity tyrosine-phosphorylation-regulated kinase 1A (DYRK1A) gene, e.g., in the DYRK1A gene, e.g., in intron 1 of DYRK1A, or in or near the Regulator of calcineurin 1 (RCAN1) gene, e.g., in the RCAN1 gene, e.g., in intron 3 of RCAN1; and a promoter operably linked to the silencing element.

In some embodiments, the vector is a plasmid or a viral vector. In some embodiments, the viral vector is vaccinia virus, adeno-associated virus (MV), or herpes virus.

In some embodiments, the silencing vector targets intron 1 of human DYRK1A and the first targeting sequence comprises a sequence obtained by performing PCR with a primer pair of: Human Chr 21 DYRK1A left arm primers: forward 5'-GCCGTATACCATTAACTCTTTACTGTTC-3' (SEQ ID NO:1), reverse 5'-TCTGTATACGTAAACTGGCAAAGGGGTGG-3' (SEQ ID NO:2); and the second targeting sequence comprises a sequence obtained by performing PCR with a primer pair of: Human Chr 21 DYRK1A right arm primers: forward 5'-ATTTCGCGAACGGGTGATGAGCAGGCTGT-3' (SEQ ID NO:3), reverse 5'-CCGTCGCGAAAACCAGAAAGTATTCTCAG-3' (SEQ ID NO:4).

In some embodiments, the silencing vector targets intron 3 of human RCAN1 and the first targeting sequence comprises a sequence obtained by performing PCR with a primer pair of: Human Chr 21 RCAN1 left arm primers: forward 5'-ATT GTATAC CCAAGAGCCC TCCTGACCTC-3' (SEQ ID NO:5), reverse 5'-AATGTATACGGGTGGAGGGGCGTGATGCA-3' (SEQ ID NO:6); and the second targeting sequence comprises a sequence obtained by performing PCR with a primer pair of: RCAN1 right arm primers: forward 5'-TAT TCGCGA CC CGCAGTGTCC CAGGAAT-3' (SEQ ID NO:7), reverse 5'-CGCTCGCGA-CAATGTTTTCAGAAATGTAA-3' (SEQ ID NO:8).

In some embodiments, the silencing element comprises a human XIST cDNA or functional fragment thereof.

In some embodiments, the silencing vector includes a selectable marker sequence, e.g., a selectable marker sequence is operably linked to a promoter.

In another aspect, provided herein are silencing vectors comprising the sequences shown in FIG. 10*a*, 10*c*-10*j* or SEQ ID NOs:14, 16, 17, 18, 19, 20, 21, 22, or 23.

In another aspect, the invention provides methods for reducing levels of expression of genes on Chromosome 21 in a cell, the method comprising contacting the cell with a silencing vector described herein, under conditions sufficient for the silencing vector to undergo homologous recombination with the genomic DNA of the cell, wherein the silencing element is inserted into intron 1 of DYRK1A or intron 3 of RCAN1.

In some embodiments, the cell is trisomic for chromosome 21.

In some embodiments, the cell is a human cell.

In some embodiments, the cell is a stem cell or a fibroblast.

In some embodiments, the stem cell is an induced pluripotent stem cell (iPSC), a hematopoietic stem cell, or a neural stem cell.

In another aspect, the invention provides cells produced by a method described herein.

In another aspect, the invention provides methods for reducing the risk of transient myeloproliferative disorder (TMD) in a subject who has Down Syndrome (Trisomy 21). The methods include obtaining a hematopoietic stem cell from the subject; contacting the cell with a silencing vector described herein, under conditions sufficient for the silencing vector to undergo homologous recombination with the genomic DNA of the cell, wherein the silencing element is inserted into intron 1 of DYRK1A or intron 3 of RCAN1, to produce a modified cell having reduced levels of expression of genes on Chromosome 21; and administering the modified cell to the subject.

In some embodiments, the methods include contacting the cell with a cleavage vector comprising a sequence that enhances or facilitates homologous recombination.

In some embodiments, the cleavage vector comprises a zinc finger nuclease (ZFN) or a transcription activator-like effector nuclease (TALEN).

In some embodiments, the cleavage vector targets a sequence in intron 1 of DYRK1A comprising GCCAC-CCCTTTGCCAGTTTACACGGGTGATGAGCA GGCT-GTT (SEQ ID NO:9).

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1:
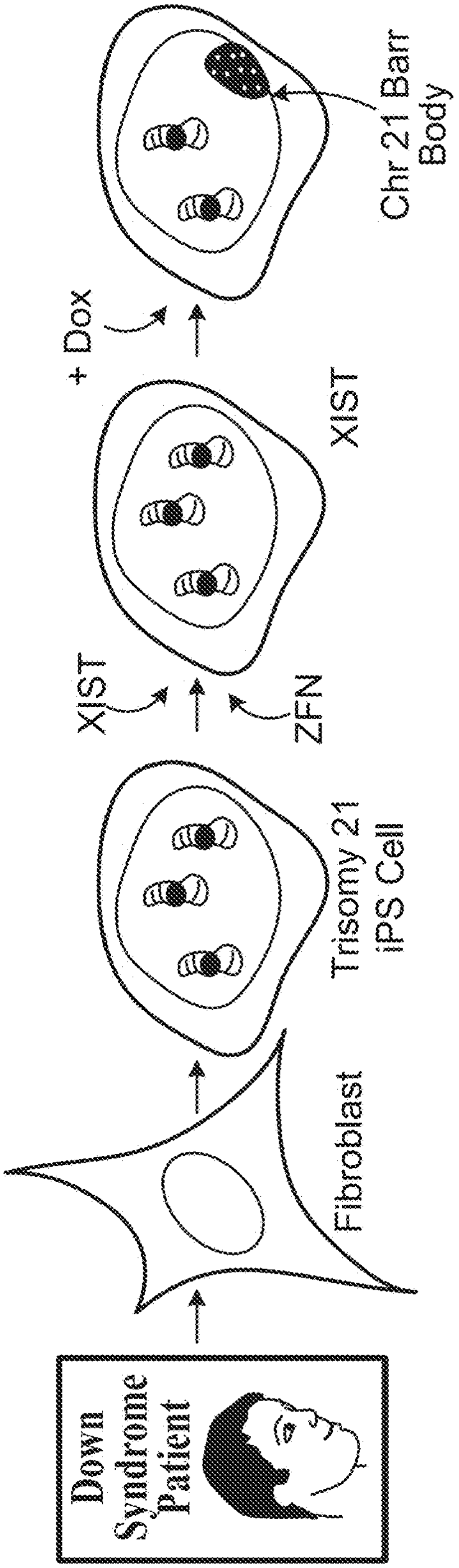
FIG. 1. Schematic outline of the trisomy 21 dosage compensation concept. The natural dosage compensation mechanism (XIST non-coding RNA) is redirected, using ZFN technology, to one trisomic chromosome in iPS cells derived from Down syndrome patient fibroblasts. Subsequent expression of XIST RNA initiates chromosome-wide silencing of the targeted Chr21, producing a stable heterochromatic Chr21-Barr body, and correcting trisomy 21 to functional disomy.

9*a:* 3G/FL/hXIST/DYRK1A. The plasmid map show the 18.5 kb inducible human XIST construct consists of two homologous arms (left arm, 690 bp; right arm, 508 bp), and a large XIST cDNA driven by an inducible pTRE3G promoter. The 14 kb XIST cDNA contains exons 1-5 and two fragments of exon 6 of XIST gene. The insert is 15.4 kb. The specifically designed ZFN cleaves the intron 1 of DYRK1A locus on Chr 21 (as shown in schematic of FIG. 2*a*).

9*b*: puro/rtTA/AAVS1. The plasmid map shows the puro/rtTA construct contains both puromycin (puro) and tetracycline transactivator (rtTA) cassettes with opposite direction. rtTA is driven by a 3G EF1α promoter that is not inactivated in hESCs and hiPSCs. The puro and rtTA plasmid is targeted the AAVS1 locus on Chr 19 by ZFN.

9*c*: FL/hXIST/DYRK1A. The plasmid map shows that the 20.7 kb selectable and inducible human XIST construct contains two homologous arms (left arm, 690 bp; right arm, 508 bp), a hygromycin selection gene, and a 14 kb full length XIST cDNA driven by a tetracycline operator inducible promoter. The large XIST transgene is targeted the DYRK1A gene on Chr 21 by ZFNs (as shown in schematic of FIG. 2*a*).

9*d:* 6.8 kb/hXIST/DYRK1A. The plasmid map shows that the 13.7 kb selectable and inducible human XIST construct contains two homologous arms (left arm, 690 bp; right arm, 508 bp), a hygromycin selection gene, and a 6.8 kb exon 1 of human XIST cDNA driven by a tetracycline operator inducible promoter. The 6.8 kb XIST transgene is targeted the DYRK1A gene on Chr 21 by ZFNs (as shown in schematic of FIG. 2*a*).

9*e*. 6.8 kb/hXIST/AAVS1. The plasmid map shows the 15.7 kb selectable and inducible human XIST construct contains two homologous arms (800 bp each arm), a hygromycin selection gene, and a 6.8 kb exon 1 of human XIST cDNA driven by a tetracycline operator inducible promoter. The 6.8 kb XIST transgene is targeted the AAVS1 locus on Chr 19 by ZFNs.

9*f:* 6.3 kb/mXist/Runx1. The plasmid map shows that the 20.6 kb selectable and inducible mouse Xist construct contains two homologous arms (4 kb each arm), a hygromycin selection gene, and a 6.3 kb exon 1 of mouse Xist cDNA driven by a tetracycline operator inducible promoter. This 6.3 kb mouse Xist transgene is targeted the Runx1 gene on Chr 16 (synteny to human Chr 21) by conventional homologous recombination.

9*g*: pEF1α/hDYRK1A/FL mXist. The plasmid map shows that the 20.6 kb construct contains full length mouse Xist cDNA, an ampicillin resistance gene, and two homologous arms that target intron 1 of DYRK1A gene on human chromosome 21.

9*h*: pEF1α/hDYRK1A/6.3 kb mXist. The plasmid map shows that the 12.2 kb construct contains 6.3 kb of mouse Xist cDNA that has been reported to function (Wutz et al., Nat Genet 30, 167-174 (2002)) and two homologous arms that target intron 1 of DYRK1A gene on human chromosome 21.

9*i*: Rosa26/pEF1x-Tet3G/hPGK-PuroR. The plasmid map shows that the 10.4 kb construct contains a puromycin resistance selection gene and rtTA cassette that is targeted to the Rosa26 locus on mouse chromosome 6 by ZFNs.

FIGS. 10A-K set forth some of the characteristics of the sequences of constructs 1-11, respectively, which are described more fully below.

DETAILED DESCRIPTION

Nature has evolved a mechanism to dosage compensate the difference in X-linked gene copies between mammalian females (XX) and males (XY)[8]. This process is driven by a large (~17 kb in human) non-coding RNA, XIST, which during early development is produced exclusively from the inactive X (Xi)[9], and "paints" (accumulates across) the interphase chromosome structure. The RNA induces a cascade of heterochromatin modifications and architectural changes which transcriptionally silence the Xi and manifest cytologically as a condensed Barr Body (reviewed in[11-14]). There is some DNA sequence specificity to XIST function, since many human genes escape X-inactivation[15-18]; however, autosomal chromatin has substantial capacity to be silenced[19-22]. The full potential of an autosome to be silenced, however, needs to be examined under conditions that avoid creation of a deleterious functional monosomy. The strategy pursued here meets that requirement and creates a tractable model to study the distinct biology of human chromosome inactivation[21].

As demonstrated herein (see FIG. 1), the present constructs and methods can be used to reroute the human X-chromosome inactivation machinery to a supernumerary Chr 21 in DS cells, and thereby enact its epigenetic transformation, in an controlled fashion. The approach directs, e.g., via zinc finger nuclease-driven targeted gene addition[23], a functional, inducible XIST transgene precisely to the gene-rich core of a trisomic chromosome 21 in induced pluripotent stem cells (iPSCs) derived from a subject with DS. The present results demonstrate (i) an unprecedented efficiency and precision of this addition using the largest transgene used for such an effort to date; (ii) the on-demand heterochromatinization of the extra Chr 21 by numerous histone modifications and DNA condensation; (iii) long-range essentially uniform transcriptional repression as gauged by in situ analyses, genome-wide expression profiling, and CpG promoter methylation status; and finally, (iv) inducible trisomy silencing in vitro can also correct a deficit in proliferation of DS stem cells as revealed in this study. Thus, these findings establish a unique system to study DS-related cellular pathologies in a developmental cell context, as well as investigate the initiation of epigenetic chromosome silencing and its relationship to genomic sequence context. In addition, as the present methods result in at least partial correction of the chromosomal imbalance in DS, the methods enable a combined genetic/epigenetic approach to "chromosome therapy" for DS as well as cell therapies using autologous cells.

Unlike random integration into a diploid cell, silencing a trisomic autosome avoids selection against full autosomal silencing and monosomy. Thus, comprehensive analysis demonstrates highly robust competence of Chr21 to be silenced, allowing dosage compensation of trisomy 21 to very near normal disomic levels. This suggests that an RNA evolved for the X-chromosome utilizes epigenome-wide mechanisms. The ability to insert a single XIST transgene in any locus, in multiple isogenic sub-clones, now provides a powerful tool to further study XIST function. The present effort also has almost tripled the size of transgenes compatible with nuclease-driven targeted gene addition, important for a host of other compelling applications that require large sequence insertions.

From a translational perspective, trisomy silencing has immediate impact as a means to define the poorly understood cellular pathways deregulated in DS. Accomplishing this in DS iPSCs provides a means to derive and study various patient-compatible cell-types potentially relevant to DS therapeutics (e.g., hematopoietic, cardiac, neuronal, endocrine, and immune). Inducible "trisomy silencing in a dish" allows discrimination of differences directly due to Chr21 over-expression apart from genetic and epigenetic differences between transgenic sub-clones or rare disomic sub-clones isolated from a trisomic population ([48,49] and this study). Induced XIST expression triggers not only global Chr21 repression, but a defined effect on the genomic expression profile, and, importantly, impacts two major aspects of cell phenotype. This can illuminate the cohort of genes and cognate pathways most consistently impacted in DS, and thus define targets for translational efforts. Our discovery that Chr21 over-expression is linked to a reversible deficit in cell proliferation, and also neural rosette formation, is significant, particularly given that DS individuals show accelerated aging and hypocellularity in certain regions of the brain[42,43]. Understanding the pathways and pathologies of DS will also inform the search for drugs that may rebalance those pathways, and the impact of whole chromosome silencing can be a benchmark to compare the impact of correcting individual genes (e.g. DYRK1A) to disomy. This general strategy can similarly be extended to study other chromosomal disorders, such as trisomy 13 and 18, so often fatal in the first 1-2 years.

Finally, the present methods and compositions can be used for gene therapy to address whole chromosome imbalance.

Nucleic Acid Constructs—Silencing Vectors

Described herein are silencing vectors, nucleic acid constructs that include a silencing sequence driven by a regulatory region comprising a promoter, and one or more targeting sequences (e.g., first and second sequences that flank the silencing sequence and direct insertion of the silencing sequence into a targeted chromosome). The silencing vectors can also include a selectable marker, driven by the same or, more preferably, a different regulatory region.

XIST Silencing Sequences

In the present application, the term "Xist" refers to an Xist gene or the encoded Xist RNA regardless of the origin of the sequence. For example, the present compositions can include, and the present methods can be carried out with, an Xist gene encoding an Xist RNA from humans or another mammal (e.g., a rodent such as a mouse, dog, cat, cow, horse, sheep, goat, or another mammalian or non-mammalian animal). The scientific literature has adopted a loose convention whereby the term is fully capitalized (XIST) when referring to a human sequence but not fully capitalized (Xist) when referring to the murine sequence. That convention is not used here, and either human or non-human sequences may be used as described herein.

The silencing sequence can be a full-length Xist gene sequence, a full-length Xist cDNA, or any biologically active fragment or other biologically active variant thereof. The sequence is "biologically active" where its activity is sufficient to silence the expression of one or more genes in cis when integrated into chromosome 21. The level of activity of a biologically active fragment or other variant may vary so long as a useful chromosomal silencing RNA is produced. Xist RNA is referred to as a chromosomal silencing RNA because it silences by binding across the chromosome or chromosome segment, and therefore silences at the level of transcription, by inducing repressive changes to chromatin. While Xist RNA is a well-studied example of a chromosomal silencing RNA, other non-coding RNAs can silence specific clusters of imprinted genes or segments of a chromosome, and in some embodiments a sequence encoding another full-length silencing RNA (examples of which are provided below) or biologically active fragment can be used in place of XIST. These other chromosomal silencing RNAs include Air RNA, HOTAIR RNA, and Kenq1ot1 RNA (see Goodrich and Kugel, Crit. Rev. Biochem. and Mol. Biol. 44:3-15, 2009), any of which can be formulated and used as described herein for Xist. Other intergenic noncoding RNAs, which may be useful in the present nucleic acid constructs and the silencing methods described herein are described by Khalil et al. (Proc. Natl. Acad. Sci. USA 106:11675-11680, 2009).

The silencing vector further includes at least one regulatory sequence (i.e., a regulatory sequence that promotes expression of the Xist RNA, and a regulatory sequence that promotes expression of a selectable marker, if any). More specifically, the regulatory sequence can include a promoter, which may be constitutively active, inducible, tissue-specific, or a developmental stage-specific promoter. Enhancers and polyadenylation sequences can also be included. For example, the Xist transgene may carry one or more regulatory elements found in the Xic region that are not a part of the Xist coding sequence. For example, deletion of the DXPas34 locus found 3' to the Xist coding sequence eliminates Xist expression in mammalian embryonic stem cells as described in Debrand et al. (Mol. Cell. Bio., 19:8513-8525, 1999) herein incorporated by reference. As a further example, silencing by mouse Xist transgenes have been shown to require a conserved repeat sequence located at the 5' end of Xist (Wutz et al., Nat. Genetics, 30:167-174, 2002).

The silencing sequence can exclude one or more introns (wholly or partially) or one or more exons (wholly or partially). However, the silencing sequence cannot exclude all exons. For example, the silencing sequence can be an Xist gene sequence exclusive of one or more introns or one or more exons (but not all exons). For example, the silencing sequence can include about 6 kb to about 10 kb of exon 1 of an Xist gene sequence (e.g., about 6-7 kb, 7-8 kb, 8-9 kb, 6.5-8.5 kb, or about 7.5 kb). More specifically, the silencing sequence can be or can include the full length human Xist cDNA sequence having accession number M97168.1 or a biologically active fragment or other variant thereof, e.g., the full length XIST shown in SEQ ID NO:10, or the variant shown in SEQ ID NO:11.

The Xist transgene need not include the whole of the Xist gene sequence, although it may. For example, the Xist transgene may be derived from an Xist cDNA cloned from one of multiple naturally occurring splice variants. This cDNA may lack sequences corresponding to one or more introns or exons or portions thereof. Additionally, the Xist transgene may include non-naturally occurring Xist coding sequences. For example, the Xist coding sequence may be mutated (e.g., truncated) or otherwise variant with respect to naturally occurring Xist coding sequences so long as it includes sequences that are required for transgene function. For example, deletion analysis demonstrates that the first exon of human Xist is sufficient for both transcript localization and the induction of silencing (Chow et al., Proc. Natl. Acad. Sci. USA 104:10104-10109, 2007). Thus, smaller Xist constructs can be generated that are more easily manipulated but still biologically active.

Non-limiting examples of Xist transgenes (derived from mouse and human sequences) that are useful in this invention are described in the following references which are herein incorporated by reference: Chow et al. (Proc. Natl. Acad. Sci. USA 104:10104-10109, 2007); Hall et al. (Proc. Natl. Acad. Sci. USA 99:8677-8682, 2002); Chow et al. (Genomics, 82:309-322, 2003); and Wutz et al. (Nat. Genet., 2002, 30:167-174, 2002).

Integrated Mouse Xist or human Xist transgenes can silence an autosome, as shown by studies in mouse embryonic stem cells (Wutz and Jaenisch, Mol. Cell, 5:695-705, 2000; Savarese et al., Mol. Cell Biol. 26:7167-7177, 2006) and in human somatic (fibrosarcoma) cells (FIG. 3; Hall et al., Hum. Mol. Genet. 11:3157-3165, 2002; Chow et al., Proc. Natl. Acad. Sci. USA 104:10104-10109, 2007). Natural autosomal silencing by Xist was also shown in patient cells, with an autosomal trisomy due to X; autosome translocations (Hall et al., Proc. Natl. Acad. Sci. USA 99:8677-8682, 2002; (FIG. 4)). Although the silencing of autosomal material may not be quite as complete or may vary somewhat between autosomal regions, autosomes studied to date are largely if not entirely silenced in response to Xist RNA.

The silencing sequence can be or can include the sequence of an XIC (X inactivation complex) locus or any portion thereof that encodes an RNA capable of silencing the chromosome into which it has been inserted. For example, the constructs can include an XIC locus lacking the sequences 3' to Xist that trigger the "counting" mechanism. Other constructs can include the Xist gene, with or without some or all of the intronic sequences, or a biologically active variant of the Xist gene (e.g., a fragment or other mutant). For information regarding the structure of XIC, one can consult Wutz and Gribnau (Curr. Opin. Genetics Dev. 17:387-393, 2007).

In some embodiments, the silencing sequence comprises one of the following:
Full Length Human XIST Sequence—SEQ ID NO:10

```
                                             (SEQ ID NO: 10)
CTAGAACATTTTCTAGTCCCCCAACACCCTTTATGGCGTATTTCTTT

AAAAAAATCACCTAAATTCCATAAAATATTTTTTTAAATTCTATACT

TTCTCCTAGTGTCTTCTTGACACGTCCTCCATATTTTTTTAAAGAAA

GTATTTGGAATATTTTGAGGCAATTTTTAATATTTAAGGAATTTTTC

TTTGGAATCATTTTTGGTGACATCTCTGTTTTTTGTGGATCAGTTTT

TTACTCTTCCACTCTCTTTTCTATATTTTGCCCATCGGGCTGCGGA

TACCTGGTTTTATTATTTTTTCTTTGCCCAACGGGGCCGTGGATACC

TGCCTTTTAATTCTTTTTTATTCGCCCATCGGGGCCGCGGATACCTG

CTTTTTATTTTTTTTTCCTTAGCCCATCGGGGTATCGGATACCTGCT

GATTCCCTTCCCCTCTGAACCCCCAACACTCTGGCCCATCGGGGTGA

CGGATATCTGCTTTTTAAAAATTTTCTTTTTTTGGCCCATCGGGGCT

TCGGATACCTGCTTTTTTTTTTTTTATTTTCCTTGCCCATCGGGGCC

TCGGATACCTGCTTTAATTTTTGTTTTTCTGCCCATCGGGGCCGCGG

ATACCTGCTTTGATTTTTTTTTTTCATCGCCCATCGGTGCTTTTTAT
```

GGATGAAAAAATGTTGGTTTTGTGGGTTGTTGCACTCTCTGGAATAT

CTACACTTTTTTTTGCTGCTGATCATTTGGTGGTGTGTGAGTGTACC

TACCGCTTTGGCAGAGAATGACTCTGCAGTTAAGCTAAGGGCGTGTT

CAGATTGTGGAGGAAAAGTGGCCGCCATTTTAGACTTGCCGCATAAC

TCGGCTTAGGGCTAGTCGTTTGTGCTAAGTTAAACTAGGGAGGCAAG

ATGGATGATAGCAGGTCAGGCAGAGGAAGTCATGTGCATTGCATGAG

CTAAACCTATCTGAATGAATTGATTTGGGGCTTGTTAGGAGCTTTGC

GTGATTGTTGTATCGGGAGGCAGTAAGAATCATCTTTTATCAGTACA

AGGGACTAGTTAAAAATGGAAGGTTAGGAAAGACTAAGGTGCAGGGC

TTAAAATGGCGATTTTGACATTGCGGCATTGCTCAGCATGGCGGGCT

GTGCTTTGTTAGGTTGTCCAAAATGGCGGATCCAGTTCTGTCGCAGT

GTTCAAGTGGCGGGAAGGCCACATCATGATGGGCGAGGCTTTGTTAA

GTGGTTAGCATGGTGGTGGACATGTGCGGTCACACAGGAAAAGATGG

CGGCTGAAGGTCTTGCCGCAGTGTAAAACATGGCGGGCCTCTTTGTC

TTTGCTGTGTGCTTTTCGTGTTGGGTTTTGCCGCAGGGACAATATGG

CAGGCGTTGTCATATGTATATCATGGCTTTTGTCACGTGGACATCAT

GGCGGGCTTGCCGCATTGTTAAAGATGGCGGGTTTTGCCGCCTAGTG

CCACGCAGAGCGGGAGAAAAGGTGGGATGGACAGTGCTGGATTGCTG

CATAACCCAACCAATTAGAAATGGGGGTGGAATTGATCACAGCCAAT

TAGAGCAGAAGATGGAATTAGACTGATGACACACTGTCCAGCTACTC

AGCGAAGACCTGGGTGAATTAGCATGGCACTTCGCAGCTGTCTTTAG

CCAGTCAGGAGAAAGAAGTGGAGGGGCCACGTGTATGTCTCCCAGTG

GGCGGTACACCAGGTGTTTTCAAGGTCTTTTCAAGGACATTTAGCCT

TTCCACCTCTGTCCCCTCTTATTTGTCCCCTCCTGTCCAGTGCTGCC

TCTTGCAGTGCTGGATATCTGGCTGTGTGGTCTGAACCTCCCTCCAT

TCCTCTGTATTGGTGCCTCACCTAAGGCTAAGTATACCTCCCCCCCC

ACCCCCCAACCCCCCCAACTCCCCACCCCCACCCCCCACCCCCCACC

TCCCCACCCCCCTACCCCCCTACCCCCCTACCCCCCTCTGGTCTGCC

CTGCACTGCACTGTTGCCATGGGCAGTGCTCCAGGCCTGCTTGGTGT

GGACATGGTGGTGAGCCGTGGCAAGGACCAGAATGGATCACAGATGA

TCGTTGGCCAACAGGTGGCAGAAGAGGAATTCCTGCCTTCCTCAAGA

GGAACACCTACCCCTTGGCTAATGCTGGGGTCGGATTTTGATTTATA

TTTATCTTTTGGATGTCAGTCATACAGTCTGATTTTGTGGTTTGCTA

GTGTTTGAATTTAAGTCTTAAGTGACTATTATAGAAATGTATTAAGA

GGCTTTATTTGTAGAATTCACTTTAATTACATTTAATGAGTTTTTGT

TTTGAGTTCCTTAAAATTCCTTAAAGTTTTTAGCTTCTCATTACAAA

TTCCTTAACCTTTTTTTGGCAGTAGATAGTCAAAGTCAAATCATTTC

TAATGTTTTAAAAATGTGCTGGTCATTTTCTTTGAAATTGACTTAAC

TATTTTCCTTTGAAGAGTCTGTAGCACAGAAACAGTAAAAAATTTAA

CTTCATGACCTAATGTAAAAAAGAGTGTTTGAAGGTTTACACAGGTC

CAGGCCTTGCTTTGTTCCCATCCTTGATGCTGCACTAATTGACTAAT

CACCTACTTATCAGACAGGAAACTTGAATTGCTGTGGTCTGGTGTCC

TCTATTCAGACTTATTATATTGGAGTATTTCAATTTTTCGTTGTATC

CTGCCTGCCTAGCATCCAGTTCCTCCCCAGCCCTGCTCCCAGCAAAC

CCCTAGTCTAGCCCCAGCCCTACTCCCACCCGGCCCCAGCCCTGCCC

CAGGCCCAGTCCCCTAACCCCCCAGCCCTAGGCCCAGTCCCAGTCCT

AGTTCCTCAGTCTGTCCAGCTTCTCTCGAAAGTCACTCTAATTTTCA

TTGATTCAGTGCTCAAAATAAGTTGTCCATTGGTATCCTATTATACT

GGGATATTCCGTTTACCCTTGGCATTGCTGATCTTCAGTACTGACTC

CTTGACCATTTTCAGTTAAGCATACAATCCCATTTGTCTGTGATCTC

AGGACAAAGAATTTCCTTACTCGGTACGTTGAAGTTAGGGAATGTCA

ATTGAGAGCTTTCTATCAGAGCATTATTGCCCACAATTTGAGTTACT

TATCATTTTCTCGATCCCCTGCCCTTAAAGGAGAAACCATTTCTCTG

TCATTGCTTCTGTAGTCACAGTCCCAATTTTGAGTAGTGATCTTTTC

TTGTGTACTGTGTTGGCCACCTAAAACTCTTTGCATTGAGTAAAATT

CTAATTGCCAATAATCCTACCCATTGGATTAGACAGCACTCTGAACC

CCATTTGCATTCAGCAGGGGGTCGCAGACAACCCGTCTTTTGTTGGA

CAGTTAAAATGCTCAGTCCCAATTGTCATAGCTTTGCCTATTAAACA

AAGGCACCCTACTGCGCTTTTTGCTGTGCTTCTGGAGAATCCTGCTG

TTCTTGGACAATTAAAGAACAAAGTAGTAATTGCTAATTGTCTCACC

CATTAATCATGAAGACTACCAGTCGCCCTTGCATTTGCCTTGAGGCA

GCGCTGACTACCTGAGATTTAAGAGTTTCTTAAATTATTGAGTAAAA

TCCCAATTATCCATAGTTCTGTTAGTTACACTATGGCCTTTGCAAAC

ATCTTTGCATAACAGCAGTGGGACTGACTCATTCTTAGAGCCCCTTC

CCTTGGAATATTAATGGATACAATAGTAATTATTCATGGTTCTGCGT

AACAGAGAAGACCCACTTATGTGTATGCCTTTATCATTGCTCCTAGA

TAGTGTGAACTACCTACCACCTTGCATTAATATGTAAAACACTAATT

GCCCATAGTCCCACTCATTAGTCTAGGATGTCCTCTTTGCCATTGCT

GCTGAGTTCTGACTACCCAAGTTTCCTTCTCTTAAACAGTTGATATG

CATAATTGCATATATTCATGGTTCTGTGCAATAAAAATGGATTCTCA

CCCCATCCCACCTTCTGTGGGATGTTGCTAACGAGTGCAGATTATTC

AATAACAGCTCTTGAACAGTTAATTTGCACAGTTGCAATTGTCCAGA

GTCCTGTCCATTAGAAAGGGACTCTGTATCCTATTTGCACGCTACAA

TGTGGGCTGATCACCCAAGGACTCTTCTTGTGCATTGATGTTCATAA

TTGTATTTGTCCACGATCTTGTGCACTAACCCTTCCACTCCCTTTGT

ATTCCAGCAGGGGACCCTTACTACTCAAGACCTCTGTACTAGGACAG

TTTATGTGCACAATCCTAATTGATTAGAACTGAGTCTTTTATATCAA

GGTCCCTGCATCATCTTTGCTTTACATCAAGAGGGTGCTGGTTACCT

AATGCCCCTCCTCCAGAAATTATTGATGTGCAAAATGCAATTTCCCT

ATCTGCTGTTAGTCTGGGGTCTCATCCCCTCATATTCCTTTTGTCTT

ACAGCAGGGGGTACTTGGGACTGTTAATGCGCATAATTGCAATTATG

-continued

GTCTTTTCCATTAAATTAAGATCCCAACTGCTCACACCCTCTTAGCA
TTACAGTAGAGGGTGCTAATCACAAGGACATTTCTTTTGTACTGTTA
ATGTGCTACTTGCATTTGTCCCTCTTCCTGTGCACTAAAGACCCCAC
TCACTTCCCTAGTGTTCAGCAGTGGATGACCTCTAGTCAAGACCTTT
GCACTAGGATAGTTAATGTGAACCATGGCAACTGATCACAACAATGT
CTTTCAGATCAGATCCATTTTATCCTCCTTGTTTTACAGCAAGGGAT
ATTAATTACCTATGTTACCTTTCCCTGGGACTATGAATGTGCAAAAT
TCCAATGTTCATGGTCTCTCCCTTTAAACCTATATTCTACCCCTTTT
ACATTATAGAAAGGGATGCTGGAAACCCAGAGTCCTTCTCTTGGGAC
TCTTAATGTGTATTTCTAATTATCCATGACTCTTAATGTGCATATTT
TCAATTGCCTAATTGATTTCAATTGTCTAAGACATTTCAAATGTCTA
ATTGATTAGAACTGAGTCTTTTATATCAAGCTAATATCTAGCTTTTA
TATCAAGCTAATATCTTGACTTCTCAGCATCATAGAAGGGGGTACTG
ATTTCCTAAAGTCTTTCTTGAATTTCTATTATGCAAAATTGCCCTGA
GGCCGGGTGTGGTGGCTCACACCTGTAATCCCAGCACTTTGGGAGGC
TGAGGTGGGAAGATCCCTTACTGCCAGGAGTTTGAGACCAGCCTGGC
CAACATTAAAAAAAAAAAAAAAAAGTAAGACAATTGCCCTGGAATCCC
ATCCCCCTCACACCTCCTTGGCAAAGCAGCAGGAGTGCTAACTAGCT
AGTGCTTCTTCTCTTATACTGCTTAAATGCGCATAATTAGCAGTAGT
TGATGTGCCCCTATGTTAGAGTAGAATCCCGCTTCCTTGCTCCATTT
GCATTACTGCAGGAGCTTCTAACTAGCCTGAATTCACTCTCTTGGAC
TGTTAATGTGCATACTTATATTTGCTGCTGTACTTTTTTACCATGTA
AGGACCCCACCCACTGTATTTACATCCCAGCTGGAAGTACCTACTAC
TTAAGACCCTTAGACTAGTAAAGTTAGCGTGCATAATCTTAGGTGTT
ATATACACATTTTCAGTTGCATACAGTTGTGCCTTTTATCAGGACTC
CTGTACTTATCAAAGCAGAGAGTGCTAATCAATATTAAGCCCTTCTC
TTCGAACTGTAGATGGCATGTAATTGCAGTTGTCAATGGTCCTTCAA
TTAGACTTGGGTTTCTGACCTATCACACCCTCTTTGCTTTATTGCAT
GGGGTACTATTCACTTAAGGCCCCTTTCTCAAACTGTTAATGTGCCT
AATGACAATTACATCAGTATCCTTCCTTTTGAAGGACAGCATGGTTG
GTGACACCTAAGGCCCCATTTCTTGGCCTCCCAATATGTGTGATTGT
ATTTGTCGAGGTTGCTATGCACTAGAGAAGGAAAGTGCTCCCCTCAT
CCCCACTTTTCCCTTCCAGCAGGAAGTGCCCACCCCATAAGACCCTT
TTATTTGGAGAGTCTAGGTGCACAATTGTAAGTGACCACAAGCATGC
ATCTTGGACATTTATGTGCGTAATCGCACACTGCTCATTCCATGTGA
ATAAGGTCCTACTCTCCGACCCCTTTTGCAATACAGAAGGGTTGCTG
ATAACGCAGTCCCCTTTTCTTGGCATGTTGTGTGTGATTATAATCGT
CTGGGATCCTATGCACTAGAAAAGGAGGGTCCTCTCCACATACCTCA
GTCTCACCTTTCCCTTCCAGCAGGGAGTGCCCACTCCATAAGACTCT
CACATTTGGACAGTCAAGGTGCGTAATTGTTAAGTGAACACAACCAT

-continued

GCACCTTAGACATGGATTTGCATAACTACACACAGCTCAACCTATCT
GAATAAAATCCTACTCTCAGACCCCTTTTGCAGTACAGCAGGGGTGC
TGATCACCAAGGCCCTTTTTCCTGGCCTGGTATGCGTGTGATTATGT
TTGTCCCGGTTCCTGTGTATTAGACATGGAAGCCTCCCCTGCCACAC
TCCACCCCCAATCTTCCTTTCCCTTCCGGCAGGAGTGCCCTCTCCAT
AAGACGCTTACGTTTGGACAATCAAGGTGCACAGTTGTAAGTGACCA
CAGGCATACACCTTGGACATTAATGTGCATAACCACTTTGCCCATTC
CATCTGAATAAGGTCCTACTCTCAGACCCCTTTTGCAGTACAGCAGG
GGTGCTGATCACCAAGGCCCCTTTTCTTGGCCTGTTATGTGCGTGAT
TATATTTGTCTGGGTTCCTGTGTATTAGACAAGGAAGCCTTCCCCCC
GCCCCCACCCCCACTCCCAGTCTTCCTTTCCCTTCCAGCAGGGAGTG
CCCCCTCCATAAGATCATTACATTTGGACAATCAAGGTGCACAATTA
TAAGTGACCACAGCCATGCACCTTGGACATTATTGGACATTAATGTG
CGTAACTGCACATGGCCCATCCCATCTGAATAAGGACCTACTCTCAG
ATGCCTTTGCAGTACAGCAGGGGTACTGAATCACCAAGGCCCTTTTT
CTTGGCCTGTTATGTGTGTGATTATATTTATCCCAGTTTCTGTGTAA
TAGACATGAAAGCCTCCCCTGCCACACCCCACCTCCAATCTTCCTTT
CCCTTCCACCAGGGAGTGTCCACTCCATATACCCTTACATTTGGACA
ATCAAGGTGCACAATTGTAAGTGAGCATAGGCACTCACCTTGGACAT
GAATGTGCATAACTGCACATGGCCCATCCCATCTGAATAAGGTCCTA
CTCTCAGACCCTTTTTGCAGTACAGCAGGGGTGCTGATCACCAAGGC
CCCTTTTCCTGGCCTGTTATGTGTGTGATTATATTTGTTCCAGTTCC
TGTGTAATAGACATGGAAGCCTCCCCTGCCACACTCCACCCCCAATC
TTCCTTTCCTTCTGGCAGGAAGTACCCGCTCCATAAGACCCTTACAT
TTGGACAGTCAAGGTGCACAATTGTATGTGACCACAACCATGCACCT
TGGACATAAATGTGTGTAACTGCACATGGCCCATCCCATCTGAATAA
GGTCCTACTCTCAGACCCCTTTTGCAGTACAGTAGGTGTGCTGATAA
CCAAGGCCCCTCTTCCTGGCCTGTTAACGTATGTGATTATATTTGTC
TGGGTTCCAGTGTATAAGACATGGAAGCCTCCCCTGCCCCACCCCAC
CCTCAATCTTCCTTTCCCTTCTGGCAGGGAGTGCCAGCTCCATAAGA
ACCTTACATTTGGACAGTCAAGGTGCACAATTCTAAGTGACCGCAGC
CATGCACCTTGGTCAATAATGTGTGTAACTGCACACGGCCTATCTCA
TCTGAATAAGGCCTTACTCTCAGACCCCTTTTGCAGTACAGCAGGGG
TGCTGATAACCAAGGCCCATTTTCCTGGCCTGTTATGTGTGTGATTA
TATTTGTCCAGGTTTCTGTGTACTAGACAAGGAAGCCTCCTCTGCCC
CATCCCATCTACGCATAATCTTTCTTTTCCTCCCAGCAGGGAGTGCT
CACTCCATAAGACCCTTACATTTGGACAATCAAGGTGCACAATTGTA
AGTGACCACAACCATGCATCTTGGAAATTTATGTGCATAACTGCACA
TGGCTTATCCTATTTGAATAAAGTCCTACTCTCAGACCCCCTTTGCA
GTATAGCTGGGGTGCTGATCACTGAGGCCTCTTTGCTTGGCTTGTCT
ATATTCTTGTGTACTAGATAAGGGCACCTTCTCATGGACTCCCTTTG

-continued

CTTTTCAACAAGGAGTACCCACTACTTTTTAAGATTCTTATATTTGT

CCAAAGTACATGGTTTTAATTGACCACAACAATGTCCCTTGGACATT

AATGTATGTAATCACCACATGGTTCATCCTAATTAAACAAAGTTCTA

CCTTCTCACCCTCCATTTGCAGTATACCAGGGTTGCTGACCCCCTAA

GTCCCCTTTTCTTGGCTTGTTGACATGCATAATTGCATTTATGTTGG

TTCTTGTGCCCTAGACAAGGATGCCCCACCTCTTTTCAATAGTGGGT

GCCCACTCCTTATGATCTTTACATTTGAACAGTTAATGTGAATAATT

GCAGTTGTCCACAACCCTATCACTTCTAGGACCATTATACCTCTTTT

GCATTACTGTGGGGTATACTGTTTCCCTCCAAGGCCCCTTCTGGTGG

ACTATCAACATATAATTGAAATTTTCTTTTGTCTTTGTCAGTAGATT

AAGGTCATACCCCATCACCTTTCCTTTGTAGTACAACAGGGTGTCCT

GATCAACCAAAGTCCTGTTGTTTTGGACTGTTAATATGTGCAATTAC

ATTTGCTCCTGATCTGTGCACTAGATAAGGATCCTACCTACTTTCTT

AGTGTTTTTAGCAGGTAGTGCCCACTACTCAAGACTGTCACTTGGAA

TGTTCATGTGCACAAACTCAATTCTCTAAGCATGTTCCTGTACCACC

TTTGCTTTAGAGCAGGGGGATGATATTCACTAAGTGCCCCTTCTTTT

GGACTTAATATGCATTAATGCAATTGTCCACCTCTTCTTTTAGACTA

AGAGTTGATCTCCACATATTCCCCTTGCATCAGGGGCATGTTAATTA

TGAATGAACCCTTTTCTTTTAATATTAATGTCATAATTGTATTTGTG

GACCTGTGTAGGAGAAAAAGACCCTATGTTCCTCCCATTACCCTTTG

GATTGCTGCTGAGAAGTGTTAACTACTCATAATCTCAGCTCTTGGAC

AATTAATAGCATTAATAACAATTATCAAGGGCACTGATCATTAGATA

AGACTCCTGCTTCCTCGTTGCTTACATCGGGGGTACTGACCCACTAA

GGCCCCTTGTACTGTTAATGTGAATATTTGCAATTATATATGTCTCC

TTCTGGTAGAGTGGGATATTATGCCCTAGTATCCCCTTTGCATTACT

GCAGGGGCTGCTGACTACTCAAAACTTCTCCTGGGACTGTTAATAGG

CACAATGGCAGTTATCAATGGTTTTCTCCCTCCCTGACCTTGTTAAG

CAAGCGCCCCACCCCACCCTTAGTTTCCCATGGCATAATAAAGTATA

AGCATTGGAGTATTCCATGCACTTGTCTATCAAACAGTGGTCCATAC

TCCCAACCCTTTTGCATTGCGCCAGTGTGTAAAATCACAGGTAGCCA

TGGTGTCATGCTTTATATACGAAGTCTTCCCTCTCTCTGCCCCTTGT

GTGCCCTTGGCCCCTTTTTACAGACTATTGCTCACAATCTCAGGTGT

CCATATTTGCAGCTATTAGGTAAGATTGTGCTGTCTCCCTCTTCCCT

TCCCTCTGCCCTGCCCCTTTTGCCTCTTTGCTGGGTAATGTTGACCA

GACAAGGCCCTTTCTCTTGGACTTAAACAATTCTCAGTTGCACTTTC

CTTGGTCCACCCATTATACATGAACCCCTCTACTTCCTTTCGCATTG

CTTCTGAGTATGCTGACTACCCAAAGCCCCTTCTGTGTTATTAATAA

ACACAGTACTGATTGTCCCATTTTTCAGCCCATCAGTCCAAGATCTC

CCTACCACTTTGGTGTGTTGGTGCAGTGTTGACTATGAAAAGCAGGC

CTGAACTAGGTGGATAAGCCTTCACTCATTTTCTTTCATTTATTAAT

-continued

GATCCTAGTTTCAATTATTGTCAGATTCTGGGGACAAGAACCATTCT

TGCCCACCTGTGTTACTGCTTTACTGTGCAAAATACTGAAGGCAAGT

CAGACCCAGGGAGCTGGATTGCCATCCTTTATTTTGTGTTTCCAGTG

TACACTATAAAATTGTCTCCCCAGGAAGGAAGGTTGGCACTTTCTCT

GCATTCTTCTTTCCAGAGCAGATTGCCTGGTTAAGAATCTCTTGTTG

TCCCTTCTGTATATTGTTATTGTAAAGTGCCAAATGCCAGGATACAG

CCAGAAAAATTGCTTATTATTATTAAAAAAATTTTTTTAAGAAAGAC

ATCTGGATTGTAGGGTGGACTCGATAACCTGGTCATTATTTTTTTGA

AGCCAAAATATCCATTTATACTATGTACCTGGTGACCAGTGTCTCTC

ATTTTAACTGAGGGTGGTGGGTCTGTGGATAGAACACTGACTCTTGC

TATTTTAATATCAAAGATATTCTAGATCCAGCACAGTGGCGGCCGCT

CTAGAGTGGAACTCTTAAGACCAGTATCTTTGTGTGGGCTTTACCAG

CATTCACTTTTAGAAAAACTACCTAAATTTTATAATCCTTTAATTTC

TTCATCTGGAGCACCTGCCCCTACTTATTTCAAGAAGATTGCAGTAA

AACGATTAAATGAGGGAACATATGCAGAGGTGCTTTTAAAAAGCATA

TGCCACCTTTTTTATTAATTATTATATAAAATGAAGCATTTAATTAT

AGTAATAATTTGAAGTAGTTTGAAGTACCACACTGAGGTGAGGACTT

AAAAATGATAAGACGAGTTCCCTATTTTATAAGAAAAATAAGCCAAA

ATTAAATATTCTTTTGGATATAAATTTCAACAGTGAGATAGCTGCCT

AGTGGAAATGAATAATATCCCAGCCACTAGTGTACAGGGTGTTTTGT

GGCACAGGATTATGTAATATGGAACTGCTCAAGCAAATAACTAGTCA

TCACAACAGCAGTTCTTTGTAATAACTGAAAAAGAATATTGTTTCTC

GGAGAAGGATGTCAAAAGATCGGCCCAGCTCAGGGAGCAGTTTGCCC

TACTAGCTCCTCGGACAGCTGTAAAGAAGAGTCTCTGGCTCTTTAGA

ATACTGATCCCATTGAAGATACCACGCTGCATGTGTCCTTAGTAGTC

ATGTCTCCTTAGGCTCCTCTTGGACATTCTGAGCATGTGAGACCTGA

GGACTGCAAACAGCTATAAGAGGCTCCAAATTAATCATATCTTTCCC

TTTGAGAATCTGGCCAAGCTCCAGCTAATCTACTTGGATGGGTTGCC

AGCTATCTGGAGAAAAAGATCTTCCTCAGAAGAATAGGCTTGTTGTT

TTACAGTGTTAGTGATCCATTCCCTTTGACGATCCCTAGGTGGAGAT

GGGGCATGAGGATCCTCCAGGGGAAAAGCTCACTACCACTGGGCAAC

AACCCTAGGTCAGGAGGTTCTGTCAAGATACTTTCCTGGTCCCAGAT

AGGAAGATAAAGTCTCAAAAACAACCACCACACGTCAAGCTCTTCAT

TGTTCCTATCTGCCAAATCATTATACTTCCTACAAGCAGTGCAGAGA

GCTGAGTCTTCAGCAGGTCCAAGAAATTTGAACACACTGAAGGAAGT

CAGCCTTCCCACCTGAAGATCAACATGCCTGGCACTCTAGCACTTGA

GGATAGCTGAATGAATGTGTATTTCTTTGTCTCTTTCTTTCTTGTCT

TTGCTCTTTGTTCTCTATCTAAAGTGTGTCTTACCCATTTCCATGTT

TCTCTTGCTAATTTCTTTCGTGTGTGCCTTTGCCTCATTTTCTCTTT

TTGTTCACAAGAGTGGTCTGTGTCTTGTCTTAGACATATCTCTCATT

TTTCATTTTGTTGCTATTTCTCTTTGCTCTCCTAGATGTGGCTCTTC

-continued

TTTCACGCTTTATTTCATGTCTCCTTTTTGGGTCACATGCTGTGTGC

TTTTTGTCCTTTTCTTGTTCTGTCTACCTCTCCTTTCTCTGCCTACC

TCTCTTTTCTCTTTGTGAACTGTGATTATTTGTTACCCCTTCCCCTT

CTCGTTCGTTTTAAATTTCACCTTTTTTCTGAGTCTGGCCTCCTTTC

TGCTGTTTCTACTTTTTATCTCACATTTCTCATTTCTGCATTTCCTT

TCTGCCTCTCTTGGGCTATTCTCTCTCTCCTCCCCTGCGTGCCTCAG

CATCTCTTGCTGTTTGTGATTTTCTATTTCAGTATTAATCTCTGTTG

GCTTGTATTTGTTCTCTGCTTCTTCCCTTTCTACTCACCTTTGAGTA

TTTCAGCCTCTTCATGAATCTATCTCCCTCTCTTTGATTTCATGTAA

TCTCTCCTTAAATATTTCTTTGCATATGTGGGCAAGTGTACGTGTGT

GTGTGTCATGTGTGGCAGAGGGGCTTCCTAACCCCTGCCTGATAGGT

GCAGAACGTCGGCTATCAGAGCAAGCATTGTGGAGCGGTTCCTTATG

CCAGGCTGCCATGTGAGATGATCCAAGACCAAAACAAGGCCCTAGAC

TGCAGTAAAACCCAGAACTCAAGTAGGGCAGAAGGTGGAAGGCTCAT

ATGGATAGAAGGCCCAAAGTATAAGACAGATGGTTTGAGACTTGAGA

CCCGAGGACTAAGATGGAAAGCCCATGTTCCAAGATAGATAGAAGCC

TCAGGCCTGAAACCAACAAAAGCCTCAAGAGCCAAGAAAACAGAGGG

TGGCCTGAATTGGACCGAAGGCCTGAGTTGGATGGAAGTCTCAAGGC

TTGAGTTAGAAGTCTTAAGACCTGGGACAGGACACATGGAAGGCCTA

AGAACTGAGACTTGTGACACAAGGCCAACGACCTAAGATTAGCCCAG

GGTTGTAGCTGGAAGACCTACAACCCAAGGATGGAAGGCCCCTGTCA

CAAAGCCTACCTAGATGGATAGAGGACCCAAGCGAAAAAGGTATCTC

AAGACTAACGGCCGGAATCTGGAGGCCCATGACCCAGAACCCAGGAA

GGATAGAAGCTTGAAGACCTGGGGAAATCCCAAGATGAGAACCCTAA

ACCCTACCTCTTTTCTATTGTTTACACTTCTTACTCTTAGATATTTC

CAGTTCTCCTGTTTATCTTTAAGCCTGATTCTTTTGAGATGTACTTT

TTGATGTTGCCGGTTACCTTTAGATTGACAGTATTATGCCTGGGCCA

GTCTTGAGCCAGCTTTAAATCACAGCTTTTACCTATTTGTTAGGCTA

TAGTGTTTTGTAAACTTCTGTTTCTATTCACATCTTCTCCACTTGAG

AGAGACACCAAAATCCAGTCAGTATCTAATCTGGCTTTTGTTAACTT

CCCTCAGGAGCAGACATTCATATAGGTGATACTGTATTTCAGTCCTT

TCTTTTGACCCCAGAAGCCCTAGACTGAGAAGATAAAATGGTCAGGT

TGTTGGGGAAAAAAAAAGTGCCAGGCTCTCTAGAGAAAAATGTGAAG

AGATGCTCCAGGCCAATGAGAAGAATTAGACAAGAAATACACAGATG

TGCCAGACTTCTGAGAAGCACCTGCCAGCAACAGCTTCCTTCTTTGA

GCTTAG

Full Length Human XIST Sequence—SEQ ID NO:10

Full Length Human XIST Sequence—SEQ ID NO:10

Full Length Human XIST Sequence—SEQ ID NO:10

Full Length Human XIST Sequence—SEQ ID NO:10

6.8 kb Human XIST Sequence—SEQ ID NO:11 tctagaacattttctagtcccccaacaccctttatggcgtatttctt taaaaaaatcacctaaattccataaaatatttttttaaattctatac tttctcctagtgtcttcttgacacgtcctccatatttttttaaagaa agtatttggaatattttgaggcaatttttaatatttaaggaatttttt ctttggaatcattttttggtgacatctctgtttttttgtggatcagttt tttactcttccactctcttttctatattttgcccatcggggctgcgg atacctggttttattatttttttctttgcccaacggggccgtggatac ctgccttttaattctttttttattcgcccatcggggccgcggatacct gctttttatttttttttccttagcccatcggggtatcggatacctgc tgattcccttcccctctgaacccccaacactctggcccatcggggtg acggatatctgctttttaaaaatttctttttttggcccatcggggc ttcggatacctgctttttttttttttatttccttgcccatcggggc ctcggatacctgctttaatttttgtttttctgcccatcggggccgcg gatacctgctttgatttttttttttcatcgcccatcggtgcttttta tggatgaaaaaatgttggttttgtgggttgttgcactctctggaata tctacacttttttttgctgctgatcatttggtggtgtgtgagtgtac ctaccgctttggcagagaatgactctgcagttaagctaagggcgtgt tcagattgtggaggaaaagtggccgccattttagacttgccgcataa ctcggcttagggctagtcgtttgtgctaagttaaactagggaggcaa gatggatgatagcaggtcaggcagaggaagtcatgtgcattgcatga gctaaacctatctgaatgaattgatttggggcttgttaggagctttg cgtgattgttgtatcgggaggcagtaagaatcatcttttatcagtac aagggactagttaaaaatggaaggttaggaaagactaaggtgcaggg cttaaaatggcgattttgacattgcggcattgctcagcatggcgggc tgtgctttgttaggttgtccaaaatggcggatccagttctgtcgcag tgttcaagtggcgggaaggccacatcatgatgggcgaggctttgtta agtggttagcatggtggtggacatgtgcggtcacacaggaaaagatg gcggctgaaggtcttgccgcagtgtaaaacatggcgggcctctttgt ctttgctgtgtgcttttcgtgttgggttttgccgcagggacaatatg gcaggcgttgtcatatgtatatcatggcttttgtcacgtggacatca tggcgggcttgccgcattgttaaagatggcgggttttgccgcctagt gccacgcagagcgggagaaaaggtgggatggacagtgctggattgct gcataacccaaccaattagaaatgggggtggaattgatcacagccaa ttagagcagaagatggaattagactgatgacacactgtccagctact cagcgaagacctgggtgaattagcatggcacttcgcagctgtcttta gccagtcaggagaaagaagtggaggggccacgtgtatgtctcccagt gggcggtacaccaggtgttttcaaggtcttttcaaggacatttagcc tttccacctctgtcccctcttatttgtcccctcctgtccagtgctgc -continued ctcttgcagtgctggatatctggctgtgtggtctgaacctccctcca ttcctctgtattggtgcctcacctaaggctaagtatacctcccccc caccccccaaccccccaactccccaccccccacccccccacccccccac ctccccaccccctacccccctacccccctaccccccctctggtctgc cctgcactgcactgttgccatgggcagtgctccaggcctgcttggtg tggacatggtggtgagccgtggcaaggaccagaatggatcacagatg atcgttggccaattggcctcccaatatgtgtgattgtatttgtcgag gttgctatgcactagagaaggaaagtgctcccctcatccccactttt cccttccagcaggaagtgcccaccccataagacccttttatttggag agtctaggtgcacaattgtaagtgaccacaagcatgcatcttggaca tttatgtgcgtaatcgcacactgctcattccatgtgaataaggtcct actctccgaccccttttgcaatacagaagggttgctgataacgcagt ccccttttcttggcatgttgtgtgtgattataatcgtctgggatcct atgcactagaaaaggagggtcctctccacatacctcagtctcacctt tcccttccagcagggagtgcccactccataagactctcacatttgga cagtcaaggtgcgtaattgttaagtgaacacaaccatgcaccttaga catggatttgcataactacacacagctcaacctatctgaataaaatc ctactctcagaccccttttgcagtacagcaggggtgctgatcaccaa ggcccttttttcctggcctggtatgcgtgtgattatgtttgtcccggt tcctgtgtattagacatggaagcctcccctgccacactccaccccca atcttcctttcccttccggcaggagtgccctctccataagacgctta cgtttggacaatcaaggtgcacagttgtaagtgaccacaggcataca ccttggacattaatgtgcataaccactttgcccattccatctgaata aggtcctactctcagaccccttttgcagtacagcaggggtgctgatc accaaggccccttttcttggcctgttatgtgcgtgattatatttgtc tgggttcctgtgtattagacaaggaagccttcccccgcccccaccc ccactcccagtcttcctttcccttccagcagggagtgccccctccat aagatcattacatttggacaatcaaggtgcacaattataagtgacca cagccatgcaccttggacattattggacattaatgtgcgtaactgca catggcccatcccatctgaataaggacctactctcagatgcctttgc agtacagcaggggtactgaatcaccaaggccctttttcttggcctgt tatgtgtgtgattatatttatcccagtttctgtgtaatagacatgaa agcctcccctgccacaccccacctccaatcttcctttcccttccacc agggagtgtccactccatatacccttacatttggacaatcaaggtgc acaattgtaagtgagcataggcactcaccttggacatgaatgtgcat aactgcacatggcccatcccatctgaataaggtcctactctcagacc ctttttgcagtacagcaggggtgctgatcaccaaggccccttttcct ggcctgttatgtgtgtgattatatttgttccagttcctgtgtaatag acatggaagcctcccctgccacactccacccccaatcttcctttcct tctggcaggaagtacccgctccataagacccttacatttggacagtc aaggtgcacaattgtatgtgaccacaaccatgcaccttggacataaa -continued tgtgtgtaactgcacatggcccatcccatctgaataaggtcctactc tcagaccccttttgcagtacagtaggtgtgctgataaccaaggcccc tcttcctggcctgttaacgtatgtgattatatttgtctgggttccag tgtataagacatggaagcctcccctgccccaccccaccctcaatctt cctttcccttctggcagggagtgccagctccataagaaccttacatt tggacagtcaaggtgcacaattctaagtgaccgcagccatgcacctt ggtcaataatgtgtgtaactgcacacggcctatctcatctgaataag gccttactctcagaccccttttgcagtacagcaggggtgctgataac caaggcccattttcctggcctgttatgtgtgtgattatatttgtcca ggtttctgtgtactagacaaggaagcctcctctgccccatcccatct acgcataatctttcttttcctcccagcagggagtgctcactccataa gacccttacatttggacaatcaaggtgcacaattgtaagtgaccaca accatgcatcttggaaatttatgtgcataactgcacatggcttatcc tatttgaataaagtcctactctcagacccccttttgcagtatagctgg ggtgctgatcactgaggcctctttgcttggcttgtctatattcttgt gtactagataagggcaccttctcatggactccctttgcttttcaaca aggagtacccactactttttaagattcttatatttgtccaaagtaca tggttttaattgaccacaacaatgtcccttggacattaatgtatgta atcaccacatggttcatcctaattaaacaaagttctaccttctcacc ctccatttgcagtataccagggttgctgacccccctaagtcccctttt cttggcttgttgacatgcataattgcatttatgttggttcttgtgcc ctagacaaggatgccccacctcttttcaatagtgggtgcccactcct tatgatctttacatttgaacagttaatgtgaataattgcagttgtcc acaaccctatcacttctaggaccattatacctcttttgcattactgt ggggtatactgtttccctccaaggccccttctggtggactatcaaca tataattgaaattttcttttgtctttgtcagtagattaaggtcatac cccatcacctttcctttgtagtacaacagggtgtcctgatcaaccaa agtcctgttgttttggactgttaatatgtgcaattacatttgctcct gatctgtgcactagataaggatcctacctactttcttagtgtttttta gcaggtagtgcccactactcaagactgtcacttggaatgttcatgtg cacaaactcaattctctaagcatgttcctgtaccacctttgctttag agcagggggatgatattcactaagtgccccttcttttggacttaata tgcattaatgcaattgtccacctcttcttttagactaagagttgatc tccacatattccccttgcatcaggggcatgttaattatgaatgaacc cttttcttttaatattaatgtcataattgtatttgtggacctgtgta ggagaaaaagaccctatgttcctcccattaccctttggattgctgct gagaagtgttaactactcataatctcagctcttggacaattaatagc attaataacaattatcaagggcactgatcattagataagactcctgc ttcctcgttgcttacatcgggggtactgacccactaaggccccttgt actgttaatgtgaatatttgcaattatatatgtctccttctggtaga -continued gtgggatattatgccctagtatcccctttgcattactgcaggggctg ctgactactcaaaacttctcctgggactgttaataggcacaatggca gttatcaatggttttctccctccctgaccttgttaagcaagcgcccc accccacccttagtttcccatggcataataaagtataagcattggag tattccatgcacttgtctatcaaacagtggtccatactcccaaccct tttgcattgcgccagtgtgtaaaatcacaggtagccatggtgtcatg ctttatatacgaagtcttccctctctctgccccttgtgtgccccttgg ccccttttacagactattgctcacaatctcaggtgtccatatttgc agctattaggtaagattgtgctgtctccctcttcccttccctctgcc ctgccccttttgcctctttgctgggtaatgttgaccGgacaaggccc tttctcttggacttaaacaattctcagttgcactttccttggtccCa cccattatacatgaacccctctacttcctttcgcattgcttctgagt atgctgactacccaaagccccttctgtgttattaataaacacagtac tgattgtcccattttcagcccatcagtccaagatctccctaccact ttggtgtgttggtgcagtgttgactatgaaaagcaggcctgaactag gtggataagccttcactcatttctttcatttattaatgatcctagt ttcaattattgtcagattctggggacaagaaccattcttgcccacct gtgttactgctttactgtgcaaaatactgaaggcaagtcagacccag ggagctggattgccatcctttatttgtgtttccagtgtacactata aaattgtctccccaggaaggaaggttggcactttctctgcattcttc tttccagagcagattgcctggttaagaatctcttgttgtccccCtTtg tatattgttattgtaaagtgccaaatgccaggatacagccagaaaaa ttgcttattattattaaaaaaatttttttaagaaagacatctggatt gtagggtggactcgataacctggtcattatttttttgaagccaaaat atccatttatactatgtacctggtgaccagtgtctctcattttaact gagggtggtgggtctgtggatagaacactgactcttgctattttaat atcaaagatattctagATCCAGCACAGTGGCggcccgataccgtcga cc 6.8 kb Human XIST Sequence—SEQ ID NO:11

6.8 kb Human XIST Sequence—SEQ ID NO:11

6.8 kb human XIST sequence—SEQ ID NO:11

Targeting Sequences

The nucleic acid constructs described herein include targeting sequences or elements (the terms are used interchangeably herein) that promote sequence specific integration of an Xist transgene into the DYRK1A or RCAN1 gene (e.g., by homologous recombination). Methods for achieving site-specific integration by ends-in or ends-out targeting are known in the art and in the nucleic acid constructs of this invention, the targeting elements are selected and oriented with respect to the Xist transgene according to whether ends-in or ends-out targeting is desired. In certain embodiments, two targeting elements flank the Xist transgene.

A targeting sequence or element may vary in size. In certain embodiments, a targeting element may be at least or about 50, 100, 200, 300, 400, 500, 600, 700, 800, 900, 1000, 2000, 3000, 4000, 5000, 6000, 7000, 8000, 9000, 10000 bp in length (or any integer value in between). In certain embodiments, a targeting element is homologous to a sequence that occurs naturally in a trisomic and/or translocated chromosomal region, including a polymorphic sequence which may be present on just one of the homologous chromosomes.

The construct elements as described here may be variants of naturally occurring DYRK1A or RCAN1 sequences. Preferably, any construct element (e.g., an Xist transgene, other non-coding, silencing RNA, or a targeting element) includes a nucleotide sequence that is at least 80% identical to its corresponding naturally occurring sequence (its reference sequence, e.g., an Xist coding region, a human Chr 21 sequence, or any duplicated or translocated genomic sequence). More preferably, the silencing sequence or the sequence of a targeting element is at least 85%, 90%, 91%, 92%, 93%, 94%, 95%, 96%, 97%, 98%, 99% identical to its reference sequence (e.g., NG_009366.1, the human refGene Sequence of DYRK1A, or NG_007071.1, the human refGene Sequence of RCAN1).

As used herein, "% identity" of two nucleic acid sequences is determined using the algorithm of Karlin and Altschul (Proc. Natl. Acad. Sci. USA, 87:2264-2268, 1990), modified as in Karlin and Altschul, Proc. Natl. Acad. Sci. USA, 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucl. Acids Res., 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

In preferred embodiments, the targeting elements comprise all or part of the following sequences, with the DYRK1A target sequences shown in bold and underlined: DYRK1A Left Arm:

(SEQ ID NO: 12)

ATGGTAATTGAGAAATGACAAGAATCATGGAACTCCAAATTCATGAC

AATATTTGGGTAAGACGTCTACCTTTCCCTCCATACCTAAATTAACT

AAACGGGTTTCGCTGTGTCTTCAACCATCGATCGATCATTTACCGTT

TTAACTTAGGTCTGAGGAATACCACAATTAACGATATCGATTTCTAC

TTTGACCTCAACACGGTGAGGAACGTGTGAAAATAGACAGTGGGAGA

ATCCGACAAAATCTTTTAGGGTACAAAATCGAACGGTAAGACAACTG

GGTCGGACGGAAAGATCGGAATTGAATGGGGAGACAGATATAAGATA

AAAGGTCGGTTTATACTCCACTGCAAATTCGACGATGAACTTTCTCT

TCACCCTCAATCCGTCTCGTCATCCCCTTAGTACAAACCCCTTCTCA

CTTCTCACATGAACTCTCTCACACCTCCACGGAACCTCCTCGACCTC

GGGTCTCCACGGGGTACTCTTGTTGTGTCCTCCGACGTCCACCTCCA

CCCACGGACTAACATCTTACGAAAGATCAACAGAAGGTGTCCTGTAA

AAACCCTCGATAAGTGTTCTAAGTACCGATGGCACGAGATTTTAAAC

TACACTTCAAGTAAAAAGGACCTGAAGAATGAATTAAGGAGACAGAA

AACCGGGT<u>CGGTGGGGAAACGGTCAAA</u>

DYRK1A Right Arm:

(SEQ ID NO: 13)

CCACTACTCGTCCGACAAACCTTTCTTGCAGGAGCTCGTCCCACGAC

AAAGGATTGGGACGCAGAAAAAGGGGAGACTCTAGTCAAATAGAAAT

AAGTGAACGTCCACAAGTTGTTAGAACAGAAAATACCCCTTAAAGAT

TACACAGAACTCGTGAAAGGGTGGGAGGATAGAACCTCCGTACCAAG

TCTCACCTTTTCCCGCGCCCGGGTGGATGGAGACCGGAAGGGTGGAG

TCGGTGGTACGAATCCCGGCACCACCTCACGAACTGGAGAAACACAC

ATGTTACGTTATGTACGACCTTATTACGGTGGAATACGTATCCCGAA

AACACCCACATTCCCGTATGGCCTTGTTCAACCGTATCTTATTCTCA

AGTCACTTACAACAGTGATGAAAAATAATGAAAAATTAACACTTTTT

GAGTGTCTAAGACATTATTTCCCAGTATCTTTGGACGAAATAGGTAT

GATAGTAATGACTCTTATGAAAGACCAAAAGC

In some embodiments, the XIST cDNA is inserted into the silencing vector in the opposite direction in order to avoid generating a fused RNA with DYRK1A exon1. In these embodiments, exemplary targeting arms comprise the sequences of SEQ ID NO:33 and SEQ ID NO: 34, set forth below.

Selection Markers

In addition, the nucleic acids may contain a marker for the selection of transfected cells (for instance, a drug resistance gene for selection by a drug such as neomycin, hygromycin, and G418). Such vectors include pMAM, pDR2, pBK-RSV, pBK-CMV, pOPRSV, pOP13, and so on. More generally, the term "marker" refers to a gene or sequence whose presence or absence conveys a detectable phenotype to the host cell or organism. Various types of markers include, but are not limited to, selection markers, screening markers, and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as green fluorescent protein (GFP), GUS or β-galactosidase. Molecular markers are, for example, sequence features that can be uniquely identified by oligonucleotide probing, for example RFLP (restriction fragment length polymorphism), or SSR markers (simple sequence repeat). To amplify the gene copies in host cell lines, the expression vector may include an aminoglycoside transferase (APH) gene, thymidine kinase (TK) gene, *E. coli* xanthine guanine phosphoribosyl transferase (Ecogpt) gene, dihydrofolate reductase (dhfr) gene, and such as a selective marker.

Expression of the selection marker can be driven by the same regulatory elements (e.g., promoters) as the silencing sequence, or can be driven by a separate regulatory element.

Recombination Facilitating Elements—Cleavage Vectors

In some embodiments, the present methods include the use of cleavage vectors, i.e., nucleic acid constructs include a sequence that enhances or facilitates homologous recombination (e.g., a zinc finger nuclease or TALEN). Zinc finger domains and TALENs can recognize and target highly specific chromosomal sequences to facilitate targeted integration of the transgene into the DYRK1A or RCAN1 gene. Alternatively, CRISPR/CAS genome editing could be used. As would be understood in the art, the term "recombination" is used to indicate the process by which genetic material at a given locus is modified as a consequence of an interaction with other genetic material. Homologous recombination indicates that recombination has occurred as a consequence of interaction between segments of genetic material that are homologous or identical. In contrast, "non-homologous" recombination indicates a recombination occurring as a consequence of the interaction between segments of genetic material that are not homologous (and therefore not identical). Non-homologous end joining (NHEJ) is an example of non-homologous recombination.

In some embodiments, targeting the present silencing constructs to DYRK1A or RCAN1 can be facilitated by introducing a chimeric zinc finger nuclease (ZFN), i.e., a DNA-cleavage domain (nuclease) operatively linked to a DNA-binding domain including at least one zinc finger, into a cell. Typically the DNA-binding domain is at the N-terminus of the chimeric protein molecule, and the DNA-cleavage domain is located at the C-terminus of the molecule. These nucleases exploit endogenous cellular mechanisms for homologous recombination and repair of double stranded breaks in genetic material. ZFNs can be used to target a wide variety of endogenous nucleic acid sequences in a cell or organism. The present compositions can include cleavage vectors that target a ZFN to a region within DYRK1A or RCAN1, and the methods include transfection or transformation of a host cell or organism by introducing a cleavage vector encoding a ZFN (e.g., a chimeric ZFN), or by introducing directly into the cell the mRNA that encodes the recombinant zinc finger nuclease, or the protein for the ZFN itself. One can then identify a resulting cell or organism in which a selected endogenous DNA sequence is cleaved and exhibits a mutation or DNA break at a specific site, into which the transgene will become integrated.

The ZFN can include multiple (e.g., at least three (e.g., 3, 4, 5, 6, 7, 8, 9 or more)) zinc fingers in order to improve its target specificity. The zinc finger domain can be derived from any class or type of zinc finger. For example, the zinc finger domain can include the Cys2His2 type of zinc finger that is very generally represented, for example, by the zinc finger transcription factors TFIIIA or Sp1. In a preferred embodiment, the zinc finger domain comprises three Cys2His2 type zinc fingers.

The ZFN DNA-cleavage domain can be derived from a class of non-specific DNA cleavage domains, for example the DNA-cleavage domain of a Type II restriction enzyme such as Fold. Thus, a chimeric ZFN useful in the present methods can include three Cys2His2 type zinc fingers and a DNA-cleavage domain derived from the Type II restriction enzyme Fold. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer."

A linker, if present, between the cleavage and recognition domains of the ZFN can be a sequence of amino acid residues that result in a flexible linker is flexible, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

A silencing sequence flanked by sequences (typically 400 bp-5 kb in length) homologous to the desired site of integration can be inserted (e.g., by homologous recombination) into the site cleaved by the endonuclease, thereby achieving a targeted insertion. When used in combination with a ZFN construct, the silencing sequence may be referred to as "donor" nucleic acid or DNA.

In some embodiments, the cleavage vector includes a transcription activator-like effector nuclease (TALEN). TALENs function in a manner somewhat similar to ZFNs, in that they can be used to induce sequence-specific cleavage; see, e.g., Hockemeyer et al., Nat Biotechnol. 29(8):731-4 (2011); Moscou et al., 2009, Science 326:1501; Boch et al., 2009, Science 326:1509-1512. Methods are known in the art for designing TALENs, see, e.g., Rayon et al., Nature Biotechnology 30:460-465 (2012).

Vectors and Transformation

The various active sequences, including the silencing sequence and the sequence encoding a chimeric ZFN can be introduced into a host cell on the same vector or separately (e.g., on separate vectors or separate types of vectors at the same time or sequentially). Methods for introducing the various nucleic acids, constructs, and vectors are discussed further below and are well known in the art.

Transformation can be carried out by a variety of known techniques which depend on the particular requirements of each cell or organism. Such techniques have been worked out for a number of organisms and cells and are readily adaptable. Stable transformation involves DNA entry into cells and into the cell nucleus. For example, transformation can be carried out in culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors.

Liposomal formulations: In certain embodiments of the invention, the oligo- or polynucleotides and/or expression vectors containing silencing sequences and/or ZFNs may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids and liposomes suitable for use in delivering the present constructs and vectors can be obtained from commercial sources or made by methods known in the art.

Microinjection: Direct microinjection of DNA into various cells, including egg or embryo cells, has also been employed effectively for transforming many species. In the mouse, the existence of pluripotent embryonic stem (ES) cells that can be cultured in vitro has been exploited to generate transformed mice. The ES cells can be transformed in culture, then micro-injected into mouse blastocysts, where they integrate into the developing embryo and ultimately generate germline chimeras. By interbreeding heterozygous siblings, homozygous animals carrying the desired gene can be obtained.

Viral Vectors as Expression Constructs: Other viral vectors may be employed as expression constructs in the present invention. Vectors derived from, for example, vaccinia virus, adeno-associated virus (AAV, e.g., MV), or herpes virus may be employed. Extensive literature is available regarding the construction and use of viral vectors. For example, see Miller et al. (Nature Biotechnol. 24:1022-1026, 2006) for information regarding adeno associated viruses. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was subsequently detected.

Non-viral Methods: Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression constructs may simply consist of naked recombinant DNA, or in some cases mRNA for the recombinant ZFN. Transfer of the construct may be performed by any of the nuclei acid transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

Pharmaceutical Compositions, RNAs, and Cells

In another embodiment, the invention features compositions (e.g., pharmaceutically acceptable compositions) that include the nucleic acid constructs or vectors described herein. Various combinations of the constructs and vectors described herein can be formulated as pharmaceutical compositions.

Also within the scope of the invention are RNAs and proteins encoded by the cleavage vector and compositions that include them (e.g., lyophilized preparations or solutions, including pharmaceutically acceptable solutions or other pharmaceutical formulations).

In another embodiment, the invention features cells that include the nucleic acid constructs, vectors (e.g., an adeno associated vector), and compositions described herein. The cell can be isolated in the sense that it can be a cell within an environment other than that in which it normally resides (e.g., the cell can be one that is removed from the organism in which it originated). The cell can be a germ cell, a stem cell (e.g., an embryonic stem cell, an adult stem cell, or an induced pluripotent stem cell (iPS cell or IPSC)), or a precursor cell. Where adult stem cells are used, the cell can be a hematopoietic stem cell, a cardiac muscle stem cell, a mesenchymal stem cell, or a neural stem cell (e.g., a neural progenitor cell). The cell can also be a differentiated cell (e.g., a fibroblast or neuron).

Methods of Treatment

The methods of the invention can be used to treat patients who have trisomy 21. Any of the methods can include the step of identifying a patient in need of treatment; any of the patients can be human; and any of the methods can be carried out by either administering the present compositions to the patient, or removing cells from the patient, treating the cells, and "readministering" those cells. For example, the invention features methods of treating a genetic disorder associated with a trisomic chromosome 21 by identifying a patient in need of treatment; and administering to the patient a nucleic acid construct, vector, and/or cleavage vector as described herein. The amount of the construct or vector administered will be an amount sufficient to improve a condition associated with the disorder. Where cells are harvested from a patient to treat a condition or disorder described herein (or an associated symptom), the methods can include the steps of identifying a patient in need of treatment; harvesting cells from the patient; transfecting the cells with one or more of the types of constructs and/or vectors described herein; and administering to the patient a sufficient number of the transfected cells to treat the condition or improve a condition or symptom associated with the disorder. The symptoms associated with many birth defects and other conditions are well known. For example, individuals having Down Syndrome often experience mental retardation, hypotonia, cardiac defects, Alzheimer's Disease, hematological abnormalities and leukemia (see Antonarakis and Epstein, *Trends Mol. Med.* 12:473-479, 2006). As noted above, treatment can also be carried out in vivo by administering present compositions to the patient via pharmaceutically acceptable compositions.

The cells can include differentiated cells (e.g., white blood cells or fibroblasts) and/or undifferentiated cells (e.g., stem cells or precursor cells). The cells can also be differentiated cells that are induced, ex vivo, into iPS cells, or multi-potent stem cells or stem cells of particular lineage, such as neural stem cells. Neural stem cells (also called neural progenitors), are characterized by the ability to form neural rosettes, a neural tube-like structure (see, e.g., FIG. 6). The condition can be a neurological or blood disorder such as Alzheimer's Disease and leukemia, respectively, or a muscular defect, including defects of the heart.

To illustrate a particular application, Xist mediated chromosomal therapy could be used to ameliorate transient myeloproliferative disorder (TMD) in Down Syndrome children and possibly prevent the later development of acute leukemia. Successful bone marrow transplants for diseases like leukemia depend upon immune compatibility, to avoid Graft versus Host Disease (GVHD). To avoid graft rejection, the patient's own cells can be used and transgenically modified prior to transplant. There are two scenarios to acquire and modify stem cells for bone marrow transplant. In the first, the patient's own bone marrow stem cells can be obtained and an Xist transgene as described herein can be introduced and targeted to chromosome 21. When Xist expression silences the trisomic chromosome, these cells can then be transplanted back into the patient following standard bone marrow transplant procedures following the destruction of the patient's bone marrow using irritation. Modified autologous (from the patient) bone marrow cells can be transplanted without first irradiating the patient to destroy the unmodified bone marrow. This would produce a situation where the patient's bone marrow would be mosaic for trisomy 21 (a mixture of modified and unmodified cells). The data presented herein indicate that the modified cells would have a growth advantage over the non-modified fully trisomic cells, and the modified cells would eventually outgrow the non-modified disease-inducing cells (see Douillard-Guilloux et al., *J. Gene Med.* 11:279-287, 2009). In the second approach, the patient's fibroblast (skin) cells can be used to produce iPS cells, into which a transgenic Xist gene is inserted and targeted to chromosome 21. IPS cells that silence one of the three trisomic chromosomes will then be differentiated into adult hemopoietic stem cells and introduced back into the patient as described herein.

EXAMPLES

The invention is further described in the following examples, which do not limit the scope of the invention described in the claims.

Materials & Methods

The following materials and methods were used in the Examples set forth below.

Cell Culture.

HT1080 TetR cells (Invitrogen) and Female DS human primary fibroblast line (Coriell) (AG13902) were cultured as recommended by supplier. DS iPSC parent line (DS1-iPS4) was provided by George Q. Daley (Children's Hospital Boston, USA) and maintained on irradiated mouse embryonic fibroblasts (iMEFs) (R & D Systems, PSC001) in hiPSC medium containing DNEM/F12 supplemented with 20% knockout Serum Replacement (Invitrogen), 1 mM glutamine (Invitrogen), 100 μM non-essential amino acids (Invitrogen), 100 μM β-mercaptoethanol (Sigma) and 10 ng/ml FGF-β (Invitrogen, PHG0024). Cultures were passaged every 5-7 days with 1 mg/ml of collagenase type IV (Invitrogen).

ZFN Design.

ZFNs against the human AAVS1 locus (PPP1R12C) on Chr19 have been previously described[25]. ZFNs against the DYRK1A locus were designed using an archive of pre-validated zinc finger modules[24,53,54], and validated for genome editing activity by transfection into K562 cells and Surveyor endonuclease-based measurement of endogenous locus disruption ("Cell" [55,56]) exactly as described[54]. Southern blotting for targeted gene addition was performed exactly as described[23,57] on SphI-digested genomic DNA probed with a fragment corresponding to positions Chr 21:38825803+38826056 (hgl 9).

iPSC reprogramming of DS fibroblasts. Three primary DS fibroblast cultures (Coriell: GM02504, AG13902, GM02067) were obtained and cultured. Two of these cultures (GM02504, AG13902) were used for reprogramming with assistance of the UConn Stem Cell Core Laboratory, using retroviral transduction with five reprogramming factors (OSKML).

It was initially noted that two of the three human primary DS fibroblast samples showed very limited proliferation even though age of donor and passage number would not predict this. In addition, a marked deficit in DS mouse tail tip fibroblast proliferation was seen. Additionally, in two attempts at reprogramming human DS fibroblasts, only the AG13902 sample was modestly successful, suggesting DS fibroblasts were more difficult to reprogram than control fibroblasts. Fewer subclones were obtained and most of these showed poor morphology and slower growth than controls.

XIST and rtTA/Puro Plasmid Construction.

14 kb human XIST cDNA, a splicing isoform of full length XIST cDNA was subcloned into pTRE3G (Clontech, Cat#: 631167). Two homologous arms (left arm, 690 bp; right arm, 508 bp) of DYRK1A gene on Chr 21 were amplified by PCR from primary DS fibroblasts (AG13902) (Coriell) and cloned into the pTRE3G vector (Human Chr 21 DYRK1A left arm primers: forward 5'-GCCGTATACCATTAACTCTTTACTGTTC-3' (SEQ ID NO:1), reverse 5'-TCTGTATACGTAAACTGGCAAAGGGGTGG-3' (SEQ ID NO:2); Human Chr 21 DYRK1A right arm primers: forward 5'-ATTTCGCGAACGGGTGATGAGCAGGCTGT-3' (SEQ ID NO:3), reverse 5'-CCGTCGCGAAAACCAGAAAGTATTCTCAG-3' (SEQ ID NO:4)).

DYRK1A Left Arm, Reverse:

(SEQ ID NO: 33)

AAACTGGCAAAGGGGTGGCTGGGCCAAAAGACAGAGGAATTAAGTAA
GAAGTCCAGGAAAAATGAACTTCACATCAAATTTTAGAGCACGGTAG
CCATGAATCTTGTGAATAGCTCCCAAAAATGTCCTGTGGAAGACAAC
TAGAAAGCATTCTACAATCAGGCACCCACCTCCACCTGCAGCCTCCT
GTGTTGTTCTCATGGGGCACCTCTGGGCTCCAGCTCCTCCAAGGCAC
CTCCACACTCTCTCAAGTACACTCTTCACTCTTCCCCAAACATGATT
CCCCTACTGCTCTGCCTAACTCCCACTTCTCTTTCAAGTAGCAGCTT
AAACGTCACCTCATATTTGGCTGGAAAATAGAATATAGACAGAGGGG
TAAGTTAAGGCTAGAAAGGCAGGCTGGGTCAACAGAATGGCAAGCTA
AAACATGGGATTTTCTAAAACAGCCTAAGAGGGTGACAGATAAAAGT
GTGCAAGGAGTGGCACAACTCCAGTTTCATCTTTAGCTATAGCAATT
AACACCATAAGGAGTCTGGATTCAATTTTGCCATTTACTAGCTAGCT
ACCAACTTCTGTGTCGCTTTGGGCAAATCAATTAAATCCATACCTCC
CTTTCCATCTGCAGAATGGGTTTATAACAGTACTTAAACCTCAAGGT
ACTAAGAACAGTAAAGAGTTAATGGTA

DYRK1A Right Arm, Reverse:

(SEQ ID NO: 34)

CGAAAACCAGAAAGTATTCTCAGTAATGATAGTATGGATAAAGCAGG
TTTCTATGACCCTTTATTACAGAATCTGTGAGTTTTTCACAATTAAA

-continued

AAGTAATAAAAAGTAGTGACAACATTCACTGAACTCTTATTCTATGC
CAACTTGTTCCGGTATGCCCTTACACCCACAAAAGCCCTATGCATAA
GGTGGCATTATTCCAGCATGTATTGCATTGTACACACAAAGAGGTCA
AGCACTCCACCACGGCCCTAAGCATGGTGGCTGAGGTGGGAAGGCCA
GAGGTAGGTGGGCCCGCGCCCTTTTCCACTCTGAACCATGCCTCCAA
GATAGGAGGGTGGGAAAGTGCTCAAGACACATTAGAAATTCCCCATA
AAAGACAAGATTGTTGAACACCTGCAAGTGAATAAAGATAAACTGAT
CTCAGAGGGGAAAAAGACGCAGGGTTAGGAAACAGCACCCTGCTCGA
GGACGTTCTTTCCAAACAGCCTGCTCATCACC

The pEF1α-3G rtTA-pA cassette from pEF1α-Tet3G vector (Clontech) was subcloned into a plasmid for targeted gene addition to the PPP1R12C/AAVS1 locus[25], which contains a unique HindIII site flanked by two 800 bp stretches of homology to the ZFN-specified position in the genome.

See FIGS. 2*a* & 9*a*, and 2*b* & 9*b*.

Constructs for Targeting DYRK1 or RCAN1:

The following constructs were made and tested. Two constructs for a dual-targeting strategy in human Down Syndrome iPSCs were made as follows:

CONSTRUCT 1 (3G/FL/hXIST/DYRK1A): The 18.5 kb inducible human XIST construct that contains 14 kb full length human XIST cDNA is targeted to the DYRK1A gene on Chr 21 by a dual-targeting strategy in human Down syndrome iPSCs. See FIG. 2*a*, 9*a*, 10*a* and SEQ ID NO:14 for the sequence.

CONSTRUCT 2 (puro/rtTA/AAVS1): The puro/rtTA construct is targeted to the AAVS1 locus on Chr 19 for the dual-targeting strategy. See FIG. 2*b*, 9*b*, 10*b*, and SEQ ID NO:15 for the sequence.

The dual-targeting strategy was specifically designed for Down Syndrome iPSCs. The 18.5 kb inducible human XIST transgene (3G/FL/hXIST/DYRK1A) is targeted to the DYRK1A gene on Chr 21, and the puro/rtTA plasmid (puro/rtTA/AAVS1) is targeted to a safe harbor of human genome (AAVS1 locus) on Chr 19. Puromycin on the puro/rtTA construct is for selection of XIST-targeted clones (by 3G/FL/hXIST/DYRK1A) and tetracycline transactivator (rtTA) is for induction of XIST transgene expression on Chr 21.

Four selectable and inducible XIST constructs targeted the RCAN1 and DYRK1A loci on Chr 21 in human somatic cells were made as follows:

CONSTRUCT 3 (FL/hXIST/RCAN1): The 21.1 kb selectable and inducible human XIST construct that contains 14 kb full length human XIST cDNA is targeted to the RCAN1 gene on Chr 21 by ZFNs in human somatic cells. See FIGS. 7A-B, 10*c*, and SEQ ID NO:16 for the sequence.

CONSTRUCT 4 (FL/hXIST/DYRK1A): The 20.7 kb selectable and inducible human XIST construct that contains 14 kb full length human XIST cDNA is targeted to the DYRK1A gene on Chr 21 by ZFNs in human somatic cells. See FIG. 9*c*, 10*d*, and SEQ ID NO:17 for the sequence.

CONSTRUCT 5 (6.8 kb/hXIST/RCAN1): The 14.0 kb selectable and inducible human XIST construct that contains 6.8 kb exon 1 of human XIST cDNA (SEQ ID NO:2, obtained from C. Brown, University of British Columbia) is targeted to the RCAN1 gene on Chr 21 by ZFNs in human somatic cells. See FIG. 7*c*, 10*e*, and SEQ ID NO:18 for the sequence.

Figure 9A:
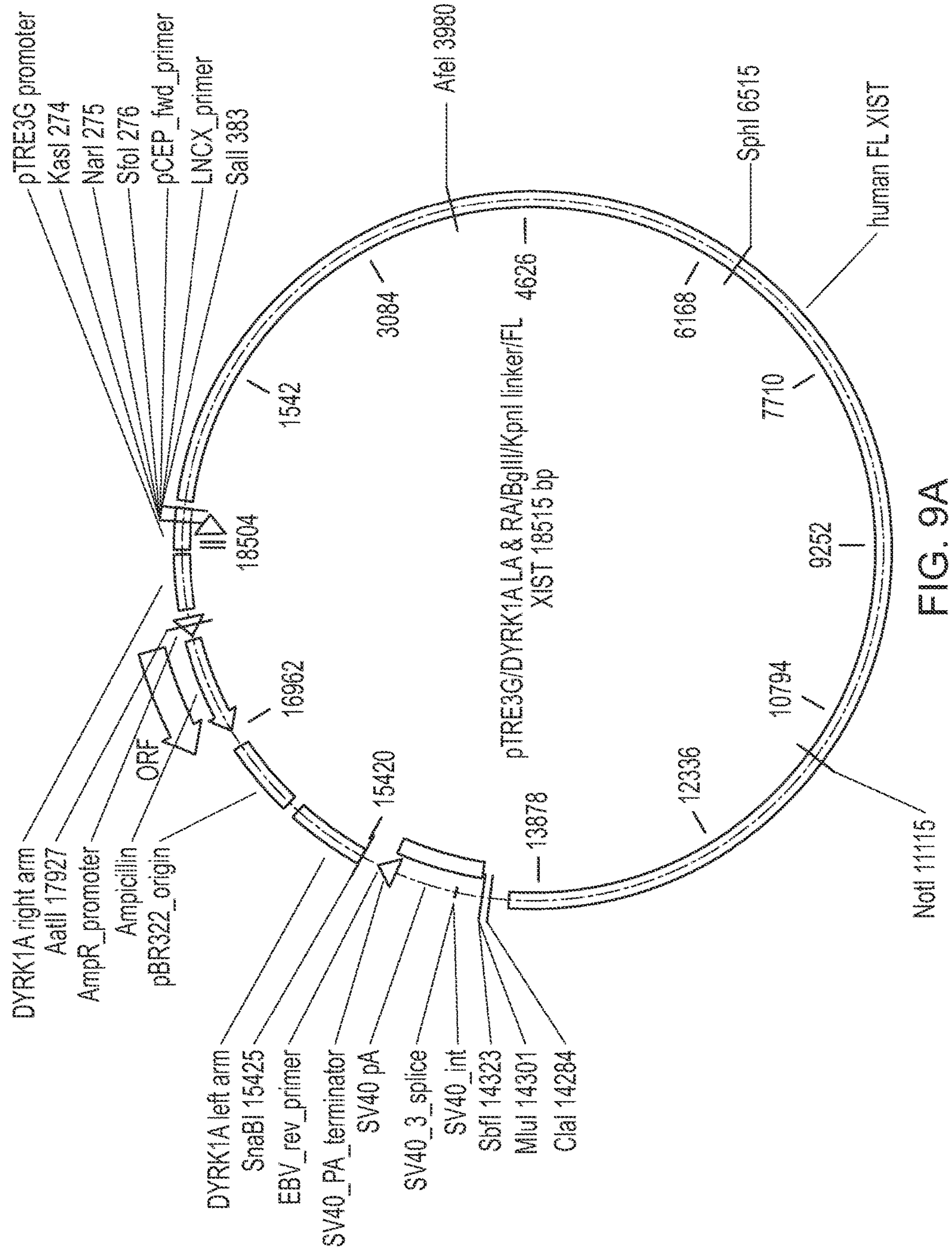
FIGS. 9A-I show schematic illustrations of some of the constructs used in the present application.
Figure 9B:
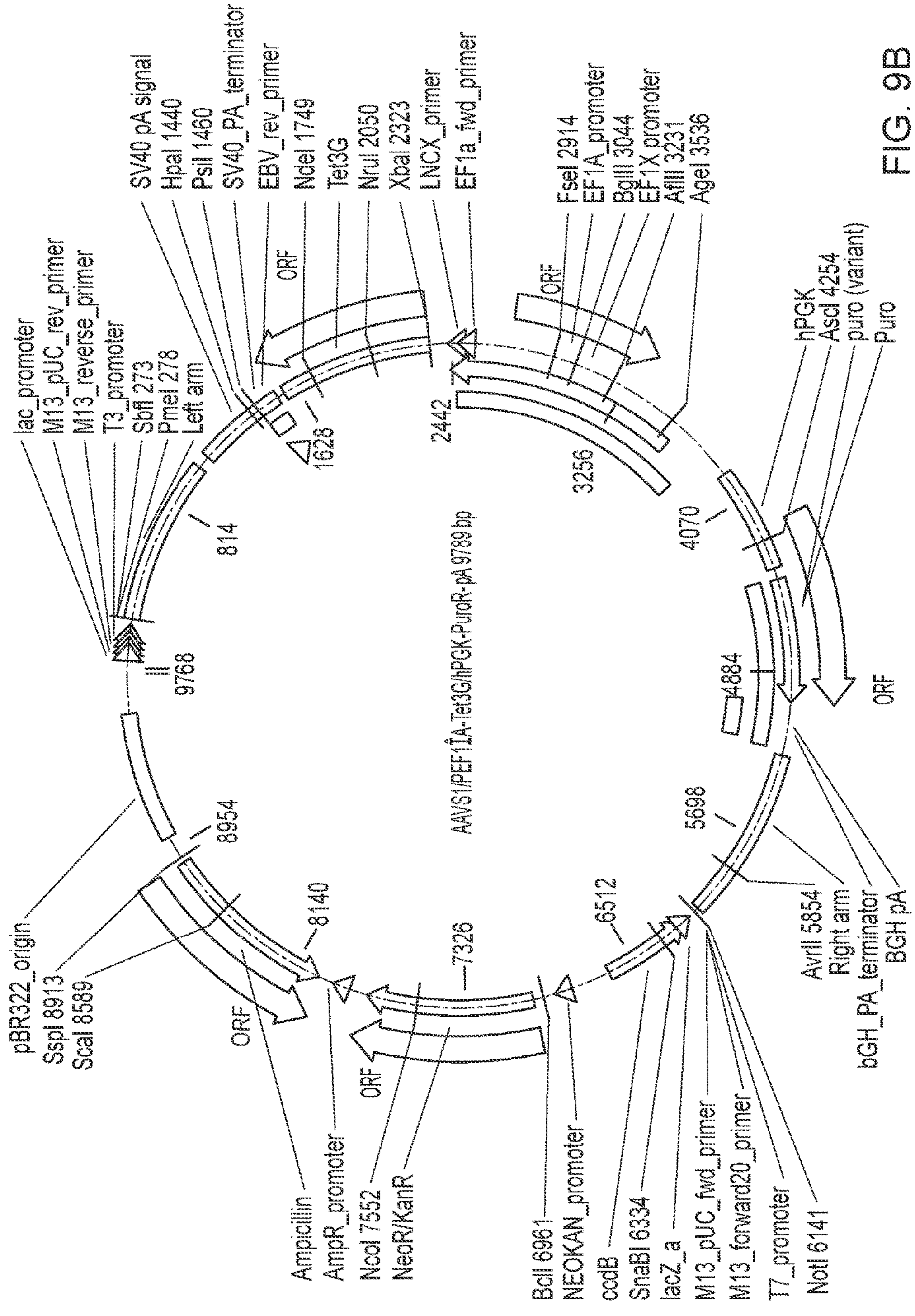

CONSTRUCT 6 (6.8 kb/hXIST/DYRK1A): The 13.7 kb selectable and inducible human XIST construct that contains 6.8 kb exon 1 of human XIST cDNA (SEQ ID NO:2, obtained from C. Brown, University of British Columbia) is targeted to the DYRK1A gene on Chr 21 by ZFNs in human somatic cells. See FIG. 9*d*, 10*f*, and SEQ ID NO:19 for the sequence.

One selectable and inducible XIST construct targeted AAVS1 locus on Chr 19 in human somatic cells was made as follows:

CONSTRUCT 7 (6.8 kb/hXIST/AAVS1): The 15.7 kb selectable and inducible human XIST construct that contains 6.8 kb exon 1 of human XIST cDNA (SEQ ID NO:2, obtained from C. Brown, University of British Columbia) is targeted to the AAVS1 locus on Chr 19 by ZFNs in human somatic cells. See FIG. 9*e*, 10*g*, and SEQ ID NO:20 for the sequence.

One selectable and inducible mouse Xist construct targeted the Runx1 gene on mouse Chr 16 was made as follows:

CONSTRUCT 8 (6.3 kb/mXist/Runx1): The 20.6 kb selectable and inducible mouse Xist construct that contains a 6.3 kb exon 1 of mouse Xist cDNA is targeted the Runx1 gene on Chr 16 (synteny to human Chr 21) by conventional homologous recombination. See FIG. 9*f*, 10*h*, and SEQ ID NO:21 for the sequence.

CONSTRUCT 9 (pEF1α/hDYRK1A/FL mXist): The 20.6 kb construct contains full length mouse Xist cDNA, an ampicillin resistance gene, and two homologous arms that target intron 1 of DYRK1A gene on human chromosome 21. See FIG. 9*g*, 10*i*, and SEQ ID NO:22 for the sequence.

CONSTRUCT 10 (pEF1α/hDYRK1A/6.3 kb mXist). The 12.2 kb construct contains 6.3 kb of mouse Xist cDNA that has been reported to function (Wutz et al., Nat Genet 30, 167-174 (2002)) and two homologous arms that target intron 1 of DYRK1A gene on human chromosome 21. See FIG. 9*h*, 10*j*, and SEQ ID NO:23 for the sequence.

CONSTRUCT 11 (Rosa26/pEF1x-Tet3G/hPGK-PuroR). The 10.3 kb construct contains a puromycin resistance selection gene and rtTA cassette that is targeted to the Rosa26 locus on mouse chromosome 6 by ZFNs. See FIG. 9*i*, 10*k*, and SEQ ID NO:24 for the sequence.

The constructs described above targeting human Chr 21 or mouse Chr 16 constitute the first "dosage compensating transgenes" designed to silence chromosome imbalance involving duplication of chromosomal material, particular trisomy with much clinical import.

Dual-Targeted-Addition of Human DS iPSCs and Generation of Stable Targeted Clones.

The DS iPSC line was cultured in 10 μM of Rho-associated protein kinases (ROCK) inhibitor (Calbiochem; Y27632) 24 h before electroporation. Single cells ($1\times10^7$) were harvested using TryPLE select (Invitrogen), resuspended in 1×PBS and electroporated with a total of 55 μg DNA including five plasmids (XIST, DYRK1A ZFN1, DYRK1A ZFN2, rtTA/puro, and AAVS1 ZFN) with both 3:1 and 5:1 ratios of XIST: rtTA/puro. The electroporation conditions were 220v, and 750 μF (BioRad Gene Pulser II System)[53]. Cells were subsequently plated on puromycin-resistant DR4 MEF feeders (Open Biosystems, Cat#: MES3948) in hiPSC medium supplemented with ROCK inhibitor for the first 24 h. Over 300 colonies remained after 12 days of 0.4 μg/ml puromycin selection and 245 randomly chosen individual colonies across 36 pooled wells were examined by interphase DNA/RNA FISH for the presence and expression of XIST, correct targeting and retention of trisomy (since some subclones lacked XIST or showed just two DYRK1A DNA signals). Over 100 individual clones were isolated and characterized, and those of interest, containing targeted XIST on one of three DYRK1A loci, were frozen. Six single target clones with good pluripotent morphology, OCT4 positive staining, correct targeting to one trisomic chromosome, and good XIST RNA paint were expanded for further characterization. One double and one triple target line, two non-target clones, and one disomic clone were also isolated and frozen. Targeting and correct chromosome number (47) was confirmed by interphase and metaphase FISH and genome integrity by high resolution G-band karyotype and CGH array.

Chromosome Preparation.

iPSCs were treated with 100 ng/ml KaryoMAX colcemid (Invitrogen) for 2-4 h at 37° C. in a 5% $CO_2$ incubator. Cells were trypsinized, treated with hypotonic solution, and fixed with methanol:acetic acid (3:1). Metaphases were spread on microscope slides, and at least 20 analyzed per clone. Karyotype analysis was done on pro-metaphase chromosomes using Standard Giemsa-trypsin G band methods.

CGH Array.

CGH was performed in the Cytogenetics Laboratory at UMASS Medical School. 1 ug of DNA was used for Genomic Microarray analysis using UMass Genomic Microarray platform (Human Genome Build hgl 9). The array contains approximately 180,000 oligonucleotides (60 mers) that represent coding and noncoding human sequences and high density coverage for clinically relevant deletion/duplication syndromes and the telomeric and pericentromeric regions of the genome. Data was analyzed by BlueFuse Multi, v3.1 (BlueGnome, Ltd).

DNA/RNA FISH, and Immunostaining.

DNA and RNA FISH were carried out as previously described[10,19,21,58]. The XIST probe is a cloned 14 kb XIST cDNA (the same sequence as XIST transgene in FIG. 2*a*) in pGEM-7Zf(+) (Promega). Six Chr 21 gene probes are BACs from BACPAC Resources (DYRK1A: Rp11-105024, APP: RP11-910G8, USP25: RP11-840D8, CXADR: RP11-1150114, ITSN1: RP11-1033C16, COL18A1: RP11-867O18). DNA probes were labeled by nick translation with either biotin-11-dUTP or digoxigenin-16-dUTP (Roche). In simultaneous DNA/RNA FISH (interphase targeting assay), cellular DNA was denatured and hybridization performed without eliminating RNA and also treated with 2 U/μl of RNasin Plus RNase inhibitor (Promega). For immunostaining with RNA FISH, cells were immunostained first with RNasin Plus and fixed in 4% paraformaldehyde before RNA FISH. Antibodies: H3K27me3 (Millipore, 07-449), UbH2A (Cell Signaling, 8240), H4K20Me (ABcam, ab9051), MacroH2A (Millipore, 07-219), OCT4 (Santa Cruz, sc-9081), PAX6 (Stemgent, 09-0075), SOX1 (R & D Systems, AF3369).

Allele-Specific SNP Analysis:

Primers were designed to amplify 3' UTR regions of chromosome 21 genes reported to contain SNPs (Table 1). Total cDNA was used from three transgenic clones with and without XIST induction for 22 days. RT-PCR products were sequenced by GENEWIZ. Of ~10 genes examined, four were heterozygous and informative in the patient DS iPS cell line used here.

TABLE 1

| Primers for Chr21 gene amplification (allele-specific SNP silencing analysis) | | | | |
|---|---|---|---|---|
| Genes | Forward primer 5'-xxx-3' | SEQ ID NO: | reverse primer 5'-xxx-3' | SEQ ID NO: |
| ADAMTS1 | TCTCTGAAACCATA GCAGCCA | 35 | CTTGTGCAGACCAT CCCTGC | 39 |
| ETS2 | GCCTTTTGCAACCA GGAACAGC | 36 | ATCACACAGAAGAA CGTGGAGC | 40 |
| SPA13 | AACTCTGCTCCAAA TGCCGA | 37 | CCTGTACATCATTC TCTGCTTGG | 41 |
| TIAM1 | TGGGGTGATTTGCT TTCCAGTGC | 38 | GTGCAGTGTCTGCC CCAAGC | 42 |

Microarray Analysis.

Three independently targeted subclones plus the parental Chr21 trisomic (non-targeted) iPS cell line were grown ±doxycycline (2 ng/ml) for 22 d. Normal male iPS and disomic isogenic lines were also cultured for 22d and total RNA was extracted with a High Pure RNA extraction kit (Roche) in triplicate for each, processed with a Gene Chip 3' IVT Express Kit (Affymetrix), and hybridized to Affymetrix human gene expression PrimeView arrays. Array normalization was performed with Affymetrix Expression Console Software with Robust Multichip Analysis (RMA)[59]. Probesets with the top 60% of signal values were considered present and "expressed" and were used for all further analysis. Data in FIG. 5 has no other threshold applied. When designated, a gene expression change significance threshold was applied using a two-tailed T-test comparing samples±doxycycline in triplicate (N=3) (FIG. 5*d*, p<0.01). For the ~200 genes found to significantly change in all three clones (in text), a T-test with p<0.001 was applied.

Microarray Data Interpretation:

Using extraction-based methods, changes on just one of three alleles (from the XIST-bearing chromosome) will be diluted by the other two. If all three chromosomes are fully expressed, this would predict a 33% reduction in Chr21 expression levels per cell when one Chr21 is fully silenced. However, 33% would apply only if Chr 21 genes are fully over-expressed to start, and prior evidence and results in this study shows this is not the case for many genes. Previous microarray studies have analyzed expression levels of Chr 21 in DS patient cells, although such analyses are hampered by the extensive genetic and epigenetic differences between any two individuals[60-62]. The fraction of Chr 21 genes detected as over-expressed varies with the study and tissue, but generally is in the 19-36% range[3,34,35,63], with individual gene increases often in the ~1.2-1.4 range (less than the theoretical 1.5). For example, one study of DS embryoid bodies showed only 6-15% of genes appeared significantly up-regulated, but this was comparing non-isogenic samples of different ES cell isolates.

Our trisomy correction system allows direct comparison of the same cells grown in identical parallel cultures, with and without XIST-mediated chromosome silencing. Our data shows a ~20% reduction in Chr 21 expression overall; importantly this level of reduction is seen either when the third chromosome is silenced in trisomic cells, or when disomic and trisomic cells are compared. This 20% reduction represents an average per cell for all three chromosomes, but corresponds to a 60% reduction in expression for just one Chr21 (the one silenced by XIST RNA, as shown here).

Apart from our goal here of trisomy dosage compensation, these results add significantly to understanding the extent of Chr 21 over-expression in Down Syndrome, by providing a more comprehensive analysis which shows expression of most genes is increased, but less than the theoretical 1.5 fold.

qRT-PCR.

qRT-PCR was performed for eight down-regulated Chr 21 genes determined by microarray on an BIO-RAD MyiQ™ Real-Time PCR Detection System in triplicate for clone 3 with/without doxycycline treatment for 22 d. The β-actin gene was used as an internal standard for calculation of expression levels. Primers for eight Chr 21 genes and β-actin were described in Table 2.

TABLE 2

| Primers for qRT-PCR | | | | |
|---|---|---|---|---|
| Genes | Forward primer 5'-xxx-3' | SEQ ID NO: | reverse primer 5'-xxx-3' | SEQ ID NO: |
| CXADR | TGCGTCTAAAC GTTGTCCCT | 43 | AGTGGACGTAC GGCTCTTTG | 52 |
| COL6A1 | ATCAGCCAGAC CATCGACAC | 44 | GCCCTTCTCTC CCTTGTAGC | 53 |
| PTTG1IP | GTTGGGTGAAC TTTGAGGCG | 45 | GTGCTGGAGCG CTTTAGTTG | 54 |
| ADAMTS1 | CCCTCACTCTG CGGAACTTTT | 46 | ATTAAGGCTGG CACACTGCTT | 55 |
| BTG3 | CCCATGTGAGG TGTGCTGT | 47 | AGGGCCCTGGT AACTTTCCT | 56 |
| TIAM1 | TCAAAACCGAG AGCCTTCCC | 48 | CGGAGACGGCA TCAGAATCA | 57 |
| USP16 | AGCCTTCAGTT TGGCTGTGT | 49 | GGCTTTGGAGT TGTAATGCTGG | 58 |
| APP | GGAGCGCTCTC GACTTTTCT | 50 | TGTGCATGTTC AGTCTGCCA | 59 |
| β-ACTIN | TTGCCGACAGG ATGCAGAAGGA | 51 | AGGTGGACAGC GAGGCCAGGAT | 60 |

DNA Methylation Analysis.

The parent line, and two independent targeted lines were grown with and without doxycycline for 22 d, in duplicate cultures. Genomic DNA was extracted using PureLink Genomic DNA Mini Kit (Invitrogen) and 750 ng bisulfite modified with the Alternative Incubation Conditions from the EZ DNA Methylation Kit (Zymo Research). 160 ng of bisulfite DNA was amplified, fragmented and hybridized to Illumina Infinium HumanMethylation450 array following standard protocol as outlined in the user guide. CpG islands were defined as high and intermediate CpG densities using the CpG density classifications based on those used by[64]. The program CpGIE[65] was used to locate HC and IC islands on the X chromosome and chromosomes 21 and 22. When multiple probes in CpG islands were associated with the same TSS, an average genic methylation value calculated. These average genic values were compared pre and post doxycycline induction using the Mann-Whitney test. Analysis was based on CpG islands within promoters of 143 Chr 21 genes.

The average methylation value was 6% on Chr 21 before XIST induction, and increased to 20-21% in both subclones after induction. Since any methylation increase on the transgenic chromosome would be diluted by the presence of three Chr 21s, this suggests the range of 60% methylation on the one XIST-coated chromosome, which is within the range seen for the inactive X chromosome[37].

Cell Proliferation Analysis.

Eight different iPSC lines (parent line, one non-targeted subclone, and six independent targeted subclones) were passaged onto 6-well plates at equal cell densities per well of each line and grown±doxycycline for 7 d. At least four replicates of each line were analyzed in two independent experiments. Rigorous measures were taken to minimize and control for any minor variations in seeding densities of iPS cells, which cannot be plated as single cell suspensions. First the analysis was done twice for six different transgenic clones, in each case comparing triplicate plates of corrected vs not corrected (Dox vs no Dox). To avoid differences in plating efficiencies of Dox and no Dox cells, we performed the experiments over a time course that did not require passage. For each of the six transgenic clones, the parental line and one negative control (non-targeted) sublcone, a single well of DS iPS cells (without Dox) was used to generate a cell suspension (cells and small disaggregated clumps). Next, equal aliquots of the cell suspension were plated into each of six wells once, then again, then a third time and then a fourth time (not relying on one measurement but the average of four for seeding each well). After plating, Dox was added to three of the six wells, and the cultures were maintained for 7 days. For images, plates were fixed, stained with 1 mg/ml crystal violet (Sigma) in 70% ethanol for 30 min and scanned to generate TIFF images. For cell counts, single cells were harvested by TryPLE select and counted using Beckman Coulter Z1 Particle Counter.

Differentiation of Neural Progenitors and Irreversibility in Cortical Neurons.

Differentiation: Independent XIST-transgenic iPSC clones, and the parental DS iPS line, were dissociated with Accutase (Innovative Cell Technologies) and $4\times10^5$ single cells were plated on Matrigel-coated 6-well plates in mTeSR1 medium (Stemcell technologies). Once the cell culture reached 90%-100% confluence, neural induction was initiated by changing the culture medium to neural induction medium, a 1:1 mixture of N2- and B27-containing media supplemented with 500 ng/ml Noggin (R&D Systems), 10 μM SB431542 (Tocris Bioscience), and 1 μM retinoic acid (Sigma, cat#: R2625), with/without treatment of doxycycline for the specified times. The neural rosettes were counted and their diameter measured, for at least 300 rosettes (sampled in random areas from triplicate dishes). At Day 14, the dox-induced culture had an average rosette diameter of 142 μm±0.55 μm in Clone 1 and 141 μm±3.49 μm in Clone 3. Rosettes could not be measured at the same time point in the uncorrected culture, since they had not formed. At day 17, the uncorrected culture had neural rosettes of similar number and size for both Clones 1 (140 μm±0.87 μm) and 3 (140 μm±1.09 μm). The corrected culture could not be accurately compared for Day 17 because the rosettes had become so mature and often had merged. After 17 d, neural rosettes were collected by dissociation with Dispase and replated on poly-ornithine and laminin-coated plastic dishes in N2- and B27-containing media including 20 ng/ml FGF2. After a further 2 d, FGF2 was withdrawn to promote differentiation of cortical neurons. Test of the irreversibility of silencing: Two independent clones were differentiated to cortical neurons in the presence of Dox for 70 days to initiate silencing. They were then split into parallel cultures grown with and without Dox for another 30 days, and XIST and APP expression analyzed by RNA FISH.

Targeted Addition to Primary Fibroblasts.

Here we used non-immortalized primary human female DS fibroblasts, which like all primary fibroblasts have a limited lifespan in culture (potentially more limited for DS fibroblasts). We reasoned that the robustness of ZFN-driven editing, combined with reduction to disomy for the DRYK1A gene, may make it possible to observe some edited cells before they senesce. We used a transgene carrying an near full length (~14 kb) XIST cDNA under a $TetO_2$ inducible promoter, and a selectable marker on the same construct, with ~600 bp homology arms to the DYRK1A gene (vector is ~21 kb total size, with a total insert size of ~17 kb) (data not shown). When introduced without the Tet-repressor construct, the $TetO_2$ CMV promoter is constitutively active. Two ZFN containing vectors as well as the 21 kb XIST transgene were transfected into the primary DS fibroblasts (ATCC) using Stemfect polymer (Stemgent) (10:1 ratio of XIST to ZFN, and 13 ug DNA to 1.3 ul Stemfect per well of 6 well plate). Surprisingly, the frequency of stable integrants was such that a sparse monolayer of transgenic fibroblasts emerged, rather than a few individual colonies following selection with hygromycin (75 ug/ml). The pooled population of selected cells was analyzed by FISH and IF for targeting, XIST expression and heterochromatin marks. XIST RNA was observed over the DYRK1A locus in ~74% of cells, indicating accurate transgene targeting, which was also verified by metaphase FISH. In many cells there was notable enrichment of H3K27me, H3K20me & UbH2A heterochromatic marks. Due to the limited lifespan of primary cells and the progressive silencing of the CMV promoter used in this construct, these cells were not more fully characterized.

Example 1. Accurate Targeted Addition of a Very Large XIST Transgene to a Trisomic Chr21 in Down Syndrome iPSCs Given its large size, neither the XIST gene nor its cDNA has previously been integrated in a targeted fashion. Thus our first goal was to demonstrate feasibility of targeted addition of by far the largest transgene targeted to date by nuclease-driven genome editing, orders of magnitude larger than sequences commonly used as templates for homology-directed double-strand break repair[24]. Therefore we first attempted targeted addition of a 16 kb XIST transgene in an easily manipulated cell line (HT1080 fibrosarcoma cells), using established ZFNs to the AAVS1 locus on Chr19[25]; see FIG. 9*e*. This proved highly successful. To extend this to Chr21, we chose the DYRK1A locus at Chr21q22 for its interest in DS (reviewed in[26]) and its potential role in pluripotency and senescence[27,28]. From this we reasoned that disrupting one of three DYRK1A alleles may enhance the likelihood of obtaining targeted trisomic pluripotent sub-clones.

Figure 9C:
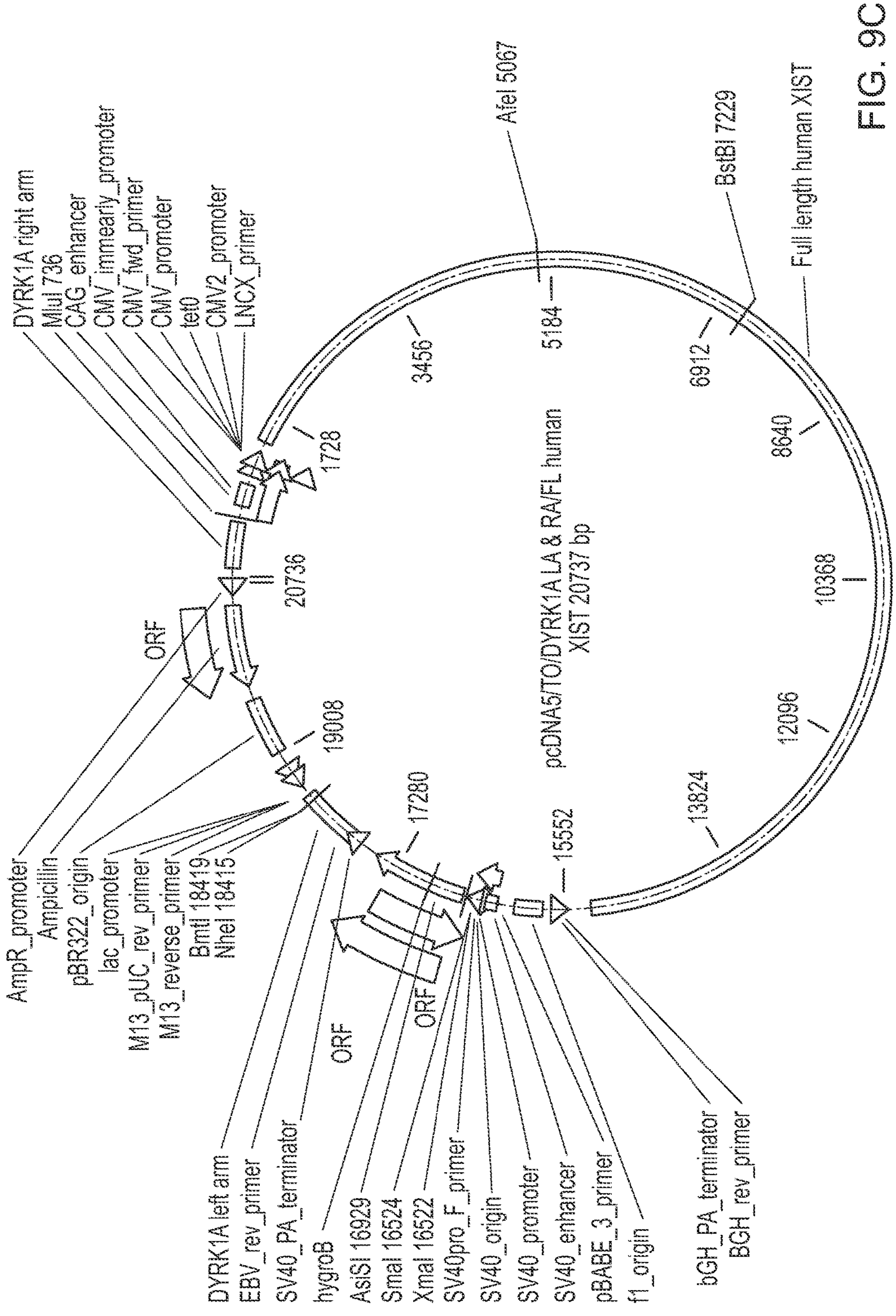
Figure 9D:
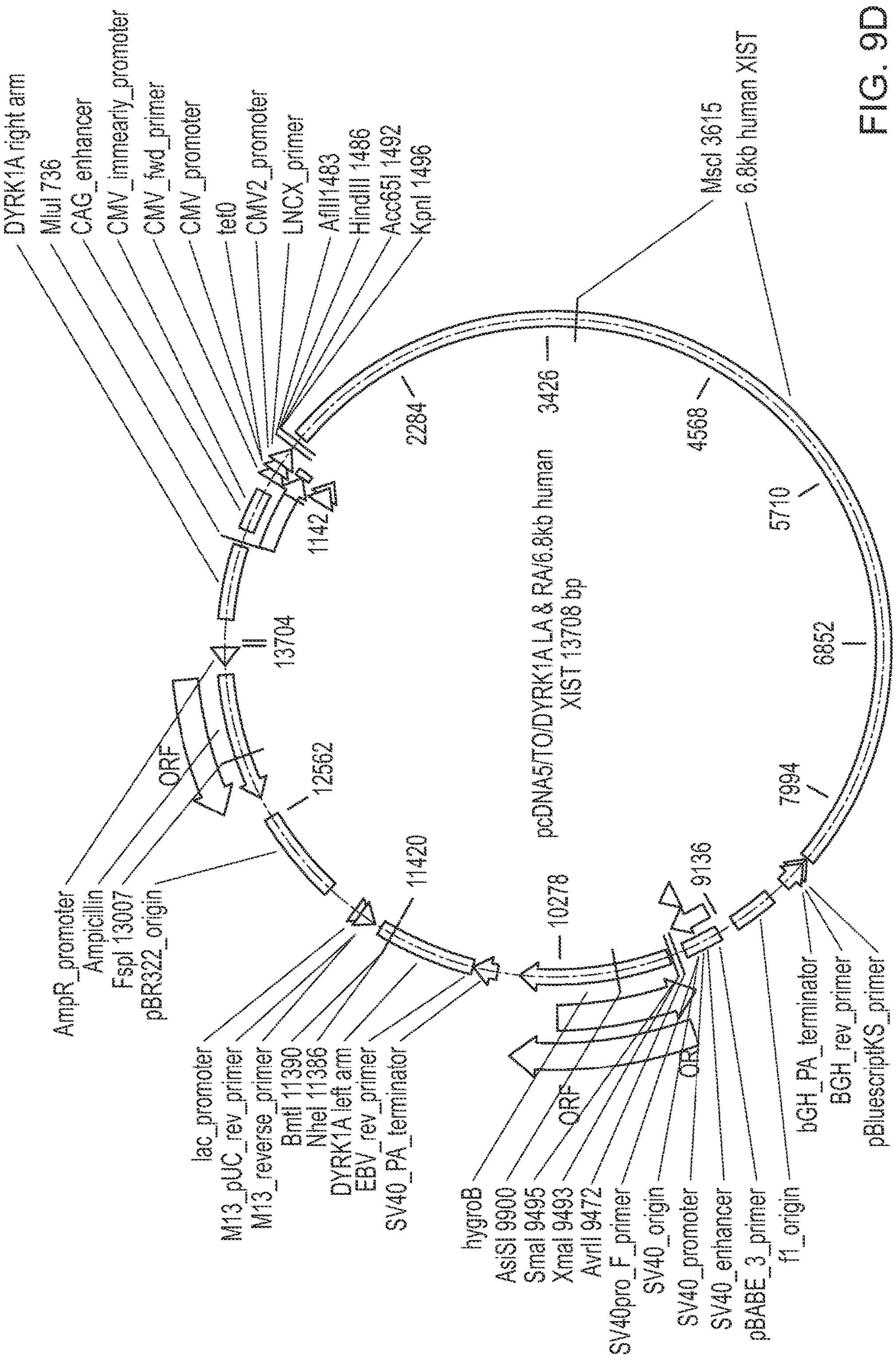
Figure 9E:
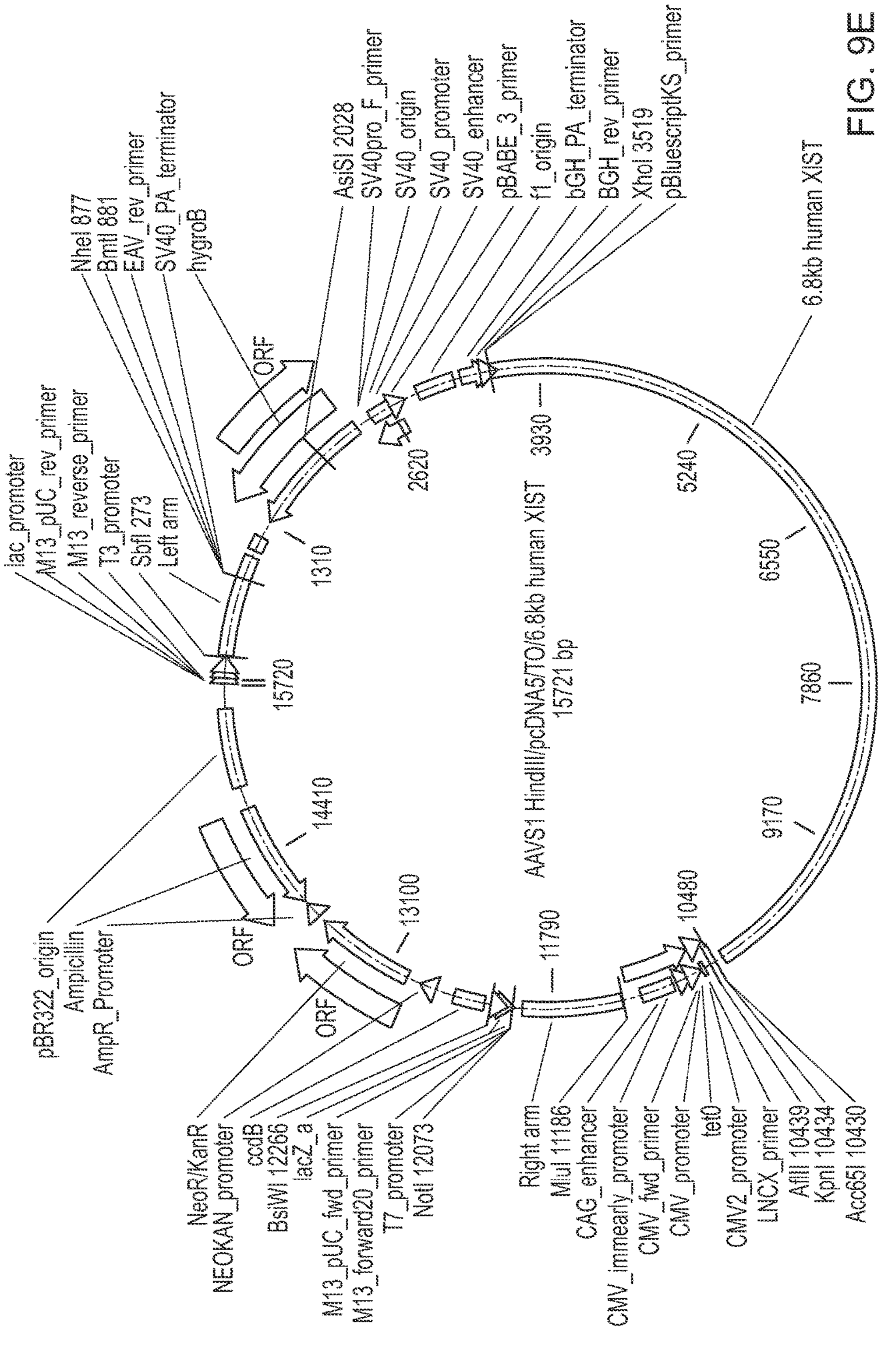
Figure 9F:
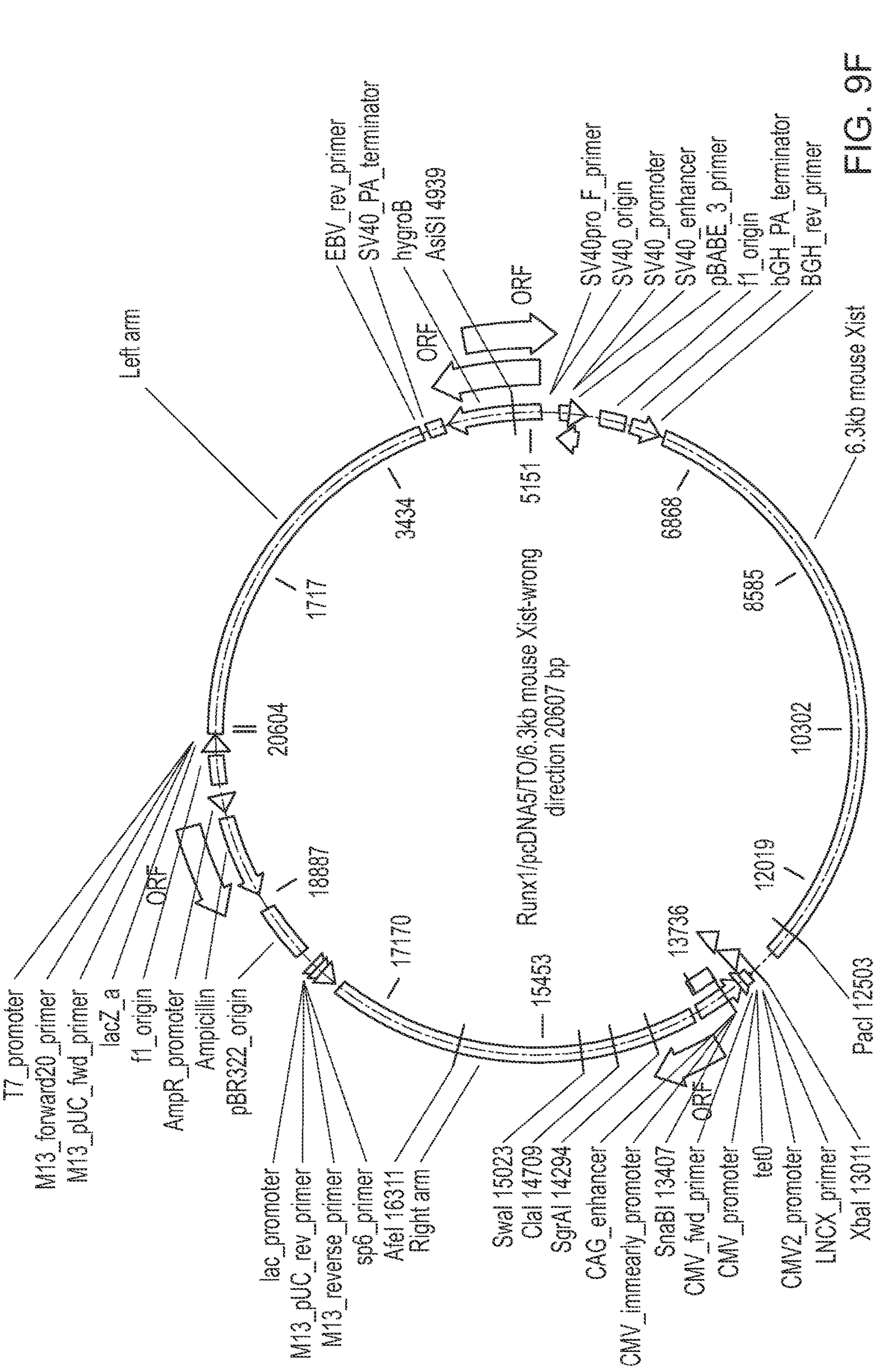
Figure 9G:
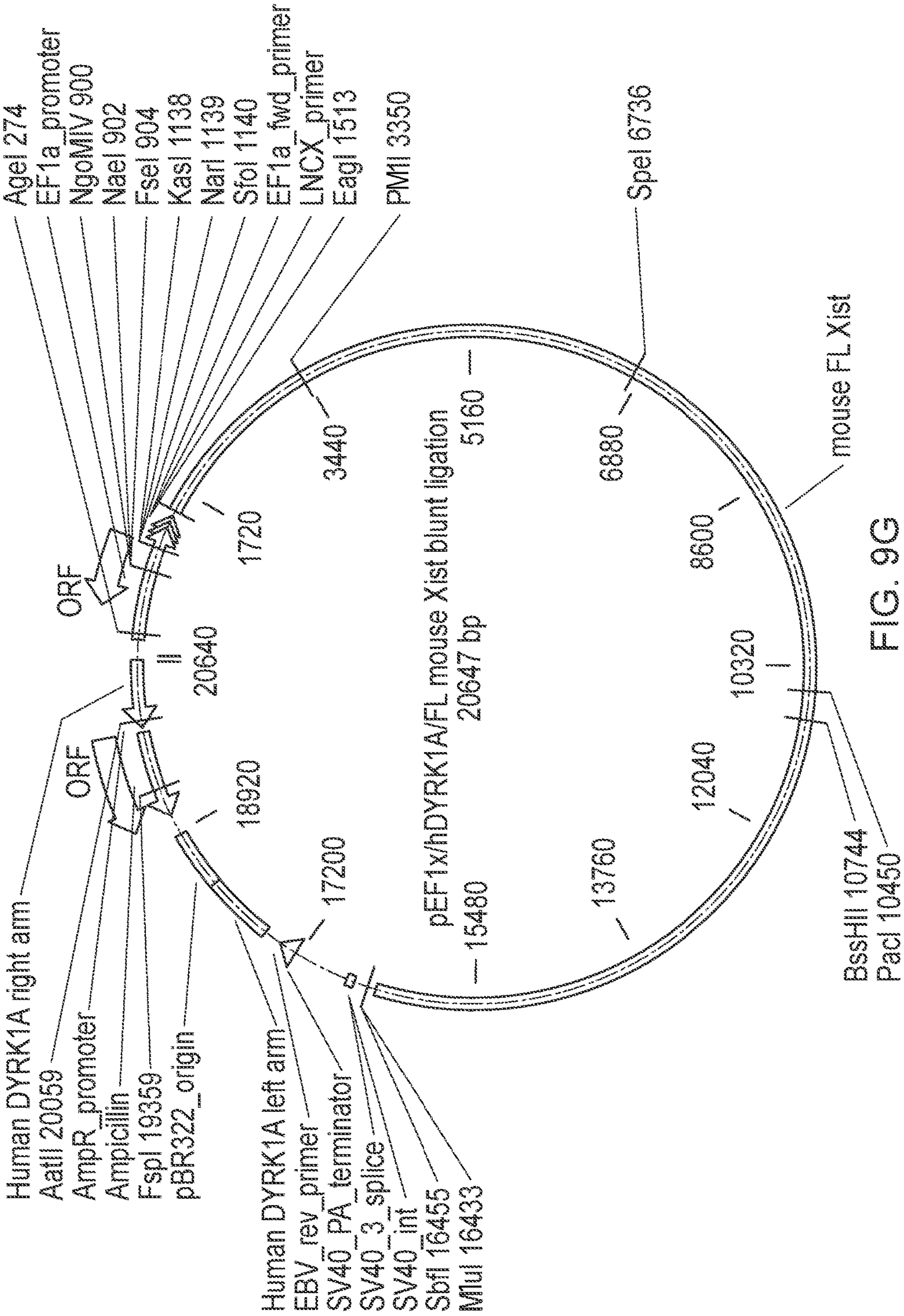
Figure 9H:
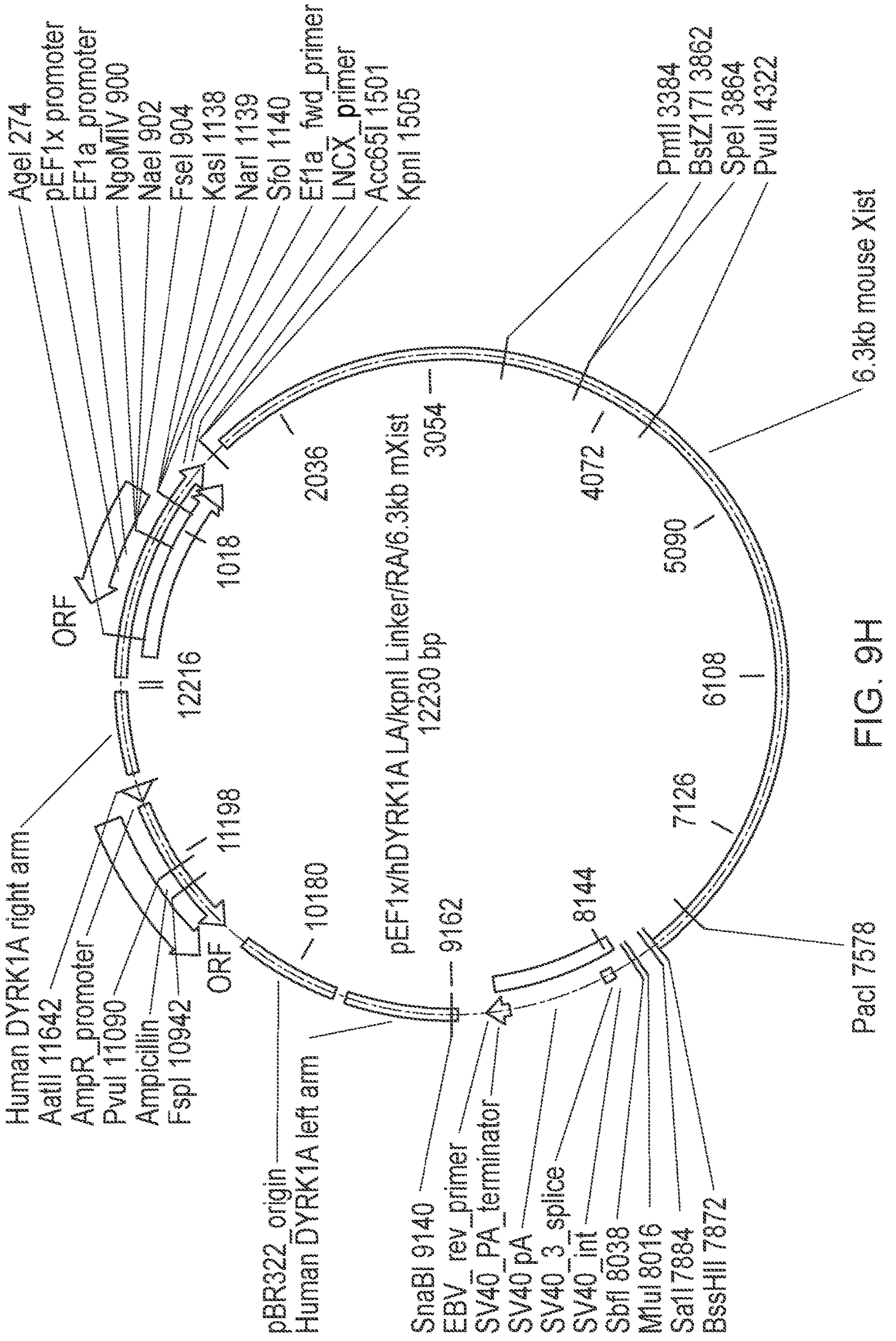
Figure 9I:
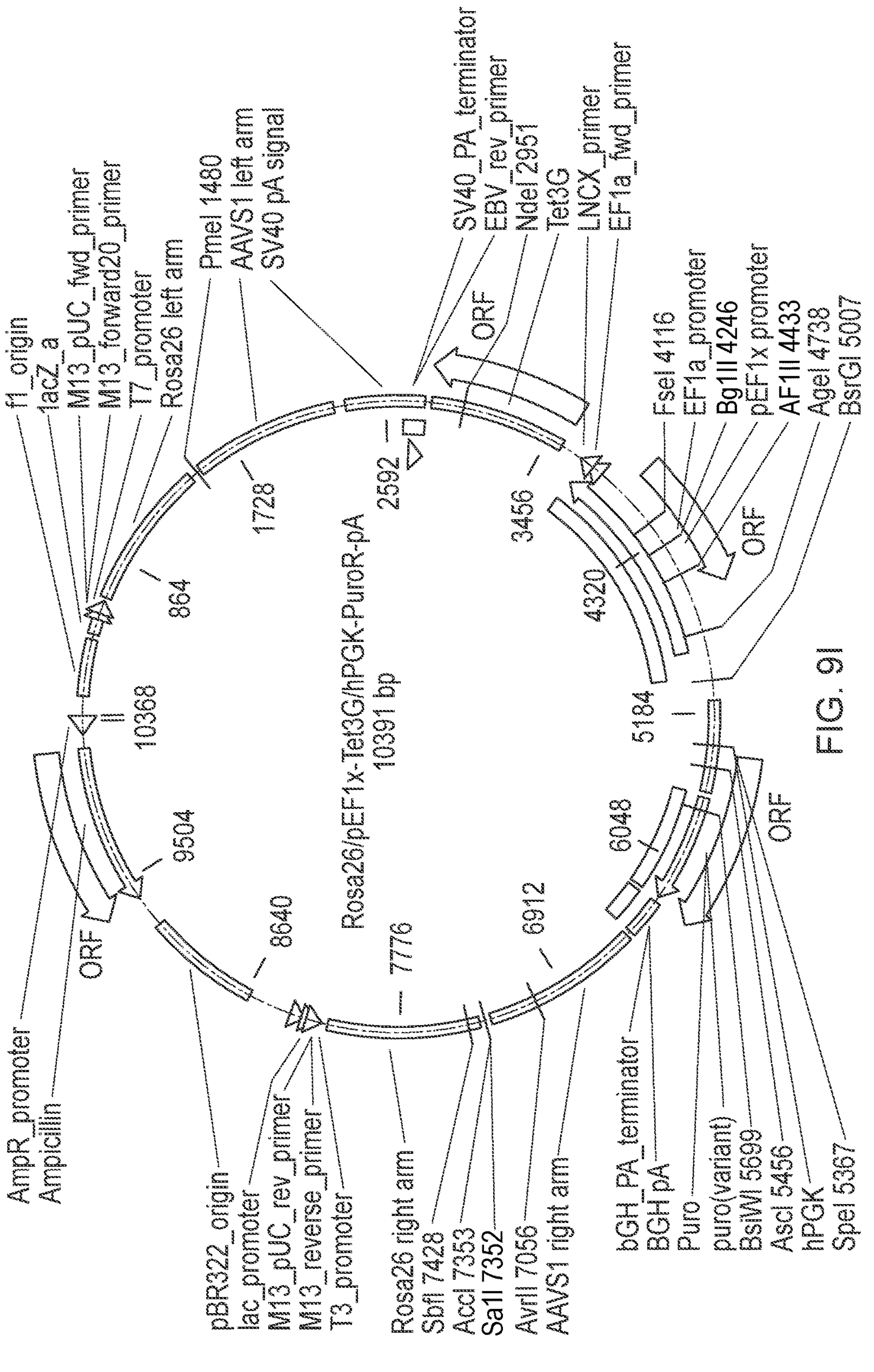

Human DYRK1A gene has at least four different splicing isoforms, which differ from each other either in the 5' UTR or in the 3' coding region. We engineered a ZFN heterodimer that binds a 36 bp target sequence in intron 1 of variants 1, 2, 5, or intron 3 of variant 3 (FIG. 2A) of DYRK1A and validated robust activity. Next, an even larger (~21 kb) construct was built containing near full-length XIST cDNA (17 kb), flanked by ~600 bp homology arms (FIG. 9*c*). Testing in the HT1080 cells demonstrated efficient, accurate addition of the entire 21 kb transgene to the "DS critical region" of Chr21.

Figures 2A, 2B:
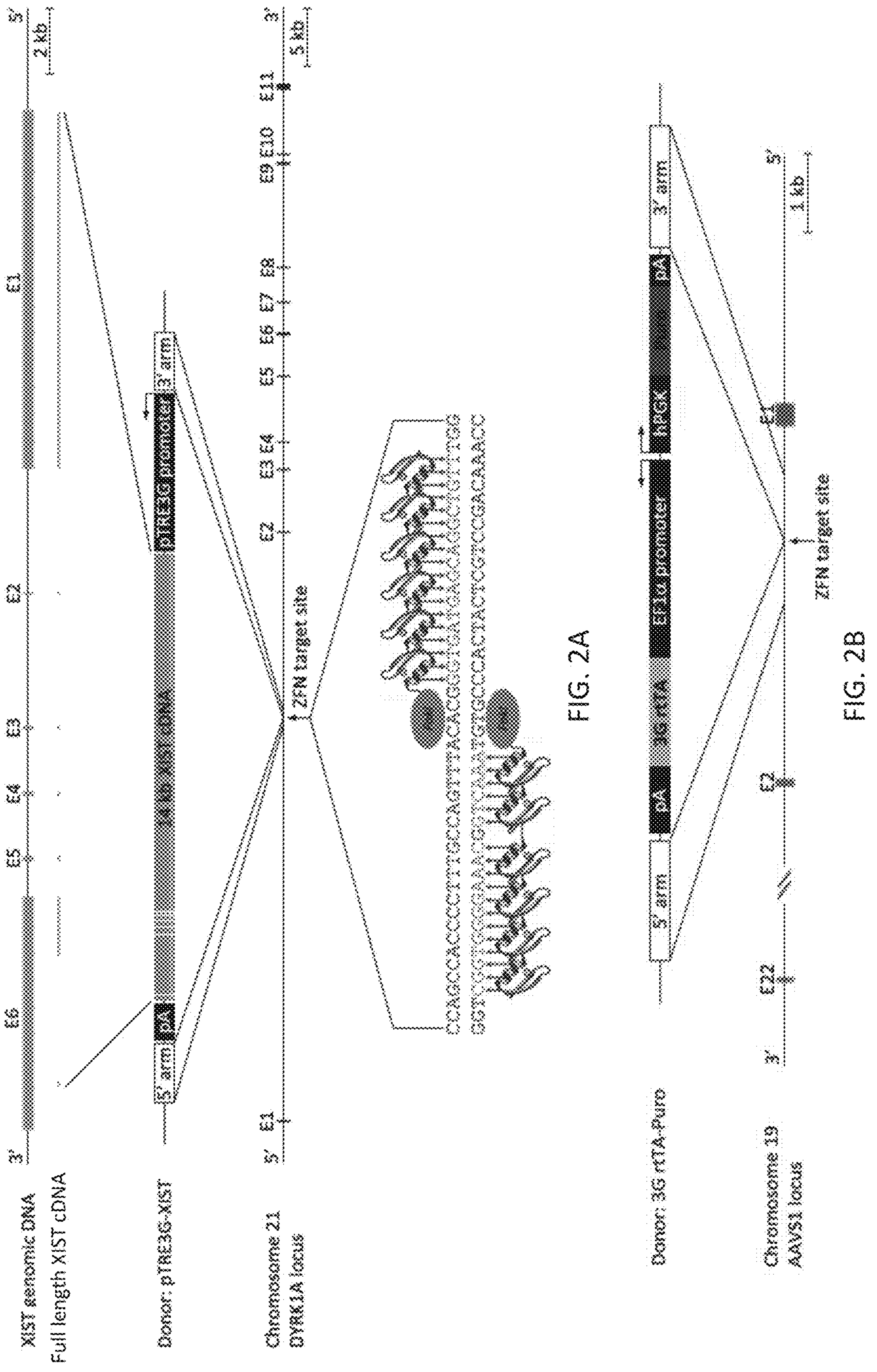
FIGS. 2A-F. Genome-editing integrates XIST into Chr 21 in trisomic iPS cells derived from DS patient cells. Both constructs in a and b were introduced simultaneously, to achieve dual-targeted-addition to two loci, in one step. a, Top, XIST transgene construct (19 kb) with two homologous Chr 21 arms and 14 kb XIST cDNA driven by inducible pTRE3G promoter. The ZFNs cleave intron 1 or intron 3 of DYRK1A locus on Chr 21. Bottom, Four DYRK1A variants. b, Construct designed to target a puromycin selection gene and rtTA cassette into the AAVS1 safe harbor locus on Chr 19 by ZFN. c. A high resolution G-band karyotype was performed to further verify genome integrity of these subclones. Only Chr21 trisomy was observed, and karyotype is consistent with a male chromosome complement. d. Genomic Microarray analysis using the UMass Genomic Microarray platform (Human Genome Build hg19) demonstrated a gain of one chromosome 21 (red arrow) (and detected addition of the XIST transgene in these male cells). All other peaks are known human polymorphic variants and are not clinically significant. Note: Chr21 is increased 1.5 fold (from 2 to 3 chromosomes) while the XIST gene is increased 2 fold (from 1 to 2 copies). e. Close-up of Chr21 CGH shows full chromosome 21 trisomy with no deletions or duplications. This analysis was done on transgenic clone 3. f. Percent of cells showing an XIST "paint" (a large, well-localized nuclear RNA territory), in six independent clones. Mean±SE from 500 nuclei.

We next determined whether this would be achievable in the technically challenging but translationally relevant iPSCs derived from reprogramming DS patient fibroblasts. These cells have unique therapeutic and developmental potential[29] due to their ability to form a variety of cell types, and thus would represent an important target of any future ex vivo cellular therapy efforts. We used a male DS iPSC line from the Daley lab[30], which we confirmed maintains pluripotency markers and trisomy 21. Although a single constitutively transcribed XIST transgene could be used, we engineered an inducible system to maximize utility for investigating the biology of DS. In one step, we targeted a doxycycline-based transgene control component (rtTA) to the AAVS1 safe harbor locus on Chr19[25] (FIGS. 2*b* & 9*b*), and the Dox-controlled XIST transgene to Chr21 (FIGS. 2*a* & 9*a*).

Figure 2C:
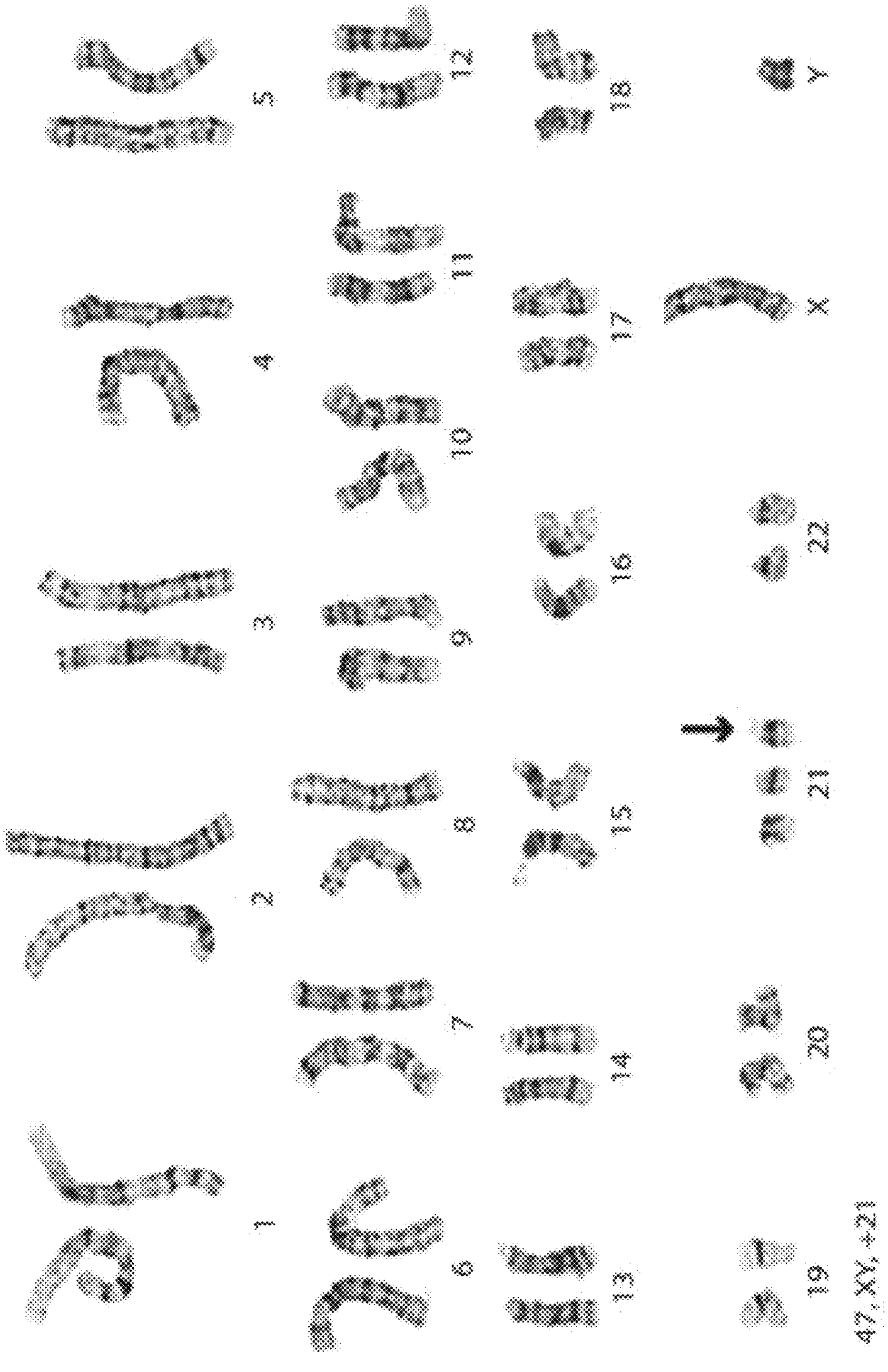
Figure 2D:
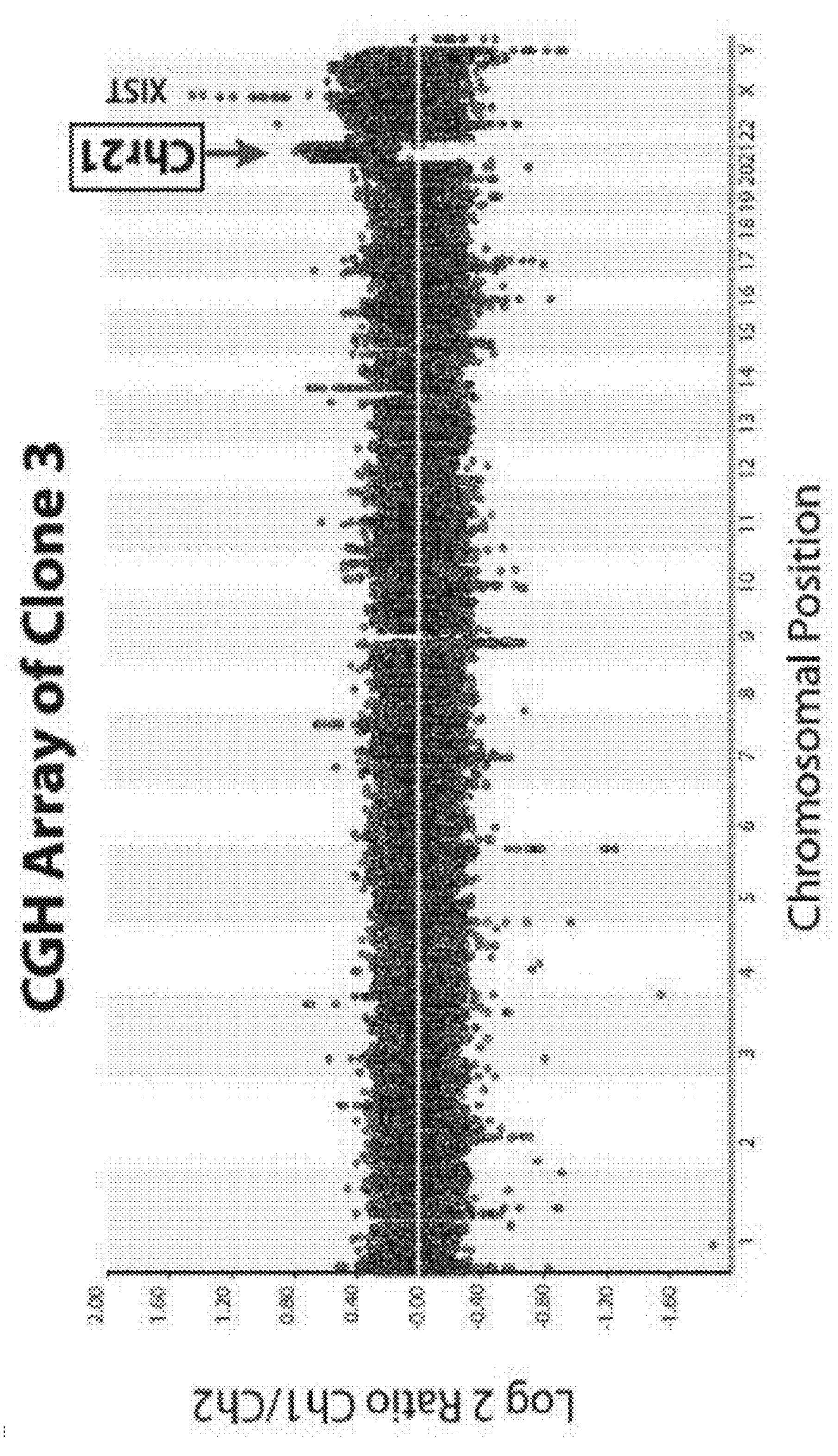
Figure 2E:
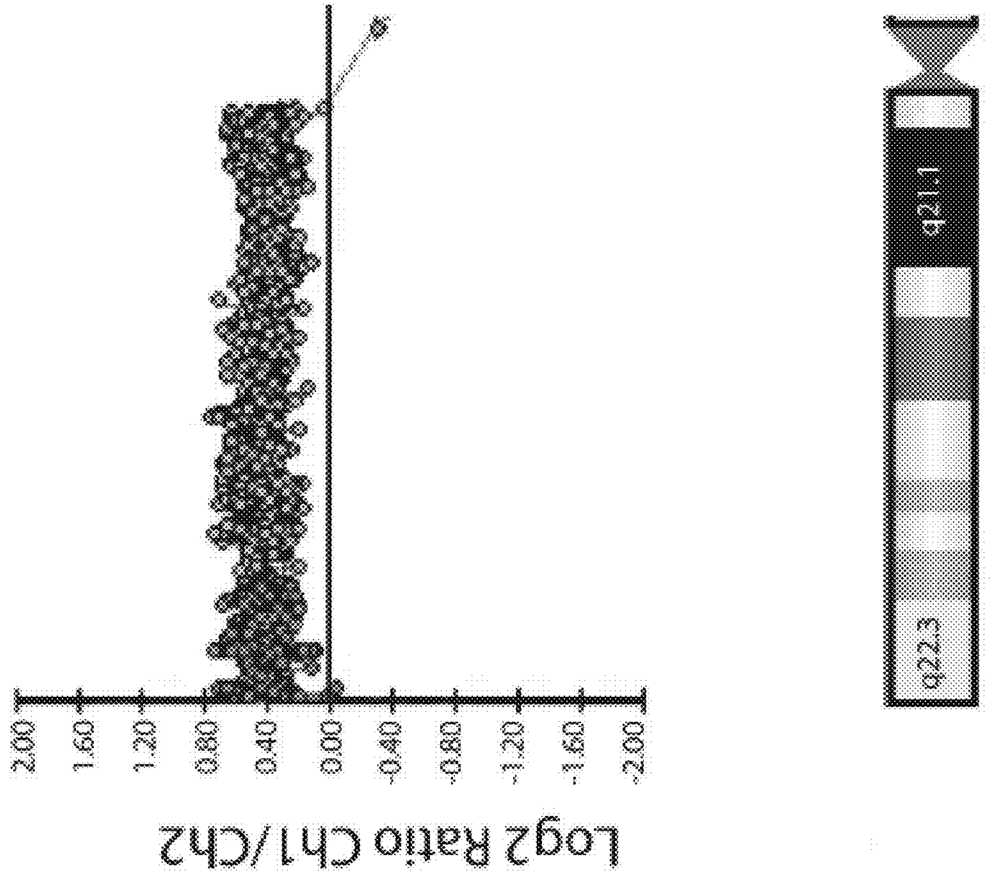

We analyzed 245 colonies from the first passage of pooled transformants by dual-color interphase in situ RNA/DNA FISH to determine if XIST was present and overlapped one of three DYRK1A alleles. Remarkably, 99% of XIST RNA-positive colonies carried the XIST transgene at this location on Chr21, and also contained rtTA/selection transgene. Efficiency was sufficiently high that, through modifications to editing conditions, we also obtained a few sub-clones with XIST integrated into two or even all three alleles of DYRK1A (see Table 3). Six independent sub-clones were chosen for further study based on: the presence of an XIST transgene on one of three copies of Chr21; pluripotent colony morphology; robust Oct4 staining; and the ability to form embryoid bodies. Southern blotting and FISH to metaphase chromosomes confirmed the interphase FISH analysis and gene addition accuracy, and all six clones retained 47 chromosomes. Selected clones were also examined by high-resolution cytogenetic banding and/or array CGH, which showed no significant abnormalities other than full trisomy for all of Chr21 (FIGS. 2*c-e*).

a heterochromatic "Chr21 Barr Body," which appeared, by multiple criteria, indistinguishable from the Xi in female cells.

Example 3. XIST RNA Drives Long-Range, Allele-Specific Gene Silencing Across the Targeted Chr21

We examined the overall transcriptional impact of XIST RNA "painting" on Chr21 using an approach we developed to broadly assay hnRNA by detecting CoT-1 repeat containing RNAs, which clearly distinguishes Xi from Xa[21]. The Chr21 XIST RNA territory is depleted for CoT-1 RNA, suggesting heterochromatic silencing, as on Xi.

We next used multi-color RNA FISH to determine the presence of transcription foci at each allele for six specific Chr21 genes, an established approach we developed to discriminate active versus silenced genes on Xi[31]. Although XIST addition disrupts the large DYRK1A gene (FIG. 2*a*), without XIST expression, three bright transcription foci remained. However, when XIST RNA was induced, the targeted allele became weaker or undetectable, indicating significant repression of DYRK1A.

Figure 4A:
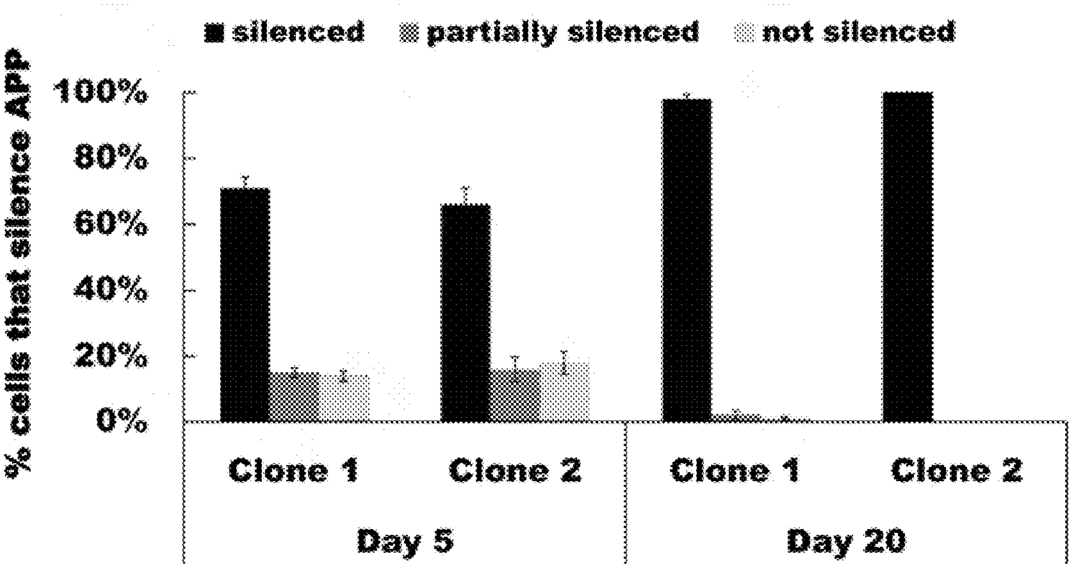
FIGS. 4A-F. XIST expression induces long-range transcriptional silencing in transgenic, pluripotent sub-clones. a. Quantification of APP silencing after 5 d and 20 d Dox induction in two independent sub-clones. Mean±SE from 100 nuclei. b. Four more Chr21-linked genes were also shown to be effectively silenced by RNA FISH, and scored before and after XIST induction. c. The silenced genes assessed by RNA FISH spanned the entire length of Chr21 (USP25 gene is ~21 Mb from XIST integration site at DYRK1A; black arrow), suggesting long range silencing of Chr21 by XIST RNA. Mean±SE from 100 nuclei. d. Sequencing analysis of gene transcripts informative for SNPs indicates one of three alleles are silenced by XIST expression. Primer pairs were used that amplified SNP-containing regions of four Chr21 genes to assess allele-specific silencing after sequencing. RNA was amplified from Dox treated and untreated samples of three different clones. Eight of 12 SNPs tested were informative in these cells, and all eight SNPs (in four genes) show reduction in one of the three alleles upon XIST induction. For example, in Clone 3 ADAMTS1 goes from TTC to TT, ETS2 from CCA to CA, TIAM1 from TTC to TC, and HSPA13 from TTC to TT. e. In two of the three transgenic clones, the same eight SNP alleles were repressed, consistent with a chromosome-wide mechanism and allows us to extrapolate the haplotype of each chromosome and surmise which carried XIST in each clone. Both clones 2 and 3 silence the far right chromosome and the center chromosome is silenced in Clone 1. f. Although XIST RNA is robustly expressed in early time points (3 days) in the double and triple targeted clones, XIST becomes almost entirely silenced in later time points (20 days). Mean±SE from 100 nuclei.
Figure 4B:
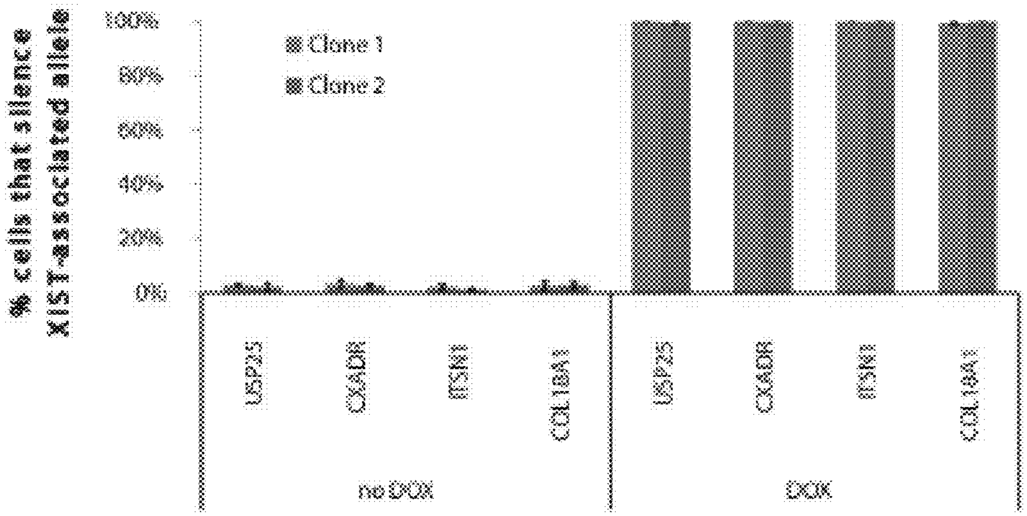
Figure 4C:
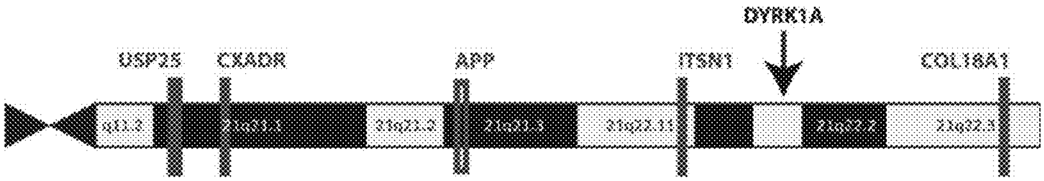

Next we examined the APP gene, which encodes amyloid beta precursor protein. Mutations in APP (causing accumulation of β-amyloid) lead to early onset familial Alzheimer disease (EOFAD)[32], and APP over-expression is linked to AD in DS as well[33]. RNA FISH data for APP are quantified in FIG. 4*a*. Without XIST induction, three bright RNA transcription foci for each allele were readily visualized. Brief XIST expression often resulted in incomplete repression of the targeted allele, which after 20 days was completely silenced in both independent clones (FIG. 4*a*).

TABLE 3

Accuracy of targeted addition for XIST transgene on Chr 21 in Down Syndrome iPCSs

| Ratio of XIST to Puro | XIST+ clones (Puro+) | Random Integration | Targeted Integration | Single Target | Double Target | Triple Target |
|---|---|---|---|---|---|---|
| 3:1 | 65 | 1 (1.5%) | 64 (98.5%) | 57 (87.7%) | 7 (10.8%) | 0 (0.0%) |
| 5:1 | 16 | 1 (6.3%) | 15 (93.8%) | 8 (50.0%) | 5 (31.3%) | 2 (12.5%) |

Figure 2F:
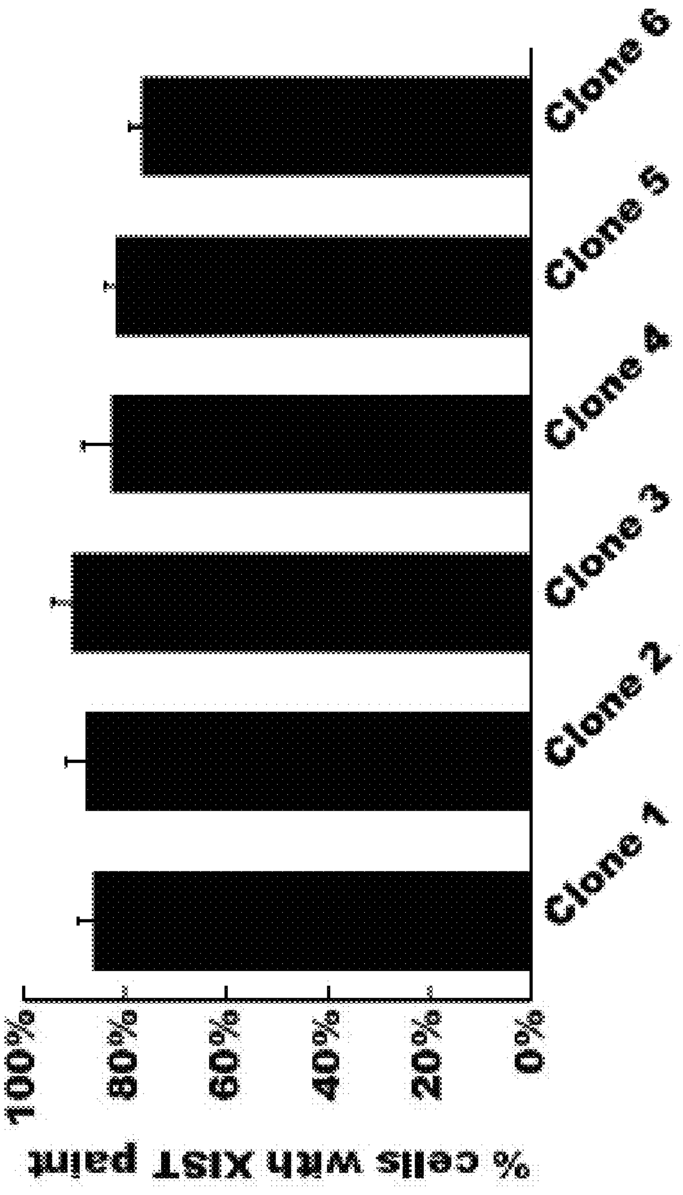

Example 2. XIST RNA Coats the Chromosome in Cis and Induces a Heterochromatic Chr21 Barr Body In the panel of six independent genome-edited clones, we induced transgene expression and detected XIST RNA by FISH three days later. XIST RNA expression was consistently robust and localized in a nuclear "territory" over one Chr21, in over 85% of cells in the six clones (FIG. 2*f*). This mirrored the unique behavior of endogenous XIST RNA which "paints" the inactive X nuclear territory[10].

Figure 3:
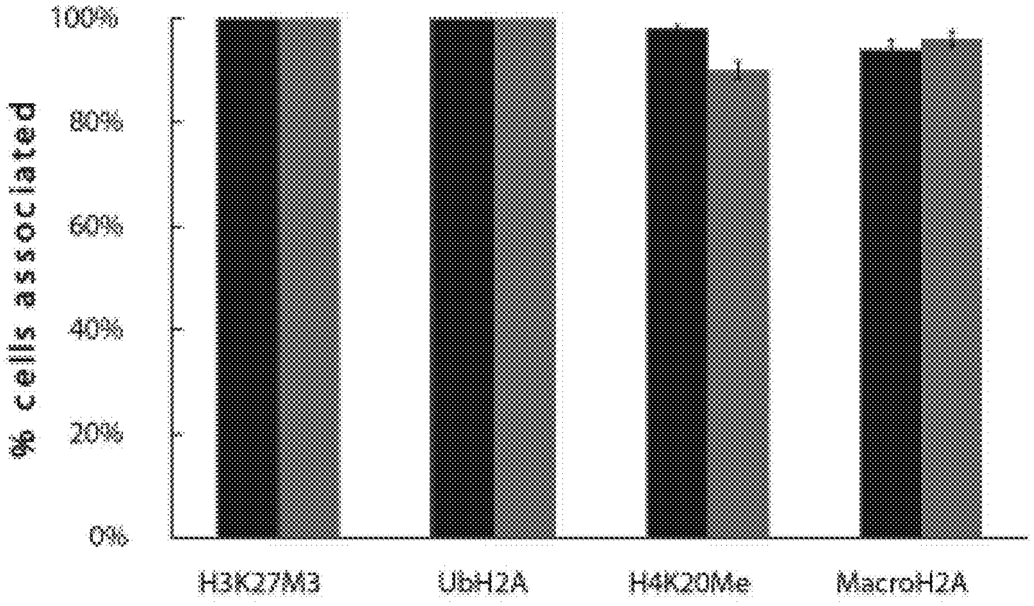
FIG. 3. XIST expression induces a cascade of heterochromatin modifications. Percentage of XIST territories with associated hallmarks H3K27me3, UbH2A, H4K20me, and MacroH2A. Mean±SE from 100 nuclei in five or more colonies.
Figure 4D:
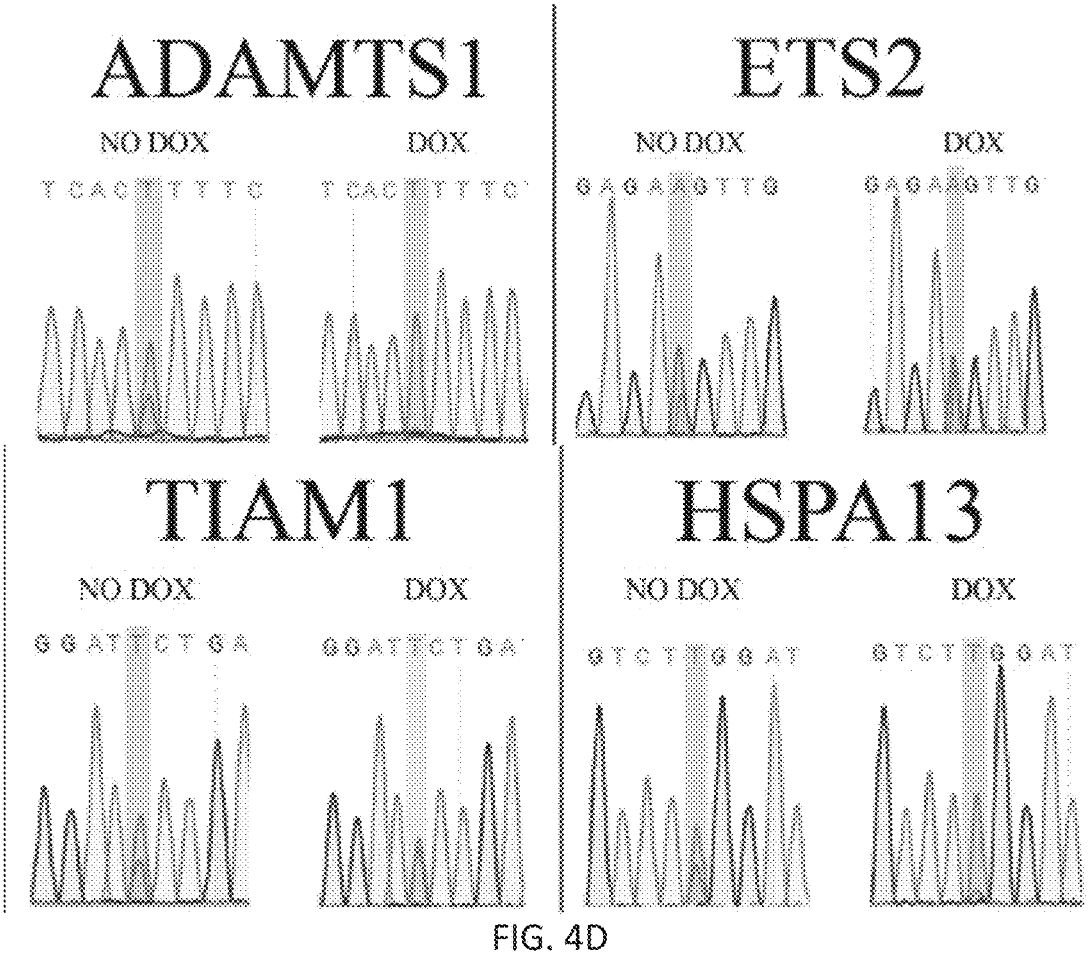
Figure 4E:
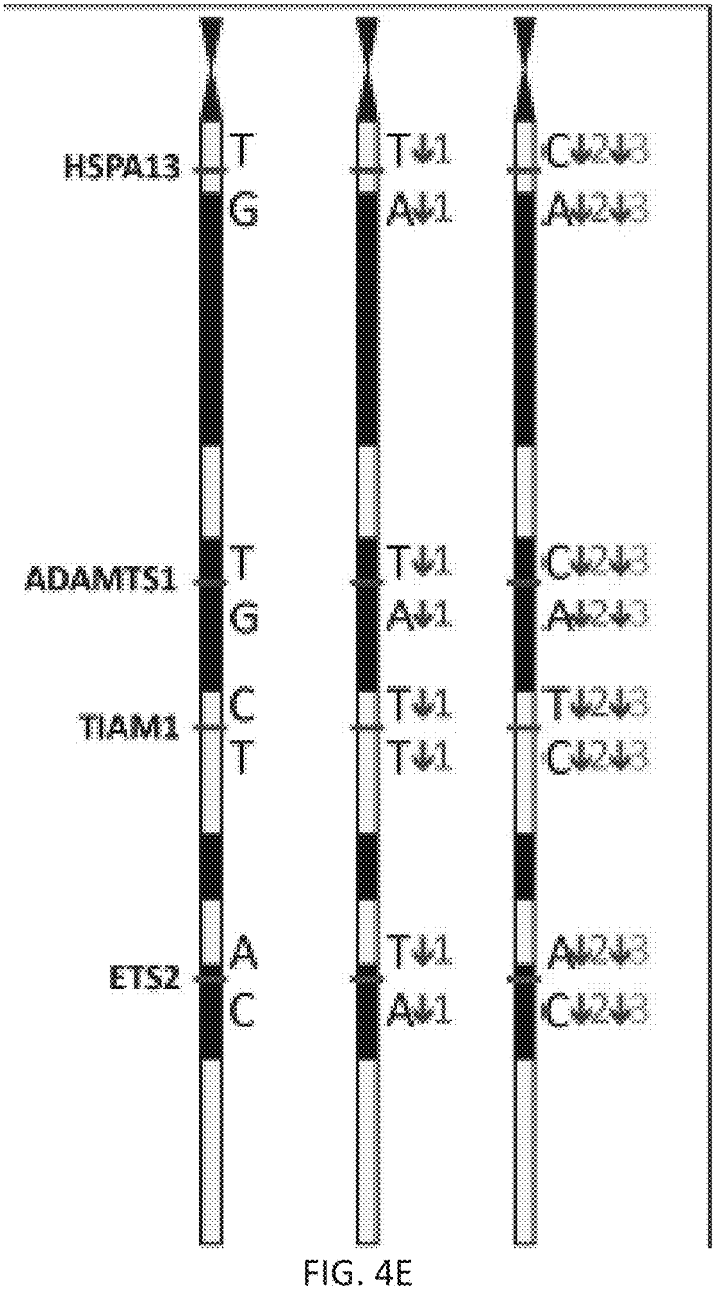
Figure 4F:
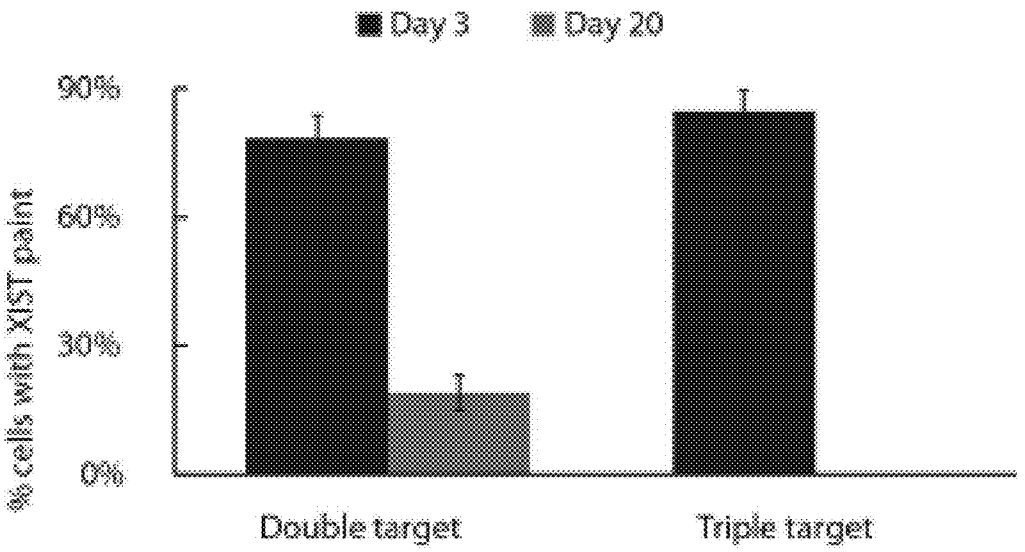

The Xi in female cells forms a visibly condensed "Barr Body" that carries an epigenetic signature of repressive histone modifications and CpG DNA methylation (reviewed in[13]). Five days after XIST induction, the edited Chr21 became markedly enriched in all heterochromatin marks examined, including H3K27Me3, UbH2A, and H4K20Me in 90%-100% of cells and, later, with macroH2A (FIG. 3). H3K27me could be seen across the metaphase Chr21. Moreover, the chromosomal DNA in many nuclei became notably condensed, further evidence that we successfully generated We extended this analysis to four more genes that ranged from 3 to 21 Mb from the XIST integration site (FIGS. 4*b-c*): ITSN1 (Intersectin-1), USP25, CXADR, and COL18A1. Complete silencing of the allele on the edited Chr21 was seen in ~100% of cells accumulating XIST RNA (FIG. 4*b*), demonstrating silencing of the XIST-associated allele. Allele-specific silencing was also validated using SNP analysis. RT-PCR products for eight known polymorphic sites (in four genes) were sequenced (ADAMTS1, ETS2, TIAM1, and HSPA13) (FIGS. 4*d-e*). Interestingly, clones 2 and 3 showed the identical pattern of eight SNP alleles repressed, whereas clone 1 showed an alternate pattern. As summarized in FIG. 4*e*, this chromosome-wide pattern allows extrapolation of the haplotype for each of the three Chr21s, and indirectly identifies for each clone which Chr21 homolog integrated XIST.

We also examined APP silencing in clones carrying XIST on two or all three copies of Chr21. After 20 days of dox, most or all cells carrying XIST on two or three Chr21s, respectively, no longer accumulated XIST RNA across the chromosome, and thus failed to silence the APP gene (FIG.

4*f*). These data argue there is in vitro selection against creating a functional monosomy or nullisomy, consistent with the lethality of any monosomy in vivo, and clinical observations that cells monosomic for Chr21 do not persist in mosaic patients.

Example 4. Genome-Wide Expression Analysis Demonstrates Transcriptional Repression Across the Edited Chr21

The above approaches demonstrate XIST RNA induces a heterochromatic Chr21 Barr Body and allele-specific repression for the nine genes examined, yet we extended this to include genome-wide expression profiling. Three independent transgenic clones and the parent line were treated with Dox for three weeks, and their transcriptome compared to parallel cultures without XIST-transcription, all in triplicate. Strikingly, only on Chr21 is there overwhelming change, in all three clones (FIG. 5*a*), with ~95% of genes significantly expressed showing repression (FIG. 5*d*).

Figure 5A:
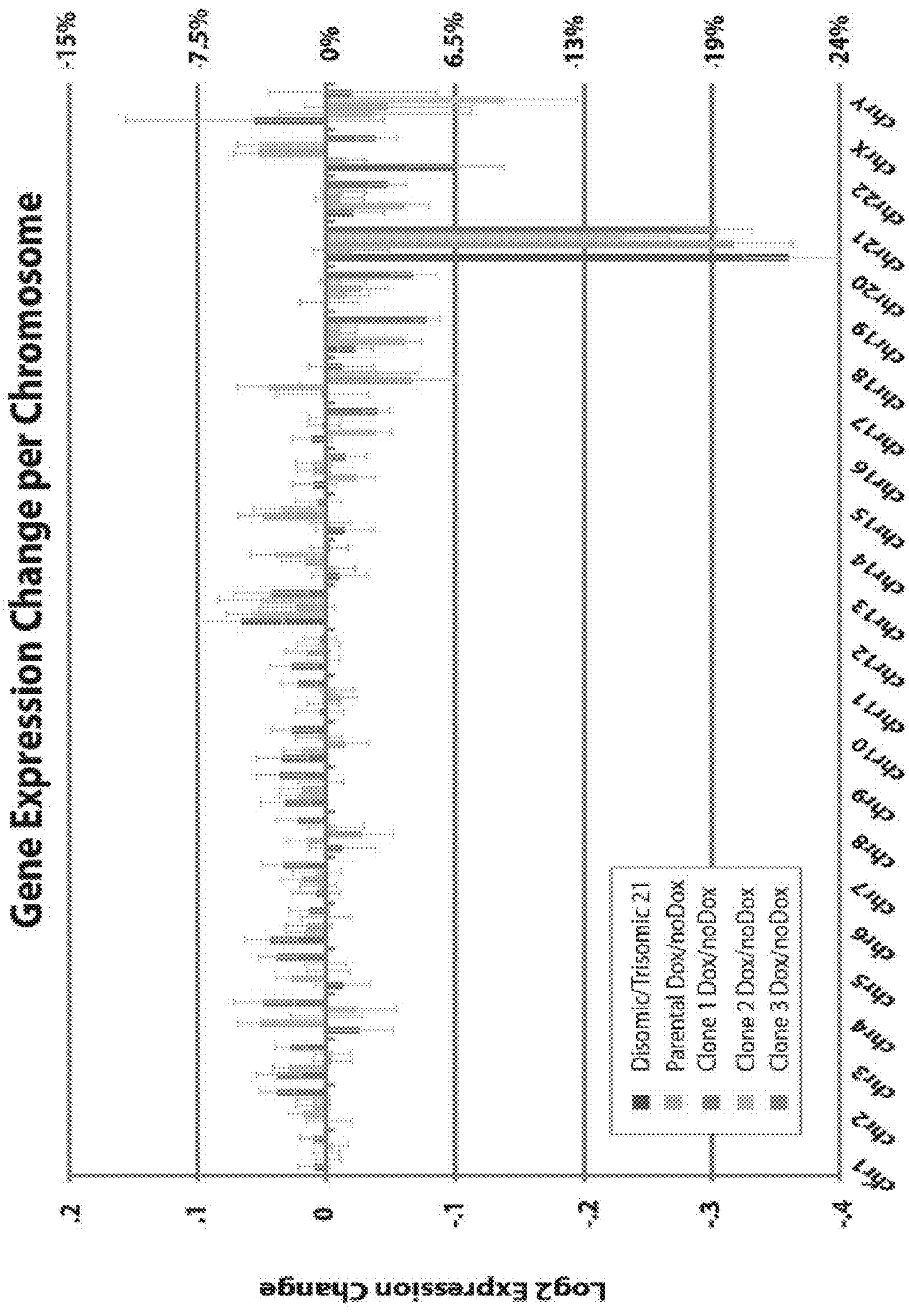
FIGS. 5A-D. Genomic expression profiling with RNA microarray and methylation levels shows widespread silencing of genes across Chr21. a. Microarray: Gene expression of parallel cultures grown with and without Dox treatment (Dox/no Dox) in clones 1, 2 &3 was compared to normal male iPS (euploid) and trisomy 21 (untargeted parent line) iPS cells (disomic/trisomic above). Total change in gene expression (N=3) per chromosome shows correction to disomic levels for XIST-expressing sub-clones on Chr21 with only limited changes on other chromosomes. Right Y-axis is scaled to reflect percent of gene expression change b. Distribution of individual repressed genes across Chr21 and corresponding level of repression for Clone 3 (Dox/no Dox) and Disomic/Trisomic. c. Methylation analysis: Genes with CpG island promoters are colored based on the levels of methylation after 22 days of Dox induction. Grey: decrease in methylation, green: no change in methylation, and red: increase in methylation. Ideograms (shown to the left of each heatmap) denote the location of genes (note: no gene probes unique to short arm of Chrs 21 and 22). Length of each chromosome is proportional to the number of gene promoters with CpG islands. Of the 143 individual Chr21 genes that had CpG islands in their promoters, 97-98% in both clones increased methylation by at least 5% (approximately two-fold increase over the average), compared to none in the parent line. d. Relative expression levels of eight genes on Chr21 by qRT-PCR for Clone 3. All 8 genes showed repression. Mean±SE from triplicate samples.
Figure 5B:
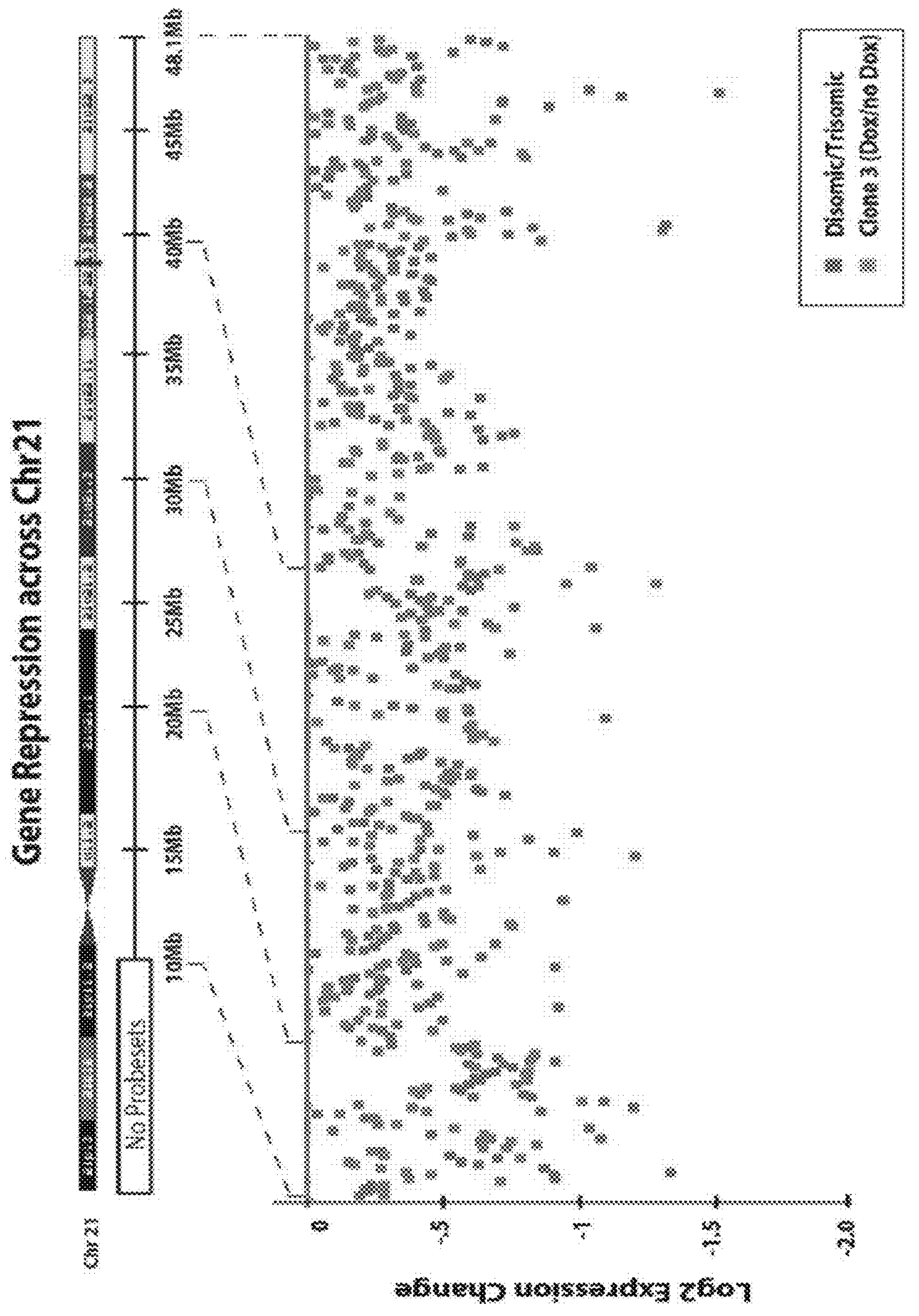
Figure 5C:
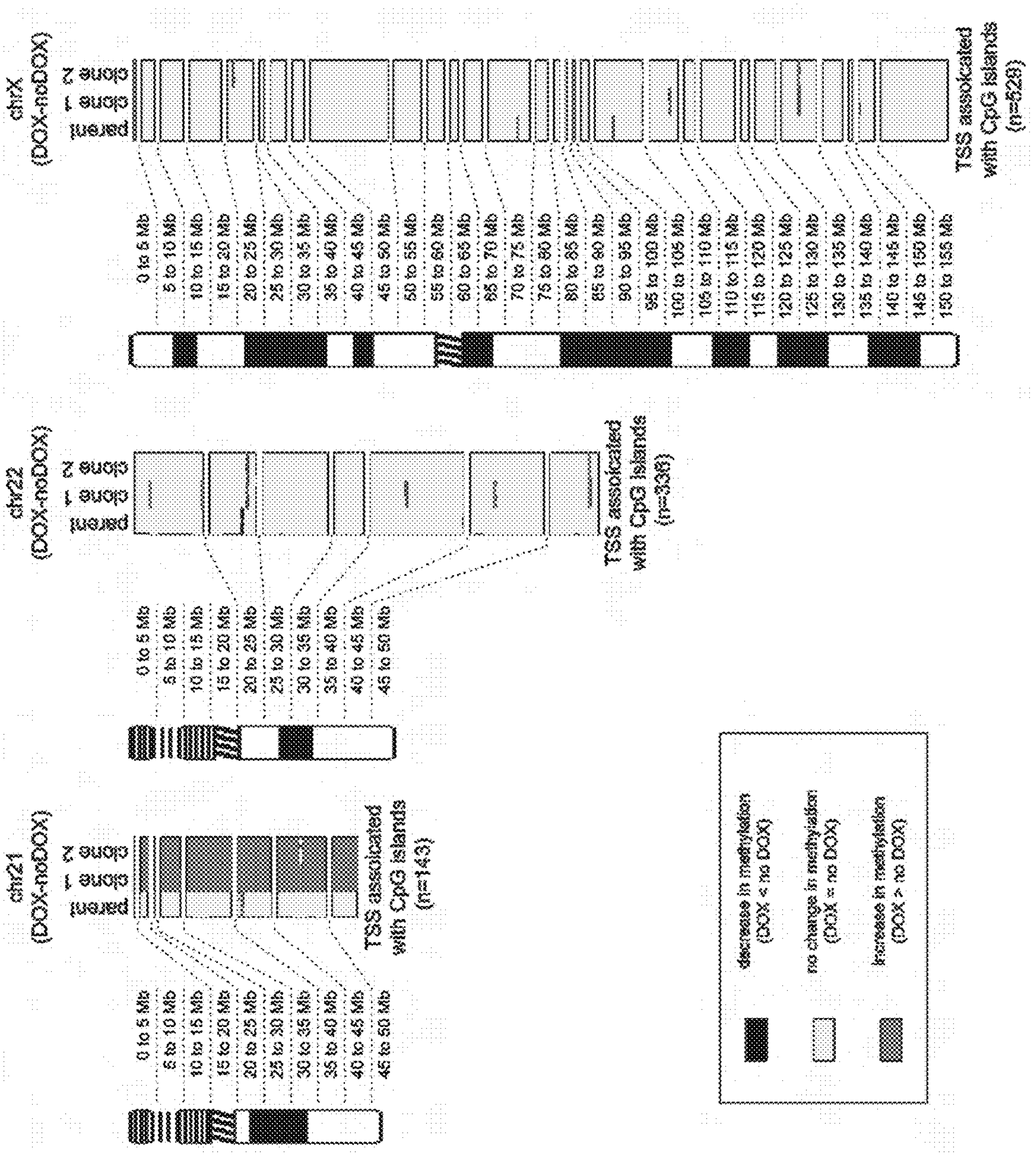
Figure 5D:
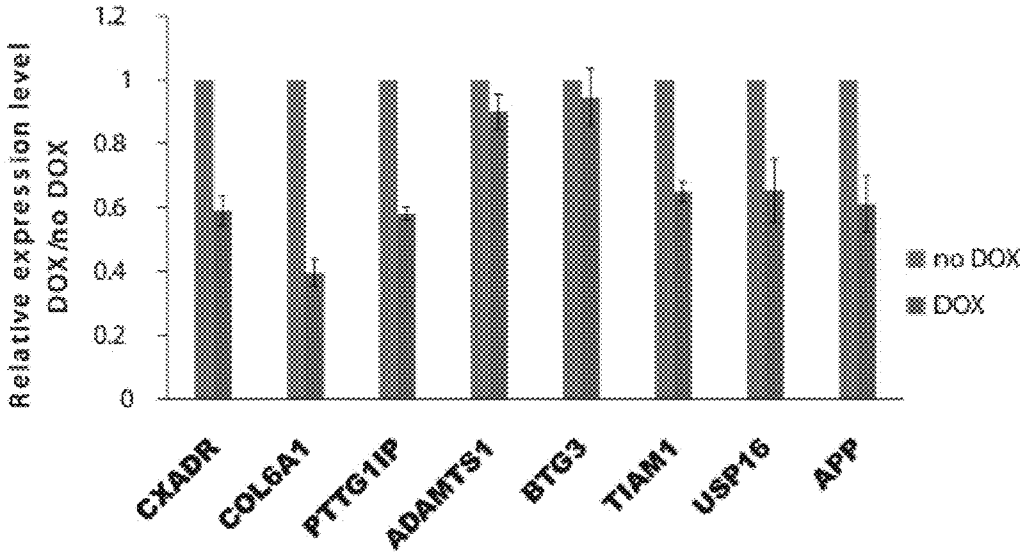

FIG. 5*a* summarizes the key finding that dosage compensation of trisomy corrects Chr21 expression to near normal disomic levels. This is based on calculation of the change in total output of expressed genes per chromosome after XIST is induced. Since evidence indicates that many Chr21 genes are not increased to the theoretical maximum of 1.5 fold in trisomic cells ([34-36] and further explained above), we included a direct comparison to trisomic versus disomic cells; this provides a baseline to evaluate the degree to which Chr21 over-expression is corrected by XIST-mediated silencing. After XIST induction, overall Chr21 expression is reduced by 20%, 15%, and 19% for clones 1, 2, and 3, respectively; this mirrors very well the 22% reduction for disomic iPS cells that lack the third Chr21 altogether (FIG. 5*a*). This disomic iPS line is representative, as a similar (21%) Chr21 difference was seen for another isogenic disomic sub-clone recently isolated from the parental DS iPS cells. FIG. 5*b* shows that individual genes repressed by XIST distribute across Chr21, as do genes over-expressed in trisomic versus disomic cells. In addition, qRT-PCR confirmed repression for all eight Chr21 genes examined (FIG. 5*d*). Taken together, these results clearly demonstrate that XIST induces robust dosage compensation of most over-expressed genes throughout the length of Chr21.

Trisomy 21 likely has broader impact on genomic expression pathways (e.g., [36]), but the differences attributable to trisomy 21 are confounded by genetic and epigenetic variability. This inducible trisomy correction system provides a new foothold into that important question. For example, microarray profiles of our three independent transgenic sub-clones reveal that even these isogenic sub-clones show many expression differences (>1000) throughout the genome, but upon XIST induction, a smaller cohort of genes (~200) change in common in all three clones (but not the dox-treated parental line); this cohort is more likely due to Chr21 over-expression. While not our focus here, these findings support the promise for "trisomy correction in a dish" as a means to identify genome-wide pathways perturbed by trisomy of Chr21.

Example 5. Chromosome-Wide Methylation of Genes on the XIST-Carrying Chr21

X-inactivation in female cells is further stabilized by hypermethylation of DNA in promoter CpG islands[37-39], which occurs late in the silencing process. Therefore, we examined the promoter methylome in two independent genome-edited clones three weeks after XIST induction. The global promoter methylome remained largely unaltered, with one striking exception (P-value<2.2e-16): the genes on Chr21 (FIG. 5*c*). Here, 97% of CpG-island-containing genes exhibited a robust increase in promoter DNA methylation on Chr21, within the range of that seen for Xi[37] (when adjusted for the number of active versus silenced chromosomes: see Methods). This change swept across the entire chromosome (FIG. 5*c*), strongly reinforcing above analyses on gene expression. Interestingly, the fact that a small subset of specific genes "escape" methylation on Chr21 in both clones demonstrates the impact of DNA sequence on XIST-mediated silencing (as long suggested[15,18,40] and reviewed in[41]).

The sum total of data, from eight different approaches, demonstrates an impressive competence of most sequences across Chr21 to undergo epigenetic modification and silencing in response to XIST RNA, an RNA evolved to silence the X-chromosome.

Example 6. Chr21 Dosage Compensation Impacts Cell Phenotype to Enhance Cell Proliferation and Neural Rosette Formation Correction of whole chromosome imbalance by manipulating just one gene presents a new paradigm, with opportunities to advance DS research in multiple directions. Currently, the specific cellular processes perturbed by trisomy 21 that generate patient pathology are largely unknown. Inducing trisomy silencing in parallel cultures of otherwise identical cells may reveal cellular pathologies due to trisomy 21, which could be obscured by differences between cell isolates. To address whether an impact in cell phenotype could be discerned, we examined two properties—cell proliferation and neural rosette formation.

Figure 6A:
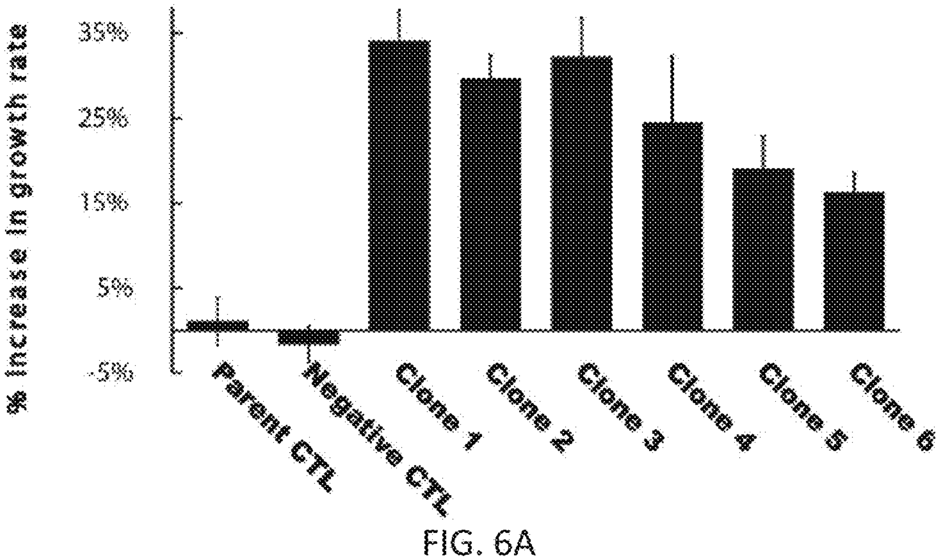
FIGS. 6A-B. "Trisomy correction" in vitro has marked effects on cell proliferation and neurogenesis, and is stable upon removal of XIST RNA. a. Changes in cell number for parent line, non-transgenic DS subclone (negative control), and six transgenic lines after 1 week of +/−Dox treatment. Mean±SE. (n=4-6). b. Quantification of number of neural rosettes at days 14 and 17 for two clones. Mean±SE from 10-12 random fields in triplicate. c. Gene silencing is stable following withdrawal of XIST RNA in cortical neurons. Transgenic cells were treated with Dox for 70 days and then Dox was removed for 30 days. Only two APP RNA transcription foci are present, as seen, with or without Dox. Mean±SE from 100 nuclei.

There is some evidence of proliferative impairment in DS[42,43], however we found this was variable between DS fibroblast cell samples, and highly sensitive to culture history and population doublings. However, a clear answer emerged from comparing multiple transgenic clones, grown in the presence or absence of doxycycline for one week. Initial analysis of clones 1 and 2 in triplicate indicated that XIST-induction rapidly resulted in larger, more numerous and more tightly packed cell colonies. This analysis was repeated for six independent transgenic sub-clones, the parental line, and a trisomic sub-clone, each replicated 4-6 times, minimizing technical variations in plating and counting iPS cells (Methods). All transgenic clones showed larger, more tightly packed colonies after just seven days of XIST induction, which contained 18-34% (average 26%) more cells than uninduced cultures (FIG. 6*a*). In contrast, Dox did not enhance growth of the parental DS cells or sub-clone (FIG. 6*a*). Thus, a proliferative impairment linked to Chr21 over-expression can be rapidly ameliorated by dosage compensation. Interestingly, this effect is not dependent on DYRK1A silencing[27,28], since the DYRK1A locus is disrupted irrespective of XIST expression.

Figure 6B:
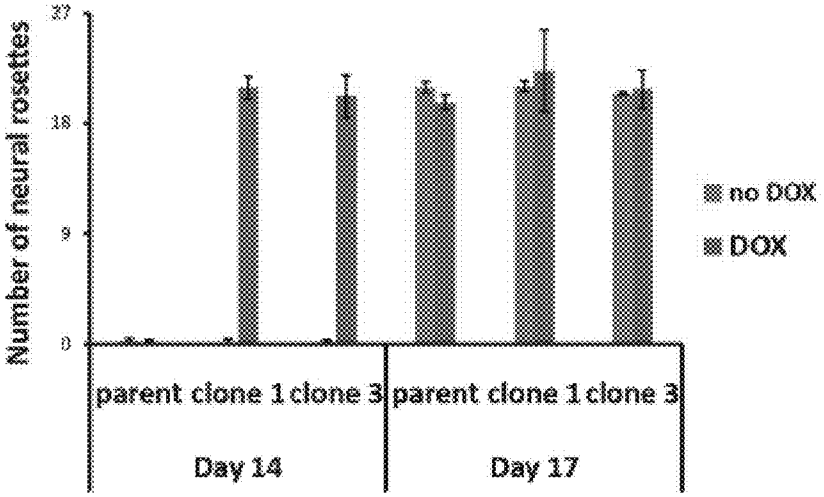
Figure 6C:
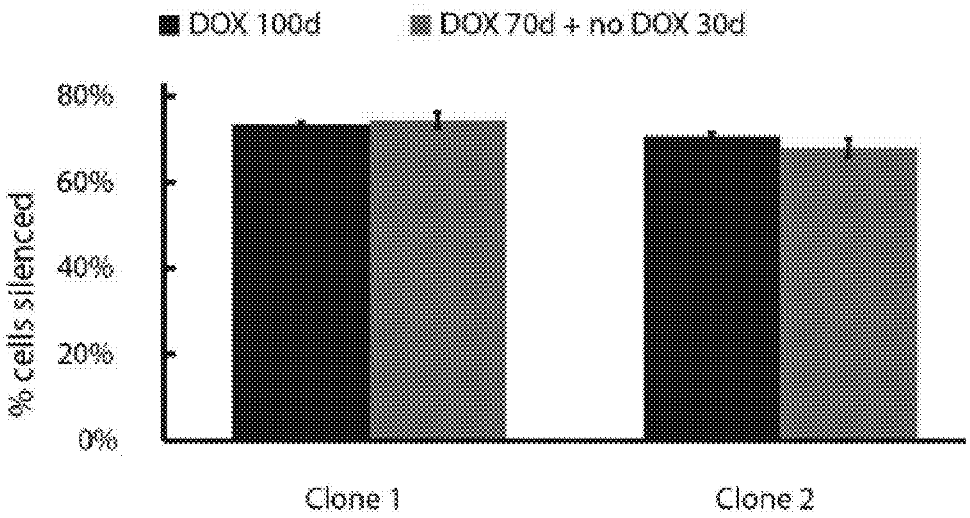

We next examined differentiation into neural progenitor cells, using a protocol to derive cortical neurons[44]. Six replicate cultures for the parental DS iPSC line and clones 1 and 3 were grown to confluency, placed in neural differentiation medium, and half of the identical samples induced to express XIST. Just 11-12 days after neural induction, all XIST-expressing cultures (in triplicate for both clones) began to form neural rosettes, and in 1-2 days were replete with neural rosettes. These cell structures are a signature of neural progenitors, and were confirmed by expression of Pax6 and Sox1. Remarkably, even at day 14, parallel uninduced cultures were still devoid of any neural rosettes (FIG. 6*b*). Thus uncorrected cultures required 4-5 more days in neural-induction media to fill with neural rosettes of similar size and number, as they did on day 17 (FIG. 6*b*). This difference is due to XIST, as there was no effect of Dox on neurogenesis in the parental DS line. This marked delay in neural differentiation appears primarily independent of cell proliferation (Methods). A similar difference occurred in repeat experiments with clones 1 and 2. Variability in the kinetics of neural differentiation that exists between various iPS cell lines[45] would likely obscure differences due to trisomy 21. We circumvented this using parallel cultures and on-demand Chr21 silencing, which made clear these important phenotypic differences.

These data highlight the potential of this new experimental model to identify and study cellular pathologies directly attributable to over-expression of Chr21 in iPSCs and their differentiated progeny.

Example 7. Stable Chr21 Silencing and Successful Targeting of XIST in DS Primary Fibroblasts Finally, we briefly consider two points relevant to any future potential for ex vivo or in vivo therapeutic strategies. While a constitutively expressed XIST transgene could be used, it is advantageous if the heterochromatic state induced by XIST RNA is stably maintained, even if XIST is no longer expressed (as reported in mouse[46]). We tested this in our human Chr21 system by removing dox and XIST expression for 30 days, after iPS cells had silenced Chr21 and differentiated to neurons. As shown (FIG. 6*c*), APP gene silencing remained indistinguishable between cultures with and without continued XIST expression, supporting other evidence that in somatic cells multi-layered chromatin modifications triggered by XIST maintain a largely irreversible silent state[39,47].

Finally, we considered the forward-looking question of whether targeted XIST addition could be achieved in primary human cells, as tested in non-immortalized female DS fibroblasts. Surprisingly, in our first attempt we generated not a few sub-clones but a sparse monolayer of edited fibroblasts, most of which carried XIST on Chr21. Due to limited lifespan, these cells were not examined in depth, but notably many showed enrichment of H3K27me3, H3K20me, and UbH2A at the transgene site. This is consistent with evidence that chromosome silencing does not necessarily require the optimal pluripotent cell context. Although pluripotent cells clearly have the optimal capacity to rapidly and fully silence chromatin in response to XIST RNA (Wutz et al., Mol Cell 5, 695-705 (2000)), several observations indicate the pluripotent cell context is not necessarily required. For example, random integration of an XIST transgene into human HT1080 cells (a transformed cell line) produced a robust Barr Body (on a Chr4 autosome), although this took longer than in pluripotent cells (Hall et al., Proc Natl Acad Sci USA 99, 8677-8682. (2002)). Similarly, gene silencing has been seen in other somatic cell lines (Chow et al., Cytogene Genome Research 99, 92-98 (2002); Chow et al., Genomics 82, 309-322 (2003)). Savarese et al. (Mol Cell Biol 26, 7167-7177 (2006)) reported that hematopoietic cells in mouse bone marrow are still capable of Xist-mediated chromosomal inactivation. The Wutz lab also reported that addition of SATB1 to mouse fibroblasts can enhance their ability to silence chromatin in response to XIST RNA (Dev Cell 16, 507-516 (2009)). Data herein suggests that primary human fibroblasts still exhibit significant capacity to induce heterochromatin modifications in response to XIST. In addition, we have data in differentiated mouse and human ES/iPS cells that demonstrate cells in the neuronal pathway can silence chromatin in response to XIST RNA. Finally, our XIST transgene lacks X-chromosome "counting" sequences, and thus is compatible with natural X-inactivation in female cells.

Example 8. DYRK1A Expression is not Disrupted by XIST Insertion

Human DYRK1A gene has at least four different splicing isoforms, which differ from each other either in the 5' UTR or in the 3' coding region. We inserted XIST transgene into intron 1 of variants 1, 2, 5, or intron 3 of variant 3 (FIG. 2A, bottom panel). To investigate whether DYRK1A expression is disrupted by XIST insertion, we performed RT-PCR and sequencing for parental line and triple target line. Parental line does not have XIST insertion and triple target line has XIST transgene inserted into all three alleles of DYRK1A gene. We designed two sets of primers for RT-PCR. The first set spans the XIST target site that contains 5' UTR and coding region between exon 1 and exon 2 of variants 1, 2, 5, or between exon 3 and exon 4 of variant 3. The second set amplifies the 3'-end of coding region that spans the sequence between exon 9 and exon 11 of variants 1, 2, 5, or between exon 11 and exon 13 of variant 3. The first set of primers is expected to generate a 202 bp product for all four variants, and the second set of primers is expected to generate a 324 bp product for variant 5 (variant 5 does not contain exon 10), a 449 bp product for variants 1 and 2, and a 580 bp product for variant 3 (Table 4). Genbank accession number: variant 1 (NM_001396.3), variant 2 (NM_130436.2), variant 3 (NM_101395.2), and variant 5 (NM_130438.2).

TABLE 4

| Primer sets | product size | amplified variants |
|---|---|---|
| set 1 | 202 bp | variants 1, 2, 3, 5 |
| set 2 | 324 bp | variant 5 |
| | 449 bp | variants 1, 2 |
| | 580 bp | variant 3 |

RT-PCR showed that the first set of primers generated a 202 bp band, and the second set of primers generated only one 449 bp of single band in both parental and triple target lines. Sequencing results confirmed that the 202 bp product from the first set of primers in both lines is the sequence spanning exon 1 and exon 2 of variants 1, 2, 5, or spanning exon 3 and exon 4 of variant 3. Sequencing for the second set of primers confirmed that the 449 bp product in both lanes was the sequence spanning exon 9 and exon 11 of variants 1 and 2, indicating that these Down syndrome iPSC lines only contain DYRK1A variant 1 and/or variant 2. These results demonstrate that DYRK1A expression was not disrupted by XIST insertion, which is consistent with the microarray data in which DYRK1A expression level in all three transgenic subclones (without Dox treatment) is not down-regulated compared with that in parental line.

Studies suggest DYRK1A plays an important role in cell proliferation and neurogenesis. This result is important because it rules out the possibility that phenotypic features of the trisomy-silencing cells are impacted by disruption of DYRK1A gene, prior to trisomy silencing by XIST RNA.

Example 9. Targeting XIST to Alternative Locations on Chr.21: Targeting RCAN1

Figure 7A:
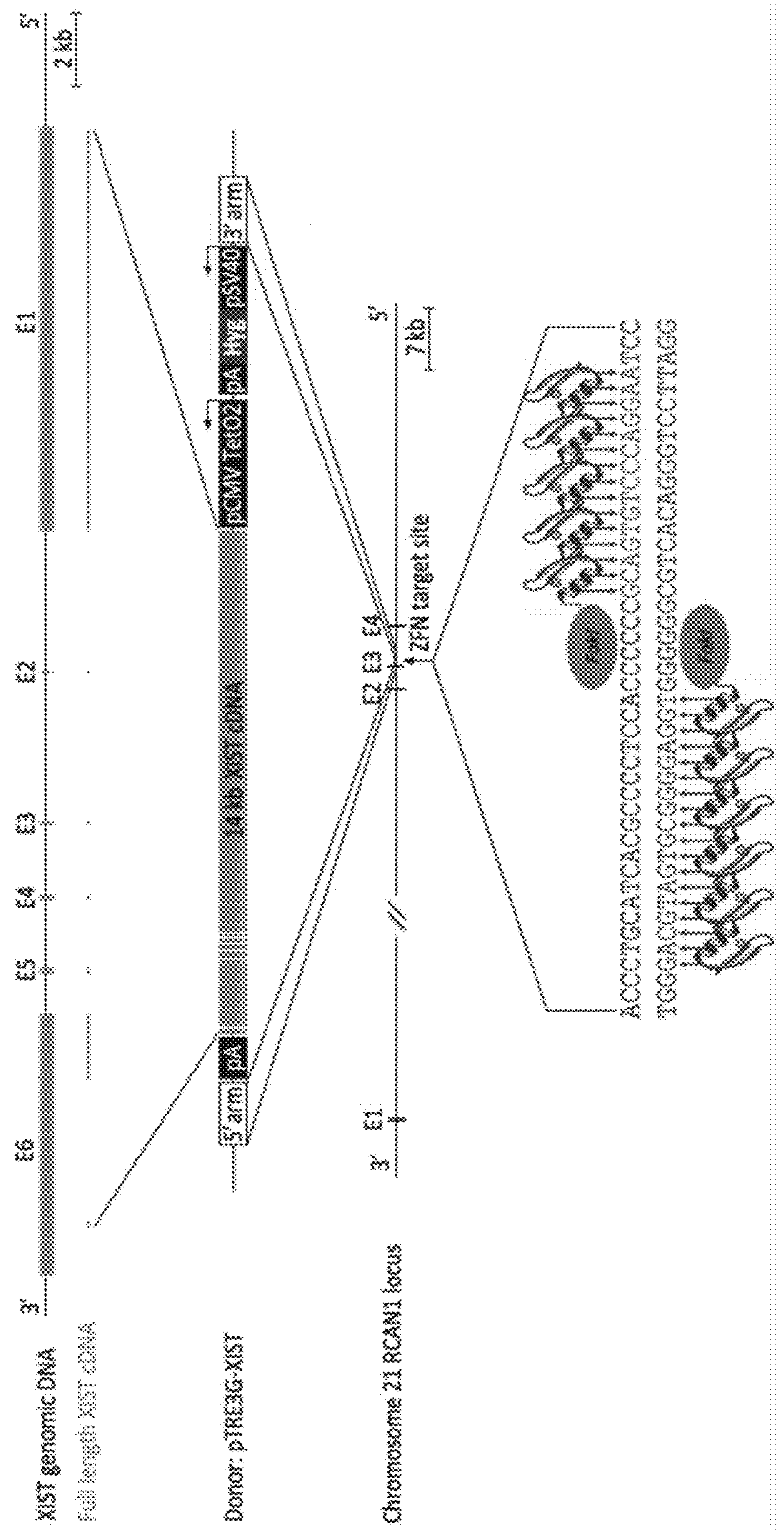
FIGS. 7A-C. RCAN1 targeting constructs. a. Schematic and b. plasmid map show that the 21.1 kb selectable and inducible human XIST construct contains two homologous arms (left arm, 759 bp; right arm, 758 bp), a hygromycin selection gene, and a 14 kb full length XIST cDNA driven by a tetracycline operator inducible promoter. The specifically designed ZFN cuts the intron 3 of RCAN1 gene on Chr 21. c. Plasmid map showing the 14.0 kb selectable and inducible human XIST construct contains two homologous arms (left arm, 759 bp; right arm, 758 bp), a hygromycin selection gene, and a 6.8 kb exon 1 of human XIST cDNA driven by a tetracycline operator inducible promoter. The 6.8 kb XIST transgene is targeted the RCAN1 gene on Chr 21 by ZFNs (as shown in schematic of FIG. 7*a*).
Figure 7B:
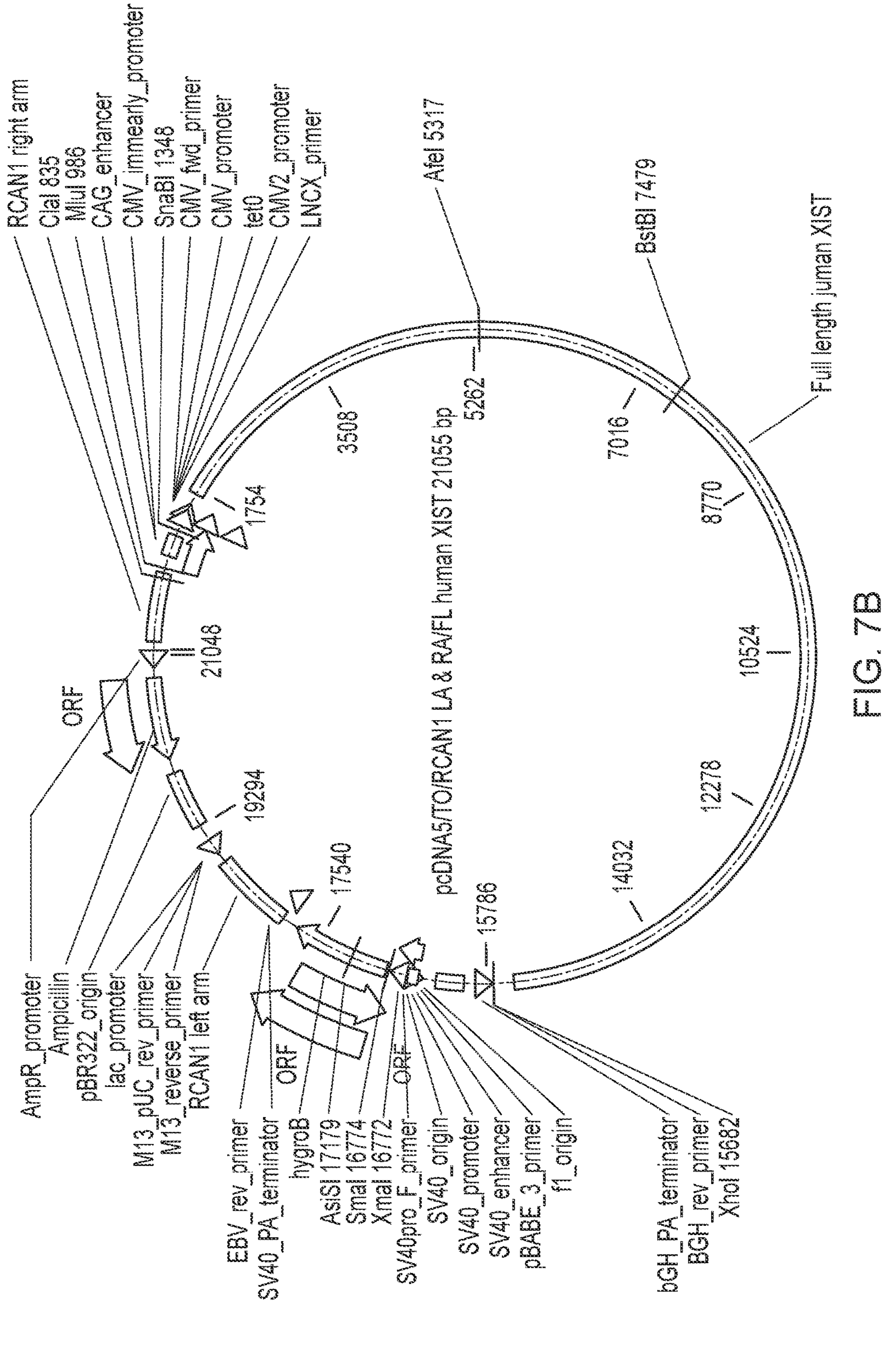
Figure 7C:
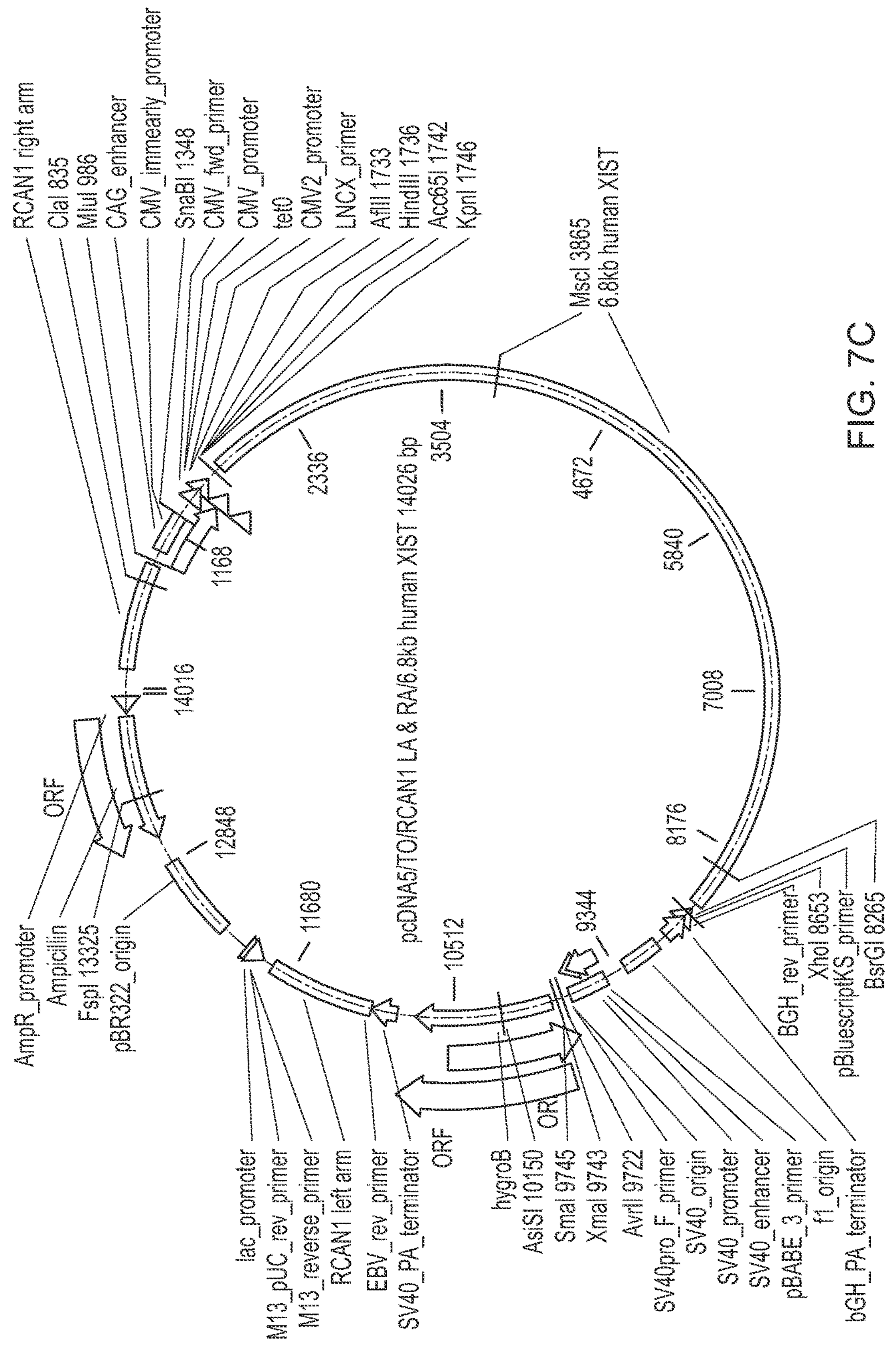
Figure 8A:
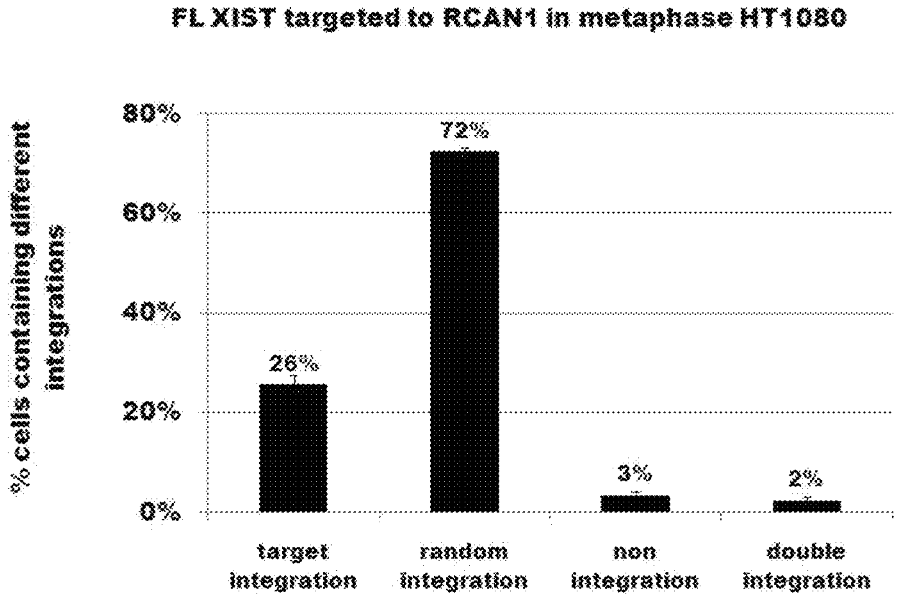
FIGS. 8A-F. ZFN Targeting XIST to RCAN1a. Cells containing the FL XIST transgene construct shown in FIGS. 7*a-b* targeted to RCAN1 locus on chr. 21 at metaphase. Graph shows quantification of cells containing different integrations. N=145 cells. b-c, Cells containing the FL XIST transgene targeted to RCAN1 locus on chr. 21 at interphase. b, Graph shows quantification of cells containing different integrations. c, Graph shows quantification of cells containing different localizations of XIST RNA. d-f. Cells containing the RCAN1 6.8 kb XIST transgene at interphase. d, Graph shows quantification of cells containing different integrations. e, Graph shows quantification of cells containing different integrations in the cells expressing XIST RNA. f, Graph shows quantification of cells containing different localizations of XIST RNA. The Distance between chr.21 BAC and RCAN1 gene is 2.3 M b.
Figure 8B:
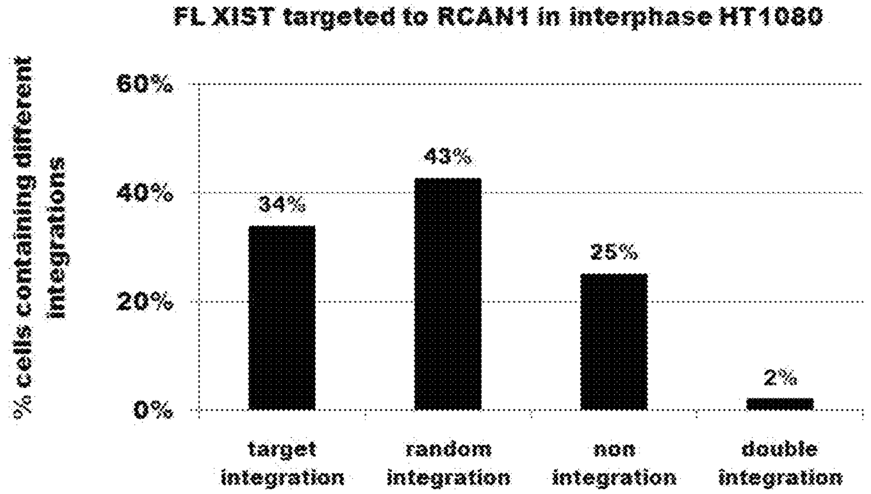
Figure 8C:
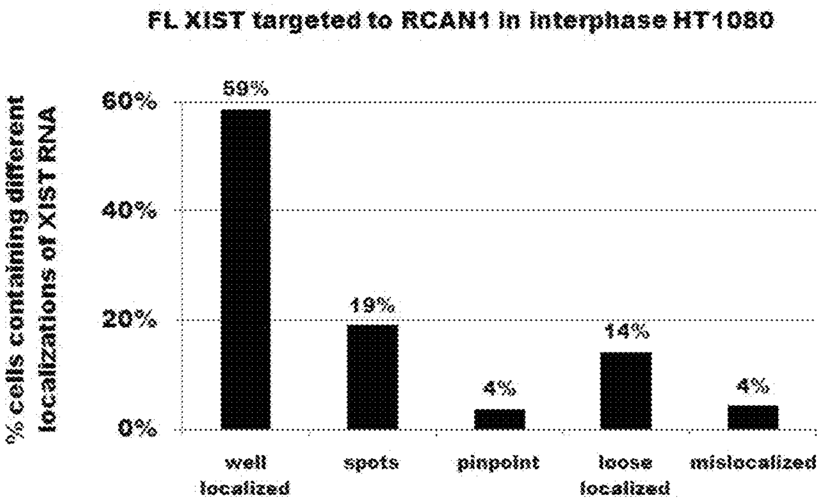
Figure 8D:
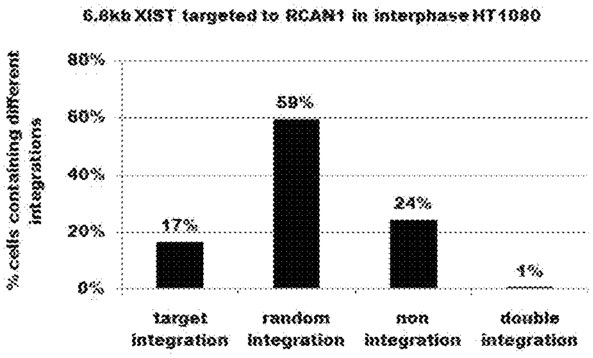
Figure 8E:
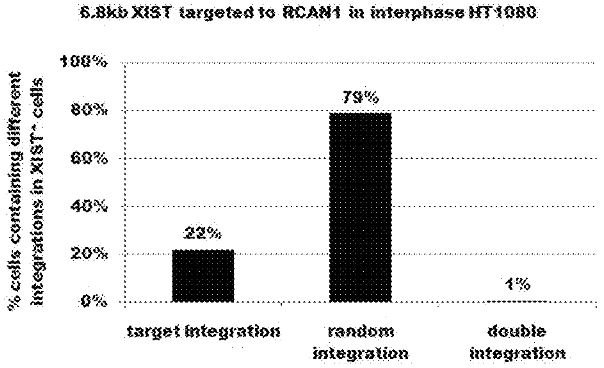
Figure 8F:
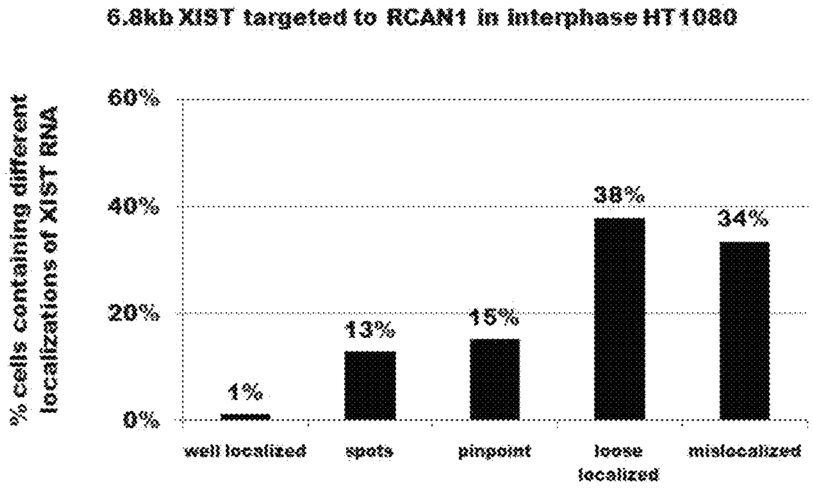

Methods as described above were used to create targeting constructs including the 6.8 kb inducible/selectable XIST transgene or the 14 kb full length XIST transgene as shown in FIGS. 7*a-c*. The lengths are shown in Table 5.

TABLE 5

| chr.21 RCAN1 targeting constructs | | | | | |
|---|---|---|---|---|---|
| | Left arm | Right arm | | Total construct length | Insert length between two arms |
| RCAN1 | 759 bp | 758 bp | 6.8 kb | 14026 bp | 10108 bp |
| | | | FL | 21055 bp | 17137 bp |

The constructs were introduced into cells as described above. Integration of the transgene and localization of XIST RNA were confirmed by interphase and metaphase FISH; the results are shown in FIGS. 8*a-f*. These data demonstrate the feasibility of using ZFN-driven genome editing to direct an entire or active XIST cassette to different loci of the "DS critical region" of Chr21.

Example 10. Generation of Trisomy Corrected Mouse Models of Down's Syndrome Carrying an Extra Human Chromosome 21

Several mouse models have been developed that recapitulate many of the phenotypic and anatomical pathologies of Down's syndrome. Two Down's syndrome mouse models (Tc1 and Ts65Dn) that are widely used have a number of well-characterized abnormalities in multiple organ systems. This example uses the Tc1 mouse model to evaluate the effects of silencing the trisomic chromosome in these mice.

The Tc1 mouse strain contains a freely segregating human fragment (~90%) of chromosome 21 containing 269 genes that have been found to contribute to human Down's syndrome. This transchromosomic mouse line represents the most complete model of Down's syndrome, exhibiting deficits in learning and memory, synaptic plasticity, motor coordination, and heart development (O'Doherty et al., Science 309, 2033-2037 (2005); Hernandez et al., Hum Mol Genet 8, 923-933 (1999); Galante et al., Hum Mol Genet 18, 1449-1463 (2009); Alford et al., Blood 115, 2928-2937). The human chromosome 21 ZFNs and doxycycline-inducible XIST constructs described herein were used to successfully target the Tc1 ES cells which were originally used to create the Tc1 Down's syndrome mouse model. XIST-targeted clones with robust XIST accumulation are being isolated.

In addition, two mouse Xist constructs were designed to target human chromosome 21. The pEF1α/hDYRK1A/FL mXist construct (20647 bp) contains full length mouse Xist cDNA and two homologous arms that are designed to target intron 1 of DYRK1A gene on human chromosome 21. The construct was generated as follows. The 15 kb of full length mouse Xist cDNA (15 kb of the 17.9 kb sequence at Genbank accession number: NR_001463.3; see SEQ ID NO:62) was subcloned into pTRE3G vector (Clontech, Cat#: 631167). Two homologous arms (left arm, 690 bp; right arm, 508 bp) of DYRK1A gene on human chromosome 21 were amplified by PCR from primary DS fibroblasts (AG13902) (Coriell) and cloned into the pTRE3G vector (Human Chr21 DYRK1A left arm primers: forward 5'-GCCGTATACCATTAACTCTTTACTGTTC-3' (SEQ ID NO:1), reverse 5'-TCTGTATACGTAAACTGGCAAAGGGGTGG-3' (SEQ ID NO:2); Human Chr21 DYRK1A right arm primers: forward 5'-ATTTCGCGAACGGGTGATGAGCAGGCTGT-3' (SEQ ID NO:3), reverse 5'-CCGTCGCGAAAACCAGAAAGTATTCTCAG-3' (SEQ ID NO:4)). The inducible pTRE3G promoter on the pTRE3G vector was replaced by a constitutive promoter PEF1α (from pEF1α-Tet3G vector, Clontech). See FIG. 9*g*, 10I and SEQ ID NO:22 for sequence information.

In order to generate a trisomy corrected Tc1 mouse model without disturbing other part of the genome, the same dual-targeted-addition strategy described above was used: to target the mouse Xist transgene into human chromosome 21 and a selection gene into chromosome 6. The Rosa26/pEF1x-Tet3G/hPGK-PuroR construct was made, which contains a puromycin resistance selection gene and rtTA cassette that is targeted to the Rosa26 locus on mouse chromosome 6 by ZFNs (Rosa26 locus is the safe harbor of mouse genome). Mouse Rosa26 ZFNs were purchased from Addgene and the pEF1x-Tet3G/hPGK-PuroR cassette from AAVS1/pEF1x-Tet3G/hPGK-PuroR vector was subcloned into a plasmid for targeted gene addition to the Rosa26 locus of mouse genome (Addgene, Cat#: 37200), which contains a unique PmeI site flanked by two 800 bp stretches of homology to the ZFN-specified position in the genome. See FIG. 9*i*, 10K and SEQ ID NO:24 for sequence information. This construct would be useful in any situation in which you do not want the selection gene directly on the transgene. This is important for Xist transgenes (which could silence the selection gene), but also in any inducible transgene which the enhancer in a tandem selection gene could cause "leaky" expression of the transgene.

These constructs were used to silence the human chromosome 21 in the Tc1 Down syndrome mouse model, which contains an extra copy of human chromosome 21 in mouse context. The Tc1 mouse embryonic stem (ES) cells were cultured in mouse ES cell growth medium. Single cells ($1\times10^7$) were harvested using trypsin (Invitrogen), resuspended in 1×PBS and electroporated with a total of 59 μg DNA including five plasmids (pEF1α/hDYRK1A/FL mXist, DYRK1A ZFN1, DYRK1A ZFN2, Rosa26/pEF1x-Tet3G/hPGK-PuroR, and Rosa26 ZFN) with 3:1 ratio of pEF1α/hDYRK1A/FL mXist:Rosa26/pEF1x-Tet3G/hPGK-PuroR. The electroporation conditions were 230v, and 500 μf (BioRad Gene Pulser II System). Cells were subsequently plated on puromycin-resistant MEF feeders in Mouse ES cell growth medium. 288 colonies were picked after 12 days of 3.0 μg/ml puromycin selection and examined by interphase DNA/RNA FISH for targeted clones. In some targeted subclones, the mouse Xist RNA did not accumulate on the targeted human chromosome 21. In another pool of Tc1 cells that contained eight different subclones, targeted cells showed robust Xist paint that appears to silence the DYRK1A gene on the trisomic human chromosome 21.

Example 11. Minimal Mouse XIST Silencing Constructs for In Vivo Delivery

In vivo chromosome therapy would have significant impact on the potential development of human therapies for Down's syndrome patients. The large size (15 kb) of the full length of mouse Xist cDNA could complicate delivery into cells using AAV-based gene delivery approach. For in vivo delivery of Xist transgene to cells within the body, a reduced size Xist (5-6 kb) was generated which can be packaged in AAV vector. This second construct, pEF1α/hDYRK1A/6.3 kb mXist (12230 bp), contains 6.3 kb of mouse Xist cDNA that has been reported to function (Wutz et al., Nat Genet 30, 167-174 (2002)) and two homologous arms that were designed to target intron 1 of DYRK1A gene on human chromosome 21. The construct was generated as follows. 6.3 kb mouse Xist cDNA that contains exon 1 of Xist gene (SEQ ID NO:61) was subcloned into pTRE3G vector (Clontech, Cat#: 631167). Two homologous arms (left arm, 690 bp; right arm, 508 bp) of DYRK1A gene on human chromosome 21 were amplified by PCR from primary DS fibroblasts (AG13902) (Coriell) and cloned into the pTRE3G vector (Human Chr21 DYRK1A left arm primers: forward 5'-GCCGTATACCATTAACTCTTTACTGTTC-3' (SEQ ID NO:1), reverse 5'-TCTGTATACGTAAACTGGCAAAGGGGTGG-3' (SEQ ID NO:2); Human Chr21 DYRK1A right arm primers: forward 5'-ATTTCGCGAACGGGTGATGAGCAGGCTGT-3' (SEQ ID NO:3), reverse 5'-CCGTCGCGAAAACCAGAAAGTATTCTCAG-3' (SEQ ID NO:4)). The inducible pTRE3G promoter on the pTRE3G vector was replaced by a constitutive promoter PEF1α (from pEF1α-Tet3G vector, Clontech). See FIG. 9*h*, 10J and SEQ ID NO:23 for sequence information. The smaller Xist transgene is used to test the Xist-mediated chromosome therapy in affected organs in vivo.

Example 12. Transplantation of Neural Stem Cells in Down's Syndrome Mouse Brain Children with Down's syndrome have variable but significant levels of cognitive impairment, which limits the independence of Down's syndrome patients and adversely impacts their quality of life. MRI studies reveal that Down's syndrome children and young adults have smaller overall brain volumes with more notable deficits in the hippocampus. Hippocampal volume continues to decrease with age in Down's syndrome individuals, which is inversely correlated with the degree of cognitive impairment (Smigielska-Kuzia et al., Neurol Neurochir Pol 45, 363-369 (2011); Pinter et al., Neurology 56, 972-974 (2001)). Neurological studies from both Down's syndrome patients and mouse models also suggest a hypocellularity in the hippocampus persists over life, indicating this may be amenable to stem cell therapies (Lorenzi & Reeves, Brain Res 1104, 153-159 (2006); Guidi et al., Brain Pathol 21, 361-373 (2011); Guidi et al., Brain Pathol 18, 180-197 (2008)).

The human iPSC-based trisomy correction model system described herein provides a uniquely powerful resource for the study of transplantation therapies in Down's syndrome. We have successfully differentiated the trisomy corrected and non-corrected cells into neural progenitors with 90% high efficiency and preliminary results indicate the human iPSC-derived neurons are capable of forming synapses in vitro. To study the in vivo function of our in vitro-produced human trisomy corrected neural progenitors, the Tc1 mouse model is used to test if the trisomy corrected human iPSC-derived neurons participate in the established mouse neural network. The trisomy corrected neural progenitors are transplanted to both sides of hippocampi of immunosupressed Tc1 mice (n=10) (group 1) and the control groups will be (1) the trisomic line without XIST induction (group 2); (2) parental trisomic line (group 3); (3) one isogenic disomic line as positive control (group 4). Each group has 10 mice (40 in total). The human-specific nuclear protein, as well as neuronal subtype and synaptic markers will be used to identify the resulting subtype of neurons and synaptic formation between human neurons and mouse neurons Human embryonic stem cell-derived neurons can functionally integrate into an existing neural circuitry and regulate the activity of an established mouse neural network after transplantation into the mouse brain (Weick et al., Proceedings of the National Academy of Sciences of the United States of America 108, 20189-20194 (2011); Espuny-Camacho et al., Neuron 77, 440-456 (2013); Muotri et al., Proceedings of the National Academy of Sciences of the United States of America 102, 18644-18648 (2005); Acharya et al., Proc Natl Acad Sci USA 106, 19150-19155 (2009)). Human ESC-derived neural progenitors transplanted into the hippocampus of mice correct learning and memory deficits (Liu et al., Nat Biotechnol 31, 440-447 (2013)). To assess whether the resulting neurons functionally integrate into neural circuits in the hippocampus of Tc1 mice, brain-slice electrophysiological recordings of human iPSC-derived neurons identified by mCherry expression under control of a synapsin promoter, which was introduced into the progenitors using a lentivirus before transplantation as described (Liu et al., Nat Biotechnol 31, 440-447 (2013)). Morris water maze test for all mice in each of the four groups, before and after cell transplantation, are used to evaluate functional improvement in hippopcampus-related learning and memory deficits.

REFERENCES

1 Antonarakis, S. E. & Epstein, C. J. The challenge of Down syndrome. Trends in molecular medicine 12, 473-479 (2006).

2 Megarbane, A. et al. The 50th anniversary of the discovery of trisomy 21: the past, present, and future of research and treatment of Down syndrome. Genetics in medicine: official journal of the American College of Medical Genetics 11, 611-616 (2009).

3 Prandini, P. et al. Natural gene-expression variation in Down syndrome modulates the outcome of gene-dosage imbalance. Am J Hum Genet 81, 252-263 (2007).

4 O'Doherty, A. et al. An aneuploid mouse strain carrying human chromosome 21 with Down syndrome phenotypes. Science 309, 2033-2037 (2005).

5 Reeves, R. H. Down syndrome mouse models are looking up. Trends Mol Med 12, 237-240 (2006).

6 Liu, C. et al. Mouse models for Down syndrome-associated developmental cognitive disabilities. Dev Neurosci 33, 404-413 (2011).

7 Gardiner, K. J. Molecular basis of pharmacotherapies for cognition in Down syndrome. Trends Pharmacol Sci 31, 66-73 (2010).

8 Lyon, M. Gene Action in the X-chromosome of the Mouse (*Mus musculus* L.). Nature 190, 372-373 (1961).

9 Brown, C. J. et al. The human XIST gene: analysis of a 17 kb inactive X-specific RNA that contains conserved repeats and is highly localized within the nucleus. Cell 71, 527-542 (1992).

10 Clemson, C. M., McNeil, J. A., Willard, H. F. & Lawrence, J. B. XIST RNA paints the inactive X chromosome at interphase: Evidence for a novel RNA involved in nuclear/chromosome structure. J. Cell Biol. 132, 259-275 (1996).

11 Hall, L. L. & Lawrence, J. B. The cell biology of a novel chromosomal RNA: chromosome painting by XIST/Xist RNA initiates a remodeling cascade. Semin Cell Dev Biol 14, 369-378 (2003).

12 Heard, E. Delving into the diversity of facultative heterochromatin: the epigenetics of the inactive X chromosome. Curr Opin Genet Dev 15, 482-489 (2005).

13 Wutz, A. Gene silencing in X-chromosome inactivation: advances in understanding facultative heterochromatin formation. Nat Rev Genet 12, 542-553 (2011).

14 Lee, J. T. Gracefully ageing at 50, X-chromosome inactivation becomes a paradigm for RNA and chromatin control. Nat Rev Mol Cell Biol 12, 815-826 (2011).

15 Bailey, J. A., Carrel, L., Chakravarti, A. & Eichler, E. E. Molecular evidence for a relationship between LINE-1 elements and X chromosome inactivation: the Lyon repeat hypothesis. Proc Natl Acad Sci USA 97, 6634-6639. (2000).

16 Brown, C. J., Carrel, L. & Willard, H. F. Expression of genes from the human active and inactive X chromosomes. Am J Hum Genet 60, 1333-1343 (1997).

17 Carrel, L. & Willard, H. F. X-inactivation profile reveals extensive variability in X-linked gene expression in females. Nature 434, 400-404 (2005).

18 McNeil, J. A., Smith, K. P., Hall, L. L. & Lawrence, J. B. Word frequency analysis reveals enrichment of dinucleotide repeats on the human X chromosome and [GATA]n in the X escape region. Genome Res 16, 477-484 (2006).

19 Hall, L. L., Clemson, C. M., Byron, M., Wydner, K. & Lawrence, J. B. Unbalanced X; autosome translocations provide evidence for sequence specificity in the association of XIST RNA with chromatin. Hum Mol Genet 11, 3157-3165. (2002).

20 Wutz, A. & Jaenisch, R. A shift from reversible to irreversible X inactivation is triggered during ES cell differentiation. Mol Cell 5, 695-705 (2000).

21 Hall, L. L. et al. An ectopic human XIST gene can induce chromosome inactivation in postdifferentiation human HT-1080 cells. Proc Natl Acad Sci USA 99, 8677-8682. (2002).

22 Lee, J. T., Strauss, W. M., Dausman, J. A. & Jaenisch, R. A 450 kb transgene displays properties of the mammalian X-inactivation center. Cell 86, 83-94 (1996).

23 Moehle, E. A. et al. Targeted gene addition into a specified location in the human genome using designed zinc finger nucleases. Proc Natl Acad Sci USA 104, 3055-3060 (2007).

24 Urnov, F. D., Rebar, E. J., Holmes, M. C., Zhang, H. S. & Gregory, P. D. Genome editing with engineered zinc finger nucleases. Nat Rev Genet 11, 636-646 (2010).

25 DeKelver, R. C. et al. Functional genomics, proteomics, and regulatory DNA analysis in isogenic settings using zinc finger nuclease-driven transgenesis into a safe harbor locus in the human genome. Genome Research 20, 1133-1142 (2010).

26 Park, J., Song, W. J. & Chung, K. C. Function and regulation of Dyrk1A: towards understanding Down syndrome. Cellular and molecular life sciences: CMLS 66, 3235-3240 (2009).

27 Yabut, O., Domogauer, J. & D'Arcangelo, G. Dyrk1A overexpression inhibits proliferation and induces premature neuronal differentiation of neural progenitor cells. J Neurosci 30, 4004-4014 (2010).

28 Litovchick, L., Florens, L. A., Swanson, S. K., Washburn, M. P. & DeCaprio, J. A. DYRK1A protein kinase promotes quiescence and senescence through DREAM complex assembly. Genes & development 25, 801-813 (2011).

29 Gurdon, J. B. & Yamanaka, S. The Nobel Prize in Physiology or Medicine 2012, nobelprize.org/nobel_prizes/medicine/laureates/2012/press.html (2012).

30 Park, I. H. et al. Disease-specific induced pluripotent stem cells. Cell 134, 877-886 (2008).

31 Clemson, C. M., Hall, L. L., Byron, M., McNeil, J. & Lawrence, J. B. The X chromosome is organized into a gene-rich outer rim and an internal core containing silenced nongenic sequences. Proc Natl Acad Sci USA 103, 7688-7693 (2006).

32 Tanzi, R. E. & Bertram, L. Twenty years of the Alzheimer's disease amyloid hypothesis: a genetic perspective. Cell 120, 545-555 (2005).

33 Webb, R. L. & Murphy, M. P. beta-Secretases, Alzheimer's Disease, and Down Syndrome. Curr Gerontol Geriatr Res 2012, 362839 (2012).

34 Biancotti, J. C. et al. Human embryonic stem cells as models for aneuploid chromosomal syndromes. Stem Cells 28, 1530-1540 (2010).

35 Lockstone, H. E. et al. Gene expression profiling in the adult Down syndrome brain. Genomics 90, 647-660 (2007).

36 Ait Yahya-Graison, E. et al. Classification of human chromosome 21 gene-expression variations in Down syndrome: impact on disease phenotypes. Am J Hum Genet 81, 475-491 (2007).

37 Cotton, A. M. et al. Chromosome-wide DNA methylation analysis predicts human tissue-specific X inactivation. Human genetics 130, 187-201 (2011).

38 Sharp, A. J. et al. DNA methylation profiles of human active and inactive X chromosomes. Genome research 21, 1592-1600 (2011).

39 Csankovszki, G., Nagy, A. & Jaenisch, R. Synergism of Xist RNA, DNA methylation, and histone hypoacetylation in maintaining X chromosome inactivation. J. of Cell Biol. 153, p. 773-783 (2001).

40 Carrel, L. et al. Genomic environment predicts expression patterns on the human inactive X chromosome. PLoS Genet 2, e151 (2006).

41 Hall, L. L. & Lawrence, J. B. XIST RNA and architecture of the inactive X chromosome: implications for the repeat genome. Cold Spring Harb Symp Quant Biol 75, 345-356 (2010).

42 Guidi, S., Ciani, E., Bonasoni, P., Santini, D. & Bartesaghi, R. Widespread proliferation impairment and hypocellularity in the cerebellum of fetuses with down syndrome. Brain Pathol 21, 361-373 (2011).

43 Haydar, T. F. & Reeves, R. H. Trisomy 21 and early brain development. Trends Neurosci 35, 81-91 (2012).

44 Shi, Y., Kirwan, P., Smith, J., Robinson, H. P. & Livesey, F. J. Human cerebral cortex development from pluripotent stem cells to functional excitatory synapses. Nat Neurosci 15, 477-486, 5471 (2012).

45 Shi, Y. et al. A human stem cell model of early Alzheimer's disease pathology in Down syndrome. Sci Transl Med 4, 124ra129 (2012).

46 Csankovszki, G., Panning, B., Bates, B., Pehrson, J. R. & Jaenisch, R. Conditional deletion of Xist disrupts histone macroH2A localization but not maintenance of X inactivation [letter]. Nat Genet 22, 323-324 (1999).

47 Ohhata, T. & Wutz, A. Reactivation of the inactive X chromosome in development and reprogramming. Cellular and molecular life sciences: CMLS (2012).

48 Li, L. B. et al. Trisomy correction in down syndrome induced pluripotent stem cells. Cell Stem Cell 11, 615-619 (2012).

49 Lavon, N. et al. Derivation of euploid human embryonic stem cells from aneuploid embryos. Stem cells 26, 1874-1882 (2008).

50 Morey, C. & Avner, P. The demoiselle of X-inactivation: 50 years old and as trendy and mesmerising as ever. PLoS genetics 7, e1002212 (2011).

51 Brockdorff, N. Chromosome silencing mechanisms in X-chromosome inactivation: unknown unknowns. Development 138, 5057-5065 (2011).

52 Minkovsky, A., Patel, S. & Plath, K. Concise review: Pluripotency and the transcriptional inactivation of the female Mammalian X chromosome. Stem cells 30, 48-54 (2012).

53 Hockemeyer, D. et al. Efficient targeting of expressed and silent genes in human ESCs and iPSCs using zinc-finger nucleases. Nat Biotechnol 27, 851-857 (2009).
54 Doyon, J. B. et al. Rapid and efficient clathrin-mediated endocytosis revealed in genome-edited mammalian cells. Nat Cell Biol (2011).
55 Miller, J. C. et al. An improved zinc-finger nuclease architecture for highly specific genome editing. Nat Biotechnol 25, 778-785 (2007).
56 Guschin, D. Y. et al. A rapid and general assay for monitoring endogenous gene modification. Methods in molecular biology 649, 247-256 (2010).
57 Urnov, F. D. et al. Highly efficient endogenous human gene correction using designed zinc-finger nucleases. Nature 435, 646-651 (2005).
58 Tam, R., Smith, K. P., and Lawrence, J. B. The 4q subtelomere harboring the FSHD locus is specifically anchored with peripheral heterochromatic unlike most human telomeres. Journal of Cell Biology 167, 269-279 (2004).
59 Irizarry, R. A. et al. Summaries of Affymetrix GeneChip probe level data. Nucleic acids research 31, e15 (2003).
60 Gardiner, K. Gene-dosage effects in Down syndrome and trisomic mouse models. Genome Biol 5, 244 (2004).
61 Antonarakis, S. E. & Epstein, C. J. The challenge of Down syndrome. Trends Mol Med 12, 473-479 (2006).
62 Antonarakis, S. E., Lyle, R., Chrast, R. & Scott, H. S. Differential gene expression studies to explore the molecular pathophysiology of Down syndrome. Brain Res Brain Res Rev 36, 265-274 (2001).
63 Tang, Y. et al. Blood expression profiles for tuberous sclerosis complex 2, neurofibromatosis type 1, and Down's syndrome. Ann Neurol 56, 808-814 (2004).
64 Weber, M. et al. Distribution, silencing potential and evolutionary impact of promoter DNA methylation in the human genome. Nat Genet 39, 457-466 (2007).
65 Wang, Y. & Leung, F. C. An evaluation of new criteria for CpG islands in the human genome as gene markers. Bioinformatics 20, 1170-1177 (2004).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A silencing vector comprising:

a silencing element comprising a silencing sequence comprising SEQ ID NO:10 or SEQ ID NO:11 flanked by first and second targeting sequences, wherein the first and second targeting sequences target insertion of the silencing sequence into a sequence comprising SEQ ID NO:9 within intron 1 of the dual specificity tyrosine-phosphorylation-regulated kinase 1A (DYRK1A) gene; and a promoter operably linked to the silencing element.

2. The silencing vector of claim 1, wherein the vector is a plasmid or a viral vector.

3. The silencing vector of claim 2, wherein the viral vector is vaccinia virus, adeno-associated virus (MV), or herpes virus.

4. The silencing vector of claim 1, wherein the silencing element comprises a human X inactive specific transcript (XIST) cDNA or functional fragment thereof.

5. The silencing vector of claim 4, further comprising a selectable marker sequence.

6. The silencing vector of claim 5, wherein the selectable marker sequence is operably linked to a promoter.

7. A method of reducing levels of expression of genes on Chromosome 21 in a cell, the method comprising contacting the cell with the silencing vector of claim 1, under conditions sufficient for the silencing vector to undergo homologous recombination with the genomic DNA of the cell, wherein the silencing element is inserted into intron 1 of DYRK1A.

8. The method of claim 7, wherein the cell is trisomic for chromosome 21.

9. The method of claim 7, wherein the cell is a human cell.

10. The method of claim 9, wherein the cell is a stem cell or a fibroblast.

11. The method of claim 10, wherein the stem cell is an induced pluripotent stem cell (iPSC), a hematopoietic stem cell, or a neural stem cell.

12. An isolated cell produced by the method of claim 7.

13. A method of reducing the risk of transient myeloproliferative disorder (TMD) in a subject who has Down Syndrome (Trisomy 21), the method comprising:

obtaining a hematopoietic stem cell from the subject;

contacting the cell with the silencing vector of claim 1, under conditions sufficient for the silencing vector to undergo homologous recombination with the genomic DNA of the cell, wherein the silencing element is inserted into DYRK1A, to produce a modified cell having reduced levels of expression of genes on Chromosome 21; and administering the modified cell to the subject.

14. The method of claim 7, further comprising contacting the cell with a cleavage vector comprising a sequence that enhances or facilitates homologous recombination.

15. The method of claim 14, wherein the cleavage vector comprises a zinc finger nuclease (ZFN) or a transcription activator-like effector nuclease (TALEN).

* * * * *

SEQUENCE LISTING

```
<160> NUMBER OF SEQ ID NOS: 62

<210> SEQ ID NO 1
<211> LENGTH: 28
<212> TYPE: DNA
<213> ORGANISM: Artificial Sequence
<220> FEATURE:
<223> OTHER INFORMATION: PCR primers

<400> SEQUENCE: 1

gccgtatacc attaactctt tactgttc                                        28


<210> SEQ ID NO 2
<211> LENGTH: 29
<212> TYPE: DNA
<213> ORGANISM: Artificial Sequence
<220> FEATURE:
<223> OTHER INFORMATION: PCR primers

<400> SEQUENCE: 2

tctgtatacg taaactggca aaggggtgg                                       29


<210> SEQ ID NO 3
<211> LENGTH: 29
<212> TYPE: DNA
<213> ORGANISM: Artificial Sequence
<220> FEATURE:
<223> OTHER INFORMATION: PCR primers

<400> SEQUENCE: 3

atttcgcgaa cgggtgatga gcaggctgt                                       29


<210> SEQ ID NO 4
<211> LENGTH: 29
<212> TYPE: DNA
<213> ORGANISM: Artificial Sequence
<220> FEATURE:
<223> OTHER INFORMATION: PCR primers

<400> SEQUENCE: 4
```

ccgtcgcgaa aaccagaaag tattctcag 29

<210> SEQ ID NO 5
<211> LENGTH: 29
<212> TYPE: DNA
<213> ORGANISM: Artificial Sequence
<220> FEATURE:
<223> OTHER INFORMATION: PCR primers

<400> SEQUENCE: 5
attgtatacc caagagccct cctgacctc 29

<210> SEQ ID NO 6
<211> LENGTH: 29
<212> TYPE: DNA
<213> ORGANISM: Artificial Sequence
<220> FEATURE:
<223> OTHER INFORMATION: PCR primers

<400> SEQUENCE: 6
aatgtatacg ggtggagggg cgtgatgca 29

<210> SEQ ID NO 7
<211> LENGTH: 28
<212> TYPE: DNA
<213> ORGANISM: Artificial Sequence
<220> FEATURE:
<223> OTHER INFORMATION: PCR primers

<400> SEQUENCE: 7
tattcgcgac ccgcagtgtc ccaggaat 28

<210> SEQ ID NO 8
<211> LENGTH: 29
<212> TYPE: DNA
<213> ORGANISM: Artificial Sequence
<220> FEATURE:
<223> OTHER INFORMATION: PCR primers

<400> SEQUENCE: 8
cgctcgcgac aatgttttca gaaatgtaa 29

<210> SEQ ID NO 9
<211> LENGTH: 42
<212> TYPE: DNA
<213> ORGANISM: Artificial Sequence
<220> FEATURE:
<223> OTHER INFORMATION: PCR primers

<400> SEQUENCE: 9
gccacccctt tgccagttta cacgggtgat gagcaggctg tt 42

<210> SEQ ID NO 10
<211> LENGTH: 13730
<212> TYPE: DNA
<213> ORGANISM: Homo sapiens

<400> SEQUENCE: 10
ctagaacatt ttctagtccc ccaacaccct ttatggcgta tttctttaaa aaaatcacct 60
aaattccata aaatattttt ttaaattcta tactttctcc tagtgtcttc ttgacacgtc 120
ctccatattt ttttaaagaa agtatttgga atattttgag gcaattttta atatttaagg 180
aatttttctt tggaatcatt tttggtgaca tctctgtttt ttgtggatca gtttttttact 240

-continued

```
cttccactct cttttctata ttttgcccat cggggctgcg gatacctggt tttattattt    300
tttctttgcc caacggggcc gtggatacct gccttttaat tctttttat tcgcccatcg     360
gggccgcgga tacctgcttt ttattttttt ttccttagcc catcggggta tcggatacct    420
gctgattccc ttcccctctg aaccccaac actctggccc atcggggtga cggatatctg     480
ctttttaaaa attttctttt tttggcccat cggggcttcg gatacctgct tttttttttt    540
ttattttcct tgcccatcgg ggcctcggat acctgcttta atttttgttt ttctgcccat    600
cggggccgcg gatacctgct ttgatttttt tttttcatcg cccatcggtg ctttttatgg    660
atgaaaaaat gttggttttg tgggttgttg cactctctgg aatatctaca cttttttttg    720
ctgctgatca tttggtggtg tgtgagtgta cctaccgctt tggcagagaa tgactctgca    780
gttaagctaa gggcgtgttc agattgtgga ggaaaagtgg ccgccatttt agacttgccg    840
cataactcgg cttagggcta gtcgtttgtg ctaagttaaa ctagggaggc aagatggatg    900
atagcaggtc aggcagagga agtcatgtgc attgcatgag ctaaacctat ctgaatgaat    960
tgatttgggg cttgttagga gctttgcgtg attgttgtat cgggaggcag taagaatcat   1020
cttttatcag tacaagggac tagttaaaaa tggaaggtta ggaaagacta aggtgcaggg   1080
cttaaaatgg cgattttgac attgcggcat tgctcagcat ggcgggctgt gctttgttag   1140
gttgtccaaa atggcggatc cagttctgtc gcagtgttca agtggcggga aggccacatc   1200
atgatgggcg aggctttgtt aagtggttag catggtggtg gacatgtgcg gtcacacagg   1260
aaaagatggc ggctgaaggt cttgccgcag tgtaaaacat ggcgggcctc tttgtctttg   1320
ctgtgtgctt ttcgtgttgg gttttgccgc agggacaata tggcaggcgt tgtcatatgt   1380
atatcatggc ttttgtcacg tggacatcat ggcgggcttg ccgcattgtt aaagatggcg   1440
ggttttgccg cctagtgcca cgcagagcgg gagaaaaggt gggatggaca gtgctggatt   1500
gctgcataac ccaaccaatt agaaatgggg gtggaattga tcacagccaa ttagagcaga   1560
agatggaatt agactgatga cacactgtcc agctactcag cgaagacctg ggtgaattag   1620
catggcactt cgcagctgtc tttagccagt caggagaaag aagtggaggg gccacgtgta   1680
tgtctcccag tgggcggtac accaggtgtt ttcaaggtct tttcaaggac atttagcctt   1740
tccacctctg tcccctctta tttgtcccct cctgtccagt gctgcctctt gcagtgctgg   1800
atatctggct gtgtggtctg aacctccctc cattcctctg tattggtgcc tcacctaagg   1860
ctaagtatac ctcccccccc accccccaac ccccccaact ccccaccccc accccccacc   1920
ccccacctcc ccaccccccct accccccctac cccccctaccc ccctctggtc tgccctgcac   1980
tgcactgttg ccatgggcag tgctccaggc ctgcttggtg tggacatggt ggtgagccgt   2040
ggcaaggacc agaatggatc acagatgatc gttggccaac aggtggcaga agaggaattc   2100
ctgccttcct caagaggaac acctacccct tggctaatgc tggggtcgga ttttgattta   2160
tatttatctt ttggatgtca gtcatacagt ctgattttgt ggtttgctag tgtttgaatt   2220
taagtcttaa gtgactatta tagaaatgta ttaagaggct ttatttgtag aattcacttt   2280
aattacattt aatgagtttt tgttttgagt tccttaaaat tccttaaagt ttttagcttc   2340
tcattacaaa ttccttaacc tttttttggc agtagatagt caaagtcaaa tcatttctaa   2400
tgttttaaaa atgtgctggt cattttcttt gaaattgact taactatttt cctttgaaga   2460
gtctgtagca cagaaacagt aaaaaattta acttcatgac ctaatgtaaa aaagagtgtt   2520
tgaaggttta cacaggtcca ggccttgctt tgttcccatc cttgatgctg cactaattga   2580
ctaatcacct acttatcaga caggaaactt gaattgctgt ggtctggtgt cctctattca   2640
```

gacttattat attggagtat ttcaattttt cgttgtatcc tgcctgccta gcatccagtt 2700
cctccccagc cctgctccca gcaaacccct agtctagccc cagccctact cccacccggc 2760
cccagccctg ccccaggccc agtcccctaa ccccccagcc ctaggcccag tcccagtcct 2820
agttcctcag tctgtccagc ttctctcgaa agtcactcta attttcattg attcagtgct 2880
caaaataagt tgtccattgg tatcctatta tactgggata ttccgtttac ccttggcatt 2940
gctgatcttc agtactgact ccttgaccat tttcagttaa gcatacaatc ccatttgtct 3000
gtgatctcag gacaaagaat ttccttactc ggtacgttga agttagggaa tgtcaattga 3060
gagctttcta tcagagcatt attgcccaca atttgagtta cttatcattt tctcgatccc 3120
ctgcccttaa aggagaaacc atttctctgt cattgcttct gtagtcacag tcccaatttt 3180
gagtagtgat cttttcttgt gtactgtgtt ggccacctaa aactctttgc attgagtaaa 3240
attctaattg ccaataatcc tacccattgg attagacagc actctgaacc ccatttgcat 3300
tcagcagggg gtcgcagaca acccgtcttt tgttggacag ttaaaatgct cagtcccaat 3360
tgtcatagct ttgcctatta aacaaaggca ccctactgcg ctttttgctg tgcttctgga 3420
gaatcctgct gttcttggac aattaaagaa caaagtagta attgctaatt gtctcaccca 3480
ttaatcatga agactaccag tcgcccttgc atttgccttg aggcagcgct gactacctga 3540
gatttaagag tttcttaaat tattgagtaa aatcccaatt atccatagtt ctgttagtta 3600
cactatggcc tttgcaaaca tctttgcata acagcagtgg gactgactca ttcttagagc 3660
cccttccctt ggaatattaa tggatacaat agtaattatt catggttctg cgtaacagag 3720
aagacccact tatgtgtatg cctttatcat tgctcctaga tagtgtgaac tacctaccac 3780
cttgcattaa tatgtaaaac actaattgcc catagtccca ctcattagtc taggatgtcc 3840
tctttgccat tgctgctgag ttctgactac ccaagtttcc ttctcttaaa cagttgatat 3900
gcataattgc atatattcat ggttctgtgc aataaaaatg gattctcacc ccatcccacc 3960
ttctgtggga tgttgctaac gagtgcagat tattcaataa cagctcttga acagttaatt 4020
tgcacagttg caattgtcca gagtcctgtc cattagaaag ggactctgta tcctatttgc 4080
acgctacaat gtgggctgat cacccaagga ctcttcttgt gcattgatgt tcataattgt 4140
atttgtccac gatcttgtgc actaaccctt ccactccctt tgtattccag caggggaccc 4200
ttactactca agacctctgt actaggacag tttatgtgca caatcctaat tgattagaac 4260
tgagtctttt atatcaaggt ccctgcatca tctttgcttt acatcaagag ggtgctggtt 4320
acctaatgcc cctcctccag aaattattga tgtgcaaaat gcaatttccc tatctgctgt 4380
tagtctgggg tctcatcccc tcatattcct tttgtcttac agcagggggt acttgggact 4440
gttaatgcgc ataattgcaa ttatggtctt ttccattaaa ttaagatccc aactgctcac 4500
accctcttag cattacagta gagggtgcta atcacaagga catttctttt gtactgttaa 4560
tgtgctactt gcatttgtcc ctcttcctgt gcactaaaga ccccactcac ttccctagtg 4620
ttcagcagtg gatgacctct agtcaagacc tttgcactag gatagttaat gtgaaccatg 4680
gcaactgatc acaacaatgt ctttcagatc agatccattt tatcctcctt gttttacagc 4740
aagggatatt aattacctat gttacctttc cctgggacta tgaatgtgca aaattccaat 4800
gttcatggtc tctcccttta aacctatatt ctaccccttt tacattatag aaagggatgc 4860
tggaaaccca gagtccttct cttgggactc ttaatgtgta tttctaatta tccatgactc 4920
ttaatgtgca tattttcaat tgcctaattg atttcaattg tctaagacat ttcaaatgtc 4980

-continued

```
taattgatta gaactgagtc ttttatatca agctaatatc tagcttttat atcaagctaa   5040
tatcttgact tctcagcatc atagaagggg gtactgattt cctaaagtct ttcttgaatt   5100
tctattatgc aaaattgccc tgaggccggg tgtggtggct cacacctgta atcccagcac   5160
tttgggaggc tgaggtggga agatccctta ctgccaggag tttgagacca gcctggccaa   5220
cattaaaaaa aaaaaaaaaa gtaagacaat tgccctggaa tcccatcccc ctcacacctc   5280
cttggcaaag cagcaggagt gctaactagc tagtgcttct tctcttatac tgcttaaatg   5340
cgcataatta gcagtagttg atgtgcccct atgttagagt agaatcccgc ttccttgctc   5400
catttgcatt actgcaggag cttctaacta gcctgaattc actctcttgg actgttaatg   5460
tgcatactta tatttgctgc tgtacttttt taccatgtaa ggaccccacc cactgtattt   5520
acatcccagc tggaagtacc tactacttaa gacccttaga ctagtaaagt tagcgtgcat   5580
aatcttaggt gttatataca cattttcagt tgcatacagt tgtgcctttt atcaggactc   5640
ctgtacttat caaagcagag agtgctaatc aatattaagc ccttctcttc gaactgtaga   5700
tggcatgtaa ttgcagttgt caatggtcct tcaattagac ttgggtttct gacctatcac   5760
accctctttg ctttattgca tggggtacta ttcacttaag gcccctttct caaactgtta   5820
atgtgcctaa tgacaattac atcagtatcc ttcctttttga aggacagcat ggttggtgac   5880
acctaaggcc ccatttcttg gcctcccaat atgtgtgatt gtatttgtcg aggttgctat   5940
gcactagaga aggaaagtgc tcccctcatc cccacttttc ccttccagca ggaagtgccc   6000
accccataag acccttttat ttggagagtc taggtgcaca attgtaagtg accacaagca   6060
tgcatcttgg acatttatgt gcgtaatcgc acactgctca ttccatgtga ataaggtcct   6120
actctccgac cccttttgca atacagaagg gttgctgata acgcagtccc cttttcttgg   6180
catgttgtgt gtgattataa tcgtctggga tcctatgcac tagaaaagga gggtcctctc   6240
cacatacctc agtctcacct ttcccttcca gcagggagtg cccactccat aagactctca   6300
catttggaca gtcaaggtgc gtaattgtta agtgaacaca accatgcacc ttagacatgg   6360
atttgcataa ctacacacag ctcaacctat ctgaataaaa tcctactctc agaccccttt   6420
tgcagtacag caggggtgct gatcaccaag gcccttttttc ctggcctggt atgcgtgtga   6480
ttatgtttgt cccggttcct gtgtattaga catggaagcc tcccctgcca cactccaccc   6540
ccaatcttcc tttcccttcc ggcaggagtg ccctctccat aagacgctta cgtttggaca   6600
atcaaggtgc acagttgtaa gtgaccacag gcatacacct tggacattaa tgtgcataac   6660
cactttgccc attccatctg aataaggtcc tactctcaga ccccttttgc agtacagcag   6720
gggtgctgat caccaaggcc ccttttcttg gcctgttatg tgcgtgatta tatttgtctg   6780
ggttcctgtg tattagacaa ggaagccttc cccccgcccc cacccccact cccagtcttc   6840
ctttcccttc cagcagggag tgccccctcc ataagatcat tacatttgga caatcaaggt   6900
gcacaattat aagtgaccac agccatgcac cttggacatt attggacatt aatgtgcgta   6960
actgcacatg gcccatccca tctgaataag gacctactct cagatgcctt tgcagtacag   7020
caggggtact gaatcaccaa ggccctttttt cttggcctgt tatgtgtgtg attatattta   7080
tcccagtttc tgtgtaatag acatgaaagc ctcccctgcc acaccccacc tccaatcttc   7140
ctttcccttc caccagggag tgtccactcc atatacccctt acatttggac aatcaaggtg   7200
cacaattgta agtgagcata ggcactcacc ttggacatga atgtgcataa ctgcacatgg   7260
cccatcccat ctgaataagg tcctactctc agaccctttt tgcagtacag caggggtgct   7320
gatcaccaag gccccttttc ctggcctgtt atgtgtgtga ttatatttgt tccagttcct   7380
```

```
gtgtaataga catggaagcc tcccctgcca cactccaccc ccaatcttcc tttccttctg   7440
gcaggaagta cccgctccat aagaccctta catttggaca gtcaaggtgc acaattgtat   7500
gtgaccacaa ccatgcacct tggacataaa tgtgtgtaac tgcacatggc ccatcccatc   7560
tgaataaggt cctactctca gaccccttt gcagtacagt aggtgtgctg ataaccaagg   7620
cccctcttcc tggcctgtta acgtatgtga ttatatttgt ctgggttcca gtgtataaga   7680
catggaagcc tcccctgccc caccccaccc tcaatcttcc tttcccttct ggcagggagt   7740
gccagctcca taagaacctt acatttggac agtcaaggtg cacaattcta agtgaccgca   7800
gccatgcacc ttggtcaata atgtgtgtaa ctgcacacgg cctatctcat ctgaataagg   7860
ccttactctc agaccccttt tgcagtacag caggggtgct gataaccaag gcccattttc   7920
ctggcctgtt atgtgtgtga ttatatttgt ccaggtttct gtgtactaga caaggaagcc   7980
tcctctgccc catcccatct acgcataatc tttcttttcc tcccagcagg gagtgctcac   8040
tccataagac ccttacattt ggacaatcaa ggtgcacaat tgtaagtgac cacaaccatg   8100
catcttggaa atttatgtgc ataactgcac atggcttatc ctatttgaat aaagtcctac   8160
tctcagaccc cctttgcagt atagctgggg tgctgatcac tgaggcctct ttgcttggct   8220
tgtctatatt cttgtgtact agataagggc accttctcat ggactccctt tgcttttcaa   8280
caaggagtac ccactacttt ttaagattct tatatttgtc caaagtacat ggttttaatt   8340
gaccacaaca atgtcccttg gacattaatg tatgtaatca ccacatggtt catcctaatt   8400
aaacaaagtt ctaccttctc accctccatt tgcagtatac cagggttgct gacccccctaa   8460
gtccccttt cttggcttgt tgacatgcat aattgcattt atgttggttc ttgtgcccta   8520
gacaaggatg ccccacctct tttcaatagt gggtgcccac tccttatgat ctttacattt   8580
gaacagttaa tgtgaataat tgcagttgtc cacaacccta tcacttctag gaccattata   8640
cctcttttgc attactgtgg ggtatactgt ttccctccaa ggccccttct ggtggactat   8700
caacatataa ttgaaatttt cttttgtctt tgtcagtaga ttaaggtcat accccatcac   8760
ctttcctttg tagtacaaca gggtgtcctg atcaaccaaa gtcctgttgt tttggactgt   8820
taatatgtgc aattacattt gctcctgatc tgtgcactag ataaggatcc tacctacttt   8880
cttagtgttt ttagcaggta gtgcccacta ctcaagactg tcacttggaa tgttcatgtg   8940
cacaaactca attctctaag catgttcctg taccaccttt gctttagagc agggggatga   9000
tattcactaa gtgccccttc ttttggactt aatatgcatt aatgcaattg tccacctctt   9060
cttttagact aagagttgat ctccacatat tccccttgca tcaggggcat gttaattatg   9120
aatgaaccct tttcttttaa tattaatgtc ataattgtat ttgtggacct gtgtaggaga   9180
aaaagaccct atgttcctcc cattaccctt tggattgctg ctgagaagtg ttaactactc   9240
ataatctcag ctcttggaca attaatagca ttaataacaa ttatcaaggg cactgatcat   9300
tagataagac tcctgcttcc tcgttgctta catcgggggt actgacccac taaggcccct   9360
tgtactgtta atgtgaatat ttgcaattat atatgtctcc ttctggtaga gtgggatatt   9420
atgccctagt atcccctttg cattactgca ggggctgctg actactcaaa acttctcctg   9480
ggactgttaa taggcacaat ggcagttatc aatggttttc tccctccctg accttgttaa   9540
gcaagcgccc caccccaccc ttagtttccc atggcataat aaagtataag cattggagta   9600
ttccatgcac ttgtctatca aacagtggtc catactccca accctttttgc attgcgccag   9660
tgtgtaaaat cacaggtagc catggtgtca tgctttatat acgaagtctt ccctctctct   9720
```

-continued

```
gccccttgtg tgcccttggc cccttttttac agactattgc tcacaatctc aggtgtccat   9780
atttgcagct attaggtaag attgtgctgt ctccctcttc ccttccctct gccctgcccc   9840
ttttgcctct ttgctgggta atgttgacca gacaaggccc tttctcttgg acttaaacaa   9900
ttctcagttg cactttcctt ggtccaccca ttatacatga acccctctac ttcctttcgc   9960
attgcttctg agtatgctga ctacccaaag ccccttctgt gttattaata aacacagtac  10020
tgattgtccc atttttcagc ccatcagtcc aagatctccc taccactttg gtgtgttggt  10080
gcagtgttga ctatgaaaag caggcctgaa ctaggtggat aagccttcac tcattttctt  10140
tcatttatta atgatcctag tttcaattat tgtcagattc tggggacaag aaccattctt  10200
gcccacctgt gttactgctt tactgtgcaa aatactgaag gcaagtcaga cccagggagc  10260
tggattgcca tcctttattt tgtgtttcca gtgtacacta taaaattgtc tccccaggaa  10320
ggaaggttgg cactttctct gcattcttct ttccagagca gattgcctgg ttaagaatct  10380
cttgttgtcc cttctgtata ttgttattgt aaagtgccaa atgccaggat acagccagaa  10440
aaattgctta ttattattaa aaaaattttt ttaagaaaga catctggatt gtagggtgga  10500
ctcgataacc tggtcattat ttttttgaag ccaaaatatc catttatact atgtacctgg  10560
tgaccagtgt ctctcatttt aactgagggt ggtgggtctg tggatagaac actgactctt  10620
gctattttaa tatcaaagat attctagatc cagcacagtg gcggccgctc tagagtggaa  10680
ctcttaagac cagtatcttt gtgtgggctt taccagcatt cacttttaga aaaactacct  10740
aaattttata atcctttaat ttcttcatct ggagcacctg cccctactta tttcaagaag  10800
attgcagtaa aacgattaaa tgagggaaca tatgcagagg tgcttttaaa aagcatatgc  10860
cacctttttt attaattatt atataaaatg aagcatttaa ttatagtaat aatttgaagt  10920
agtttgaagt accacactga ggtgaggact taaaaatgat aagacgagtt ccctatttta  10980
taagaaaaat aagccaaaat taaatattct tttggatata aatttcaaca gtgagatagc  11040
tgcctagtgg aaatgaataa tatcccagcc actagtgtac agggtgtttt gtggcacagg  11100
attatgtaat atggaactgc tcaagcaaat aactagtcat cacaacagca gttctttgta  11160
ataactgaaa aagaatattg tttctcggag aaggatgtca aaagatcggc ccagctcagg  11220
gagcagtttg ccctactagc tcctcggaca gctgtaaaga agagtctctg gctctttaga  11280
atactgatcc cattgaagat accacgctgc atgtgtcctt agtagtcatg tctccttagg  11340
ctcctcttgg acattctgag catgtgagac ctgaggactg caaacagcta taagaggctc  11400
caaattaatc atatctttcc ctttgagaat ctggccaagc tccagctaat ctacttggat  11460
gggttgccag ctatctggag aaaaagatct tcctcagaag aataggcttg ttgttttaca  11520
gtgttagtga tccattccct ttgacgatcc ctaggtggag atggggcatg aggatcctcc  11580
aggggaaaag ctcactacca ctgggcaaca accctaggtc aggaggttct gtcaagatac  11640
tttcctggtc ccagatagga agataaagtc tcaaaaacaa ccaccacacg tcaagctctt  11700
cattgttcct atctgccaaa tcattatact tcctacaagc agtgcagaga gctgagtctt  11760
cagcaggtcc aagaaatttg aacacactga aggaagtcag ccttcccacc tgaagatcaa  11820
catgcctggc actctagcac ttgaggatag ctgaatgaat gtgtatttct ttgtctcttt  11880
ctttcttgtc tttgctcttt gttctctatc taaagtgtgt cttacccatt tccatgtttc  11940
tcttgctaat ttctttcgtg tgtgcctttg cctcatttc tctttttgtt cacaagagtg  12000
gtctgtgtct tgtcttagac atatctctca tttttcattt tgttgctatt tctctttgct  12060
ctcctagatg tggctcttct ttcacgcttt atttcatgtc tccttttttgg gtcacatgct  12120
```

gtgtgctttt tgtccttttc ttgttctgtc tacctctcct ttctctgcct acctctcttt 12180
tctctttgtg aactgtgatt atttgttacc ccttcccctt ctcgttcgtt ttaaatttca 12240
ccttttttct gagtctggcc tcctttctgc tgtttctact ttttatctca catttctcat 12300
ttctgcattt cctttctgcc tctcttgggc tattctctct ctcctcccct gcgtgcctca 12360
gcatctcttg ctgtttgtga ttttctattt cagtattaat ctctgttggc ttgtatttgt 12420
tctctgcttc ttccctttct actcaccttt gagtatttca gcctcttcat gaatctatct 12480
ccctctcttt gatttcatgt aatctctcct taaatatttc tttgcatatg tgggcaagtg 12540
tacgtgtgtg tgtgtcatgt gtggcagagg ggcttcctaa cccctgcctg ataggtgcag 12600
aacgtcggct atcagagcaa gcattgtgga gcggttcctt atgccaggct gccatgtgag 12660
atgatccaag accaaaacaa ggccctagac tgcagtaaaa cccagaactc aagtagggca 12720
gaaggtggaa ggctcatatg gatagaaggc ccaaagtata agacagatgg tttgagactt 12780
gagacccgag gactaagatg gaaagcccat gttccaagat agatagaagc ctcaggcctg 12840
aaaccaacaa aagcctcaag agccaagaaa acagagggtg gcctgaattg gaccgaaggc 12900
ctgagttgga tggaagtctc aaggcttgag ttagaagtct taagacctgg gacaggacac 12960
atggaaggcc taagaactga gacttgtgac acaaggccaa cgacctaaga ttagcccagg 13020
gttgtagctg gaagacctac aacccaagga tggaaggccc ctgtcacaaa gcctacctag 13080
atggatagag gacccaagcg aaaaaggtat ctcaagacta acggccggaa tctggaggcc 13140
catgacccag aacccaggaa ggatagaagc ttgaagacct ggggaaatcc caagatgaga 13200
accctaaacc ctacctcttt tctattgttt acacttctta ctcttagata tttccagttc 13260
tcctgtttat ctttaagcct gattcttttg agatgtactt tttgatgttg ccggttacct 13320
ttagattgac agtattatgc ctgggccagt cttgagccag ctttaaatca cagcttttac 13380
ctatttgtta ggctatagtg ttttgtaaac ttctgtttct attcacatct tctccacttg 13440
agagagacac caaaatccag tcagtatcta atctggcttt tgttaacttc cctcaggagc 13500
agacattcat ataggtgata ctgtatttca gtcctttctt ttgaccccag aagccctaga 13560
ctgagaagat aaaatggtca ggttgttggg gaaaaaaaaa gtgccaggct ctctagagaa 13620
aaatgtgaag agatgctcca ggccaatgag aagaattaga caagaaatac acagatgtgc 13680
cagacttctg agaagcacct gccagcaaca gcttccttct ttgagcttag 13730

<210> SEQ ID NO 11
<211> LENGTH: 6864
<212> TYPE: DNA
<213> ORGANISM: Artificial Sequence
<220> FEATURE:
<223> OTHER INFORMATION: truncated human XIST

<400> SEQUENCE: 11
tctagaacat tttctagtcc cccaacaccc tttatggcgt atttctttaa aaaaatcacc 60
taaattccat aaaatatttt tttaaattct atactttctc ctagtgtctt cttgacacgt 120
cctccatatt tttttaaaga aagtatttgg aatattttga ggcaattttt aatatttaag 180
gaatttttct ttggaatcat ttttggtgac atctctgttt tttgtggatc agttttttac 240
tcttccactc tcttttctat attttgccca tcggggctgc ggatacctgg ttttattatt 300
ttttctttgc ccaacggggc cgtggatacc tgccttttaa ttcttttttta ttcgcccatc 360 ggggccgcgg atacctgctt tttatttttt tttccttagc ccatcggggt atcggatacc 420

-continued

```
tgctgattcc cttcccctct gaaccccca cactctggcc catcggggtg acggatatct    480
gctttttaaa aattttcttt ttttggccca tcggggcttc ggatacctgc ttttttttt    540
tttattttcc ttgcccatcg gggcctcgga tacctgcttt aatttttgtt tttctgccca    600
tcggggccgc ggatacctgc tttgattttt ttttttcatc gcccatcggt gctttttatg    660
gatgaaaaaa tgttggtttt gtgggttgtt gcactctctg gaatatctac actttttttt    720
gctgctgatc atttggtggt gtgtgagtgt acctaccgct ttggcagaga atgactctgc    780
agttaagcta agggcgtgtt cagattgtgg aggaaaagtg gccgccattt tagacttgcc    840
gcataactcg gcttagggct agtcgtttgt gctaagttaa actagggagg caagatggat    900
gatagcaggt caggcagagg aagtcatgtg cattgcatga gctaaaccta tctgaatgaa    960
ttgatttggg gcttgttagg agctttgcgt gattgttgta tcgggaggca gtaagaatca   1020
tcttttatca gtacaaggga ctagttaaaa atggaaggtt aggaaagact aaggtgcagg   1080
gcttaaaatg gcgattttga cattgcggca ttgctcagca tggcgggctg tgctttgtta   1140
ggttgtccaa aatggcggat ccagttctgt cgcagtgttc aagtggcggg aaggccacat   1200
catgatgggc gaggctttgt taagtggtta gcatggtggt ggacatgtgc ggtcacacag   1260
gaaaagatgg cggctgaagg tcttgccgca gtgtaaaaca tggcgggcct ctttgtcttt   1320
gctgtgtgct tttcgtgttg ggttttgccg cagggacaat atggcaggcg ttgtcatatg   1380
tatatcatgg cttttgtcac gtggacatca tggcgggctt gccgcattgt taaagatggc   1440
gggttttgcc gcctagtgcc acgcagagcg ggagaaaagg tgggatggac agtgctggat   1500
tgctgcataa cccaaccaat tagaaatggg ggtggaattg atcacagcca attagagcag   1560
aagatggaat tagactgatg acacactgtc cagctactca gcgaagacct gggtgaatta   1620
gcatggcact tcgcagctgt ctttagccag tcaggagaaa gaagtggagg ggccacgtgt   1680
atgtctccca gtgggcggta caccaggtgt tttcaaggtc ttttcaagga catttagcct   1740
ttccacctct gtcccctctt atttgtcccc tcctgtccag tgctgcctct tgcagtgctg   1800
gatatctggc tgtgtggtct gaacctccct ccattcctct gtattggtgc ctcacctaag   1860
gctaagtata cctccccccc cacccccaa ccccccaac tccccacccc cacccccac    1920
cccccacctc cccacccccc taccccccta cccccctacc cccctctggt ctgccctgca   1980
ctgcactgtt gccatgggca gtgctccagg cctgcttggt gtggacatgg tggtgagccg   2040
tggcaaggac cagaatggat cacagatgat cgttggccaa ttggcctccc aatatgtgtg   2100
attgtatttg tcgaggttgc tatgcactag agaaggaaag tgctcccctc atccccactt   2160
ttcccttcca gcaggaagtg cccaccccat aagacccttt tatttggaga gtctaggtgc   2220
acaattgtaa gtgaccacaa gcatgcatct tggacattta tgtgcgtaat cgcacactgc   2280
tcattccatg tgaataaggt cctactctcc gacccctttt gcaatacaga agggttgctg   2340
ataacgcagt cccctttctt tggcatgttg tgtgtgatta taatcgtctg ggatcctatg   2400
cactagaaaa ggagggtcct ctccacatac ctcagtctca cctttccctt ccagcaggga   2460
gtgcccactc cataagactc tcacatttgg acagtcaagg tgcgtaattg ttaagtgaac   2520
acaaccatgc accttagaca tggatttgca taactacaca cagctcaacc tatctgaata   2580
aaatcctact ctcagacccc ttttgcagta cagcaggggt gctgatcacc aaggcccttt   2640
ttcctggcct ggtatgcgtg tgattatgtt tgtcccggtt cctgtgtatt agacatggaa   2700
gcctcccctg ccacactcca cccccaatct tcctttccct tccggcagga gtgccctctc   2760
cataagacgc ttacgtttgg acaatcaagg tgcacagttg taagtgacca caggcataca   2820
```

-continued

```
ccttggacat taatgtgcat aaccactttg cccattccat ctgaataagg tcctactctc   2880
agaccccttt tgcagtacag caggggtgct gatcaccaag gccccttttc ttggcctgtt   2940
atgtgcgtga ttatatttgt ctgggttcct gtgtattaga caaggaagcc ttccccccgc   3000
ccccaccccc actcccagtc ttcctttccc ttccagcagg gagtgccccc tccataagat   3060
cattacattt ggacaatcaa ggtgcacaat tataagtgac cacagccatg caccttggac   3120
attattggac attaatgtgc gtaactgcac atggcccatc ccatctgaat aaggacctac   3180
tctcagatgc ctttgcagta cagcaggggt actgaatcac caaggccctt tttcttggcc   3240
tgttatgtgt gtgattatat ttatcccagt ttctgtgtaa tagacatgaa agcctcccct   3300
gccacacccc acctccaatc ttcctttccc ttccaccagg gagtgtccac tccatatacc   3360
cttacatttg gacaatcaag gtgcacaatt gtaagtgagc ataggcactc accttggaca   3420
tgaatgtgca taactgcaca tggcccatcc catctgaata aggtcctact ctcagaccct   3480
ttttgcagta cagcaggggt gctgatcacc aaggcccctt ttcctggcct gttatgtgtg   3540
tgattatatt tgttccagtt cctgtgtaat agacatggaa gcctcccctg ccacactcca   3600
cccccaatct tcctttcctt ctggcaggaa gtacccgctc cataagaccc ttacatttgg   3660
acagtcaagg tgcacaattg tatgtgacca caaccatgca ccttggacat aaatgtgtgt   3720
aactgcacat ggcccatccc atctgaataa ggtcctactc tcagacccct tttgcagtac   3780
agtaggtgtg ctgataacca aggcccctct tcctggcctg ttaacgtatg tgattatatt   3840
tgtctgggtt ccagtgtata agacatggaa gcctcccctg ccccacccca ccctcaatct   3900
tcctttccct tctggcaggg agtgccagct ccataagaac cttacatttg gacagtcaag   3960
gtgcacaatt ctaagtgacc gcagccatgc accttggtca ataatgtgtg taactgcaca   4020
cggcctatct catctgaata aggccttact ctcagacccc ttttgcagta cagcaggggt   4080
gctgataacc aaggcccatt ttcctggcct gttatgtgtg tgattatatt tgtccaggtt   4140
tctgtgtact agacaaggaa gcctcctctg ccccatccca tctacgcata atctttcttt   4200
tcctcccagc agggagtgct cactccataa gacccttaca tttggacaat caaggtgcac   4260
aattgtaagt gaccacaacc atgcatcttg gaaatttatg tgcataactg cacatggctt   4320
atcctatttg aataaagtcc tactctcaga ccccctttgc agtatagctg ggtgctgat    4380
cactgaggcc tctttgcttg gcttgtctat attcttgtgt actagataag ggcaccttct   4440
catggactcc ctttgctttt caacaaggag tacccactac tttttaagat tcttatattt   4500
gtccaaagta catggtttta attgaccaca acaatgtccc ttggacatta atgtatgtaa   4560
tcaccacatg gttcatccta attaaacaaa gttctacctt ctcaccctcc atttgcagta   4620
taccagggtt gctgaccccc taagtcccct tttcttggct tgttgacatg cataattgca   4680
tttatgttgg ttcttgtgcc ctagacaagg atgccccacc tcttttcaat agtgggtgcc   4740
cactccttat gatctttaca tttgaacagt taatgtgaat aattgcagtt gtccacaacc   4800
ctatcacttc taggaccatt atacctcttt tgcattactg tggggtatac tgtttccctc   4860
caaggcccct tctggtggac tatcaacata taattgaaat tttcttttgt ctttgtcagt   4920
agattaaggt cataccccat cacctttcct ttgtagtaca acagggtgtc ctgatcaacc   4980
aaagtcctgt tgttttggac tgttaatatg tgcaattaca tttgctcctg atctgtgcac   5040
tagataagga tcctacctac tttcttagtg tttttagcag gtagtgccca ctactcaaga   5100
ctgtcacttg gaatgttcat gtgcacaaac tcaattctct aagcatgttc ctgtaccacc   5160
```

-continued

```
tttgctttag agcaggggga tgatattcac taagtgcccc ttcttttgga cttaatatgc   5220
attaatgcaa ttgtccacct cttcttttag actaagagtt gatctccaca tattcccctt   5280
gcatcagggg catgttaatt atgaatgaac ccttttcttt taatattaat gtcataattg   5340
tatttgtgga cctgtgtagg agaaaaagac cctatgttcc tcccattacc ctttggattg   5400
ctgctgagaa gtgttaacta ctcataatct cagctcttgg acaattaata gcattaataa   5460
caattatcaa gggcactgat cattagataa gactcctgct tcctcgttgc ttacatcggg   5520
ggtactgacc cactaaggcc ccttgtactg ttaatgtgaa tatttgcaat tatatatgtc   5580
tccttctggt agagtgggat attatgccct agtatcccct ttgcattact gcaggggctg   5640
ctgactactc aaaacttctc ctgggactgt taataggcac aatggcagtt atcaatggtt   5700
ttctccctcc ctgaccttgt taagcaagcg ccccacccca cccttagttt cccatggcat   5760
aataaagtat aagcattgga gtattccatg cacttgtcta tcaaacagtg gtccatactc   5820
ccaacccttt tgcattgcgc cagtgtgtaa aatcacaggt agccatggtg tcatgcttta   5880
tatacgaagt cttccctctc tctgcccctt gtgtgccctt ggcccctttt tacagactat   5940
tgctcacaat ctcaggtgtc catatttgca gctattaggt aagattgtgc tgtctccctc   6000
ttcccttccc tctgccctgc ccttttttgcc tctttgctgg gtaatgttga ccggacaagg   6060
ccctttctct tggacttaaa caattctcag ttgcactttc cttggtccca cccattatac   6120
atgaacccct ctacttcctt tcgcattgct tctgagtatg ctgactaccc aaagcccctt   6180
ctgtgttatt aataaacaca gtactgattg tcccattttt cagcccatca gtccaagatc   6240
tccctaccac tttggtgtgt tggtgcagtg ttgactatga aaagcaggcc tgaactaggt   6300
ggataagcct tcactcattt tctttcattt attaatgatc ctagtttcaa ttattgtcag   6360
attctgggga caagaaccat tcttgcccac ctgtgttact gctttactgt gcaaaatact   6420
gaaggcaagt cagacccagg gagctggatt gccatccttt attttgtgtt tccagtgtac   6480
actataaaat tgtctcccca ggaaggaagg ttggcacttt ctctgcattc ttctttccag   6540
agcagattgc ctggttaaga atctcttgtt gtcccctttg tatattgtta ttgtaaagtg   6600
ccaaatgcca ggatacagcc agaaaaattg cttattatta ttaaaaaaat ttttttaaga   6660
aagacatctg gattgtaggg tggactcgat aacctggtca ttattttttt gaagccaaaa   6720
tatccattta tactatgtac ctggtgacca gtgtctctca ttttaactga gggtggtggg   6780
tctgtggata gaacactgac tcttgctatt ttaatatcaa agatattcta gatccagcac   6840
agtggcggcc cgataccgtc gacc                                          6864
```

```
<210> SEQ ID NO 12
<211> LENGTH: 685
<212> TYPE: DNA
<213> ORGANISM: Artificial Sequence
<220> FEATURE:
<223> OTHER INFORMATION: DYRK1A LEFT ARM

<400> SEQUENCE: 12

atggtaattg agaaatgaca agaatcatgg aactccaaat tcatgacaat atttgggtaa     60
gacgtctacc tttccctcca tacctaaatt aactaaacgg gtttcgctgt gtcttcaacc    120
atcgatcgat catttaccgt tttaacttag gtctgaggaa taccacaatt aacgatatcg    180
atttctactt tgacctcaac acggtgagga acgtgtgaaa atagacagtg ggagaatccg    240
acaaaatctt ttagggtaca aaatcgaacg gtaagacaac tgggtcggac ggaaagatcg    300
gaattgaatg gggagacaga tataagataa aaggtcggtt tatactccac tgcaaattcg    360
```

```
acgatgaact ttctcttcac cctcaatccg tctcgtcatc cccttagtac aaacccccttc    420

tcacttctca catgaactct ctcacacctc cacggaacct cctcgacctc gggtctccac    480

ggggtactct tgttgtgtcc tccgacgtcc acctccaccc acggactaac atcttacgaa    540

agatcaacag aaggtgtcct gtaaaaaccc tcgataagtg ttctaagtac cgatggcacg    600

agattttaaa ctacacttca agtaaaaagg acctgaagaa tgaattaagg agacagaaaa    660

ccgggtcggt ggggaaacgg tcaaa                                          685
```

<210> SEQ ID NO 13
<211> LENGTH: 502
<212> TYPE: DNA
<213> ORGANISM: Artificial Sequence
<220> FEATURE:
<223> OTHER INFORMATION: DYRK1A RIGHT ARM

<400> SEQUENCE: 13

```
ccactactcg tccgacaaac ctttcttgca ggagctcgtc ccacgacaaa ggattgggac     60

gcagaaaaag gggagactct agtcaaatag aaataagtga acgtccacaa gttgttagaa    120

cagaaaatac cccttaaaga ttacacagaa ctcgtgaaag ggtgggagga tagaacctcc    180

gtaccaagtc tcacctttc ccgcgcccgg gtggatggag accggaaggg tggagtcggt    240

ggtacgaatc ccggcaccac ctcacgaact ggagaaacac acatgttacg ttatgtacga    300

ccttattacg gtggaatacg tatcccgaaa acacccacat tcccgtatgg ccttgttcaa    360

ccgtatctta ttctcaagtc acttacaaca gtgatgaaaa ataatgaaaa attaacactt    420

tttgagtgtc taagacatta tttcccagta tctttggacg aaataggtat gatagtaatg    480

actcttatga aagaccaaaa gc                                             502
```

<210> SEQ ID NO 14
<211> LENGTH: 18515
<212> TYPE: DNA
<213> ORGANISM: Artificial Sequence
<220> FEATURE:
<223> OTHER INFORMATION: targeting CONSTRUCT 1 (3G/FL/hXIST/DYRK1A)

<400> SEQUENCE: 14

```
ctcgagttta ctccctatca gtgatagaga acgtatgaag agtttactcc ctatcagtga     60

tagagaacgt atgcagactt tactccctat cagtgataga gaacgtataa ggagtttact    120

ccctatcagt gatagagaac gtatgaccag tttactccct atcagtgata gagaacgtat    180

ctacagttta ctccctatca gtgatagaga acgtatatcc agtttactcc ctatcagtga    240

tagagaacgt ataagcttta ggcgtgtacg gtgggcgcct ataaaagcag agctcgttta    300

gtgaaccgtc agatcgcctg gagcaattcc acaacacttt tgtcttatac caactttccg    360

taccacttcc taccctcgta aagtcgacac cggggcccag atctggtacc gagctcggat    420

ccactagtcc agtgtggtgg aattctgcag attctagaac attttctagt cccccaacac    480

cctttatggc gtatttcttt aaaaaaatca cctaaattcc ataaaatatt tttttaaatt    540

ctatactttc tcctagtgtc ttcttgacac gtcctccata ttttttttaaa gaaagtattt    600

ggaatatttt gaggcaattt ttaatattta aggaattttt ctttggaatc atttttggtg    660

acatctctgt tttttgtgga tcagtttttt actcttccac tctcttttct atattttgcc    720

catcggggct gcggatacct ggttttatta ttttttcttt gcccaacggg gccgtggata    780

cctgcctttt aattcttttt tattcgccca tcggggccgc ggatacctgc tttttatttt    840
```

-continued

```
tttttcctta gcccatcggg gtatcggata cctgctgatt cccttcccct ctgaaccccc    900
aacactctgg cccatcgggg tgacggatat ctgcttttta aaaattttct ttttttggcc    960
catcggggct tcggatacct gctttttttt tttttatttt ccttgcccat cggggcctcg   1020
gatacctgct ttaatttttg tttttctgcc catcggggcc gcggatacct gctttgattt   1080
tttttttca tcgcccatcg gtgcttttta tggatgaaaa aatgttggtt ttgtgggttg   1140
ttgcactctc tggaatatct acactttttt ttgctgctga tcatttggtg gtgtgtgagt   1200
gtacctaccg ctttggcaga gaatgactct gcagttaagc taagggcgtg ttcagattgt   1260
ggaggaaaag tggccgccat tttagacttg ccgcataact cggcttaggg ctagtcgttt   1320
gtgctaagtt aaactaggga ggcaagatgg atgatagcag gtcaggcaga ggaagtcatg   1380
tgcattgcat gagctaaacc tatctgaatg aattgatttg gggcttgtta ggagctttgc   1440
gtgattgttg tatcgggagg cagtaagaat catcttttat cagtacaagg gactagttaa   1500
aaatggaagg ttaggaaaga ctaaggtgca gggcttaaaa tggcgatttt gacattgcgg   1560
cattgctcag catggcgggc tgtgctttgt taggttgtcc aaaatggcgg atccagttct   1620
gtcgcagtgt tcaagtggcg ggaaggccac atcatgatgg gcgaggcttt gttaagtggt   1680
tagcatggtg gtggacatgt gcggtcacac aggaaaagat ggcggctgaa ggtcttgccg   1740
cagtgtaaaa catggcgggc ctctttgtct ttgctgtgtg cttttcgtgt tgggttttgc   1800
cgcagggaca atatggcagg cgttgtcata tgtatatcat ggcttttgtc acgtggacat   1860
catggcgggc ttgccgcatt gttaaagatg gcgggttttg ccgcctagtg ccacgcagag   1920
cgggagaaaa ggtgggatgg acagtgctgg attgctgcat aacccaacca attagaaatg   1980
ggggtggaat tgatcacagc caattagagc agaagatgga attagactga tgacacactg   2040
tccagctact cagcgaagac ctgggtgaat tagcatggca cttcgcagct gtctttagcc   2100
agtcaggaga aagaagtgga ggggccacgt gtatgtctcc cagtgggcgg tacaccaggt   2160
gttttcaagg tcttttcaag gacatttagc ctttccacct ctgtcccctc ttatttgtcc   2220
cctcctgtcc agtgctgcct cttgcagtgc tggatatctg gctgtgtggt ctgaacctcc   2280
ctccattcct ctgtattggt gcctcaccta aggctaagta tacctccccc cccacccccc   2340
aacccccccca actccccacc cccacccccc accccccacc tccccacccc cctaccccccc   2400
tacccccccta cccccctctg gtctgccctg cactgcactg ttgccatggg cagtgctcca   2460
ggcctgcttg gtgtggacat ggtggtgagc cgtggcaagg accagaatgg atcacagatg   2520
atcgttggcc aacaggtggc agaagaggaa ttcctgcctt cctcaagagg aacacctacc   2580
ccttggctaa tgctggggtc ggattttgat ttatatttat cttttggatg tcagtcatac   2640
agtctgattt tgtggtttgc tagtgtttga atttaagtct taagtgacta ttatagaaat   2700
gtattaagag gctttatttg tagaattcac tttaattaca tttaatgagt ttttgttttg   2760
agttccttaa aattccttaa agtttttagc ttctcattac aaattcctta accttttttt   2820
ggcagtagat agtcaaagtc aaatcatttc taatgtttta aaaatgtgct ggtcattttc   2880
tttgaaattg acttaactat tttcctttga agagtctgta gcacagaaac agtaaaaaat   2940
ttaacttcat gacctaatgt aaaaaagagt gtttgaaggt ttacacaggt ccaggccttg   3000
ctttgttccc atccttgatg ctgcactaat tgactaatca cctacttatc agacaggaaa   3060
cttgaattgc tgtggtctgg tgtcctctat tcagacttat tatattggag tatttcaatt   3120
tttcgttgta tcctgcctgc ctagcatcca gttcctcccc agccctgctc ccagcaaacc   3180
cctagtctag ccccagccct actcccaccc ggccccagcc ctgccccagg cccagtcccc   3240
```

-continued taacccccca gccctaggcc cagtcccagt cctagttcct cagtctgtcc agcttctctc 3300
gaaagtcact ctaattttca ttgattcagt gctcaaaata agttgtccat tggtatccta 3360
ttatactggg atattccgtt tacccttggc attgctgatc ttcagtactg actccttgac 3420
cattttcagt taagcataca atcccatttg tctgtgatct caggacaaag aatttcctta 3480
ctcggtacgt tgaagttagg gaatgtcaat tgagagcttt ctatcagagc attattgccc 3540
acaatttgag ttacttatca ttttctcgat cccctgccct taaaggagaa accatttctc 3600
tgtcattgct tctgtagtca cagtcccaat tttgagtagt gatcttttct tgtgtactgt 3660
gttggccacc taaaactctt tgcattgagt aaaattctaa ttgccaataa tcctacccat 3720
tggattagac agcactctga accccatttg cattcagcag ggggtcgcag acaacccgtc 3780
ttttgttgga cagttaaaat gctcagtccc aattgtcata gctttgccta ttaaacaaag 3840
gcaccctact gcgctttttg ctgtgcttct ggagaatcct gctgttcttg gacaattaaa 3900
gaacaaagta gtaattgcta attgtctcac ccattaatca tgaagactac cagtcgccct 3960
tgcatttgcc ttgaggcagc gctgactacc tgagatttaa gagtttctta aattattgag 4020
taaaatccca attatccata gttctgttag ttacactatg gcctttgcaa acatctttgc 4080
ataacagcag tgggactgac tcattcttag agccccttcc cttggaatat taatggatac 4140
aatagtaatt attcatggtt ctgcgtaaca gagaagaccc acttatgtgt atgcctttat 4200
cattgctcct agatagtgtg aactacctac caccttgcat taatatgtaa aacactaatt 4260
gcccatagtc ccactcatta gtctaggatg tcctctttgc cattgctgct gagttctgac 4320
tacccaagtt tccttctctt aaacagttga tatgcataat tgcatatatt catggttctg 4380
tgcaataaaa atggattctc accccatccc accttctgtg ggatgttgct aacgagtgca 4440
gattattcaa taacagctct tgaacagtta atttgcacag ttgcaattgt ccagagtcct 4500
gtccattaga aagggactct gtatcctatt tgcacgctac aatgtgggct gatcacccaa 4560
ggactcttct tgtgcattga tgttcataat tgtatttgtc cacgatcttg tgcactaacc 4620
cttccactcc ctttgtattc cagcagggga cccttactac tcaagacctc tgtactagga 4680
cagtttatgt gcacaatcct aattgattag aactgagtct tttatatcaa ggtccctgca 4740
tcatctttgc tttacatcaa gagggtgctg gttacctaat gcccctcctc cagaaattat 4800
tgatgtgcaa aatgcaattt ccctatctgc tgttagtctg gggtctcatc ccctcatatt 4860
ccttttgtct tacagcaggg ggtacttggg actgttaatg cgcataattg caattatggt 4920
cttttccatt aaattaagat cccaactgct cacaccctct tagcattaca gtagagggtg 4980
ctaatcacaa ggacatttct tttgtactgt taatgtgcta cttgcatttg tccctcttcc 5040
tgtgcactaa agaccccact cacttcccta gtgttcagca gtggatgacc tctagtcaag 5100
acctttgcac taggatagtt aatgtgaacc atggcaactg atcacaacaa tgtctttcag 5160
atcagatcca ttttatcctc cttgttttac agcaagggat attaattacc tatgttacct 5220
ttccctggga ctatgaatgt gcaaaattcc aatgttcatg gtctctccct ttaaacctat 5280
attctacccc ttttacatta tagaaaggga tgctggaaac ccagagtcct tctcttggga 5340
ctcttaatgt gtatttctaa ttatccatga ctcttaatgt gcatattttc aattgcctaa 5400
ttgatttcaa ttgtctaaga catttcaaat gtctaattga ttagaactga gtcttttata 5460
tcaagctaat atctagcttt tatatcaagc taatatcttg acttctcagc atcatagaag 5520
ggggtactga tttcctaaag tctttcttga atttctatta tgcaaaattg ccctgaggcc 5580
gggtgtggtg gctcacacct gtaatcccag cactttggga ggctgaggtg ggaagatccc 5640
ttactgccag gagtttgaga ccagcctggc caacattaaa aaaaaaaaaa aaagtaagac 5700
aattgccctg gaatcccatc cccctcacac ctccttggca aagcagcagg agtgctaact 5760
agctagtgct tcttctctta tactgcttaa atgcgcataa ttagcagtag ttgatgtgcc 5820
cctatgttag agtagaatcc cgcttccttg ctccatttgc attactgcag gagcttctaa 5880
ctagcctgaa ttcactctct tggactgtta atgtgcatac ttatatttgc tgctgtactt 5940
ttttaccatg taaggacccc acccactgta tttacatccc agctggaagt acctactact 6000
taagaccctt agactagtaa agttagcgtg cataatctta ggtgttatat acacattttc 6060
agttgcatac agttgtgcct tttatcagga ctcctgtact tatcaaagca gagagtgcta 6120
atcaatatta agcccttctc ttcgaactgt agatggcatg taattgcagt tgtcaatggt 6180
ccttcaatta gacttgggtt tctgacctat cacaccctct ttgctttatt gcatggggta 6240
ctattcactt aaggcccctt tctcaaactg ttaatgtgcc taatgacaat tacatcagta 6300
tccttccttt tgaaggacag catggttggt gacacctaag gccccatttc ttggcctccc 6360
aatatgtgtg attgtatttg tcgaggttgc tatgcactag agaaggaaag tgctcccctc 6420
atccccactt ttcccttcca gcaggaagtg cccaccccat aagacccttt tatttggaga 6480
gtctaggtgc acaattgtaa gtgaccacaa gcatgcatct tggacattta tgtgcgtaat 6540
cgcacactgc tcattccatg tgaataaggt cctactctcc gaccccttt gcaatacaga 6600
agggttgctg ataacgcagt cccctttct tggcatgttg tgtgtgatta taatcgtctg 6660
ggatcctatg cactagaaaa ggagggtcct ctccacatac ctcagtctca cctttccctt 6720
ccagcaggga gtgcccactc cataagactc tcacatttgg acagtcaagg tgcgtaattg 6780
ttaagtgaac acaaccatgc accttagaca tggatttgca taactacaca cagctcaacc 6840
tatctgaata aaatcctact ctcagacccc ttttgcagta cagcaggggt gctgatcacc 6900
aaggcccttt ttcctggcct ggtatgcgtg tgattatgtt tgtcccggtt cctgtgtatt 6960
agacatggaa gcctcccctg ccacactcca cccccaatct tcctttccct tccggcagga 7020
gtgccctctc cataagacgc ttacgtttgg acaatcaagg tgcacagttg taagtgacca 7080
caggcataca ccttggacat taatgtgcat aaccactttg cccattccat ctgaataagg 7140
tcctactctc agaccccttt tgcagtacag caggggtgct gatcaccaag gccccttttc 7200
ttggcctgtt atgtgcgtga ttatatttgt ctgggttcct gtgtattaga caaggaagcc 7260
ttccccccgc ccccaccccc actcccagtc ttcctttccc ttccagcagg gagtgccccc 7320
tccataagat cattacattt ggacaatcaa ggtgcacaat tataagtgac cacagccatg 7380
caccttggac attattggac attaatgtgc gtaactgcac atggcccatc ccatctgaat 7440
aaggacctac tctcagatgc ctttgcagta cagcaggggt actgaatcac caaggccctt 7500
tttcttggcc tgttatgtgt gtgattatat ttatcccagt ttctgtgtaa tagacatgaa 7560
agcctcccct gccacacccc acctccaatc ttcctttccc ttccaccagg gagtgtccac 7620
tccatatacc cttacatttg gacaatcaag gtgcacaatt gtaagtgagc ataggcactc 7680
accttggaca tgaatgtgca taactgcaca tggcccatcc catctgaata aggtcctact 7740
ctcagaccct ttttgcagta cagcaggggt gctgatcacc aaggcccctt ttcctggcct 7800
gttatgtgtg tgattatatt tgttccagtt cctgtgtaat agacatggaa gcctcccctg 7860
ccacactcca cccccaatct tcctttcctt ctggcaggaa gtacccgctc cataagaccc 7920
ttacatttgg acagtcaagg tgcacaattg tatgtgacca caaccatgca ccttggacat 7980

-continued

```
aaatgtgtgt aactgcacat ggcccatccc atctgaataa ggtcctactc tcagacccct   8040
tttgcagtac agtaggtgtg ctgataacca aggcccctct tcctggcctg ttaacgtatg   8100
tgattatatt tgtctgggtt ccagtgtata agacatggaa gcctcccctg ccccacccca   8160
ccctcaatct tcctttccct tctggcaggg agtgccagct ccataagaac cttacatttg   8220
gacagtcaag gtgcacaatt ctaagtgacc gcagccatgc accttggtca ataatgtgtg   8280
taactgcaca cggcctatct catctgaata aggccttact ctcagacccc ttttgcagta   8340
cagcaggggt gctgataacc aaggcccatt ttcctggcct gttatgtgtg tgattatatt   8400
tgtccaggtt tctgtgtact agacaaggaa gcctcctctg ccccatccca tctacgcata   8460
atctttcttt tcctcccagc agggagtgct cactccataa gacccttaca tttggacaat   8520
caaggtgcac aattgtaagt gaccacaacc atgcatcttg gaaatttatg tgcataactg   8580
cacatggctt atcctatttg aataaagtcc tactctcaga ccccctttgc agtatagctg   8640
gggtgctgat cactgaggcc tctttgcttg gcttgtctat attcttgtgt actagataag   8700
ggcaccttct catggactcc ctttgctttt caacaaggag tacccactac tttttaagat   8760
tcttatattt gtccaaagta catggtttta attgaccaca acaatgtccc ttggacatta   8820
atgtatgtaa tcaccacatg gttcatccta attaaacaaa gttctacctt ctcaccctcc   8880
atttgcagta taccagggtt gctgaccccc taagtcccct tttcttggct tgttgacatg   8940
cataattgca tttatgttgg ttcttgtgcc ctagacaagg atgccccacc tcttttcaat   9000
agtgggtgcc cactccttat gatctttaca tttgaacagt taatgtgaat aattgcagtt   9060
gtccacaacc ctatcacttc taggaccatt atacctcttt tgcattactg tggggtatac   9120
tgtttccctc caaggcccct tctggtggac tatcaacata taattgaaat tttcttttgt   9180
ctttgtcagt agattaaggt cataccccat cacctttcct ttgtagtaca acagggtgtc   9240
ctgatcaacc aaagtcctgt tgttttggac tgttaatatg tgcaattaca tttgctcctg   9300
atctgtgcac tagataagga tcctacctac tttcttagtg tttttagcag gtagtgccca   9360
ctactcaaga ctgtcacttg gaatgttcat gtgcacaaac tcaattctct aagcatgttc   9420
ctgtaccacc tttgctttag agcaggggga tgatattcac taagtgcccc ttcttttgga   9480
cttaatatgc attaatgcaa ttgtccacct cttcttttag actaagagtt gatctccaca   9540
tattcccctt gcatcagggg catgttaatt atgaatgaac ccttttcttt taatattaat   9600
gtcataattg tatttgtgga cctgtgtagg agaaaaagac cctatgttcc tcccattacc   9660
ctttggattg ctgctgagaa gtgttaacta ctcataatct cagctcttgg acaattaata   9720
gcattaataa caattatcaa gggcactgat cattagataa gactcctgct tcctcgttgc   9780
ttacatcggg ggtactgacc cactaaggcc ccttgtactg ttaatgtgaa tatttgcaat   9840
tatatatgtc tccttctggt agagtgggat attatgccct agtatcccct ttgcattact   9900
gcaggggctg ctgactactc aaaacttctc ctgggactgt taataggcac aatggcagtt   9960
atcaatggtt ttctccctcc ctgaccttgt taagcaagcg ccccacccca cccttagttt  10020
cccatggcat aataaagtat aagcattgga gtattccatg cacttgtcta tcaaacagtg  10080
gtccatactc ccaacccttt tgcattgcgc cagtgtgtaa aatcacaggt agccatggtg  10140
tcatgcttta tatacgaagt cttccctctc tctgcccctt gtgtgccctt ggccccttttt  10200
tacagactat tgctcacaat ctcaggtgtc catatttgca gctattaggt aagattgtgc  10260
tgtctccctc ttcccttccc tctgccctgc cccttttgcc tctttgctgg gtaatgttga  10320
```

-continued

```
ccagacaagg ccctttctct tggacttaaa caattctcag ttgcactttc cttggtccac  10380
ccattataca tgaacccctc tacttccttt cgcattgctt ctgagtatgc tgactaccca  10440
aagccccttc tgtgttatta ataaacacag tactgattgt cccatttttc agcccatcag  10500
tccaagatct ccctaccact ttggtgtgtt ggtgcagtgt tgactatgaa aagcaggcct  10560
gaactaggtg gataagcctt cactcatttt ctttcattta ttaatgatcc tagtttcaat  10620
tattgtcaga ttctggggac aagaaccatt cttgcccacc tgtgttactg ctttactgtg  10680
caaaatactg aaggcaagtc agacccaggg agctggattg ccatcccttta ttttgtgttt  10740
ccagtgtaca ctataaaatt gtctccccag gaaggaaggt tggcactttc tctgcattct  10800
tctttccaga gcagattgcc tggttaagaa tctcttgttg tcccttctgt atattgttat  10860
tgtaaagtgc caaatgccag gatacagcca gaaaaattgc ttattattat taaaaaaatt  10920
tttttaagaa agacatctgg attgtagggt ggactcgata acctggtcat tatttttttg  10980
aagccaaaat atccatttat actatgtacc tggtgaccag tgtctctcat tttaactgag  11040
ggtggtgggt ctgtggatag aacactgact cttgctattt taatatcaaa gatattctag  11100
atccagcaca gtggcggccg ctctagagtg gaactcttaa gaccagtatc tttgtgtggg  11160
ctttaccagc attcactttt agaaaaacta cctaaatttt ataatccttt aatttcttca  11220
tctggagcac ctgcccctac ttatttcaag aagattgcag taaaacgatt aaatgaggga  11280
acatatgcag aggtgctttt aaaaagcata tgccaccttt tttattaatt attatataaa  11340
atgaagcatt taattatagt aataatttga agtagtttga agtaccacac tgaggtgagg  11400
acttaaaaat gataagacga gttccctatt ttataagaaa aataagccaa aattaaatat  11460
tcttttggat ataaatttca acagtgagat agctgcctag tggaaatgaa taatatccca  11520
gccactagtg tacagggtgt tttgtggcac aggattatgt aatatggaac tgctcaagca  11580
aataactagt catcacaaca gcagttcttt gtaataactg aaaaagaata ttgtttctcg  11640
gagaaggatg tcaaaagatc ggcccagctc agggagcagt ttgccctact agctcctcgg  11700
acagctgtaa agaagagtct ctggctcttt agaatactga tcccattgaa gataccacgc  11760
tgcatgtgtc cttagtagtc atgtctcctt aggctcctct tggacattct gagcatgtga  11820
gacctgagga ctgcaaacag ctataagagg ctccaaatta atcatatctt tccctttgag  11880
aatctggcca agctccagct aatctacttg gatgggttgc cagctatctg gagaaaaaga  11940
tcttcctcag aagaataggc ttgttgtttt acagtgttag tgatccattc cctttgacga  12000
tccctaggtg gagatggggc atgaggatcc tccaggggaa aagctcacta ccactgggca  12060
acaaccctag gtcaggaggt tctgtcaaga tactttcctg gtcccagata ggaagataaa  12120
gtctcaaaaa caaccaccac acgtcaagct cttcattgtt cctatctgcc aaatcattat  12180
acttcctaca agcagtgcag agagctgagt cttcagcagg tccaagaaat ttgaacacac  12240
tgaaggaagt cagccttccc acctgaagat caacatgcct ggcactctag cacttgagga  12300
tagctgaatg aatgtgtatt tctttgtctc tttctttctt gtctttgctc tttgttctct  12360
atctaaagtg tgtcttaccc atttccatgt ttctcttgct aatttctttc gtgtgtgcct  12420
ttgcctcatt ttctcttttt gttcacaaga gtggtctgtg tcttgtctta gacatatctc  12480
tcatttttca ttttgttgct atttctcttt gctctcctag atgtggctct tctttcacgc  12540
tttatttcat gtctcctttt tgggtcacat gctgtgtgct ttttgtcctt ttcttgttct  12600
gtctacctct cctttctctg cctacctctc ttttctcttt gtgaactgtg attatttgtt  12660
accccttccc cttctcgttc gttttaaatt tcaccttttt tctgagtctg gcctcctttc  12720
```

tgctgtttct actttttatc tcacatttct catttctgca tttcctttct gcctctcttg 12780
ggctattctc tctctcctcc cctgcgtgcc tcagcatctc ttgctgtttg tgattttcta 12840
tttcagtatt aatctctgtt ggcttgtatt tgttctctgc ttcttccctt tctactcacc 12900
tttgagtatt tcagcctctt catgaatcta tctccctctc tttgatttca tgtaatctct 12960
ccttaaatat ttctttgcat atgtgggcaa gtgtacgtgt gtgtgtgtca tgtgtggcag 13020
aggggcttcc taacccctgc ctgataggtg cagaacgtcg gctatcagag caagcattgt 13080
ggagcggttc cttatgccag gctgccatgt gagatgatcc aagaccaaaa caaggcccta 13140
gactgcagta aaacccagaa ctcaagtagg gcagaaggtg gaaggctcat atggatagaa 13200
ggcccaaagt ataagacaga tggtttgaga cttgagaccc gaggactaag atggaaagcc 13260
catgttccaa gatagataga agcctcaggc ctgaaaccaa caaaagcctc aagagccaag 13320
aaaacagagg gtggcctgaa ttggaccgaa ggcctgagtt ggatggaagt ctcaaggctt 13380
gagttagaag tcttaagacc tgggacagga cacatggaag gcctaagaac tgagacttgt 13440
gacacaaggc caacgaccta agattagccc agggttgtag ctggaagacc tacaacccaa 13500
ggatggaagg cccctgtcac aaagcctacc tagatggata gaggacccaa gcgaaaaagg 13560
tatctcaaga ctaacggccg gaatctggag gcccatgacc cagaacccag gaaggataga 13620
agcttgaaga cctggggaaa tcccaagatg agaaccctaa accctacctc ttttctattg 13680
tttacacttc ttactcttag atatttccag ttctcctgtt tatctttaag cctgattctt 13740
ttgagatgta ctttttgatg ttgccggtta cctttagatt gacagtatta tgcctgggcc 13800
agtcttgagc cagctttaaa tcacagcttt tacctatttg ttaggctata gtgttttgta 13860
aacttctgtt tctattcaca tcttctccac ttgagagaga caccaaaatc cagtcagtat 13920
ctaatctggc ttttgttaac ttccctcagg agcagacatt catataggtg atactgtatt 13980
tcagtccttt cttttgaccc cagaagccct agactgagaa gataaaatgg tcaggttgtt 14040
ggggaaaaaa aaagtgccag gctctctaga gaaaaatgtg aagagatgct ccaggccaat 14100
gagaagaatt agacaagaaa tacacagatg tgccagactt ctgagaagca cctgccagca 14160
acagcttcct tctttgagct tagattttcc tagtccatcc ctcatgaaaa atgactgacc 14220
actgctgggc agcaggaggg atgatgacca actaattccc aaaccccagt ctcattggta 14280
ccatcgatcg gccggatatc acgcgtcata tggctagcct gcagggatcc aatgtaactg 14340
tattcagcga tgacgaaatt cttagctatt gtaatactct agaggatctt tgtgaaggaa 14400
ccttacttct gtggtgtgac ataattggac aaactaccta cagagattta aagctctaag 14460
gtaaatataa aatttttaag tgtataatgt gttaaactac tgattctaat tgtttgtgta 14520
ttttagattc caacctatgg aactgatgaa tgggagcagt ggtggaatgc ctttaatgag 14580
gaaaacctgt tttgctcaga agaaatgcca tctagtgatg atgaggctac tgctgactct 14640
caacattcta ctcctccaaa aaagaagaga aaggtagaag accccaagga ctttccttca 14700
gaattgctaa gttttttgag tcatgctgtg tttagtaata gaactcttgc ttgctttgct 14760
atttacacca caaaggaaaa agctgcactg ctatacaaga aaattatgga aaaatattct 14820
gtaaccttta taagtaggca taacagttat aatcataaca tactgttttt tcttactcca 14880
cacaggcata gagtgtctgc tattaataac tatgctcaaa aattgtgtac ctttagcttt 14940
ttaatttgta aaggggttaa taaggaatat ttgatgtata gtgccttgac tagagatcat 15000
aatcagccat accacatttg tagaggtttt acttgcttta aaaaacctcc cacacctccc 15060
cctgaacctg aaacataaaa tgaatgcaat tgttgttgtt aacttgttta ttgcagctta 15120
taatggttac aaataaagca atagcatcac aaatttcaca aataaagcat ttttttcact 15180
gcattctagt tgtggtttgt ccaaactcat caatgtatct tatcatgtct gcggctctag 15240
agctgcatta atgaatcggc caacgcgcgg ggagaggcgg tttgcgtatt gggcgctctt 15300
ccgcttcctc gctcactgac tcgctgcgct cggtcgttcg gctgcggcga gcggtatcag 15360
ctcactcaaa ggcggtaata cggttatcca cagaatcagg ggataacgca ggaaagaaca 15420
tgtacgtaaa ctggcaaagg ggtggctggg ccaaaagaca gaggaattaa gtaagaagtc 15480
caggaaaaat gaacttcaca tcaaatttta gagcacggta gccatgaatc ttgtgaatag 15540
ctcccaaaaa tgtcctgtgg aagacaacta gaaagcattc tacaatcagg cacccacctc 15600
cacctgcagc ctcctgtgtt gttctcatgg ggcacctctg ggctccagct cctccaaggc 15660
acctccacac tctctcaagt acactcttca ctcttcccca aacatgattc ccctactgct 15720
ctgcctaact cccacttctc tttcaagtag cagcttaaac gtcacctcat atttggctgg 15780
aaaatagaat atagacagag ggtaagttta aggctagaaa ggcaggctgg gtcaacagaa 15840
tggcaagcta aaacatggga ttttctaaaa cagcctaaga gggtgacaga taaaagtgtg 15900
caaggagtgg cacaactcca gtttcatctt tagctatagc aattaacacc ataaggagtc 15960
tggattcaat tttgccattt actagctagc taccaacttc tgtgtcgctt tgggcaaatc 16020
aattaaatcc atacctccct ttccatctgc agaatgggtt tataacagta cttaaacctc 16080
aaggtactaa gaacagtaaa gagttaatgg tacatgtgag caaaaggcca gcaaaaggcc 16140
aggaaccgta aaaaggccgc gttgctggcg tttttccata ggctccgccc ccctgacgag 16200
catcacaaaa atcgacgctc aagtcagagg tggcgaaacc cgacaggact ataaagatac 16260
caggcgtttc cccctggaag ctccctcgtg cgctctcctg ttccgaccct gccgcttacc 16320
ggatacctgt ccgcctttct cccttcggga agcgtggcgc tttctcatag ctcacgctgt 16380
aggtatctca gttcggtgta ggtcgttcgc tccaagctgg gctgtgtgca cgaacccccc 16440
gttcagcccg accgctgcgc cttatccggt aactatcgtc ttgagtccaa cccggtaaga 16500
cacgacttat cgccactggc agcagccact ggtaacagga ttagcagagc gaggtatgta 16560
ggcggtgcta cagagttctt gaagtggtgg cctaactacg gctacactag aagaacagta 16620
tttggtatct gcgctctgct gaagccagtt accttcggaa aaagagttgg tagctcttga 16680
tccggcaaac aaaccaccgc tggtagcggt ggtttttttg tttgcaagca gcagattacg 16740
cgcagaaaaa aaggatctca agaagatcct ttgatctttt ctacggggtc tgacgctcag 16800
tggaacgaaa actcacgtta agggattttg gtcatgagat tatcaaaaag gatcttcacc 16860
tagatccttt taaattaaaa atgaagtttt aaatcaatct aaagtatata tgagtaaact 16920
tggtctgaca gttaccaatg cttaatcagt gaggcaccta tctcagcgat ctgtctattt 16980
cgttcatcca tagttgcctg actccccgtc gtgtagataa ctacgatacg ggagggctta 17040
ccatctggcc ccagtgctgc aatgataccg cgagacccac gctcaccggc tccagattta 17100
tcagcaataa accagccagc cggaagggcc gagcgcagaa gtggtcctgc aactttatcc 17160
gcctccatcc agtctattaa ttgttgccgg gaagctagag taagtagttc gccagttaat 17220
agtttgcgca acgttgttgc cattgctaca ggcatcgtgg tgtcacgctc gtcgtttggt 17280
atggcttcat tcagctccgg ttcccaacga tcaaggcgag ttacatgatc ccccatgttg 17340
tgcaaaaaag cggttagctc cttcggtcct ccgatcgttg tcagaagtaa gttggccgca 17400
gtgttatcac tcatggttat ggcagcactg cataattctc ttactgtcat gccatccgta 17460
agatgctttt ctgtgactgg tgagtactca accaagtcat tctgagaata gtgtatgcgg 17520
cgaccgagtt gctcttgccc ggcgtcaata cgggataata ccgcgccaca tagcagaact 17580
ttaaaagtgc tcatcattgg aaaacgttct tcggggcgaa aactctcaag gatcttaccg 17640
ctgttgagat ccagttcgat gtaacccact cgtgcaccca actgatcttc agcatctttt 17700
actttcacca gcgtttctgg gtgagcaaaa acaggaaggc aaaatgccgc aaaaaaggga 17760
ataagggcga cacggaaatg ttgaatactc atactcttcc tttttcaata ttattgaagc 17820
atttatcagg gttattgtct catgagcgga tacatatttg aatgtattta gaaaaataaa 17880
caaatagggg ttccgcgcac atttccccga aaagtgccac ctgacgtcta agaaaccatt 17940
attatcatga cattaaccta taaaaatagg cgtatcacga ggccctttcg tcttcaagaa 18000
ttcgaaaacc agaaagtatt ctcagtaatg atagtatgga taaagcaggt ttctatgacc 18060
ctttattaca gaatctgtga gtttttcaca attaaaaagt aataaaaagt agtgacaaca 18120
ttcactgaac tcttattcta tgccaacttg ttccggtatg cccttacacc cacaaaagcc 18180
ctatgcataa ggtggcatta ttccagcatg tattgcattg tacacacaaa gaggtcaagc 18240
actccaccac ggccctaagc atggtggctg aggtgggaag gccagaggta ggtgggcccg 18300 cgccctttc cactctgaac catgcctcca agataggagg gtgggaaagt gctcaagaca 18360
cattagaaat tccccataaa agacaagatt gttgaacacc tgcaagtgaa taaagataaa 18420
ctgatctcag aggggaaaaa gacgcagggt taggaaacag caccctgctc gaggacgttc 18480
tttccaaaca gcctgctcat cacccgttcg aattc 18515

<210> SEQ ID NO 15
<211> LENGTH: 9789
<212> TYPE: DNA
<213> ORGANISM: Artificial Sequence
<220> FEATURE:
<223> OTHER INFORMATION: puro/rtTA/AAVS1 construct

<400> SEQUENCE: 15
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagctca 240
gaattaaccc tcactaaagg gactagtcct gcaggtttaa acgaattcgc cctttgcttt 300
ctctgaccag cattctctcc cctgggcctg tgccgctttc tgtctgcagc ttgtggcctg 360
ggtcacctct acggctggcc cagatccttc cctgccgcct ccttcaggtt ccgtcttcct 420
ccactccctc ttccccttgc tctctgctgt gttgctgccc aaggatgctc tttccggagc 480
acttccttct cggcgctgca ccacgtgatg tcctctgagc ggatcctccc cgtgtctggg 540
tcctctccgg gcatctctcc tccctcaccc aaccccatgc cgtcttcact cgctgggttc 600
ccttttcctt ctccttctgg ggcctgtgcc atctctcgtt tcttaggatg gccttctccg 660
acggatgtct cccttgcgtc ccgcctcccc ttcttgtagg cctgcatcat caccgttttt 720
ctggacaacc ccaaagtacc ccgtctccct ggctttagcc acctctccat cctcttgctt 780
tctttgcctg gacaccccgt tctcctgtgg attcgggtca cctctcactc ctttcatttg 840
ggcagctccc ctaccccccct tacctctcta gtctgtgcta gctcttccag ccccctgtca 900
tggcatcttc caggggtccg agagctcagc tagtcttctt cctccaaccc gggcccctat 960

-continued

```
gtccacttca ggacagcatg tttgctgcct ccagggatcc tgtgtccccg agctgggacc   1020
accttatatt cccagggccg gttaatgtgg ctctggttct gggtactttt atctgtcccc   1080
tccaccccac agtggggcaa gctagcttgg tcgagctgga tacttcccgt ccgccagggg   1140
gacatgccgg cgatgctgaa ggtcgcgcgc attcccgatg aagaggccgg ttaccgcctg   1200
ttgacctggt gggacgggca gggcgccgcc cgagtcttcg cctcggcggc gggcgctctg   1260
ctcatggagc gcgcgtccgg ggccggggac cttgcacaga tagcgtggtc cggccaggac   1320
gacgaggctt gcaggatcat aatcagccat accacatttg tagaggtttt acttgcttta   1380
aaaaacctcc cacacctccc cctgaacctg aaacataaaa tgaatgcaat tgttgttgtt   1440
aacttgttta ttgcagctta taatggttac aaataaagca atagcatcac aaatttcaca   1500
aataaagcat ttttttcact gcattctagt tgtggtttgt ccaaactcat caatgtatct   1560
tatcatgtct ggatccttac ttagttaccc ggggagcatg tcaaggtcaa aatcgtcaag   1620
agcgtcagca ggcagcatat caaggtcaaa gtcgtcaagg gcatcggctg ggagcatgtc   1680
taagtcaaaa tcgtcaaggg cgtcggtcgg cccgccgctt tcgcacttta gctgtttctc   1740
caggccacat atgattagtt ccaggccgaa aaggaaggca ggttcggctc cctgccggtc   1800
gaacagctca attgcttgtt tcagaagtgg gggcatagaa tcggtggtag gtgtctctct   1860
ttcctctttt gctacttgat gctcctgttc ctccaatacg cagcccagtg taaagtggcc   1920
cacggcggac agagcgtaca gtgcgttctc cagggagaag ccttgctgac acaggaacgc   1980
gagctgattt tccagggttt cgtactgttt ctctgttggg cgggtgccga gatgcacttt   2040
agccccgtcg cgatgtgaga ggagagcaca gcggtatgac ttggcgttgt tccgcagaaa   2100
gtcttgccat gactcgcctt ccagggggca ggagtgggta tgatgcctgt ccagcatctc   2160
gattggcagg gcatcgagca gggcccgctt gttcttcacg tgccagtaca gggtaggctg   2220
ctcaactccc agcttttgag cgagtttcct tgtcgtcagg ccttcgatac cgactccatt   2280
gagtaattcc agagcagagt ttatgacttt gctcttgtcc agtctagaca tggtgaattc   2340
ggggccgcgg aggctggatc ggtcccggtg tcttctatgg aggtcaaaac agcgtggatg   2400
gcgtctccag gcgatctgac ggttcactaa acgagctcac gacacctgaa atggaagaaa   2460
aaaactttga accactgtct gaggcttgag aatgaaccaa gatccaaact caaaaagggc   2520
aaattccaag gagaattaca tcaagtgcca agctggccta acttcagtct ccacccactc   2580
agtgtgggga aactccatcg cataaaaccc ctccccccaa cctaaagacg acgtactcca   2640
aaagctcgag aactaatcga ggtgcctgga cggcgcccgg tactccgtgg agtcacatga   2700
agcgacggct gaggacggaa aggccctttt cctttgtgtg ggtgactcac ccgcccgctc   2760
tcccgagcgc cgcgtcctcc attttgagct ccctgcagca gggccgggaa gcggccatct   2820
ttccgctcac gcaactggtg ccgaccgggc cagccttgcc gcccagggcg gggcgataca   2880
cggcggcgcg aggccaggca ccagagcagg ccggccagct tgagactacc cccgtccgat   2940
tctcggtggc cgcgctcgca ggccccgcct cgccgaacat gtgcgctggg acgcacgggc   3000
cccgtcgccg cccgcggccc caaaaaccga aataccagtg tgcagatctt ggcccgcatt   3060
tacaagacta tcttgccaga aaaaaagcgt cgcagcaggt catcaaaaat tttaaatggc   3120
tagagactta tcgaaagcag cgagacaggc gcgaaggtgc caccagattc gcacgcggcg   3180
gccccagcgc ccaagccagg cctcaactca agcacgaggc gaaggggctc cttaagcgca   3240
aggcctcgaa ctctcccacc cacttccaac ccgaagctcg ggatcaagaa tcacgtactg   3300
cagccagggg cgtggaagta attcaaggca cgcaagggcc ataacccgta aagaggccag   3360
```

-continued

```
gcccgcggga accacacacg gcacttacct gtgttctggc ggcaaacccg ttgcgaaaaa   3420
gaacgttcac ggcgactact gcacttatat acggttctcc cccaccctcg ggaaaaaggc   3480
ggagccagta cacgacatca ctttcccagt ttaccccgcg ccaccttctc taggcaccgg   3540
ttcaattgcc gacccctccc cccaacttct cggggactgt gggcgatgtg cgctctgccc   3600
actgacgggc accggagcct cacgcatgct cttctccacc tcagtgatga cgagagcggg   3660
cgggtgaggg ggcgggaacg cagcgatctc tgggttctac gttagtggga gtttaacgac   3720
ggtccctggg attccccaag gcaggggcga gtccttttgt atgaattact catggcggta   3780
atgttggaca tgagccaata taaatgtaca tattatgata tggatacaac gtatgcaatg   3840
ggccaagctc ctcgaggtgg tgcactctca gtacaatctg ctctgatgcc gcatagttaa   3900
gccagtaagc ttttggggtt gcgccttttc caaggcagcc ctgggtttgc gcagggacgc   3960
ggctgctctg ggcgtggttc cgggaaacgc agcggcgccg accctgggtc tcgcacattc   4020
ttcacgtccg ttcgcagcgt cacccggatc ttcgccgcta cccttgtggg ccccccggcg   4080
acgcttcctg ctccgcccct aagtcgggaa ggttccttgc ggttcgcggc gtgccggacg   4140
tgacaaacgg aagccgcacg tctcactagt accctcgcag acggacagcg ccagggagca   4200
atggcagcgc gccgaccgcg atgggctgtg gccaatagcg gctgctcagc agggcgcgcc   4260
gagagcagcg gccgggaagg ggcggtgcgg gaggcggggt gtggggcggt agtgtgggcc   4320
ctgttcctgc ccgcgcggtg ttccgcattc tgcaagcctc cggagcgcac gtcggcagtc   4380
ggctccctcg ttgaccgaat caccgacctc tctccccagg gggatccacc ggagcttacc   4440
atgaccgagt acaagcccac ggtgcgcctc gccacccgcg acgacgtccc cagggccgta   4500
cgcaccctcg ccgccgcgtt cgccgactac cccgccacgc gccacaccgt cgatccggac   4560
cgccacatcg agcgggtcac cgagctgcaa gaactcttcc tcacgcgcgt cgggctcgac   4620
atcggcaagg tgtgggtcgc ggacgacggc gccgcggtgg cggtctggac cacgccggag   4680
agcgtcgaag cgggggcggt gttcgccgag atcggcccgc gcatggccga gttgagcggt   4740
tcccggctgg ccgcgcagca acagatggaa ggcctcctgg cgccgcaccg gcccaaggag   4800
cccgcgtggt tcctggccac cgtcggcgtc tcgcccgacc accagggcaa gggtctgggc   4860
agcgccgtcg tgctccccgg agtggaggcg gccgagcgcg ccggggtgcc cgccttcctg   4920
gagacctccg cgccccgcaa cctccccttc tacgagcggc tcggcttcac cgtcaccgcc   4980
gacgtcgagg tgcccgaagg accgcgcacc tggtgcatga cccgcaagcc cggtgcctga   5040
ggtaccctgt gccttctagt tgccagccat ctgttgtttg cccctccccc gtgccttcct   5100
tgaccctgga aggtgccact cccactgtcc tttcctaata aaatgaggaa attgcatcgc   5160
attgtctgag taggtgtcat tctattctgg ggggtggggt ggggcaggac agcaaggggg   5220
aggattggga agacaatagc aggcatgctg gggatgcggt gggctctatg ggtaccaag    5280
ctttactagg gacaggattg gtgacagaaa agccccatcc ttaggcctcc tccttcctag   5340
tctcctgata ttgggtctaa cccccacctc ctgttaggca gattccttat ctggtgacac   5400
acccccattt cctggagcca tctctctcct tgccagaacc tctaaggttt gcttacgatg   5460
gagccagaga ggatcctggg agggagagct tggcaggggg tgggagggaa gggggggatg   5520
cgtgacctgc ccggttctca gtggccaccc tgcgctaccc tctcccagaa cctgagctgc   5580
tctgacgcgg ctgtctggtg cgtttcactg atcctggtgc tgcagcttcc ttacacttcc   5640
caagaggaga agcagtttgg aaaaacaaaa tcagaataag ttggtcctga gttctaactt   5700
```

-continued

```
tggctcttca cctttctagt ccccaattta tattgttcct ccgtgcgtca gttttacctg   5760
tgagataagg ccagtagcca gccccgtcct ggcagggctg tggtgaggag gggggtgtcc   5820
gtgtggaaaa ctccctttgt gagaatggtg cgtcctaggt gttcaccagg tcgtggccgc   5880
ctctactccc tttctctttc tccatccttc tttccttaaa gagtccccag tgctatctgg   5940
gacatattcc tccgcccaga gcagggtccc gcttccctaa ggccctgctc tgggcttctg   6000
ggtttgagtc cttggcaagc ccaggagagg cgctcaggct tccctgtccc ccttcctcgt   6060
ccaccatctc atgcccctgg ctctcctgcc ccttccctac aggggttcct ggctctgctc   6120
taagggcaag ggcgaattcg cggccgctaa attcaattcg ccctatagtg agtcgtatta   6180
caattcactg gccgtcgttt tacaacgtcg tgactgggaa aaccctggcg ttacccaact   6240
taatcgcctt gcagcacatc ccccttttcgc cagctggcgt aatagcgaag aggcccgcac   6300
cgatcgccct tcccaacagt tgcgcagcct atacgtacgg cagtttaagg tttacaccta   6360
taaaagagag agccgttatc gtctgtttgt ggatgtacag agtgatatta ttgacacgcc   6420
ggggcgacgg atggtgatcc ccctggccag tgcacgtctg ctgtcagata aagtctcccg   6480
tgaactttac ccggtggtgc atatcgggga tgaaagctgg cgcatgatga ccaccgatat   6540
ggccagtgtg ccggtctccg ttatcgggga agaagtggct gatctcagcc accgcgaaaa   6600
tgacatcaaa aacgccatta acctgatgtt ctggggaata taaatgtcag gcatgagatt   6660
atcaaaaagg atcttcacct agatcctttt cacgtagaaa gccagtccgc agaaacggtg   6720
ctgaccccgg atgaatgtca gctactgggc tatctggaca agggaaaacg caagcgcaaa   6780
gagaaagcag gtagcttgca gtgggcttac atggcgatag ctagactggg cggttttatg   6840
gacagcaagc gaaccggaat tgccagctgg ggcgccctct ggtaaggttg ggaagccctg   6900
caaagtaaac tggatggctt tcttgccgcc aaggatctga tggcgcaggg gatcaagctc   6960
tgatcaagag acaggatgag gatcgtttcg catgattgaa caagatggat tgcacgcagg   7020
ttctccggcc gcttgggtgg agaggctatt cggctatgac tgggcacaac agacaatcgg   7080
ctgctctgat gccgccgtgt tccggctgtc agcgcagggg cgcccggttc tttttgtcaa   7140
gaccgacctg tccggtgccc tgaatgaact gcaagacgag gcagcgcggc tatcgtggct   7200
ggccacgacg ggcgttcctt gcgcagctgt gctcgacgtt gtcactgaag cgggaaggga   7260
ctggctgcta ttgggcgaag tgccggggca ggatctcctg tcatctcacc ttgctcctgc   7320
cgagaaagta tccatcatgg ctgatgcaat gcggcggctg catacgcttg atccggctac   7380
ctgcccattc gaccaccaag cgaaacatcg catcgagcga gcacgtactc ggatggaagc   7440
cggtcttgtc gatcaggatg atctggacga agagcatcag gggctcgcgc cagccgaact   7500
gttcgccagg ctcaaggcga gcatgcccga cggcgaggat ctcgtcgtga cccatggcga   7560
tgcctgcttg ccgaatatca tggtggaaaa tggccgcttt tctggattca tcgactgtgg   7620
ccggctgggt gtggcggacc gctatcagga catagcgttg gctacccgtg atattgctga   7680
agagcttggc ggcgaatggg ctgaccgctt cctcgtgctt tacggtatcg ccgctcccga   7740
ttcgcagcgc atcgccttct atcgccttct tgacgagttc ttctgaatta ttaacgctta   7800
caatttcctg atgcggtatt ttctccttac gcatctgtgc ggtatttcac accgcatcag   7860
gtggcacttt tcggggaaat gtgcgcggaa cccctatttg tttatttttc taaatacatt   7920
caaatatgta tccgctcatg agattatcaa aaaggatctt cacctagatc cttttaaatt   7980
aaaaatgaag ttttaaatca atctaaagta tatatgagta aacttggtct gacagttacc   8040
aatgcttaat cagtgaggca cctatctcag cgatctgtct atttcgttca tccatagttg   8100
```

cctgactccc cgtcgtgtag ataactacga tacgggaggg cttaccatct ggccccagtg 8160
ctgcaatgat accgcgagac ccacgctcac cggctccaga tttatcagca ataaaccagc 8220
cagccggaag ggccgagcgc agaagtggtc ctgcaacttt atccgcctcc atccagtcta 8280
ttaattgttg ccgggaagct agagtaagta gttcgccagt taatagtttg cgcaacgttg 8340
ttgccattgc tacaggcatc gtggtgtcac gctcgtcgtt tggtatggct tcattcagct 8400
ccggttccca acgatcaagg cgagttacat gatcccccat gttgtgcaaa aaagcggtta 8460
gctccttcgg tcctccgatc gttgtcagaa gtaagttggc cgcagtgtta tcactcatgg 8520
ttatggcagc actgcataat tctcttactg tcatgccatc cgtaagatgc ttttctgtga 8580
ctggtgagta ctcaaccaag tcattctgag aatagtgtat gcggcgaccg agttgctctt 8640
gcccggcgtc aatacgggat aataccgcgc cacatagcag aactttaaaa gtgctcatca 8700
ttggaaaacg ttcttcgggg cgaaaactct caaggatctt accgctgttg agatccagtt 8760
cgatgtaacc cactcgtgca cccaactgat cttcagcatc ttttactttc accagcgttt 8820
ctgggtgagc aaaaacagga aggcaaaatg ccgcaaaaaa gggaataagg gcgacacgga 8880
aatgttgaat actcatactc ttcctttttc aatattattg aagcatttat cagggttatt 8940
gtctcatgac caaaatccct taacgtgagt tttcgttcca ctgagcgtca gaccccgtag 9000
aaaagatcaa aggatcttct tgagatcctt tttttctgcg cgtaatctgc tgcttgcaaa 9060
caaaaaaacc accgctacca gcggtggttt gtttgccgga tcaagagcta ccaactcttt 9120
ttccgaaggt aactggcttc agcagagcgc agataccaaa tactgttctt ctagtgtagc 9180
cgtagttagg ccaccacttc aagaactctg tagcaccgcc tacatacctc gctctgctaa 9240
tcctgttacc agtggctgct gccagtggcg ataagtcgtg tcttaccggg ttggactcaa 9300
gacgatagtt accggataag gcgcagcggt cgggctgaac ggggggttcg tgcacacagc 9360
ccagcttgga gcgaacgacc tacaccgaac tgagatacct acagcgtgag ctatgagaaa 9420
gcgccacgct tcccgaaggg agaaaggcgg acaggtatcc ggtaagcggc agggtcggaa 9480
caggagagcg cacgagggag cttccagggg gaaacgcctg gtatctttat agtcctgtcg 9540
ggtttcgcca cctctgactt gagcgtcgat ttttgtgatg ctcgtcaggg gggcggagcc 9600
tatggaaaaa cgccagcaac gcggcctttt tacggttcct ggccttttgc tggccttttg 9660
ctcacatgtt ctttcctgcg ttatcccctg attctgtgga taaccgtatt accgcctttg 9720
agtgagctga taccgctcgc cgcagccgaa cgaccgagcg cagcgagtca gtgagcgagg 9780
aagcggaag 9789

<210> SEQ ID NO 16
<211> LENGTH: 21055
<212> TYPE: DNA
<213> ORGANISM: Artificial Sequence
<220> FEATURE:
<223> OTHER INFORMATION: FL/hXIST/RCAN1 construct

<400> SEQUENCE: 16
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg acaatgtttt cagaaatgta atcttttcaa 240
tatgaaactg ctgatggacc aagaaaacaa aaccctcaac ccaagggaac atcagattgc 300

-continued

```
tggtcaagga gaaatgagga gctgacggtc tcagcattta tttgacttgc tccacggaca    360
gagcaggaga aggctcaaac ctcttcaccc caagactctc cctcacacct gcctcctcac    420
ccaaacccta gaggacagga caggaaccac caacatttta tggttttcaa aaatcctgca    480
ttgaacactg actgtgagcc aggtgctgat ggaagtgcct ttcactcgat gatctcatct    540
actgctcaca attccaccag ttaaggccca cattttggac aaagagcctg aggaacctac    600
cccctccccg cagtgctcac acttttgtcc ctccagagga cgggaacttc ctctttcttt    660
agcaagctct gtaggggacc agcccacagg ccctggggta gggcagcccg accgcggccc    720
ttccctcacc atggcctatg gttctccttc ccttttcctt taagaaggcc aggtgagaat    780
cacaggaaag ggagaattta ttttgattaa aaataacatt tcttaaaggg ggcatcgatt    840
ttccctttcc aaagtccaat cactcatccc tatccggagc gacagaacct ggggccgggg    900
ctcaggcctc ccacgcaggc tgtgctcagt ggacacagga atggattcct gggacactgc    960
gggtcgcgat gtacgggcca gatatacgcg ttgacattga ttattgacta gttattaata   1020
gtaatcaatt acggggtcat tagttcatag cccatatatg gagttccgcg ttacataact   1080
tacggtaaat ggcccgcctg gctgaccgcc caacgacccc cgcccattga cgtcaataat   1140
gacgtatgtt cccatagtaa cgccaatagg gactttccat tgacgtcaat gggtggagta   1200
tttacggtaa actgcccact tggcagtaca tcaagtgtat catatgccaa gtacgccccc   1260
tattgacgtc aatgacggta aatggcccgc ctggcattat gcccagtaca tgaccttatg   1320
ggactttcct acttggcagt acatctacgt attagtcatc gctattacca tggtgatgcg   1380
gttttggcag tacatcaatg ggcgtggata gcggtttgac tcacggggat ttccaagtct   1440
ccaccccatt gacgtcaatg ggagtttgtt ttggcaccaa aatcaacggg actttccaaa   1500
atgtcgtaac aactccgccc cattgacgca aatgggcggt aggcgtgtac ggtgggaggt   1560
ctatataagc agagctctcc ctatcagtga tagagatctc cctatcagtg atagagatcg   1620
tcgacgagct cgtttagtga accgtcagat cgcctggaga cgccatccac gctgttttga   1680
cctccataga agacaccggg accgatccag cctccggact ctagcgttta aacttaagct   1740
tggtaccgag ctcggatcca ctagtccagt gtggtggaat tctgcagatt ctagaacatt   1800
ttctagtccc ccaacaccct ttatggcgta tttctttaaa aaaatcacct aaattccata   1860
aaatattttt ttaaattcta tactttctcc tagtgtcttc ttgacacgtc ctccatattt   1920
ttttaaagaa agtatttgga atattttgag gcaattttta atatttaagg aatttttctt   1980
tggaatcatt tttggtgaca tctctgtttt ttgtggatca gtttttttact cttccactct   2040
cttttctata ttttgcccat cggggctgcg gatacctggt tttattattt tttctttgcc   2100
caacggggcc gtggatacct gccttttaat tctttttttat tcgcccatcg gggccgcgga   2160
tacctgcttt ttattttttt ttccttagcc catcggggta tcggatacct gctgattccc   2220
ttcccctctg aacccccaac actctggccc atcggggtga cggatatctg ctttttaaaa   2280
atttctttt tttggcccat cggggcttcg gatacctgct ttttttttt ttatttcct      2340
tgcccatcgg ggcctcggat acctgcttta atttttgttt ttctgcccat cggggccgcg   2400
gatacctgct ttgattttttt tttttcatcg cccatcggtg ctttttatgg atgaaaaaat   2460
gttggttttg tgggttgttg cactctctgg aatatctaca cttttttttg ctgctgatca   2520
tttggtggtg tgtgagtgta cctaccgctt tggcagagaa tgactctgca gttaagctaa   2580
gggcgtgttc agattgtgga ggaaaagtgg ccgccatttt agacttgccg cataactcgg   2640
cttagggcta gtcgtttgtg ctaagttaaa ctagggaggc aagatggatg atagcaggtc   2700
```

-continued aggcagagga agtcatgtgc attgcatgag ctaaacctat ctgaatgaat tgatttgggg 2760
cttgttagga gctttgcgtg attgttgtat cgggaggcag taagaatcat cttttatcag 2820
tacaagggac tagttaaaaa tggaaggtta ggaaagacta aggtgcaggg cttaaaatgg 2880
cgattttgac attgcggcat tgctcagcat ggcgggctgt gctttgttag gttgtccaaa 2940
atggcggatc cagttctgtc gcagtgttca agtggcggga aggccacatc atgatgggcg 3000
aggctttgtt aagtggttag catggtggtg gacatgtgcg gtcacacagg aaaagatggc 3060
ggctgaaggt cttgccgcag tgtaaaacat ggcgggcctc tttgtctttg ctgtgtgctt 3120
ttcgtgttgg gttttgccgc agggacaata tggcaggcgt tgtcatatgt atatcatggc 3180
ttttgtcacg tggacatcat ggcgggcttg ccgcattgtt aaagatggcg ggttttgccg 3240
cctagtgcca cgcagagcgg gagaaaaggt gggatggaca gtgctggatt gctgcataac 3300
ccaaccaatt agaaatgggg gtggaattga tcacagccaa ttagagcaga agatggaatt 3360
agactgatga cacactgtcc agctactcag cgaagacctg ggtgaattag catggcactt 3420
cgcagctgtc tttagccagt caggagaaag aagtggaggg gccacgtgta tgtctcccag 3480
tgggcggtac accaggtgtt ttcaaggtct tttcaaggac atttagcctt tccacctctg 3540
tcccctctta tttgtcccct cctgtccagt gctgcctctt gcagtgctgg atatctggct 3600
gtgtggtctg aacctccctc cattcctctg tattggtgcc tcacctaagg ctaagtatac 3660
ctcccccccc accccccaac ccccccaact ccccaccccc accccccacc ccccacctcc 3720 ccaccccccct accccccctac cccccctaccc ccctctggtc tgccctgcac tgcactgttg 3780
ccatgggcag tgctccaggc ctgcttggtg tggacatggt ggtgagccgt ggcaaggacc 3840
agaatggatc acagatgatc gttggccaac aggtggcaga agaggaattc ctgccttcct 3900
caagaggaac acctacccct tggctaatgc tggggtcgga ttttgattta tatttatctt 3960
ttggatgtca gtcatacagt ctgattttgt ggtttgctag tgtttgaatt taagtcttaa 4020
gtgactatta tagaaatgta ttaagaggct ttatttgtag aattcacttt aattacattt 4080
aatgagtttt tgttttgagt tccttaaaat tccttaaagt ttttagcttc tcattacaaa 4140
ttccttaacc tttttttggc agtagatagt caaagtcaaa tcatttctaa tgttttaaaa 4200
atgtgctggt cattttcttt gaaattgact taactatttt cctttgaaga gtctgtagca 4260
cagaaacagt aaaaaattta acttcatgac ctaatgtaaa aaagagtgtt tgaaggttta 4320
cacaggtcca ggccttgctt tgttcccatc cttgatgctg cactaattga ctaatcacct 4380
acttatcaga caggaaactt gaattgctgt ggtctggtgt cctctattca gacttattat 4440
attggagtat ttcaattttt cgttgtatcc tgcctgccta gcatccagtt cctccccagc 4500
cctgctccca gcaaacccct agtctagccc cagccctact cccacccggc cccagccctg 4560
ccccaggccc agtcccctaa ccccccagcc ctaggcccag tcccagtcct agttcctcag 4620
tctgtccagc ttctctcgaa agtcactcta attttcattg attcagtgct caaaataagt 4680
tgtccattgg tatcctatta tactgggata ttccgtttac ccttggcatt gctgatcttc 4740
agtactgact ccttgaccat tttcagttaa gcatacaatc ccatttgtct gtgatctcag 4800
gacaaagaat ttccttactc ggtacgttga agttagggaa tgtcaattga gagctttcta 4860
tcagagcatt attgcccaca atttgagtta cttatcattt tctcgatccc ctgcccttaa 4920
aggagaaacc atttctctgt cattgcttct gtagtcacag tcccaatttt gagtagtgat 4980
cttttcttgt gtactgtgtt ggccacctaa aactctttgc attgagtaaa attctaattg 5040

-continued

```
ccaataatcc tacccattgg attagacagc actctgaacc ccatttgcat tcagcagggg   5100
gtcgcagaca acccgtcttt tgttggacag ttaaaatgct cagtcccaat tgtcatagct   5160
ttgcctatta aacaaaggca ccctactgcg ctttttgctg tgcttctgga gaatcctgct   5220
gttcttggac aattaaagaa caaagtagta attgctaatt gtctcaccca ttaatcatga   5280
agactaccag tcgcccttgc atttgccttg aggcagcgct gactacctga gatttaagag   5340
tttcttaaat tattgagtaa aatcccaatt atccatagtt ctgttagtta cactatggcc   5400
tttgcaaaca tctttgcata acagcagtgg gactgactca ttcttagagc cccttccctt   5460
ggaatattaa tggatacaat agtaattatt catggttctg cgtaacagag aagacccact   5520
tatgtgtatg cctttatcat tgctcctaga tagtgtgaac tacctaccac cttgcattaa   5580
tatgtaaaac actaattgcc catagtccca ctcattagtc taggatgtcc tctttgccat   5640
tgctgctgag ttctgactac ccaagtttcc ttctcttaaa cagttgatat gcataattgc   5700
atatattcat ggttctgtgc aataaaaatg gattctcacc ccatcccacc ttctgtggga   5760
tgttgctaac gagtgcagat tattcaataa cagctcttga acagttaatt tgcacagttg   5820
caattgtcca gagtcctgtc cattagaaag ggactctgta tcctatttgc acgctacaat   5880
gtgggctgat cacccaagga ctcttcttgt gcattgatgt tcataattgt atttgtccac   5940
gatcttgtgc actaaccctt ccactccctt tgtattccag caggggaccc ttactactca   6000
agacctctgt actaggacag tttatgtgca caatcctaat tgattagaac tgagtctttt   6060
atatcaaggt ccctgcatca tctttgcttt acatcaagag ggtgctggtt acctaatgcc   6120
cctcctccag aaattattga tgtgcaaaat gcaatttccc tatctgctgt tagtctgggg   6180
tctcatcccc tcatattcct tttgtcttac agcagggggt acttgggact gttaatgcgc   6240
ataattgcaa ttatggtctt ttccattaaa ttaagatccc aactgctcac accctcttag   6300
cattacagta gagggtgcta atcacaagga catttctttt gtactgttaa tgtgctactt   6360
gcatttgtcc ctcttcctgt gcactaaaga ccccactcac ttccctagtg ttcagcagtg   6420
gatgacctct agtcaagacc tttgcactag gatagttaat gtgaaccatg gcaactgatc   6480
acaacaatgt ctttcagatc agatccattt tatcctcctt gttttacagc aagggatatt   6540
aattacctat gttacctttc cctgggacta tgaatgtgca aaattccaat gttcatggtc   6600
tctcccttta aacctatatt ctaccccttt tacattatag aaagggatgc tggaaaccca   6660
gagtccttct cttgggactc ttaatgtgta tttctaatta tccatgactc ttaatgtgca   6720
tattttcaat tgcctaattg atttcaattg tctaagacat ttcaaatgtc taattgatta   6780
gaactgagtc ttttatatca agctaatatc tagcttttat atcaagctaa tatcttgact   6840
tctcagcatc atagaagggg gtactgattt cctaaagtct ttcttgaatt tctattatgc   6900
aaaattgccc tgaggccggg tgtggtggct cacacctgta atcccagcac tttgggaggc   6960
tgaggtggga agatccctta ctgccaggag tttgagacca gcctggccaa cattaaaaaa   7020
aaaaaaaaaa gtaagacaat tgccctggaa tcccatcccc ctcacacctc cttggcaaag   7080
cagcaggagt gctaactagc tagtgcttct tctcttatac tgcttaaatg cgcataatta   7140
gcagtagttg atgtgcccct atgttagagt agaatcccgc ttccttgctc catttgcatt   7200
actgcaggag cttctaacta gcctgaattc actctcttgg actgttaatg tgcatactta   7260
tatttgctgc tgtacttttt taccatgtaa ggaccccacc cactgtattt acatcccagc   7320
tggaagtacc tactacttaa gacccttaga ctagtaaagt tagcgtgcat aatcttaggt   7380
gttatataca cattttcagt tgcatacagt tgtgcctttt atcaggactc ctgtacttat   7440
```

```
caaagcagag agtgctaatc aatattaagc ccttctcttc gaactgtaga tggcatgtaa   7500
ttgcagttgt caatggtcct tcaattagac ttgggtttct gacctatcac accctctttg   7560
ctttattgca tggggtacta ttcacttaag gcccctttct caaactgtta atgtgcctaa   7620
tgacaattac atcagtatcc ttccttttga aggacagcat ggttggtgac acctaaggcc   7680
ccatttcttg gcctcccaat atgtgtgatt gtatttgtcg aggttgctat gcactagaga   7740
aggaaagtgc tcccctcatc cccacttttc ccttccagca ggaagtgccc accccataag   7800
acccttttat ttggagagtc taggtgcaca attgtaagtg accacaagca tgcatcttgg   7860
acatttatgt gcgtaatcgc acactgctca ttccatgtga ataaggtcct actctccgac   7920
ccctttgca atacagaagg gttgctgata acgcagtccc cttttcttgg catgttgtgt   7980
gtgattataa tcgtctggga tcctatgcac tagaaaagga gggtcctctc cacatacctc   8040
agtctcacct ttcccttcca gcagggagtg cccactccat aagactctca catttggaca   8100
gtcaaggtgc gtaattgtta agtgaacaca accatgcacc ttagacatgg atttgcataa   8160
ctacacacag ctcaacctat ctgaataaaa tcctactctc agacccttt tgcagtacag   8220
caggggtgct gatcaccaag gccctttttc ctggcctggt atgcgtgtga ttatgtttgt   8280
cccggttcct gtgtattaga catggaagcc tcccctgcca cactccaccc ccaatcttcc   8340
tttcccttcc ggcaggagtg ccctctccat aagacgctta cgtttggaca atcaaggtgc   8400
acagttgtaa gtgaccacag gcatacacct tggacattaa tgtgcataac cactttgccc   8460
attccatctg aataaggtcc tactctcaga cccctttgc agtacagcag gggtgctgat   8520
caccaaggcc cctttcttg gcctgttatg tgcgtgatta tatttgtctg ggttcctgtg   8580
tattagacaa ggaagccttc cccccgcccc cacccccact cccagtcttc ctttcccttc   8640
cagcagggag tgccccctcc ataagatcat tacatttgga caatcaaggt gcacaattat   8700
aagtgaccac agccatgcac cttggacatt attggacatt aatgtgcgta actgcacatg   8760
gcccatccca tctgaataag gacctactct cagatgcctt tgcagtacag caggggtact   8820
gaatcaccaa ggcccttttt cttggcctgt tatgtgtgtg attatattta tcccagtttc   8880
tgtgtaatag acatgaaagc ctcccctgcc acaccccacc tccaatcttc ctttcccttc   8940
caccagggag tgtccactcc atatacccttacatttggac aatcaaggtg cacaattgta   9000
agtgagcata ggcactcacc ttggacatga atgtgcataa ctgcacatgg cccatcccat   9060
ctgaataagg tcctactctc agacccttt tgcagtacag caggggtgct gatcaccaag   9120
gcccctttc ctggcctgtt atgtgtgtga ttatatttgt tccagttcct gtgtaataga   9180
catggaagcc tcccctgcca cactccaccc ccaatcttcc tttccttctg gcaggaagta   9240
cccgctccat aagaccctta catttggaca gtcaaggtgc acaattgtat gtgaccacaa   9300
ccatgcacct tggacataaa tgtgtgtaac tgcacatggc ccatcccatc tgaataaggt   9360
cctactctca gacccctttt gcagtacagt aggtgtgctg ataaccaagg cccctcttcc   9420
tggcctgtta acgtatgtga ttatatttgt ctgggttcca gtgtataaga catggaagcc   9480
tcccctgccc caccccaccc tcaatcttcc tttcccttct ggcagggagt gccagctcca   9540
taagaacctt acatttggac agtcaaggtg cacaattcta agtgaccgca gccatgcacc   9600
ttggtcaata atgtgtgtaa ctgcacacgg cctatctcat ctgaataagg ccttactctc   9660
agacccctt tgcagtacag caggggtgct gataaccaag gcccattttc ctggcctgtt   9720
atgtgtgtga ttatatttgt ccaggtttct gtgtactaga caaggaagcc tcctctgccc   9780
```

```
catcccatct acgcataatc tttcttttcc tcccagcagg gagtgctcac tccataagac   9840
ccttacattt ggacaatcaa ggtgcacaat tgtaagtgac cacaaccatg catcttggaa   9900
atttatgtgc ataactgcac atggcttatc ctatttgaat aaagtcctac tctcagaccc   9960
cctttgcagt atagctgggg tgctgatcac tgaggcctct ttgcttggct tgtctatatt  10020
cttgtgtact agataagggc accttctcat ggactccctt tgcttttcaa caaggagtac  10080
ccactacttt ttaagattct tatatttgtc caaagtacat ggttttaatt gaccacaaca  10140
atgtcccttg gacattaatg tatgtaatca ccacatggtt catcctaatt aaacaaagtt  10200
ctaccttctc accctccatt tgcagtatac cagggttgct gaccccctaa gtcccctttt  10260
cttggcttgt tgacatgcat aattgcattt atgttggttc ttgtgcccta gacaaggatg  10320
ccccacctct tttcaatagt gggtgcccac tccttatgat ctttacattt gaacagttaa  10380
tgtgaataat tgcagttgtc cacaacccta tcacttctag gaccattata cctcttttgc  10440
attactgtgg ggtatactgt ttccctccaa ggccccttct ggtggactat caacatataa  10500
ttgaaatttt cttttgtctt tgtcagtaga ttaaggtcat accccatcac ctttcctttg  10560
tagtacaaca gggtgtcctg atcaaccaaa gtcctgttgt tttggactgt taatatgtgc  10620
aattacattt gctcctgatc tgtgcactag ataaggatcc tacctacttt cttagtgttt  10680
ttagcaggta gtgcccacta ctcaagactg tcacttggaa tgttcatgtg cacaaactca  10740
attctctaag catgttcctg taccaccttt gctttagagc agggggatga tattcactaa  10800
gtgccccttc ttttggactt aatatgcatt aatgcaattg tccacctctt cttttagact  10860
aagagttgat ctccacatat tccccttgca tcaggggcat gttaattatg aatgaaccct  10920
tttcttttaa tattaatgtc ataattgtat ttgtggacct gtgtaggaga aaaagaccct  10980
atgttcctcc cattaccctt tggattgctg ctgagaagtg ttaactactc ataatctcag  11040
ctcttggaca attaatagca ttaataacaa ttatcaaggg cactgatcat tagataagac  11100
tcctgcttcc tcgttgctta catcgggggt actgacccac taaggcccct tgtactgtta  11160
atgtgaatat ttgcaattat atatgtctcc ttctggtaga gtgggatatt atgccctagt  11220
atccccttg cattactgca ggggctgctg actactcaaa acttctcctg ggactgttaa  11280
taggcacaat ggcagttatc aatggttttc tccctccctg accttgttaa gcaagcgccc  11340
caccccaccc ttagtttccc atggcataat aaagtataag cattggagta ttccatgcac  11400
ttgtctatca aacagtggtc catactccca accctttgc attgcgccag tgtgtaaaat  11460
cacaggtagc catggtgtca tgctttatat acgaagtctt ccctctctct gccccttgtg  11520
tgcccttggc cccttttac agactattgc tcacaatctc aggtgtccat atttgcagct  11580
attaggtaag attgtgctgt ctccctcttc ccttccctct gccctgcccc ttttgcctct  11640
ttgctgggta atgttgacca gacaaggccc tttctcttgg acttaaacaa ttctcagttg  11700
cactttcctt ggtccaccca ttatacatga acccctctac ttcctttcgc attgcttctg  11760
agtatgctga ctacccaaag ccccttctgt gttattaata aacacagtac tgattgtccc  11820
atttttcagc ccatcagtcc aagatctccc taccactttg gtgtgttggt gcagtgttga  11880
ctatgaaaag caggcctgaa ctaggtggat aagccttcac tcattttctt tcatttatta  11940
atgatcctag tttcaattat tgtcagattc tggggacaag aaccattctt gcccacctgt  12000
gttactgctt tactgtgcaa aatactgaag gcaagtcaga cccagggagc tggattgcca  12060
tcctttattt tgtgtttcca gtgtacacta taaaattgtc tccccaggaa ggaaggttgg  12120
cactttctct gcattcttct ttccagagca gattgcctgg ttaagaatct cttgttgtcc  12180
```

cttctgtata ttgttattgt aaagtgccaa atgccaggat acagccagaa aaattgctta 12240
ttattattaa aaaaattttt ttaagaaaga catctggatt gtagggtgga ctcgataacc 12300
tggtcattat ttttttgaag ccaaaatatc catttatact atgtacctgg tgaccagtgt 12360
ctctcatttt aactgagggt ggtgggtctg tggatagaac actgactctt gctattttaa 12420
tatcaaagat attctagatc cagcacagtg gcggccgctc tagagtggaa ctcttaagac 12480
cagtatcttt gtgtgggctt taccagcatt cacttttaga aaaactacct aaattttata 12540
atcctttaat ttcttcatct ggagcacctg cccctactta tttcaagaag attgcagtaa 12600
aacgattaaa tgagggaaca tatgcagagg tgcttttaaa aagcatatgc cacctttttt 12660
attaattatt atataaaatg aagcatttaa ttatagtaat aatttgaagt agtttgaagt 12720
accacactga ggtgaggact taaaaatgat aagacgagtt ccctatttta taagaaaaat 12780
aagccaaaat taaatattct tttggatata aatttcaaca gtgagatagc tgcctagtgg 12840
aaatgaataa tatcccagcc actagtgtac agggtgtttt gtggcacagg attatgtaat 12900
atggaactgc tcaagcaaat aactagtcat cacaacagca gttctttgta ataactgaaa 12960
aagaatattg tttctcggag aaggatgtca aaagatcggc ccagctcagg gagcagtttg 13020
ccctactagc tcctcggaca gctgtaaaga agagtctctg gctctttaga atactgatcc 13080
cattgaagat accacgctgc atgtgtcctt agtagtcatg tctccttagg ctcctcttgg 13140
acattctgag catgtgagac ctgaggactg caaacagcta taagaggctc caaattaatc 13200
atatctttcc ctttgagaat ctggccaagc tccagctaat ctacttggat gggttgccag 13260
ctatctggag aaaaagatct tcctcagaag aataggcttg ttgttttaca gtgttagtga 13320
tccattccct ttgacgatcc ctaggtggag atggggcatg aggatcctcc aggggaaaag 13380
ctcactacca ctgggcaaca accctaggtc aggaggttct gtcaagatac tttcctggtc 13440
ccagatagga agataaagtc tcaaaaacaa ccaccacacg tcaagctctt cattgttcct 13500
atctgccaaa tcattatact tcctacaagc agtgcagaga gctgagtctt cagcaggtcc 13560
aagaaatttg aacacactga aggaagtcag ccttcccacc tgaagatcaa catgcctggc 13620
actctagcac ttgaggatag ctgaatgaat gtgtatttct ttgtctcttt ctttcttgtc 13680
tttgctcttt gttctctatc taaagtgtgt cttacccatt tccatgtttc tcttgctaat 13740
ttctttcgtg tgtgcctttg cctcattttc tctttttgtt cacaagagtg gtctgtgtct 13800
tgtcttagac atatctctca tttttcattt tgttgctatt tctctttgct ctcctagatg 13860
tggctcttct ttcacgcttt atttcatgtc tcctttttgg gtcacatgct gtgtgctttt 13920
tgtccttttc ttgttctgtc tacctctcct ttctctgcct acctctcttt tctctttgtg 13980
aactgtgatt atttgttacc ccttcccctt ctcgttcgtt ttaaatttca ccttttttct 14040
gagtctggcc tcctttctgc tgtttctact ttttatctca catttctcat ttctgcattt 14100
cctttctgcc tctcttgggc tattctctct ctcctcccct gcgtgcctca gcatctcttg 14160
ctgtttgtga ttttctattt cagtattaat ctctgttggc ttgtatttgt tctctgcttc 14220
ttccctttct actcaccttt gagtatttca gcctcttcat gaatctatct ccctctcttt 14280
gatttcatgt aatctctcct taaatatttc tttgcatatg tgggcaagtg tacgtgtgtg 14340
tgtgtcatgt gtggcagagg ggcttcctaa cccctgcctg ataggtgcag aacgtcggct 14400
atcagagcaa gcattgtgga gcggttcctt atgccaggct gccatgtgag atgatccaag 14460
accaaaacaa ggccctagac tgcagtaaaa cccagaactc aagtagggca gaaggtggaa 14520

-continued

```
ggctcatatg gatagaaggc ccaaagtata agacagatgg tttgagactt gagacccgag  14580
gactaagatg gaaagcccat gttccaagat agatagaagc ctcaggcctg aaaccaacaa  14640
aagcctcaag agccaagaaa acagagggtg gcctgaattg gaccgaaggc ctgagttgga  14700
tggaagtctc aaggcttgag ttagaagtct taagacctgg gacaggacac atggaaggcc  14760
taagaactga gacttgtgac acaaggccaa cgacctaaga ttagcccagg gttgtagctg  14820
gaagacctac aacccaagga tggaaggccc ctgtcacaaa gcctacctag atggatagag  14880
gacccaagcg aaaaaggtat ctcaagacta acggccggaa tctggaggcc catgacccag  14940
aacccaggaa ggatagaagc ttgaagacct ggggaaatcc caagatgaga accctaaacc  15000
ctacctcttt tctattgttt acacttctta ctcttagata tttccagttc tcctgtttat  15060
ctttaagcct gattcttttg agatgtactt tttgatgttg ccggttacct ttagattgac  15120
agtattatgc ctgggccagt cttgagccag ctttaaatca cagcttttac ctatttgtta  15180
ggctatagtg ttttgtaaac ttctgtttct attcacatct tctccacttg agagagacac  15240
caaaatccag tcagtatcta atctggcttt tgttaacttc cctcaggagc agacattcat  15300
ataggtgata ctgtatttca gtcctttctt ttgaccccag aagccctaga ctgagaagat  15360
aaaatggtca ggttgttggg gaaaaaaaaa gtgccaggct ctctagagaa aaatgtgaag  15420
agatgctcca ggccaatgag aagaattaga caagaaatac acagatgtgc cagacttctg  15480
agaagcacct gccagcaaca gcttccttct ttgagcttag attttcctag tccatccctc  15540
atgaaaaatg actgaccact gctgggcagc aggagggatg atgaccaact aattcccaaa  15600
ccccagtctc attggtaccg agctcggatc cactagtcca gtgtggtgga attctgcaga  15660
tatccagcac agtggcggcc gctcgagtct agagggcccg tttaaacccg ctgatcagcc  15720
tcgactgtgc cttctagttg ccagccatct gttgtttgcc cctcccccgt gccttccttg  15780
accctggaag gtgccactcc cactgtcctt tcctaataaa atgaggaaat tgcatcgcat  15840
tgtctgagta ggtgtcattc tattctgggg ggtggggtgg ggcaggacag caagggggag  15900
gattgggaag acaatagcag gcatgctggg gatgcggtgg gctctatggc ttctgaggcg  15960
gaaagaacca gctggggctc tagggggtat ccccacgcgc cctgtagcgg cgcattaagc  16020
gcggcgggtg tggtggttac gcgcagcgtg accgctacac ttgccagcgc cctagcgccc  16080
gctcctttcg ctttcttccc ttcctttctc gccacgttcg ccggctttcc ccgtcaagct  16140
ctaaatcggg ggctcccttt agggttccga tttagtgctt tacggcacct cgaccccaaa  16200
aaacttgatt agggtgatgg ttcacgtagt gggccatcgc cctgatagac ggtttttcgc  16260
cctttgacgt tggagtccac gttctttaat agtggactct tgttccaaac tggaacaaca  16320
ctcaacccta tctcggtcta ttcttttgat ttataaggga ttttgccgat ttcggcctat  16380
tggttaaaaa atgagctgat ttaacaaaaa tttaacgcga attaattctg tggaatgtgt  16440
gtcagttagg gtgtggaaag tccccaggct ccccagcagg cagaagtatg caaagcatgc  16500
atctcaatta gtcagcaacc aggtgtggaa agtccccagg ctccccagca ggcagaagta  16560
tgcaaagcat gcatctcaat tagtcagcaa ccatagtccc gcccctaact ccgcccatcc  16620
cgcccctaac tccgcccagt tccgcccatt ctccgcccca tggctgacta atttttttta  16680
tttatgcaga ggccgaggcc gcctctgcct ctgagctatt ccagaagtag tgaggaggct  16740
tttttggagg cctaggcttt tgcaaaaagc tcccgggagc ttgtatatcc attttcggat  16800
ctgatcagca cgtgatgaaa aagcctgaac tcaccgcgac gtctgtcgag aagtttctga  16860
tcgaaaagtt cgacagcgtc tccgacctga tgcagctctc ggagggcgaa gaatctcgtg  16920
```

```
ctttcagctt cgatgtagga gggcgtggat atgtcctgcg ggtaaatagc tgcgccgatg  16980
gtttctacaa agatcgttat gtttatcggc actttgcatc ggccgcgctc ccgattccgg  17040
aagtgcttga cattggggaa ttcagcgaga gcctgaccta ttgcatctcc cgccgtgcac  17100
agggtgtcac gttgcaagac ctgcctgaaa ccgaactgcc cgctgttctg cagccggtcg  17160
cggaggccat ggatgcgatc gctgcggccg atcttagcca gacgagcggg ttcggcccat  17220
tcggaccgca aggaatcggt caatacacta catggcgtga tttcatatgc gcgattgctg  17280
atccccatgt gtatcactgg caaactgtga tggacgacac cgtcagtgcg tccgtcgcgc  17340
aggctctcga tgagctgatg ctttgggccg aggactgccc cgaagtccgg cacctcgtgc  17400
acgcggattt cggctccaac aatgtcctga cggacaatgg ccgcataaca gcggtcattg  17460
actggagcga ggcgatgttc ggggattccc aatacgaggt cgccaacatc ttcttctgga  17520
ggccgtggtt ggcttgtatg gagcagcaga cgcgctactt cgagcggagg catccggagc  17580
ttgcaggatc gccgcggctc cgggcgtata tgctccgcat tggtcttgac caactctatc  17640
agagcttggt tgacggcaat ttcgatgatg cagcttgggc gcagggtcga tgcgacgcaa  17700
tcgtccgatc cggagccggg actgtcgggc gtacacaaat cgcccgcaga agcgcggccg  17760
tctggaccga tggctgtgta gaagtactcg ccgatagtgg aaaccgacgc cccagcactc  17820
gtccgagggc aaaggaatag cacgtgctac gagatttcga ttccaccgcc gccttctatg  17880
aaaggttggg cttcggaatc gttttccggg acgccggctg gatgatcctc cagcgcgggg  17940
atctcatgct ggagttcttc gcccacccca acttgtttat tgcagcttat aatggttaca  18000
aataaagcaa tagcatcaca aatttcacaa ataaagcatt tttttcactg cattctagtt  18060
gtggtttgtc caaactcatc aatgtatctt atcatgtctg tatacgggtg gaggggcgtg  18120
atgcagggtc cccacgatca gccgcagtct ctctaacact gcaggtggtg ccaagaggca  18180
ggcatgctcc cagcacaagg gacggtggcg cagaagaata cagagaagct cacaaaacat  18240
gccggcatgg gctcaggaga gctacggggg tagtggtggt actgctccct ggtgcagggc  18300
agcagctgtg tctcccccctg cctccctccc acccgagggc cctgctcacc tggccccagc  18360
ttggagatgg catataagag atcatagttt atgactgggg tcgcatcttc cacttgtttc  18420
catcccactg gcggagaggc gggaggggag atcagaaact gcttgtctgg atttggcgga  18480
gccaggtgtg agcttcctat gtgtaaggtc tgaggagaga aaataagcac aggtcagttg  18540
ttgccaggga agaactgcag tgaggcaaca gcacctaacg ccagttccgg gagatgggca  18600
ggtcaatgtc caggcgtcag gacaggtgtg attccaggac caattgtaag atggtctgta  18660
atggggaggg caaaaggaca tatgaactct ggttgtggca cagataggat gacagccccc  18720
tcccagggct atgggagtca caggcacagg gactgcaaat aattacgctt gacctagatg  18780
gacagaaaat cagcagaggt gactttagta tatatggaaa tttaagtcac tgtcattgag  18840
gtcaggaggg ctcttgggta taccgtcgac ctctagctag agcttggcgt aatcatggtc  18900
atagctgttt cctgtgtgaa attgttatcc gctcacaatt ccacacaaca tacgagccgg  18960
aagcataaag tgtaaagcct ggggtgccta atgagtgagc taactcacat taattgcgtt  19020
gcgctcactg cccgctttcc agtcgggaaa cctgtcgtgc cagctgcatt aatgaatcgg  19080
ccaacgcgcg gggagaggcg gtttgcgtat tgggcgctct tccgcttcct cgctcactga  19140
ctcgctgcgc tcggtcgttc ggctgcggcg agcggtatca gctcactcaa aggcggtaat  19200
acggttatcc acagaatcag gggataacgc aggaaagaac atgtgagcaa aaggccagca  19260
```

aaaggccagg aaccgtaaaa aggccgcgtt gctggcgttt ttccataggc tccgcccccc 19320
tgacgagcat cacaaaaatc gacgctcaag tcagaggtgg cgaaacccga caggactata 19380
aagataccag gcgtttcccc ctggaagctc cctcgtgcgc tctcctgttc cgaccctgcc 19440
gcttaccgga tacctgtccg cctttctccc ttcgggaagc gtggcgcttt ctcatagctc 19500
acgctgtagg tatctcagtt cggtgtaggt cgttcgctcc aagctgggct gtgtgcacga 19560
accccccgtt cagcccgacc gctgcgcctt atccggtaac tatcgtcttg agtccaaccc 19620
ggtaagacac gacttatcgc cactggcagc agccactggt aacaggatta gcagagcgag 19680
gtatgtaggc ggtgctacag agttcttgaa gtggtggcct aactacggct acactagaag 19740
aacagtattt ggtatctgcg ctctgctgaa gccagttacc ttcggaaaaa gagttggtag 19800
ctcttgatcc ggcaaacaaa ccaccgctgg tagcggttgg tttttttgttt gcaagcagca 19860 gattacgcgc agaaaaaaag gatctcaaga agatcctttg atcttttcta cggggtctga 19920
cgctcagtgg aacgaaaact cacgttaagg gattttggtc atgagattat caaaaaggat 19980
cttcacctag atccttttaa attaaaaatg aagttttaaa tcaatctaaa gtatatatga 20040
gtaaacttgg tctgacagtt accaatgctt aatcagtgag gcacctatct cagcgatctg 20100
tctatttcgt tcatccatag ttgcctgact ccccgtcgtg tagataacta cgatacggga 20160
gggcttacca tctggcccca gtgctgcaat gataccgcga gacccacgct caccggctcc 20220
agatttatca gcaataaacc agccagccgg aagggccgag cgcagaagtg gtcctgcaac 20280
tttatccgcc tccatccagt ctattaattg ttgccgggaa gctagagtaa gtagttcgcc 20340
agttaatagt ttgcgcaacg ttgttgccat tgctacaggc atcgtggtgt cacgctcgtc 20400
gtttggtatg gcttcattca gctccggttc ccaacgatca aggcgagtta catgatcccc 20460
catgttgtgc aaaaaagcgg ttagctcctt cggtcctccg atcgttgtca gaagtaagtt 20520
ggccgcagtg ttatcactca tggttatggc agcactgcat aattctctta ctgtcatgcc 20580
atccgtaaga tgcttttctg tgactggtga gtactcaacc aagtcattct gagaatagtg 20640
tatgcggcga ccgagttgct cttgcccggc gtcaatacgg gataataccg cgccacatag 20700
cagaacttta aaagtgctca tcattggaaa acgttcttcg gggcgaaaac tctcaaggat 20760
cttaccgctg ttgagatcca gttcgatgta acccactcgt gcacccaact gatcttcagc 20820
atcttttact ttcaccagcg tttctgggtg agcaaaaaca ggaaggcaaa atgccgcaaa 20880
aaagggaata agggcgacac ggaaatgttg aatactcata ctcttccttt ttcaatatta 20940
ttgaagcatt tatcagggtt attgtctcat gagcggatac atatttgaat gtatttagaa 21000
aaataaacaa ataggggttc cgcgcacatt tccccgaaaa gtgccacctg acgtc 21055

<210> SEQ ID NO 17
<211> LENGTH: 20737
<212> TYPE: DNA
<213> ORGANISM: Artificial Sequence
<220> FEATURE:
<223> OTHER INFORMATION: FL/hXIST/DYRK1A construct

<400> SEQUENCE: 17
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg aaaaccagaa agtattctca gtaatgatag 240
tatggataaa gcaggtttct atgacccttt attacagaat ctgtgagttt ttcacaatta 300

-continued

```
aaaagtaata aaaagtagtg acaacattca ctgaactctt attctatgcc aacttgttcc    360
ggtatgccct tacacccaca aaagccctat gcataaggtg gcattattcc agcatgtatt    420
gcattgtaca cacaaagagg tcaagcactc caccacggcc ctaagcatgg tggctgaggt    480
gggaaggcca gaggtaggtg ggcccgcgcc cttttccact ctgaaccatg cctccaagat    540
aggagggtgg gaaagtgctc aagacacatt agaaattccc cataaaagac aagattgttg    600
aacacctgca agtgaataaa gataaactga tctcagaggg gaaaaagacg cagggttagg    660
aaacagcacc ctgctcgagg acgttctttc caaacagcct gctcatcacc cgttcgcgat    720
gtacgggcca gatatacgcg ttgacattga ttattgacta gttattaata gtaatcaatt    780
acggggtcat tagttcatag cccatatatg gagttccgcg ttacataact tacggtaaat    840
ggcccgcctg gctgaccgcc caacgacccc cgcccattga cgtcaataat gacgtatgtt    900
cccatagtaa cgccaatagg gactttccat tgacgtcaat gggtggagta tttacggtaa    960
actgcccact tggcagtaca tcaagtgtat catatgccaa gtacgccccc tattgacgtc   1020
aatgacggta aatggcccgc ctggcattat gcccagtaca tgaccttatg ggactttcct   1080
acttggcagt acatctacgt attagtcatc gctattacca tggtgatgcg gttttggcag   1140
tacatcaatg ggcgtggata gcggtttgac tcacggggat ttccaagtct ccaccccatt   1200
gacgtcaatg ggagtttgtt ttggcaccaa aatcaacggg actttccaaa atgtcgtaac   1260
aactccgccc cattgacgca aatgggcggt aggcgtgtac ggtgggaggt ctatataagc   1320
agagctctcc ctatcagtga tagagatctc cctatcagtg atagagatcg tcgacgagct   1380
cgtttagtga accgtcagat cgcctggaga cgccatccac gctgttttga cctccataga   1440
agacaccggg accgatccag cctccggact ctagcgttta aacttaagct tggtaccgag   1500
ctcggatcca ctagtccagt gtggtggaat tctgcagatt ctagaacatt ttctagtccc   1560
ccaacaccct ttatggcgta tttctttaaa aaaatcacct aaattccata aaatattttt   1620
ttaaattcta tactttctcc tagtgtcttc ttgacacgtc ctccatattt ttttaaagaa   1680
agtatttgga atattttgag gcaattttta atatttaagg aatttttctt tggaatcatt   1740
tttggtgaca tctctgtttt ttgtggatca gtttttttact cttccactct cttttctata   1800
ttttgcccat cggggctgcg gatacctggt tttattattt tttctttgcc caacggggcc   1860
gtggatacct gccttttaat tctttttttat tcgcccatcg gggccgcgga tacctgcttt   1920
ttattttttt ttccttagcc catcggggta tcggatacct gctgattccc ttcccctctg   1980
aacccccaac actctggccc atcggggtga cggatatctg ctttttaaaa attttctttt   2040
tttggcccat cggggcttcg gatacctgct tttttttttt ttattttcct tgcccatcgg   2100
ggcctcggat acctgcttta atttttgttt ttctgcccat cggggccgcg gatacctgct   2160
ttgatttttt tttttcatcg cccatcggtg ctttttatgg atgaaaaaat gttggttttg   2220
tgggttgttg cactctctgg aatatctaca cttttttttg ctgctgatca tttggtggtg   2280
tgtgagtgta cctaccgctt tggcagagaa tgactctgca gttaagctaa gggcgtgttc   2340
agattgtgga ggaaaagtgg ccgccatttt agacttgccg cataactcgg cttagggcta   2400
gtcgtttgtg ctaagttaaa ctagggaggc aagatggatg atagcaggtc aggcagagga   2460
agtcatgtgc attgcatgag ctaaacctat ctgaatgaat tgatttgggg cttgttagga   2520
gctttgcgtg attgttgtat cgggaggcag taagaatcat cttttatcag tacaagggac   2580
tagttaaaaa tggaaggtta ggaaagacta aggtgcaggg cttaaaatgg cgattttgac   2640
```

-continued

```
attgcggcat tgctcagcat ggcgggctgt gctttgttag gttgtccaaa atggcggatc   2700
cagttctgtc gcagtgttca agtggcggga aggccacatc atgatgggcg aggctttgtt   2760
aagtggttag catggtggtg gacatgtgcg gtcacacagg aaaagatggc ggctgaaggt   2820
cttgccgcag tgtaaaacat ggcgggcctc tttgtctttg ctgtgtgctt ttcgtgttgg   2880
gttttgccgc agggacaata tggcaggcgt tgtcatatgt atatcatggc ttttgtcacg   2940
tggacatcat ggcgggcttg ccgcattgtt aaagatggcg ggttttgccg cctagtgcca   3000
cgcagagcgg gagaaaaggt gggatggaca gtgctggatt gctgcataac ccaaccaatt   3060
agaaatgggg gtggaattga tcacagccaa ttagagcaga agatggaatt agactgatga   3120
cacactgtcc agctactcag cgaagacctg ggtgaattag catggcactt cgcagctgtc   3180
tttagccagt caggagaaag aagtggaggg gccacgtgta tgtctcccag tgggcggtac   3240
accaggtgtt ttcaaggtct tttcaaggac atttagcctt tccacctctg tcccctctta   3300
tttgtcccct cctgtccagt gctgcctctt gcagtgctgg atatctggct gtgtggtctg   3360
aacctccctc cattcctctg tattggtgcc tcacctaagg ctaagtatac ctcccccccc   3420
accccccaac ccccccaact ccccaccccc accccccacc ccccacctcc ccaccccccct   3480
acccccctac ccccctaccc ccctctggtc tgccctgcac tgcactgttg ccatgggcag   3540
tgctccaggc ctgcttggtg tggacatggt ggtgagccgt ggcaaggacc agaatggatc   3600
acagatgatc gttggccaac aggtggcaga agaggaattc ctgccttcct caagaggaac   3660
acctacccct tggctaatgc tggggtcgga ttttgattta tatttatctt ttggatgtca   3720
gtcatacagt ctgattttgt ggtttgctag tgtttgaatt taagtcttaa gtgactatta   3780
tagaaatgta ttaagaggct ttatttgtag aattcacttt aattacattt aatgagtttt   3840
tgttttgagt tccttaaaat tccttaaagt ttttagcttc tcattacaaa ttccttaacc   3900
tttttttggc agtagatagt caaagtcaaa tcatttctaa tgttttaaaa atgtgctggt   3960
cattttcttt gaaattgact taactatttt cctttgaaga gtctgtagca cagaaacagt   4020
aaaaaattta acttcatgac ctaatgtaaa aaagagtgtt tgaaggttta cacaggtcca   4080
ggccttgctt tgttcccatc cttgatgctg cactaattga ctaatcacct acttatcaga   4140
caggaaactt gaattgctgt ggtctggtgt cctctattca gacttattat attggagtat   4200
ttcaattttt cgttgtatcc tgcctgccta gcatccagtt cctccccagc cctgctccca   4260
gcaaacccct agtctagccc cagccctact cccacccggc cccagccctg ccccaggccc   4320
agtcccctaa ccccccagcc ctaggcccag tcccagtcct agttcctcag tctgtccagc   4380
ttctctcgaa agtcactcta attttcattg attcagtgct caaaataagt tgtccattgg   4440
tatcctatta tactgggata ttccgtttac ccttggcatt gctgatcttc agtactgact   4500
ccttgaccat tttcagttaa gcatacaatc ccatttgtct gtgatctcag gacaaagaat   4560
ttccttactc ggtacgttga agttagggaa tgtcaattga gagctttcta tcagagcatt   4620
attgcccaca atttgagtta cttatcattt tctcgatccc ctgcccttaa aggagaaacc   4680
atttctctgt cattgcttct gtagtcacag tcccaatttt gagtagtgat cttttcttgt   4740
gtactgtgtt ggccacctaa aactctttgc attgagtaaa attctaattg ccaataatcc   4800
tacccattgg attagacagc actctgaacc ccatttgcat tcagcagggg gtcgcagaca   4860
acccgtcttt tgttggacag ttaaaatgct cagtcccaat tgtcatagct ttgcctatta   4920
aacaaaggca ccctactgcg ctttttgctg tgcttctgga gaatcctgct gttcttggac   4980
aattaaagaa caaagtagta attgctaatt gtctcaccca ttaatcatga agactaccag   5040
```

```
tcgcccttgc atttgccttg aggcagcgct gactacctga gatttaagag tttcttaaat   5100
tattgagtaa aatcccaatt atccatagtt ctgttagtta cactatggcc tttgcaaaca   5160
tctttgcata acagcagtgg gactgactca ttcttagagc cccttccctt ggaatattaa   5220
tggatacaat agtaattatt catggttctg cgtaacagag aagacccact tatgtgtatg   5280
cctttatcat tgctcctaga tagtgtgaac tacctaccac cttgcattaa tatgtaaaac   5340
actaattgcc catagtccca ctcattagtc taggatgtcc tctttgccat tgctgctgag   5400
ttctgactac ccaagtttcc ttctcttaaa cagttgatat gcataattgc atatattcat   5460
ggttctgtgc aataaaaatg gattctcacc ccatcccacc ttctgtggga tgttgctaac   5520
gagtgcagat tattcaataa cagctcttga acagttaatt tgcacagttg caattgtcca   5580
gagtcctgtc cattagaaag ggactctgta tcctatttgc acgctacaat gtgggctgat   5640
cacccaagga ctcttcttgt gcattgatgt tcataattgt atttgtccac gatcttgtgc   5700
actaaccctt ccactccctt tgtattccag caggggaccc ttactactca agacctctgt   5760
actaggacag tttatgtgca caatcctaat tgattagaac tgagtctttt atatcaaggt   5820
ccctgcatca tctttgcttt acatcaagag ggtgctggtt acctaatgcc cctcctccag   5880
aaattattga tgtgcaaaat gcaatttccc tatctgctgt tagtctgggg tctcatcccc   5940
tcatattcct tttgtcttac agcagggggt acttgggact gttaatgcgc ataattgcaa   6000
ttatggtctt ttccattaaa ttaagatccc aactgctcac accctcttag cattacagta   6060
gagggtgcta atcacaagga catttctttt gtactgttaa tgtgctactt gcatttgtcc   6120
ctcttcctgt gcactaaaga ccccactcac ttccctagtg ttcagcagtg gatgacctct   6180
agtcaagacc tttgcactag gatagttaat gtgaaccatg gcaactgatc acaacaatgt   6240
ctttcagatc agatccattt tatcctcctt gttttacagc aagggatatt aattacctat   6300
gttacctttc cctgggacta tgaatgtgca aaattccaat gttcatggtc tctcccttta   6360
aacctatatt ctaccccttt tacattatag aaagggatgc tggaaaccca gagtccttct   6420
cttgggactc ttaatgtgta tttctaatta tccatgactc ttaatgtgca tattttcaat   6480
tgcctaattg atttcaattg tctaagacat ttcaaatgtc taattgatta gaactgagtc   6540
ttttatatca agctaatatc tagcttttat atcaagctaa tatcttgact tctcagcatc   6600
atagaagggg gtactgattt cctaaagtct ttcttgaatt tctattatgc aaaattgccc   6660
tgaggccggg tgtggtggct cacacctgta atcccagcac tttgggaggc tgaggtggga   6720
agatccctta ctgccaggag tttgagacca gcctggccaa cattaaaaaa aaaaaaaaaa   6780
gtaagacaat tgccctggaa tcccatcccc ctcacacctc cttggcaaag cagcaggagt   6840
gctaactagc tagtgcttct tctcttatac tgcttaaatg cgcataatta gcagtagttg   6900
atgtgcccct atgttagagt agaatcccgc ttccttgctc catttgcatt actgcaggag   6960
cttctaacta gcctgaattc actctcttgg actgttaatg tgcatactta tatttgctgc   7020
tgtacttttt taccatgtaa ggaccccacc cactgtattt acatcccagc tggaagtacc   7080
tactacttaa gacccttaga ctagtaaagt tagcgtgcat aatcttaggt gttatataca   7140
cattttcagt tgcatacagt tgtgcctttt atcaggactc ctgtacttat caaagcagag   7200
agtgctaatc aatattaagc ccttctcttc gaactgtaga tggcatgtaa ttgcagttgt   7260
caatggtcct tcaattagac ttgggtttct gacctatcac accctctttg ctttattgca   7320
tggggtacta ttcacttaag gccccttttct caaactgtta atgtgcctaa tgacaattac   7380
```

atcagtatcc ttccttttga aggacagcat ggttggtgac acctaaggcc ccatttcttg 7440
gcctcccaat atgtgtgatt gtatttgtcg aggttgctat gcactagaga aggaaagtgc 7500
tcccctcatc cccacttttc ccttccagca ggaagtgccc accccataag accctttat 7560 ttggagagtc taggtgcaca attgtaagtg accacaagca tgcatcttgg acatttatgt 7620
gcgtaatcgc acactgctca ttccatgtga ataaggtcct actctccgac cccttttgca 7680
atacagaagg gttgctgata acgcagtccc cttttcttgg catgttgtgt gtgattataa 7740
tcgtctggga tcctatgcac tagaaaagga gggtcctctc cacatacctc agtctcacct 7800
ttcccttcca gcagggagtg cccactccat aagactctca catttggaca gtcaaggtgc 7860
gtaattgtta agtgaacaca accatgcacc ttagacatgg atttgcataa ctacacacag 7920
ctcaacctat ctgaataaaa tcctactctc agaccccttt tgcagtacag caggggtgct 7980
gatcaccaag gcccttttc ctggcctggt atgcgtgtga ttatgtttgt cccggttcct 8040
gtgtattaga catggaagcc tcccctgcca cactccaccc ccaatcttcc tttcccttcc 8100
ggcaggagtg ccctctccat aagacgctta cgtttggaca atcaaggtgc acagttgtaa 8160
gtgaccacag gcatacacct tggacattaa tgtgcataac cactttgccc attccatctg 8220
aataaggtcc tactctcaga cccctttgc agtacagcag ggtgctgat caccaaggcc 8280 ccttttcttg gcctgttatg tgcgtgatta tatttgtctg ggttcctgtg tattagacaa 8340
ggaagccttc cccccgcccc cacccccact cccagtcttc ctttcccttc cagcagggag 8400
tgccccctcc ataagatcat tacatttgga caatcaaggt gcacaattat aagtgaccac 8460
agccatgcac cttggacatt attggacatt aatgtgcgta actgcacatg gcccatccca 8520
tctgaataag gacctactct cagatgcctt tgcagtacag caggggtact gaatcaccaa 8580
ggcccttttt cttggcctgt tatgtgtgtg attatattta tcccagtttc tgtgtaatag 8640
acatgaaagc ctcccctgcc acaccccacc tccaatcttc ctttcccttc caccagggag 8700
tgtccactcc atataccctt acatttggac aatcaaggtg cacaattgta agtgagcata 8760
ggcactcacc ttggacatga atgtgcataa ctgcacatgg cccatcccat ctgaataagg 8820
tcctactctc agacccttt tgcagtacag caggggtgct gatcaccaag gccccttttc 8880
ctggcctgtt atgtgtgtga ttatatttgt tccagttcct gtgtaataga catggaagcc 8940
tcccctgcca cactccaccc ccaatcttcc tttccttctg gcaggaagta cccgctccat 9000
aagaccctta catttggaca gtcaaggtgc acaattgtat gtgaccacaa ccatgcacct 9060
tggacataaa tgtgtgtaac tgcacatggc ccatcccatc tgaataaggt cctactctca 9120
gacccctttt gcagtacagt aggtgtgctg ataaccaagg cccctcttcc tggcctgtta 9180
acgtatgtga ttatatttgt ctgggttcca gtgtataaga catggaagcc tcccctgccc 9240
caccccaccc tcaatcttcc tttcccttct ggcagggagt gccagctcca taagaacctt 9300
acatttggac agtcaaggtg cacaattcta agtgaccgca gccatgcacc ttggtcaata 9360
atgtgtgtaa ctgcacacgg cctatctcat ctgaataagg ccttactctc agaccccttt 9420
tgcagtacag caggggtgct gataaccaag gcccattttc ctggcctgtt atgtgtgtga 9480
ttatatttgt ccaggtttct gtgtactaga caaggaagcc tcctctgccc catcccatct 9540
acgcataatc tttcttttcc tcccagcagg gagtgctcac tccataagac ccttacattt 9600
ggacaatcaa ggtgcacaat tgtaagtgac cacaaccatg catcttggaa atttatgtgc 9660
ataactgcac atggcttatc ctatttgaat aaagtcctac tctcagaccc cctttgcagt 9720
atagctgggg tgctgatcac tgaggcctct ttgcttggct tgtctatatt cttgtgtact 9780

-continued

```
agataagggc accttctcat ggactccctt tgcttttcaa caaggagtac ccactacttt   9840
ttaagattct tatatttgtc caaagtacat ggttttaatt gaccacaaca atgtcccttg   9900
gacattaatg tatgtaatca ccacatggtt catcctaatt aaacaaagtt ctaccttctc   9960
accctccatt tgcagtatac cagggttgct gaccccctaa gtcccctttt cttggcttgt  10020
tgacatgcat aattgcattt atgttggttc ttgtgcccta gacaaggatg ccccacctct  10080
tttcaatagt gggtgcccac tccttatgat ctttacattt gaacagttaa tgtgaataat  10140
tgcagttgtc cacaacccta tcacttctag gaccattata cctcttttgc attactgtgg  10200
ggtatactgt ttccctccaa ggccccttct ggtggactat caacatataa ttgaaatttt  10260
cttttgtctt tgtcagtaga ttaaggtcat accccatcac ctttcctttg tagtacaaca  10320
gggtgtcctg atcaaccaaa gtcctgttgt tttggactgt taatatgtgc aattacattt  10380
gctcctgatc tgtgcactag ataaggatcc tacctacttt cttagtgttt ttagcaggta  10440
gtgcccacta ctcaagactg tcacttggaa tgttcatgtg cacaaactca attctctaag  10500
catgttcctg taccaccttt gctttagagc agggggatga tattcactaa gtgccccttc  10560
ttttggactt aatatgcatt aatgcaattg tccacctctt cttttagact aagagttgat  10620
ctccacatat tccccttgca tcaggggcat gttaattatg aatgaaccct tttcttttaa  10680
tattaatgtc ataattgtat ttgtggacct gtgtaggaga aaaagaccct atgttcctcc  10740
cattaccctt tggattgctg ctgagaagtg ttaactactc ataatctcag ctcttggaca  10800
attaatagca ttaataacaa ttatcaaggg cactgatcat tagataagac tcctgcttcc  10860
tcgttgctta catcgggggt actgacccac taaggcccct tgtactgtta atgtgaatat  10920
ttgcaattat atatgtctcc ttctggtaga gtgggatatt atgccctagt atcccctttg  10980
cattactgca ggggctgctg actactcaaa acttctcctg ggactgttaa taggcacaat  11040
ggcagttatc aatggttttc tccctccctg accttgttaa gcaagcgccc caccccaccc  11100
ttagtttccc atggcataat aaagtataag cattggagta ttccatgcac ttgtctatca  11160
aacagtggtc catactccca accctttttgc attgcgccag tgtgtaaaat cacaggtagc  11220
catggtgtca tgctttatat acgaagtctt ccctctctct gccccttgtg tgcccttggc  11280
cccttttttac agactattgc tcacaatctc aggtgtccat atttgcagct attaggtaag  11340
attgtgctgt ctccctcttc ccttccctct gccctgcccc ttttgcctct ttgctgggta  11400
atgttgacca gacaaggccc tttctcttgg acttaaacaa ttctcagttg cactttcctt  11460
ggtccaccca ttatacatga acccctctac ttcctttcgc attgcttctg agtatgctga  11520
ctacccaaag ccccttctgt gttattaata aacacagtac tgattgtccc atttttcagc  11580
ccatcagtcc aagatctccc taccactttg gtgtgttggt gcagtgttga ctatgaaaag  11640
caggcctgaa ctaggtggat aagccttcac tcattttctt tcatttatta atgatcctag  11700
tttcaattat tgtcagattc tggggacaag aaccattctt gcccacctgt gttactgctt  11760
tactgtgcaa aatactgaag gcaagtcaga cccagggagc tggattgcca tcctttattt  11820
tgtgtttcca gtgtacacta taaaattgtc tccccaggaa ggaaggttgg cactttctct  11880
gcattcttct ttccagagca gattgcctgg ttaagaatct cttgttgtcc cttctgtata  11940
ttgttattgt aaagtgccaa atgccaggat acagccagaa aaattgctta ttattattaa  12000
aaaaattttt ttaagaaaga catctggatt gtagggtgga ctcgataacc tggtcattat  12060
tttttgaag ccaaaatatc catttatact atgtacctgg tgaccagtgt ctctcatttt  12120
```

aactgagggt ggtgggtctg tggatagaac actgactctt gctattttaa tatcaaagat 12180
attctagatc cagcacagtg gcggccgctc tagagtggaa ctcttaagac cagtatcttt 12240
gtgtgggctt taccagcatt cacttttaga aaaactacct aaattttata atcctttaat 12300
ttcttcatct ggagcacctg cccctactta tttcaagaag attgcagtaa aacgattaaa 12360
tgagggaaca tatgcagagg tgcttttaaa aagcatatgc caccttttt attaattatt 12420
atataaaatg aagcatttaa ttatagtaat aatttgaagt agtttgaagt accacactga 12480
ggtgaggact taaaaatgat aagacgagtt ccctatttta taagaaaaat aagccaaaat 12540
taaatattct tttggatata aatttcaaca gtgagatagc tgcctagtgg aaatgaataa 12600
tatcccagcc actagtgtac agggtgtttt gtggcacagg attatgtaat atggaactgc 12660
tcaagcaaat aactagtcat cacaacagca gttctttgta ataactgaaa aagaatattg 12720
tttctcggag aaggatgtca aaagatcggc ccagctcagg gagcagtttg ccctactagc 12780
tcctcggaca gctgtaaaga agagtctctg gctctttaga atactgatcc cattgaagat 12840
accacgctgc atgtgtcctt agtagtcatg tctccttagg ctcctcttgg acattctgag 12900
catgtgagac ctgaggactg caaacagcta taagaggctc caaattaatc atatctttcc 12960
ctttgagaat ctggccaagc tccagctaat ctacttggat gggttgccag ctatctggag 13020
aaaaagatct tcctcagaag aataggcttg ttgttttaca gtgttagtga tccattccct 13080
ttgacgatcc ctaggtggag atggggcatg aggatcctcc aggggaaaag ctcactacca 13140
ctgggcaaca accctaggtc aggaggttct gtcaagatac tttcctggtc ccagatagga 13200
agataaagtc tcaaaaacaa ccaccacacg tcaagctctt cattgttcct atctgccaaa 13260
tcattatact tcctacaagc agtgcagaga gctgagtctt cagcaggtcc aagaaatttg 13320
aacacactga aggaagtcag ccttcccacc tgaagatcaa catgcctggc actctagcac 13380
ttgaggatag ctgaatgaat gtgtatttct ttgtctcttt ctttcttgtc tttgctcttt 13440
gttctctatc taaagtgtgt cttacccatt tccatgtttc tcttgctaat ttctttcgtg 13500
tgtgcctttg cctcattttc tctttttgtt cacaagagtg gtctgtgtct tgtcttagac 13560
atatctctca tttttcattt tgttgctatt tctctttgct ctcctagatg tggctcttct 13620
ttcacgcttt atttcatgtc tcctttttgg gtcacatgct gtgtgctttt tgtccttttc 13680
ttgttctgtc tacctctcct ttctctgcct acctctcttt tctctttgtg aactgtgatt 13740
atttgttacc ccttcccctt ctcgttcgtt ttaaatttca cctttttctt gagtctggcc 13800
tcctttctgc tgtttctact ttttatctca catttctcat ttctgcattt cctttctgcc 13860
tctcttgggc tattctctct ctcctcccct gcgtgcctca gcatctcttg ctgtttgtga 13920
ttttctattt cagtattaat ctctgttggc ttgtatttgt tctctgcttc ttccctttct 13980
actcaccttt gagtatttca gcctcttcat gaatctatct ccctctcttt gatttcatgt 14040
aatctctcct taaatatttc tttgcatatg tgggcaagtg tacgtgtgtg tgtgtcatgt 14100
gtggcagagg ggcttcctaa cccctgcctg ataggtgcag aacgtcggct atcagagcaa 14160
gcattgtgga gcggttcctt atgccaggct gccatgtgag atgatccaag accaaaacaa 14220
ggccctagac tgcagtaaaa cccagaactc aagtagggca gaaggtggaa ggctcatatg 14280
gatagaaggc ccaaagtata agacagatgg tttgagactt gagacccgag gactaagatg 14340
gaaagcccat gttccaagat agatagaagc ctcaggcctg aaaccaacaa aagcctcaag 14400
agccaagaaa acagagggtg gcctgaattg gaccgaaggc ctgagttgga tggaagtctc 14460
aaggcttgag ttagaagtct taagacctgg gacaggacac atggaaggcc taagaactga 14520

```
gacttgtgac acaaggccaa cgacctaaga ttagcccagg gttgtagctg gaagacctac  14580
aacccaagga tggaaggccc ctgtcacaaa gcctacctag atggatagag gacccaagcg  14640
aaaaaggtat ctcaagacta acggccggaa tctggaggcc catgacccag aacccaggaa  14700
ggatagaagc ttgaagacct ggggaaatcc caagatgaga accctaaacc ctacctcttt  14760
tctattgttt acacttctta ctcttagata tttccagttc tcctgtttat ctttaagcct  14820
gattcttttg agatgtactt tttgatgttg ccggttacct ttagattgac agtattatgc  14880
ctgggccagt cttgagccag ctttaaatca cagcttttac ctatttgtta ggctatagtg  14940
ttttgtaaac ttctgtttct attcacatct tctccacttg agagagacac caaaatccag  15000
tcagtatcta atctggcttt tgttaacttc cctcaggagc agacattcat ataggtgata  15060
ctgtatttca gtcctttctt ttgaccccag aagccctaga ctgagaagat aaaatggtca  15120
ggttgttggg gaaaaaaaaa gtgccaggct ctctagagaa aaatgtgaag agatgctcca  15180
ggccaatgag aagaattaga caagaaatac acagatgtgc cagacttctg agaagcacct  15240
gccagcaaca gcttccttct ttgagcttag attttcctag tccatccctc atgaaaaatg  15300
actgaccact gctgggcagc aggagggatg atgaccaact aattcccaaa ccccagtctc  15360
attggtaccg agctcggatc cactagtcca gtgtggtgga attctgcaga tatccagcac  15420
agtggcggcc gctcgagtct agagggcccg tttaaacccg ctgatcagcc tcgactgtgc  15480
cttctagttg ccagccatct gttgtttgcc cctcccccgt gccttccttg accctggaag  15540
gtgccactcc cactgtcctt tcctaataaa atgaggaaat tgcatcgcat tgtctgagta  15600
ggtgtcattc tattctgggg ggtggggtgg ggcaggacag caagggggag gattgggaag  15660
acaatagcag gcatgctggg gatgcggtgg gctctatggc ttctgaggcg gaaagaacca  15720
gctggggctc taggggggtat ccccacgcgc cctgtagcgg cgcattaagc gcggcgggtg  15780
tggtggttac gcgcagcgtg accgctacac ttgccagcgc cctagcgccc gctcctttcg  15840
ctttcttccc ttcctttctc gccacgttcg ccggctttcc ccgtcaagct ctaaatcggg  15900
ggctcccttt agggttccga tttagtgctt tacggcacct cgaccccaaa aaacttgatt  15960
agggtgatgg ttcacgtagt gggccatcgc cctgatagac ggtttttcgc cctttgacgt  16020
tggagtccac gttctttaat agtggactct tgttccaaac tggaacaaca ctcaacccta  16080
tctcggtcta ttcttttgat ttataaggga ttttgccgat ttcggcctat tggttaaaaa  16140
atgagctgat ttaacaaaaa tttaacgcga attaattctg tggaatgtgt gtcagttagg  16200
gtgtggaaag tccccaggct ccccagcagg cagaagtatg caaagcatgc atctcaatta  16260
gtcagcaacc aggtgtggaa agtccccagg ctccccagca ggcagaagta tgcaaagcat  16320
gcatctcaat tagtcagcaa ccatagtccc gcccctaact ccgcccatcc cgcccctaac  16380
tccgcccagt tccgcccatt ctccgcccca tggctgacta attttttttta tttatgcaga  16440
ggccgaggcc gcctctgcct ctgagctatt ccagaagtag tgaggaggct tttttggagg  16500
cctaggcttt tgcaaaaagc tcccgggagc ttgtatatcc attttcggat ctgatcagca  16560
cgtgatgaaa aagcctgaac tcaccgcgac gtctgtcgag aagtttctga tcgaaaagtt  16620
cgacagcgtc tccgacctga tgcagctctc ggagggcgaa gaatctcgtg ctttcagctt  16680
cgatgtagga gggcgtggat atgtcctgcg ggtaaatagc tgcgccgatg gtttctacaa  16740
agatcgttat gtttatcggc actttgcatc ggccgcgctc ccgattccgg aagtgcttga  16800
cattggggaa ttcagcgaga gcctgaccta ttgcatctcc cgccgtgcac agggtgtcac  16860
```

-continued gttgcaagac ctgcctgaaa ccgaactgcc cgctgttctg cagccggtcg cggaggccat 16920
ggatgcgatc gctgcggccg atcttagcca gacgagcggg ttcggcccat tcggaccgca 16980
aggaatcggt caatacacta catggcgtga tttcatatgc gcgattgctg atccccatgt 17040
gtatcactgg caaactgtga tggacgacac cgtcagtgcg tccgtcgcgc aggctctcga 17100
tgagctgatg ctttgggccg aggactgccc cgaagtccgg cacctcgtgc acgcggattt 17160
cggctccaac aatgtcctga cggacaatgg ccgcataaca gcggtcattg actggagcga 17220
ggcgatgttc ggggattccc aatacgaggt cgccaacatc ttcttctgga ggccgtggtt 17280
ggcttgtatg gagcagcaga cgcgctactt cgagcggagg catccggagc ttgcaggatc 17340
gccgcggctc cgggcgtata tgctccgcat tggtcttgac caactctatc agagcttggt 17400
tgacggcaat ttcgatgatg cagcttgggc gcagggtcga tgcgacgcaa tcgtccgatc 17460
cggagccggg actgtcgggc gtacacaaat cgcccgcaga agcgcggccg tctggaccga 17520
tggctgtgta gaagtactcg ccgatagtgg aaaccgacgc cccagcactc gtccgagggc 17580
aaaggaatag cacgtgctac gagatttcga ttccaccgcc gccttctatg aaaggttggg 17640
cttcggaatc gttttccggg acgccggctg gatgatcctc cagcgcgggg atctcatgct 17700
ggagttcttc gcccacccca acttgtttat tgcagcttat aatggttaca aataaagcaa 17760
tagcatcaca aatttcacaa ataaagcatt tttttcactg cattctagtt gtggtttgtc 17820
caaactcatc aatgtatctt atcatgtctg tatacgtaaa ctggcaaagg ggtggctggg 17880
ccaaaagaca gaggaattaa gtaagaagtc caggaaaaat gaacttcaca tcaaatttta 17940
gagcacggta gccatgaatc ttgtgaatag ctcccaaaaa tgtcctgtgg aagacaacta 18000
gaaagcattc tacaatcagg cacccacctc cacctgcagc ctcctgtgtt gttctcatgg 18060
ggcacctctg ggctccagct cctccaaggc acctccacac tctctcaagt acactcttca 18120
ctcttcccca aacatgattc ccctactgct ctgcctaact cccacttctc tttcaagtag 18180
cagcttaaac gtcacctcat atttggctgg aaaatagaat atagacagag gggtaagtta 18240
aggctagaaa ggcaggctgg gtcaacagaa tggcaagcta aaacatggga ttttctaaaa 18300
cagcctaaga gggtgacaga taaaagtgtg caaggagtgg cacaactcca gtttcatctt 18360
tagctatagc aattaacacc ataaggagtc tggattcaat tttgccattt actagctagc 18420
taccaacttc tgtgtcgctt tgggcaaatc aattaaatcc atacctccct ttccatctgc 18480
agaatgggtt tataacagta cttaaacctc aaggtactaa gaacagtaaa gagttaatgg 18540
tataccgtcg acctctagct agagcttggc gtaatcatgg tcatagctgt ttcctgtgtg 18600
aaattgttat ccgctcacaa ttccacacaa catacgagcc ggaagcataa agtgtaaagc 18660
ctggggtgcc taatgagtga gctaactcac attaattgcg ttgcgctcac tgcccgcttt 18720
ccagtcggga aacctgtcgt gccagctgca ttaatgaatc ggccaacgcg cggggagagg 18780
cggtttgcgt attgggcgct cttccgcttc ctcgctcact gactcgctgc gctcggtcgt 18840
tcggctgcgg cgagcggtat cagctcactc aaaggcggta atacggttat ccacagaatc 18900
aggggataac gcaggaaaga acatgtgagc aaaaggccag caaaaggcca ggaaccgtaa 18960
aaaggccgcg ttgctggcgt ttttccatag gctccgcccc cctgacgagc atcacaaaaa 19020
tcgacgctca agtcagaggt ggcgaaaccc gacaggacta taaagatacc aggcgtttcc 19080
ccctggaagc tccctcgtgc gctctcctgt tccgaccctg ccgcttaccg gatacctgtc 19140
cgcctttctc ccttcgggaa gcgtggcgct ttctcatagc tcacgctgta ggtatctcag 19200
ttcggtgtag gtcgttcgct ccaagctggg ctgtgtgcac gaaccccccg ttcagcccga 19260
ccgctgcgcc ttatccggta actatcgtct tgagtccaac ccggtaagac acgacttatc 19320
gccactggca gcagccactg gtaacaggat tagcagagcg aggtatgtag gcggtgctac 19380
agagttcttg aagtggtggc ctaactacgg ctacactaga agaacagtat ttggtatctg 19440
cgctctgctg aagccagtta ccttcggaaa aagagttggt agctcttgat ccggcaaaca 19500
aaccaccgct ggtagcggtt ggtttttttgt ttgcaagcag cagattacgc gcagaaaaaa 19560
aggatctcaa gaagatcctt tgatcttttc tacggggtct gacgctcagt ggaacgaaaa 19620
ctcacgttaa gggattttgg tcatgagatt atcaaaaagg atcttcacct agatcctttt 19680
aaattaaaaa tgaagtttta aatcaatcta aagtatatat gagtaaactt ggtctgacag 19740
ttaccaatgc ttaatcagtg aggcacctat ctcagcgatc tgtctatttc gttcatccat 19800
agttgcctga ctccccgtcg tgtagataac tacgatacgg gagggcttac catctggccc 19860
cagtgctgca atgataccgc gagacccacg ctcaccggct ccagatttat cagcaataaa 19920
ccagccagcc ggaagggccg agcgcagaag tggtcctgca actttatccg cctccatcca 19980
gtctattaat tgttgccggg aagctagagt aagtagttcg ccagttaata gtttgcgcaa 20040
cgttgttgcc attgctacag gcatcgtggt gtcacgctcg tcgtttggta tggcttcatt 20100
cagctccggt tcccaacgat caaggcgagt tacatgatcc cccatgttgt gcaaaaaagc 20160
ggttagctcc ttcggtcctc cgatcgttgt cagaagtaag ttggccgcag tgttatcact 20220
catggttatg gcagcactgc ataattctct tactgtcatg ccatccgtaa gatgcttttc 20280
tgtgactggt gagtactcaa ccaagtcatt ctgagaatag tgtatgcggc gaccgagttg 20340
ctcttgcccg gcgtcaatac gggataatac cgcgccacat agcagaactt taaaagtgct 20400
catcattgga aaacgttctt cggggcgaaa actctcaagg atcttaccgc tgttgagatc 20460
cagttcgatg taacccactc gtgcacccaa ctgatcttca gcatctttta ctttcaccag 20520
cgtttctggg tgagcaaaaa caggaaggca aaatgccgca aaaaagggaa taagggcgac 20580
acggaaatgt tgaatactca tactcttcct ttttcaatat tattgaagca tttatcaggg 20640
ttattgtctc atgagcggat acatatttga atgtatttag aaaaataaac aaataggggt 20700
tccgcgcaca tttccccgaa aagtgccacc tgacgtc 20737

<210> SEQ ID NO 18
<211> LENGTH: 14026
<212> TYPE: DNA
<213> ORGANISM: Artificial Sequence
<220> FEATURE:
<223> OTHER INFORMATION: 6.8 kb/hXIST/RCAN1 construct

<400> SEQUENCE: 18
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg acaatgtttt cagaaatgta atcttttcaa 240
tatgaaactg ctgatggacc aagaaaacaa aaccctcaac ccaagggaac atcagattgc 300
tggtcaagga gaaatgagga gctgacggtc tcagcattta tttgacttgc tccacggaca 360
gagcaggaga aggctcaaac ctcttcaccc caagactctc cctcacacct gcctcctcac 420
ccaaacccta gaggacagga caggaaccac caacatttta tggttttcaa aaatcctgca 480
ttgaacactg actgtgagcc aggtgctgat ggaagtgcct ttcactcgat gatctcatct 540

-continued

```
actgctcaca attccaccag ttaaggccca cattttggac aaagagcctg aggaacctac    600
cccctccccg cagtgctcac acttttgtcc ctccagagga cgggaacttc ctctttcttt    660
agcaagctct gtaggggacc agcccacagg ccctggggta gggcagcccg accgcggccc    720
ttccctcacc atggcctatg gttctccttc ccttttcctt taagaaggcc aggtgagaat    780
cacaggaaag ggagaattta ttttgattaa aaataacatt tcttaaaggg ggcatcgatt    840
ttccctttcc aaagtccaat cactcatccc tatccggagc gacagaacct ggggccgggg    900
ctcaggcctc ccacgcaggc tgtgctcagt ggacacagga atggattcct gggacactgc    960
gggtcgcgat gtacgggcca gatatacgcg ttgacattga ttattgacta gttattaata   1020
gtaatcaatt acggggtcat tagttcatag cccatatatg gagttccgcg ttacataact   1080
tacggtaaat ggcccgcctg gctgaccgcc caacgacccc cgcccattga cgtcaataat   1140
gacgtatgtt cccatagtaa cgccaatagg gactttccat tgacgtcaat gggtggagta   1200
tttacggtaa actgcccact tggcagtaca tcaagtgtat catatgccaa gtacgccccc   1260
tattgacgtc aatgacggta aatggcccgc ctggcattat gcccagtaca tgaccttatg   1320
ggactttcct acttggcagt acatctacgt attagtcatc gctattacca tggtgatgcg   1380
gttttggcag tacatcaatg ggcgtggata gcggtttgac tcacggggat ttccaagtct   1440
ccaccccatt gacgtcaatg ggagtttgtt ttggcaccaa aatcaacggg actttccaaa   1500
atgtcgtaac aactccgccc cattgacgca aatgggcggt aggcgtgtac ggtgggaggt   1560
ctatataagc agagctctcc ctatcagtga tagagatctc cctatcagtg atagagatcg   1620
tcgacgagct cgtttagtga accgtcagat cgcctggaga cgccatccac gctgttttga   1680
cctccataga agacaccggg accgatccag cctccggact ctagcgttta aacttaagct   1740
tggtaccgag ctcggatcca ctagtccagt gtggtggaat tctgcagatt ctagaacatt   1800
ttctagtccc ccaacaccct ttatggcgta tttctttaaa aaaatcacct aaattccata   1860
aaatattttt ttaaattcta tactttctcc tagtgtcttc ttgacacgtc ctccatattt   1920
ttttaaagaa agtatttgga atattttgag gcaattttta atatttaagg aatttttctt   1980
tggaatcatt tttggtgaca tctctgtttt ttgtggatca gtttttttact cttccactct   2040
cttttctata ttttgcccat cggggctgcg gatacctggt tttattattt tttctttgcc   2100
caacggggcc gtggatacct gccttttaat tcttttttat tcgcccatcg gggccgcgga   2160
tacctgcttt ttattttttt ttccttagcc catcggggta tcggatacct gctgattccc   2220
ttcccctctg aacccccaac actctggccc atcggggtga cggatatctg ctttttaaaa   2280
attttctttt tttggcccat cggggcttcg gatacctgct tttttttttt ttattttcct   2340
tgcccatcgg ggcctcggat acctgcttta atttttgttt ttctgcccat cggggccgcg   2400
gatacctgct ttgatttttt tttttcatcg cccatcggtg ctttttatgg atgaaaaaat   2460
gttggttttg tgggttgttg cactctctgg aatatctaca cttttttttg ctgctgatca   2520
tttggtggtg tgtgagtgta cctaccgctt tggcagagaa tgactctgca gttaagctaa   2580
gggcgtgttc agattgtgga ggaaaagtgg ccgccatttt agacttgccg cataactcgg   2640
cttagggcta gtcgtttgtg ctaagttaaa ctagggaggc aagatggatg atagcaggtc   2700
aggcagagga agtcatgtgc attgcatgag ctaaacctat ctgaatgaat tgatttgggg   2760
cttgttagga gctttgcgtg attgttgtat cgggaggcag taagaatcat cttttatcag   2820
tacaagggac tagttaaaaa tggaaggtta ggaaagacta aggtgcaggg cttaaaatgg   2880
cgattttgac attgcggcat tgctcagcat ggcgggctgt gctttgttag gttgtccaaa   2940
```

-continued atggcggatc cagttctgtc gcagtgttca agtggcggga aggccacatc atgatgggcg 3000
aggctttgtt aagtggttag catggtggtg gacatgtgcg gtcacacagg aaaagatggc 3060
ggctgaaggt cttgccgcag tgtaaaacat ggcgggcctc tttgtctttg ctgtgtgctt 3120
ttcgtgttgg gttttgccgc agggacaata tggcaggcgt tgtcatatgt atatcatggc 3180
ttttgtcacg tggacatcat ggcgggcttg ccgcattgtt aaagatggcg ggttttgccg 3240
cctagtgcca cgcagagcgg gagaaaaggt gggatggaca gtgctggatt gctgcataac 3300
ccaaccaatt agaaatgggg gtggaattga tcacagccaa ttagagcaga agatggaatt 3360
agactgatga cacactgtcc agctactcag cgaagacctg ggtgaattag catggcactt 3420
cgcagctgtc tttagccagt caggagaaag aagtggaggg gccacgtgta tgtctcccag 3480
tgggcggtac accaggtgtt ttcaaggtct tttcaaggac atttagcctt tccacctctg 3540
tcccctctta tttgtcccct cctgtccagt gctgcctctt gcagtgctgg atatctggct 3600
gtgtggtctg aacctccctc cattcctctg tattggtgcc tcacctaagg ctaagtatac 3660
ctcccccccc accccccaac ccccccaact ccccaccccc accccccacc ccccacctcc 3720 ccaccccccct accccccctac ccccctaccc ccctctggtc tgccctgcac tgcactgttg 3780
ccatgggcag tgctccaggc ctgcttggtg tggacatggt ggtgagccgt ggcaaggacc 3840
agaatggatc acagatgatc gttggccaat tggcctccca atatgtgtga ttgtatttgt 3900
cgaggttgct atgcactaga gaaggaaagt gctcccctca tccccacttt tcccttccag 3960
caggaagtgc ccaccccata agaccctttt atttggagag tctaggtgca caattgtaag 4020
tgaccacaag catgcatctt ggacatttat gtgcgtaatc gcacactgct cattccatgt 4080
gaataaggtc ctactctccg accccttttg caatacagaa gggttgctga taacgcagtc 4140 ccctttctt ggcatgttgt gtgtgattat aatcgtctgg gatcctatgc actagaaaag 4200
gagggtcctc tccacatacc tcagtctcac ctttcccttc cagcagggag tgcccactcc 4260
ataagactct cacatttgga cagtcaaggt gcgtaattgt taagtgaaca caaccatgca 4320
ccttagacat ggatttgcat aactacacac agctcaacct atctgaataa aatcctactc 4380
tcagacccct tttgcagtac agcaggggtg ctgatcacca aggccctttt tcctggcctg 4440
gtatgcgtgt gattatgttt gtcccggttc ctgtgtatta gacatggaag cctcccctgc 4500
cacactccac ccccaatctt cctttccctt ccggcaggag tgccctctcc ataagacgct 4560
tacgtttgga caatcaaggt gcacagttgt aagtgaccac aggcatacac cttggacatt 4620
aatgtgcata accactttgc ccattccatc tgaataaggt cctactctca gaccccttt 4680 gcagtacagc aggggtgctg atcaccaagg cccctttct tggcctgtta tgtgcgtgat 4740
tatatttgtc tgggttcctg tgtattagac aaggaagcct tccccccgcc cccacccca 4800 ctcccagtct tcctttccct tccagcaggg agtgccccct ccataagatc attacatttg 4860
gacaatcaag gtgcacaatt ataagtgacc acagccatgc accttggaca ttattggaca 4920
ttaatgtgcg taactgcaca tggcccatcc catctgaata aggacctact ctcagatgcc 4980
tttgcagtac agcaggggta ctgaatcacc aaggcccttt ttcttggcct gttatgtgtg 5040
tgattatatt tatcccagtt tctgtgtaat agacatgaaa gcctcccctg ccacacccca 5100
cctccaatct tcctttccct tccaccaggg agtgtccact ccatataccc ttacatttgg 5160
acaatcaagg tgcacaattg taagtgagca taggcactca ccttggacat gaatgtgcat 5220
aactgcacat ggcccatccc atctgaataa ggtcctactc tcagaccctt tttgcagtac 5280
agcaggggtg ctgatcacca aggccccttt tcctggcctg ttatgtgtgt gattatattt 5340
gttccagttc ctgtgtaata gacatggaag cctcccctgc cacactccac ccccaatctt 5400
cctttccttc tggcaggaag tacccgctcc ataagaccct tacatttgga cagtcaaggt 5460
gcacaattgt atgtgaccac aaccatgcac cttggacata aatgtgtgta actgcacatg 5520
gcccatccca tctgaataag gtcctactct cagacccctt ttgcagtaca gtaggtgtgc 5580
tgataaccaa ggcccctctt cctggcctgt taacgtatgt gattatattt gtctgggttc 5640
cagtgtataa gacatggaag cctcccctgc cccaccccac cctcaatctt cctttccctt 5700
ctggcaggga gtgccagctc cataagaacc ttacatttgg acagtcaagg tgcacaattc 5760
taagtgaccg cagccatgca ccttggtcaa taatgtgtgt aactgcacac ggcctatctc 5820
atctgaataa ggccttactc tcagacccct tttgcagtac agcaggggtg ctgataacca 5880
aggcccattt tcctggcctg ttatgtgtgt gattatattt gtccaggttt ctgtgtacta 5940
gacaaggaag cctcctctgc cccatcccat ctacgcataa tctttctttt cctcccagca 6000
gggagtgctc actccataag acccttacat ttggacaatc aaggtgcaca attgtaagtg 6060
accacaacca tgcatcttgg aaatttatgt gcataactgc acatggctta tcctatttga 6120
ataaagtcct actctcagac cccctttgca gtatagctgg ggtgctgatc actgaggcct 6180
ctttgcttgg cttgtctata ttcttgtgta ctagataagg gcaccttctc atggactccc 6240
tttgcttttc aacaaggagt acccactact ttttaagatt cttatatttg tccaaagtac 6300
atggttttaa ttgaccacaa caatgtccct tggacattaa tgtatgtaat caccacatgg 6360
ttcatcctaa ttaaacaaag ttctaccttc tcaccctcca tttgcagtat accagggttg 6420 ctgacccccct aagtcccctt ttcttggctt gttgacatgc ataattgcat ttatgttggt 6480
tcttgtgccc tagacaagga tgccccacct cttttcaata gtgggtgccc actccttatg 6540
atctttacat ttgaacagtt aatgtgaata attgcagttg tccacaaccc tatcacttct 6600
aggaccatta tacctctttt gcattactgt ggggtatact gtttccctcc aaggcccctt 6660
ctggtggact atcaacatat aattgaaatt ttcttttgtc tttgtcagta gattaaggtc 6720
ataccccatc acctttcctt tgtagtacaa cagggtgtcc tgatcaacca aagtcctgtt 6780
gttttggact gttaatatgt gcaattacat ttgctcctga tctgtgcact agataaggat 6840
cctacctact ttcttagtgt ttttagcagg tagtgcccac tactcaagac tgtcacttgg 6900
aatgttcatg tgcacaaact caattctcta agcatgttcc tgtaccacct ttgctttaga 6960
gcagggggat gatattcact aagtgcccct tcttttggac ttaatatgca ttaatgcaat 7020
tgtccacctc ttcttttaga ctaagagttg atctccacat attccccttg catcaggggc 7080
atgttaatta tgaatgaacc cttttctttt aatattaatg tcataattgt atttgtggac 7140
ctgtgtagga gaaaaagacc ctatgttcct cccattaccc tttggattgc tgctgagaag 7200
tgttaactac tcataatctc agctcttgga caattaatag cattaataac aattatcaag 7260
ggcactgatc attagataag actcctgctt cctcgttgct tacatcgggg gtactgaccc 7320
actaaggccc cttgtactgt taatgtgaat atttgcaatt atatatgtct ccttctggta 7380
gagtgggata ttatgcccta gtatcccctt tgcattactg caggggctgc tgactactca 7440
aaacttctcc tgggactgtt aataggcaca atggcagtta tcaatggttt tctccctccc 7500
tgaccttgtt aagcaagcgc cccaccccac ccttagtttc ccatggcata ataaagtata 7560
agcattggag tattccatgc acttgtctat caaacagtgg tccatactcc caacccttttt 7620 gcattgcgcc agtgtgtaaa atcacaggta gccatggtgt catgctttat atacgaagtc 7680

-continued

```
ttccctctct ctgccccttg tgtgcccttg gccccttttt acagactatt gctcacaatc   7740
tcaggtgtcc atatttgcag ctattaggta agattgtgct gtctccctct tcccttccct   7800
ctgccctgcc ccttttgcct ctttgctggg taatgttgac cggacaaggc cctttctctt   7860
ggacttaaac aattctcagt tgcactttcc ttggtcccac ccattataca tgaacccctc   7920
tacttccttt cgcattgctt ctgagtatgc tgactaccca aagccccttc tgtgttatta   7980
ataaacacag tactgattgt cccatttttc agcccatcag tccaagatct ccctaccact   8040
ttggtgtgtt ggtgcagtgt tgactatgaa aagcaggcct gaactaggtg gataagcctt   8100
cactcatttt ctttcattta ttaatgatcc tagtttcaat tattgtcaga ttctggggac   8160
aagaaccatt cttgcccacc tgtgttactg ctttactgtg caaaatactg aaggcaagtc   8220
agacccaggg agctggattg ccatccttta ttttgtgttt ccagtgtaca ctataaaatt   8280
gtctccccag gaaggaaggt tggcactttc tctgcattct tctttccaga gcagattgcc   8340
tggttaagaa tctcttgttg tcccctttgt atattgttat tgtaaagtgc caaatgccag   8400
gatacagcca gaaaaattgc ttattattat taaaaaaatt tttttaagaa agacatctgg   8460
attgtagggt ggactcgata acctggtcat tatttttttg aagccaaaat atccatttat   8520
actatgtacc tggtgaccag tgtctctcat tttaactgag ggtggtgggt ctgtggatag   8580
aacactgact cttgctattt taatatcaaa gatattctag atccagcaca gtggcggccc   8640
gataccgtcg acctcgagtc tagagggccc gtttaaaccc gctgatcagc ctcgactgtg   8700
ccttctagtt gccagccatc tgttgtttgc ccctcccccg tgccttcctt gaccctggaa   8760
ggtgccactc ccactgtcct ttcctaataa aatgaggaaa ttgcatcgca ttgtctgagt   8820
aggtgtcatt ctattctggg gggtggggtg gggcaggaca gcaaggggga ggattgggaa   8880
gacaatagca ggcatgctgg ggatgcggtg ggctctatgg cttctgaggc ggaaagaacc   8940
agctggggct ctagggggta tccccacgcg ccctgtagcg gcgcattaag cgcggcgggt   9000
gtggtggtta cgcgcagcgt gaccgctaca cttgccagcg ccctagcgcc cgctcctttc   9060
gctttcttcc cttcctttct cgccacgttc gccggctttc cccgtcaagc tctaaatcgg   9120
gggctccctt tagggttccg atttagtgct ttacggcacc tcgaccccaa aaaacttgat   9180
tagggtgatg gttcacgtag tgggccatcg ccctgataga cggtttttcg ccctttgacg   9240
ttggagtcca cgttctttaa tagtggactc ttgttccaaa ctggaacaac actcaaccct   9300
atctcggtct attcttttga tttataaggg attttgccga tttcggccta ttggttaaaa   9360
aatgagctga tttaacaaaa atttaacgcg aattaattct gtggaatgtg tgtcagttag   9420
ggtgtggaaa gtccccaggc tccccagcag gcagaagtat gcaaagcatg catctcaatt   9480
agtcagcaac caggtgtgga aagtccccag gctccccagc aggcagaagt atgcaaagca   9540
tgcatctcaa ttagtcagca accatagtcc cgcccctaac tccgcccatc ccgcccctaa   9600
ctccgcccag ttccgcccat tctccgcccc atggctgact aatttttttt atttatgcag   9660
aggccgaggc cgcctctgcc tctgagctat tccagaagta gtgaggaggc ttttttggag   9720
gcctaggctt ttgcaaaaag ctcccgggag cttgtatatc cattttcgga tctgatcagc   9780
acgtgatgaa aaagcctgaa ctcaccgcga cgtctgtcga gaagtttctg atcgaaaagt   9840
tcgacagcgt ctccgacctg atgcagctct cggagggcga agaatctcgt gctttcagct   9900
tcgatgtagg agggcgtgga tatgtcctgc gggtaaatag ctgcgccgat ggtttctaca   9960
aagatcgtta tgtttatcgg cactttgcat cggccgcgct cccgattccg gaagtgcttg  10020
```

-continued

```
acattgggga attcagcgag agcctgacct attgcatctc ccgccgtgca cagggtgtca  10080
cgttgcaaga cctgcctgaa accgaactgc ccgctgttct gcagccggtc gcggaggcca  10140
tggatgcgat cgctgcggcc gatcttagcc agacgagcgg gttcggccca ttcggaccgc  10200
aaggaatcgg tcaatacact acatggcgtg atttcatatg cgcgattgct gatccccatg  10260
tgtatcactg gcaaactgtg atggacgaca ccgtcagtgc gtccgtcgcg caggctctcg  10320
atgagctgat gctttgggcc gaggactgcc ccgaagtccg gcacctcgtg cacgcggatt  10380
tcggctccaa caatgtcctg acggacaatg gccgcataac agcggtcatt gactggagcg  10440
aggcgatgtt cggggattcc caatacgagg tcgccaacat cttcttctgg aggccgtggt  10500
tggcttgtat ggagcagcag acgcgctact tcgagcggag gcatccggag cttgcaggat  10560
cgccgcggct ccgggcgtat atgctccgca ttggtcttga ccaactctat cagagcttgg  10620
ttgacggcaa tttcgatgat gcagcttggg cgcagggtcg atgcgacgca atcgtccgat  10680
ccggagccgg gactgtcggg cgtacacaaa tcgcccgcag aagcgcggcc gtctggaccg  10740
atggctgtgt agaagtactc gccgatagtg gaaaccgacg ccccagcact cgtccgaggg  10800
caaaggaata gcacgtgcta cgagatttcg attccaccgc cgccttctat gaaaggttgg  10860
gcttcggaat cgttttccgg gacgccggct ggatgatcct ccagcgcggg gatctcatgc  10920
tggagttctt cgcccacccc aacttgttta ttgcagctta taatggttac aaataaagca  10980
atagcatcac aaatttcaca aataaagcat ttttttcact gcattctagt tgtggtttgt  11040
ccaaactcat caatgtatct tatcatgtct gtatacgggt ggaggggcgt gatgcagggt  11100
ccccacgatc agccgcagtc tctctaacac tgcaggtggt gccaagaggc aggcatgctc  11160
ccagcacaag ggacggtggc gcagaagaat acagagaagc tcacaaaaca tgccggcatg  11220
ggctcaggag agctacgggg gtagtggtgg tactgctccc tggtgcaggg cagcagctgt  11280
gtctccccct gcctccctcc cacccgaggg ccctgctcac ctggccccag cttggagatg  11340
gcatataaga gatcatagtt tatgactggg gtcgcatctt ccacttgttt ccatccccact  11400
ggcggagagg cgggagggga gatcagaaac tgcttgtctg gatttggcgg agccaggtgt  11460
gagcttccta tgtgtaaggt ctgaggagag aaaataagca caggtcagtt gttgccaggg  11520
aagaactgca gtgaggcaac agcacctaac gccagttccg ggagatgggc aggtcaatgt  11580
ccaggcgtca ggacaggtgt gattccagga ccaattgtaa gatggtctgt aatggggagg  11640
gcaaaaggac atatgaactc tggttgtggc acagatagga tgacagcccc ctcccagggc  11700
tatgggagtc acaggcacag ggactgcaaa taattacgct tgacctagat ggacagaaaa  11760
tcagcagagg tgactttagt atatatggaa atttaagtca ctgtcattga ggtcaggagg  11820
gctcttgggt ataccgtcga cctctagcta gagcttggcg taatcatggt catagctgtt  11880
tcctgtgtga aattgttatc cgctcacaat tccacacaac atacgagccg gaagcataaa  11940
gtgtaaagcc tggggtgcct aatgagtgag ctaactcaca ttaattgcgt tgcgctcact  12000
gcccgctttc cagtcgggaa acctgtcgtg ccagctgcat taatgaatcg gccaacgcgc  12060
ggggagaggc ggtttgcgta ttgggcgctc ttccgcttcc tcgctcactg actcgctgcg  12120
ctcggtcgtt cggctgcggc gagcggtatc agctcactca aaggcggtaa tacggttatc  12180
cacagaatca ggggataacg caggaaagaa catgtgagca aaaggccagc aaaaggccag  12240
gaaccgtaaa aaggccgcgt tgctggcgtt tttccatagg ctccgccccc ctgacgagca  12300
tcacaaaaat cgacgctcaa gtcagaggtg gcgaaacccg acaggactat aaagatacca  12360
ggcgtttccc cctggaagct ccctcgtgcg ctctcctgtt ccgaccctgc cgcttaccgg  12420
```

atacctgtcc gcctttctcc cttcgggaag cgtggcgctt tctcatagct cacgctgtag 12480
gtatctcagt tcggtgtagg tcgttcgctc caagctgggc tgtgtgcacg aaccccccgt 12540
tcagcccgac cgctgcgcct tatccggtaa ctatcgtctt gagtccaacc cggtaagaca 12600
cgacttatcg ccactggcag cagccactgg taacaggatt agcagagcga ggtatgtagg 12660
cggtgctaca gagttcttga agtggtggcc taactacggc tacactagaa gaacagtatt 12720
tggtatctgc gctctgctga agccagttac cttcggaaaa agagttggta gctcttgatc 12780
cggcaaacaa accaccgctg gtagcggtgg tttttttgtt tgcaagcagc agattacgcg 12840
cagaaaaaaa ggatctcaag aagatccttt gatcttttct acggggtctg acgctcagtg 12900
gaacgaaaac tcacgttaag ggattttggt catgagatta tcaaaaagga tcttcaccta 12960
gatcctttta aattaaaaat gaagttttaa atcaatctaa agtatatatg agtaaacttg 13020
gtctgacagt taccaatgct taatcagtga ggcacctatc tcagcgatct gtctatttcg 13080
ttcatccata gttgcctgac tccccgtcgt gtagataact acgatacggg agggcttacc 13140
atctggcccc agtgctgcaa tgataccgcg agacccacgc tcaccggctc cagatttatc 13200
agcaataaac cagccagccg gaagggccga gcgcagaagt ggtcctgcaa ctttatccgc 13260
ctccatccag tctattaatt gttgccggga agctagagta agtagttcgc cagttaatag 13320
tttgcgcaac gttgttgcca ttgctacagg catcgtggtg tcacgctcgt cgtttggtat 13380
ggcttcattc agctccggtt cccaacgatc aaggcgagtt acatgatccc ccatgttgtg 13440
caaaaaagcg gttagctcct tcggtcctcc gatcgttgtc agaagtaagt tggccgcagt 13500
gttatcactc atggttatgg cagcactgca taattctctt actgtcatgc catccgtaag 13560
atgcttttct gtgactggtg agtactcaac caagtcattc tgagaatagt gtatgcggcg 13620
accgagttgc tcttgcccgg cgtcaatacg ggataatacc gcgccacata gcagaacttt 13680
aaaagtgctc atcattggaa aacgttcttc ggggcgaaaa ctctcaagga tcttaccgct 13740
gttgagatcc agttcgatgt aacccactcg tgcacccaac tgatcttcag catcttttac 13800
tttcaccagc gtttctgggt gagcaaaaac aggaaggcaa aatgccgcaa aaaagggaat 13860
aagggcgaca cggaaatgtt gaatactcat actcttcctt tttcaatatt attgaagcat 13920
ttatcagggt tattgtctca tgagcggata catatttgaa tgtatttaga aaaataaaca 13980
aataggggtt ccgcgcacat ttccccgaaa agtgccacct gacgtc 14026

<210> SEQ ID NO 19
<211> LENGTH: 13708
<212> TYPE: DNA
<213> ORGANISM: Artificial Sequence
<220> FEATURE:
<223> OTHER INFORMATION: 6.8 kb/hXIST/DYRK1A construct

<400> SEQUENCE: 19
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg aaaaccagaa agtattctca gtaatgatag 240
tatggataaa gcaggtttct atgacccttt attacagaat ctgtgagttt ttcacaatta 300
aaaagtaata aaaagtagtg acaacattca ctgaactctt attctatgcc aacttgttcc 360
ggtatgccct tacacccaca aaagccctat gcataaggtg gcattattcc agcatgtatt 420

-continued

```
gcattgtaca cacaaagagg tcaagcactc caccacggcc ctaagcatgg tggctgaggt    480
gggaaggcca gaggtaggtg ggcccgcgcc cttttccact ctgaaccatg cctccaagat    540
aggagggtgg gaaagtgctc aagacacatt agaaattccc cataaaagac aagattgttg    600
aacacctgca agtgaataaa gataaactga tctcagaggg gaaaaagacg cagggttagg    660
aaacagcacc ctgctcgagg acgttctttc caaacagcct gctcatcacc cgttcgcgat    720
gtacgggcca gatatacgcg ttgacattga ttattgacta gttattaata gtaatcaatt    780
acggggtcat tagttcatag cccatatatg gagttccgcg ttacataact tacggtaaat    840
ggcccgcctg gctgaccgcc caacgacccc cgcccattga cgtcaataat gacgtatgtt    900
cccatagtaa cgccaatagg gactttccat tgacgtcaat gggtggagta tttacggtaa    960
actgcccact tggcagtaca tcaagtgtat catatgccaa gtacgccccc tattgacgtc   1020
aatgacggta aatggcccgc ctggcattat gcccagtaca tgaccttatg ggactttcct   1080
acttggcagt acatctacgt attagtcatc gctattacca tggtgatgcg gttttggcag   1140
tacatcaatg ggcgtggata gcggtttgac tcacggggat ttccaagtct ccaccccatt   1200
gacgtcaatg ggagtttgtt ttggcaccaa aatcaacggg actttccaaa atgtcgtaac   1260
aactccgccc cattgacgca aatgggcggt aggcgtgtac ggtgggaggt ctatataagc   1320
agagctctcc ctatcagtga tagagatctc cctatcagtg atagagatcg tcgacgagct   1380
cgtttagtga accgtcagat cgcctggaga cgccatccac gctgttttga cctccataga   1440
agacaccggg accgatccag cctccggact ctagcgttta aacttaagct tggtaccgag   1500
ctcggatcca ctagtccagt gtggtggaat tctgcagatt ctagaacatt ttctagtccc   1560
ccaacaccct ttatggcgta tttctttaaa aaaatcacct aaattccata aaatattttt   1620
ttaaattcta tactttctcc tagtgtcttc ttgacacgtc ctccatattt ttttaaagaa   1680
agtatttgga atattttgag gcaattttta atatttaagg aatttttctt tggaatcatt   1740
tttggtgaca tctctgtttt ttgtggatca gtttttttact cttccactct cttttctata   1800
ttttgcccat cggggctgcg gatacctggt tttattattt tttctttgcc caacggggcc   1860
gtggatacct gccttttaat tctttttttat tcgcccatcg gggccgcgga tacctgcttt   1920
ttattttttt ttccttagcc catcggggta tcggatacct gctgattccc ttcccctctg   1980
aacccccaac actctggccc atcggggtga cggatatctg ctttttaaaa attttctttt   2040
tttggcccat cggggcttcg gatacctgct tttttttttt ttattttcct tgcccatcgg   2100
ggcctcggat acctgcttta atttttgttt ttctgcccat cggggccgcg gatacctgct   2160
ttgatttttt tttttcatcg cccatcggtg ctttttatgg atgaaaaaat gttggttttg   2220
tgggttgttg cactctctgg aatatctaca cttttttttg ctgctgatca tttggtggtg   2280
tgtgagtgta cctaccgctt tggcagagaa tgactctgca gttaagctaa gggcgtgttc   2340
agattgtgga ggaaaagtgg ccgccatttt agacttgccg cataactcgg cttagggcta   2400
gtcgtttgtg ctaagttaaa ctagggaggc aagatggatg atagcaggtc aggcagagga   2460
agtcatgtgc attgcatgag ctaaacctat ctgaatgaat tgatttgggg cttgttagga   2520
gctttgcgtg attgttgtat cgggaggcag taagaatcat cttttatcag tacaagggac   2580
tagttaaaaa tggaaggtta ggaaagacta aggtgcaggg cttaaaatgg cgattttgac   2640
attgcggcat tgctcagcat ggcgggctgt gctttgttag gttgtccaaa atggcggatc   2700
cagttctgtc gcagtgttca agtggcggga aggccacatc atgatgggcg aggctttgtt   2760
aagtggttag catggtggtg gacatgtgcg gtcacacagg aaaagatggc ggctgaaggt   2820
```

cttgccgcag tgtaaaacat ggcgggcctc tttgtctttg ctgtgtgctt ttcgtgttgg 2880
gttttgccgc agggacaata tggcaggcgt tgtcatatgt atatcatggc ttttgtcacg 2940
tggacatcat ggcgggcttg ccgcattgtt aaagatggcg ggttttgccg cctagtgcca 3000
cgcagagcgg gagaaaaggt gggatggaca gtgctggatt gctgcataac ccaaccaatt 3060
agaaatgggg gtggaattga tcacagccaa ttagagcaga agatggaatt agactgatga 3120
cacactgtcc agctactcag cgaagacctg ggtgaattag catggcactt cgcagctgtc 3180
tttagccagt caggagaaag aagtggaggg gccacgtgta tgtctcccag tgggcggtac 3240
accaggtgtt ttcaaggtct tttcaaggac atttagcctt tccacctctg tcccctctta 3300
tttgtcccct cctgtccagt gctgcctctt gcagtgctgg atatctggct gtgtggtctg 3360
aacctccctc cattcctctg tattggtgcc tcacctaagg ctaagtatac ctcccccccc 3420
accccccaac ccccccaact ccccaccccc accccccacc ccccacctcc ccacccccct 3480
accccccctac cccccctaccc ccctctggtc tgccctgcac tgcactgttg ccatgggcag 3540
tgctccaggc ctgcttggtg tggacatggt ggtgagccgt ggcaaggacc agaatggatc 3600
acagatgatc gttggccaat tggcctccca atatgtgtga ttgtatttgt cgaggttgct 3660
atgcactaga gaaggaaagt gctcccctca tccccacttt tcccttccag caggaagtgc 3720
ccaccccata agaccctttt atttggagag tctaggtgca caattgtaag tgaccacaag 3780
catgcatctt ggacatttat gtgcgtaatc gcacactgct cattccatgt gaataaggtc 3840
ctactctccg accccttttg caatacagaa gggttgctga taacgcagtc cccttttctt 3900
ggcatgttgt gtgtgattat aatcgtctgg gatcctatgc actagaaaag gagggtcctc 3960
tccacatacc tcagtctcac ctttcccttc cagcagggag tgcccactcc ataagactct 4020
cacatttgga cagtcaaggt gcgtaattgt taagtgaaca caaccatgca ccttagacat 4080
ggatttgcat aactacacac agctcaacct atctgaataa aatcctactc tcagacccct 4140
tttgcagtac agcaggggtg ctgatcacca aggccctttt tcctggcctg gtatgcgtgt 4200
gattatgttt gtcccggttc ctgtgtatta gacatggaag cctcccctgc cacactccac 4260
ccccaatctt cctttccctt ccggcaggag tgccctctcc ataagacgct tacgtttgga 4320
caatcaaggt gcacagttgt aagtgaccac aggcatacac cttggacatt aatgtgcata 4380
accactttgc ccattccatc tgaataaggt cctactctca gaccccttttt gcagtacagc 4440
aggggtgctg atcaccaagg cccctttttct tggcctgtta tgtgcgtgat tatatttgtc 4500
tgggttcctg tgtattagac aaggaagcct tccccccgcc cccaccccca ctcccagtct 4560
tcctttccct tccagcaggg agtgccccct ccataagatc attacatttg gacaatcaag 4620
gtgcacaatt ataagtgacc acagccatgc accttggaca ttattggaca ttaatgtgcg 4680
taactgcaca tggcccatcc catctgaata aggacctact ctcagatgcc tttgcagtac 4740
agcaggggta ctgaatcacc aaggcccttt ttcttggcct gttatgtgtg tgattatatt 4800
tatcccagtt tctgtgtaat agacatgaaa gcctcccctg ccacacccca cctccaatct 4860
tcctttccct tccaccaggg agtgtccact ccatataccc ttacatttgg acaatcaagg 4920
tgcacaattg taagtgagca taggcactca ccttggacat gaatgtgcat aactgcacat 4980
ggcccatccc atctgaataa ggtcctactc tcagaccctt tttgcagtac agcaggggtg 5040
ctgatcacca aggcccccttt tcctggcctg ttatgtgtgt gattatattt gttccagttc 5100
ctgtgtaata gacatggaag cctcccctgc cacactccac ccccaatctt cctttccttc 5160

-continued

```
tggcaggaag tacccgctcc ataagaccct tacatttgga cagtcaaggt gcacaattgt   5220
atgtgaccac aaccatgcac cttggacata aatgtgtgta actgcacatg gcccatccca   5280
tctgaataag gtcctactct cagacccctt ttgcagtaca gtaggtgtgc tgataaccaa   5340
ggcccctctt cctggcctgt taacgtatgt gattatattt gtctgggttc cagtgtataa   5400
gacatggaag cctcccctgc cccaccccac cctcaatctt cctttccctt ctggcaggga   5460
gtgccagctc cataagaacc ttacatttgg acagtcaagg tgcacaattc taagtgaccg   5520
cagccatgca ccttggtcaa taatgtgtgt aactgcacac ggcctatctc atctgaataa   5580
ggccttactc tcagacccct tttgcagtac agcaggggtg ctgataacca aggcccattt   5640
tcctggcctg ttatgtgtgt gattatattt gtccaggttt ctgtgtacta gacaaggaag   5700
cctcctctgc cccatcccat ctacgcataa tctttctttt cctcccagca gggagtgctc   5760
actccataag acccttacat ttggacaatc aaggtgcaca attgtaagtg accacaacca   5820
tgcatcttgg aaatttatgt gcataactgc acatggctta tcctatttga ataaagtcct   5880
actctcagac cccctttgca gtatagctgg ggtgctgatc actgaggcct ctttgcttgg   5940
cttgtctata ttcttgtgta ctagataagg gcaccttctc atggactccc tttgcttttc   6000
aacaaggagt acccactact ttttaagatt cttatatttg tccaaagtac atggttttaa   6060
ttgaccacaa caatgtccct tggacattaa tgtatgtaat caccacatgg ttcatcctaa   6120
ttaaacaaag ttctaccttc tcaccctcca tttgcagtat accagggttg ctgacccccct   6180
aagtcccctt ttcttggctt gttgacatgc ataattgcat ttatgttggt tcttgtgccc   6240
tagacaagga tgccccacct cttttcaata gtgggtgccc actccttatg atctttacat   6300
ttgaacagtt aatgtgaata attgcagttg tccacaaccc tatcacttct aggaccatta   6360
tacctctttt gcattactgt ggggtatact gtttccctcc aaggcccctt ctggtggact   6420
atcaacatat aattgaaatt ttcttttgtc tttgtcagta gattaaggtc ataccccatc   6480
acctttcctt tgtagtacaa cagggtgtcc tgatcaacca aagtcctgtt gttttggact   6540
gttaatatgt gcaattacat ttgctcctga tctgtgcact agataaggat cctacctact   6600
ttcttagtgt ttttagcagg tagtgcccac tactcaagac tgtcacttgg aatgttcatg   6660
tgcacaaact caattctcta agcatgttcc tgtaccacct ttgctttaga gcagggggat   6720
gatattcact aagtgcccct tcttttggac ttaatatgca ttaatgcaat tgtccacctc   6780
ttcttttaga ctaagagttg atctccacat attccccttg catcaggggc atgttaatta   6840
tgaatgaacc cttttctttt aatattaatg tcataattgt atttgtggac ctgtgtagga   6900
gaaaaagacc ctatgttcct cccattaccc tttggattgc tgctgagaag tgttaactac   6960
tcataatctc agctcttgga caattaatag cattaataac aattatcaag ggcactgatc   7020
attagataag actcctgctt cctcgttgct tacatcgggg gtactgaccc actaaggccc   7080
cttgtactgt taatgtgaat atttgcaatt atatatgtct ccttctggta gagtgggata   7140
ttatgcccta gtatcccctt tgcattactg caggggctgc tgactactca aaacttctcc   7200
tgggactgtt aataggcaca atggcagtta tcaatggttt tctccctccc tgaccttgtt   7260
aagcaagcgc cccaccccac ccttagtttc ccatggcata ataaagtata agcattggag   7320
tattccatgc acttgtctat caaacagtgg tccatactcc caaccctttt gcattgcgcc   7380
agtgtgtaaa atcacaggta gccatggtgt catgctttat atacgaagtc ttccctctct   7440
ctgccccttg tgtgcccttg gccccttttt acagactatt gctcacaatc tcaggtgtcc   7500
atatttgcag ctattaggta agattgtgct gtctccctct tcccttccct ctgccctgcc   7560
```

-continued

```
ccttttgcct ctttgctggg taatgttgac cggacaaggc cctttctctt ggacttaaac   7620
aattctcagt tgcactttcc ttggtcccac ccattataca tgaacccctc tacttccttt   7680
cgcattgctt ctgagtatgc tgactaccca aagccccttc tgtgttatta ataaacacag   7740
tactgattgt cccatttttc agcccatcag tccaagatct ccctaccact ttggtgtgtt   7800
ggtgcagtgt tgactatgaa aagcaggcct gaactaggtg gataagcctt cactcatttt   7860
ctttcattta ttaatgatcc tagtttcaat tattgtcaga ttctggggac aagaaccatt   7920
cttgcccacc tgtgttactg ctttactgtg caaaatactg aaggcaagtc agacccaggg   7980
agctggattg ccatccttta ttttgtgttt ccagtgtaca ctataaaatt gtctccccag   8040
gaaggaaggt tggcactttc tctgcattct tctttccaga gcagattgcc tggttaagaa   8100
tctcttgttg tccccttttgt atattgttat tgtaaagtgc caaatgccag gatacagcca   8160
gaaaaattgc ttattattat taaaaaaatt tttttaagaa agacatctgg attgtagggt   8220
ggactcgata acctggtcat tattttttttg aagccaaaat atccatttat actatgtacc   8280
tggtgaccag tgtctctcat tttaactgag ggtggtgggt ctgtggatag aacactgact   8340
cttgctattt taatatcaaa gatattctag atccagcaca gtggcggccc gataccgtcg   8400
acctcgagtc tagagggccc gtttaaaccc gctgatcagc ctcgactgtg ccttctagtt   8460
gccagccatc tgttgtttgc ccctcccccg tgccttcctt gaccctggaa ggtgccactc   8520
ccactgtcct ttcctaataa aatgaggaaa ttgcatcgca ttgtctgagt aggtgtcatt   8580
ctattctggg gggtggggtg gggcaggaca gcaaggggga ggattgggaa gacaatagca   8640
ggcatgctgg ggatgcggtg ggctctatgg cttctgaggc ggaaagaacc agctggggct   8700
ctagggggta tccccacgcg ccctgtagcg gcgcattaag cgcggcgggt gtggtggtta   8760
cgcgcagcgt gaccgctaca cttgccagcg ccctagcgcc cgctcctttc gctttcttcc   8820
cttcctttct cgccacgttc gccggctttc cccgtcaagc tctaaatcgg gggctccctt   8880
tagggttccg atttagtgct ttacggcacc tcgaccccaa aaaacttgat tagggtgatg   8940
gttcacgtag tgggccatcg ccctgataga cggtttttcg ccctttgacg ttggagtcca   9000
cgttctttaa tagtggactc ttgttccaaa ctggaacaac actcaaccct atctcggtct   9060
attcttttga tttataaggg attttgccga tttcggccta ttggttaaaa aatgagctga   9120
tttaacaaaa atttaacgcg aattaattct gtggaatgtg tgtcagttag ggtgtggaaa   9180
gtccccaggc tccccagcag gcagaagtat gcaaagcatg catctcaatt agtcagcaac   9240
caggtgtgga aagtccccag gctccccagc aggcagaagt atgcaaagca tgcatctcaa   9300
ttagtcagca accatagtcc cgcccctaac tccgcccatc ccgcccctaa ctccgcccag   9360
ttccgcccat tctccgcccc atggctgact aattttttttt atttatgcag aggccgaggc   9420
cgcctctgcc tctgagctat tccagaagta gtgaggaggc ttttttggag gcctaggctt   9480
ttgcaaaaag ctcccgggag cttgtatatc cattttcgga tctgatcagc acgtgatgaa   9540
aaagcctgaa ctcaccgcga cgtctgtcga gaagtttctg atcgaaaagt tcgacagcgt   9600
ctccgacctg atgcagctct cggagggcga agaatctcgt gctttcagct tcgatgtagg   9660
agggcgtgga tatgtcctgc gggtaaatag ctgcgccgat ggtttctaca aagatcgtta   9720
tgtttatcgg cactttgcat cggccgcgct cccgattccg gaagtgcttg acattgggga   9780
attcagcgag agcctgacct attgcatctc ccgccgtgca cagggtgtca cgttgcaaga   9840
cctgcctgaa accgaactgc ccgctgttct gcagccggtc gcggaggcca tggatgcgat   9900
```

```
cgctgcggcc gatcttagcc agacgagcgg gttcggccca ttcggaccgc aaggaatcgg   9960
tcaatacact acatggcgtg atttcatatg cgcgattgct gatccccatg tgtatcactg  10020
gcaaactgtg atggacgaca ccgtcagtgc gtccgtcgcg caggctctcg atgagctgat  10080
gctttgggcc gaggactgcc ccgaagtccg gcacctcgtg cacgcggatt tcggctccaa  10140
caatgtcctg acggacaatg gccgcataac agcggtcatt gactggagcg aggcgatgtt  10200
cggggattcc caatacgagg tcgccaacat cttcttctgg aggccgtggt tggcttgtat  10260
ggagcagcag acgcgctact tcgagcggag gcatccggag cttgcaggat cgccgcggct  10320
ccgggcgtat atgctccgca ttggtcttga ccaactctat cagagcttgg ttgacggcaa  10380
tttcgatgat gcagcttggg cgcagggtcg atgcgacgca atcgtccgat ccggagccgg  10440
gactgtcggg cgtacacaaa tcgcccgcag aagcgcggcc gtctggaccg atggctgtgt  10500
agaagtactc gccgatagtg gaaaccgacg ccccagcact cgtccgaggg caaaggaata  10560
gcacgtgcta cgagatttcg attccaccgc cgccttctat gaaaggttgg gcttcggaat  10620
cgttttccgg gacgccggct ggatgatcct ccagcgcggg gatctcatgc tggagttctt  10680
cgcccacccc aacttgttta ttgcagctta taatggttac aaataaagca atagcatcac  10740
aaatttcaca aataaagcat ttttttcact gcattctagt tgtggtttgt ccaaactcat  10800
caatgtatct tatcatgtct gtatacgtaa actggcaaag ggtggctgg gccaaaagac  10860
agaggaatta agtaagaagt ccaggaaaaa tgaacttcac atcaaatttt agagcacggt  10920
agccatgaat cttgtgaata gctcccaaaa atgtcctgtg gaagacaact agaaagcatt  10980
ctacaatcag gcacccacct ccacctgcag cctcctgtgt tgttctcatg ggcacctct  11040
gggctccagc tcctccaagg cacctccaca ctctctcaag tacactcttc actcttcccc  11100
aaacatgatt cccctactgc tctgcctaac tcccacttct ctttcaagta gcagcttaaa  11160
cgtcacctca tatttggctg gaaaatagaa tatagacaga ggggtaagtt aaggctagaa  11220
aggcaggctg ggtcaacaga atggcaagct aaaacatggg attttctaaa acagcctaag  11280
agggtgacag ataaaagtgt gcaaggagtg gcacaactcc agtttcatct ttagctatag  11340
caattaacac cataaggagt ctggattcaa ttttgccatt tactagctag ctaccaactt  11400
ctgtgtcgct ttgggcaaat caattaaatc catacctccc tttccatctg cagaatgggt  11460
ttataacagt acttaaacct caaggtacta agaacagtaa agagttaatg gtataccgtc  11520
gacctctagc tagagcttgg cgtaatcatg gtcatagctg tttcctgtgt gaaattgtta  11580
tccgctcaca attccacaca acatacgagc cggaagcata aagtgtaaag cctggggtgc  11640
ctaatgagtg agctaactca cattaattgc gttgcgctca ctgcccgctt tccagtcggg  11700
aaacctgtcg tgccagctgc attaatgaat cggccaacgc gcggggagag gcggtttgcg  11760
tattgggcgc tcttccgctt cctcgctcac tgactcgctg cgctcggtcg ttcggctgcg  11820
gcgagcggta tcagctcact caaaggcggt aatacggtta tccacagaat caggggataa  11880
cgcaggaaag aacatgtgag caaaaggcca gcaaaaggcc aggaaccgta aaaaggccgc  11940
gttgctggcg tttttccata ggctccgccc ccctgacgag catcacaaaa atcgacgctc  12000
aagtcagagg tggcgaaacc cgacaggact ataaagatac caggcgtttc cccctggaag  12060
ctccctcgtg cgctctcctg ttccgaccct gccgcttacc ggatacctgt ccgcctttct  12120
cccttcggga agcgtggcgc tttctcatag ctcacgctgt aggtatctca gttcggtgta  12180
ggtcgttcgc tccaagctgg gctgtgtgca cgaacccccc gttcagcccg accgctgcgc  12240
cttatccggt aactatcgtc ttgagtccaa cccggtaaga cacgacttat cgccactggc  12300
```

-continued

```
agcagccact ggtaacagga ttagcagagc gaggtatgta ggcggtgcta cagagttctt  12360

gaagtggtgg cctaactacg gctacactag aagaacagta tttggtatct gcgctctgct  12420

gaagccagtt accttcggaa aaagagttgg tagctcttga tccggcaaac aaaccaccgc  12480

tggtagcggt tggtttttg tttgcaagca gcagattacg cgcagaaaaa aaggatctca  12540

agaagatcct ttgatctttt ctacggggtc tgacgctcag tggaacgaaa actcacgtta  12600

agggattttg gtcatgagat tatcaaaaag gatcttcacc tagatccttt taaattaaaa  12660

atgaagtttt aaatcaatct aaagtatata tgagtaaact tggtctgaca gttaccaatg  12720

cttaatcagt gaggcaccta tctcagcgat ctgtctattt cgttcatcca tagttgcctg  12780

actccccgtc gtgtagataa ctacgatacg ggagggctta ccatctggcc ccagtgctgc  12840

aatgataccg cgagacccac gctcaccggc tccagattta tcagcaataa accagccagc  12900

cggaagggcc gagcgcagaa gtggtcctgc aactttatcc gcctccatcc agtctattaa  12960

ttgttgccgg gaagctagag taagtagttc gccagttaat agtttgcgca acgttgttgc  13020

cattgctaca ggcatcgtgg tgtcacgctc gtcgtttggt atggcttcat tcagctccgg  13080

ttcccaacga tcaaggcgag ttacatgatc ccccatgttg tgcaaaaaag cggttagctc  13140

cttcggtcct ccgatcgttg tcagaagtaa gttggccgca gtgttatcac tcatggttat  13200

ggcagcactg cataattctc ttactgtcat gccatccgta agatgctttt ctgtgactgg  13260

tgagtactca accaagtcat tctgagaata gtgtatgcgg cgaccgagtt gctcttgccc  13320

ggcgtcaata cgggataata ccgcgccaca tagcagaact ttaaaagtgc tcatcattgg  13380

aaaacgttct tcggggcgaa aactctcaag gatcttaccg ctgttgagat ccagttcgat  13440

gtaacccact cgtgcaccca actgatcttc agcatctttt actttcacca gcgtttctgg  13500

gtgagcaaaa acaggaaggc aaaatgccgc aaaaaaggga ataagggcga cacggaaatg  13560

ttgaatactc atactcttcc tttttcaata ttattgaagc atttatcagg gttattgtct  13620

catgagcgga tacatatttg aatgtattta gaaaaataaa caaatagggg ttccgcgcac  13680

atttccccga aaagtgccac ctgacgtc                                    13708

<210> SEQ ID NO 20
<211> LENGTH: 15721
<212> TYPE: DNA
<213> ORGANISM: Artificial Sequence
<220> FEATURE:
<223> OTHER INFORMATION: 6.8 kb/hXIST/AAVS1 construct

<400> SEQUENCE: 20

agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagctca    240

gaattaaccc tcactaaagg gactagtcct gcaggtttaa acgaattcgc cctttgcttt    300

ctctgaccag cattctctcc cctgggcctg tgccgctttc tgtctgcagc ttgtggcctg    360

ggtcacctct acggctggcc cagatccttc cctgccgcct ccttcaggtt ccgtcttcct    420

ccactccctc ttccccttgc tctctgctgt gttgctgccc aaggatgctc tttccggagc    480

acttccttct cggcgctgca ccacgtgatg tcctctgagc ggatcctccc cgtgtctggg    540

tcctctccgg gcatctctcc tccctcaccc aaccccatgc cgtcttcact cgctgggttc    600
```

-continued

```
ccttttcctt ctccttctgg ggcctgtgcc atctctcgtt tcttaggatg gccttctccg    660
acggatgtct cccttgcgtc ccgcctcccc ttcttgtagg cctgcatcat caccgttttt    720
ctggacaacc ccaaagtacc ccgtctccct ggctttagcc acctctccat cctcttgctt    780
tctttgcctg gacaccccgt tctcctgtgg attcgggtca cctctcactc ctttcatttg    840
ggcagctccc ctaccccccct tacctctcta gtctgtgcta gctcttccag ccccctgtca    900
tggcatcttc caggggtccg agagctcagc tagtcttctt cctccaaccc gggcccctat    960
gtccacttca ggacagcatg tttgctgcct ccagggatcc tgtgtccccg agctgggacc   1020
accttatatt cccagggccg gttaatgtgg ctctggttct gggtactttt atctgtcccc   1080
tccaccccac agtggggcaa gcttacagac atgataagat acattgatga gtttggacaa   1140
accacaacta gaatgcagtg aaaaaaatgc tttatttgtg aaatttgtga tgctattgct   1200
ttatttgtaa ccattataag ctgcaataaa caagttgggg tgggcgaaga actccagcat   1260
gagatccccg cgctggagga tcatccagcc ggcgtcccgg aaaacgattc cgaagcccaa   1320
cctttcatag aaggcggcgg tggaatcgaa atctcgtagc acgtgctatt cctttgccct   1380
cggacgagtg ctggggcgtc ggtttccact atcggcgagt acttctacac agccatcggt   1440
ccagacggcc gcgcttctgc gggcgatttg tgtacgcccg acagtcccgg ctccggatcg   1500
gacgattgcg tcgcatcgac cctgcgccca agctgcatca tcgaaattgc cgtcaaccaa   1560
gctctgatag agttggtcaa gaccaatgcg gagcatatac gcccggagcc gcggcgatcc   1620
tgcaagctcc ggatgcctcc gctcgaagta gcgcgtctgc tgctccatac aagccaacca   1680
cggcctccag aagaagatgt tggcgacctc gtattgggaa tccccgaaca tcgcctcgct   1740
ccagtcaatg accgctgtta tgcggccatt gtccgtcagg acattgttgg agccgaaatc   1800
cgcgtgcacg aggtgccgga cttcggggca gtcctcggcc caaagcatca gctcatcgag   1860
agcctgcgcg acggacgcac tgacggtgtc gtccatcaca gtttgccagt gatacacatg   1920
gggatcagca atcgcgcata tgaaatcacg ccatgtagtg tattgaccga ttccttgcgg   1980
tccgaatggg ccgaacccgc tcgtctggct aagatcggcc gcagcgatcg catccatggc   2040
ctccgcgacc ggctgcagaa cagcgggcag ttcggtttca ggcaggtctt gcaacgtgac   2100
accctgtgca cggcgggaga tgcaataggt caggctctcg ctgaattccc caatgtcaag   2160
cacttccgga atcgggagcg cggccgatgc aaagtgccga taaacataac gatctttgta   2220
gaaaccatcg gcgcagctat ttacccgcag gacatatcca cgccctccta catcgaagct   2280
gaaagcacga gattcttcgc cctccgagag ctgcatcagg tcggagacgc tgtcgaactt   2340
ttcgatcaga aacttctcga cagacgtcgc ggtgagttca ggcttttca tcacgtgctg   2400
atcagatccg aaaatggata tacaagctcc cgggagcttt ttgcaaaagc ctaggcctcc   2460
aaaaaagcct cctcactact tctggaatag ctcagaggca gaggcggcct cggcctctgc   2520
ataaataaaa aaaattagtc agccatgggg cggagaatgg gcggaactgg gcggagttag   2580
gggcgggatg ggcggagtta ggggcgggac tatggttgct gactaattga gatgcatgct   2640
ttgcatactt ctgcctgctg gggagcctgg ggactttcca cacctggttg ctgactaatt   2700
gagatgcatg ctttgcatac ttctgcctgc tggggagcct ggggactttc cacaccctaa   2760
ctgacacaca ttccacagaa ttaattcgcg ttaaattttt gttaaatcag ctcatttttt   2820
aaccaatagg ccgaaatcgg caaaatccct tataaatcaa aagaatagac cgagataggg   2880
ttgagtgttg ttccagtttg gaacaagagt ccactattaa agaacgtgga ctccaacgtc   2940
aaagggcgaa aaaccgtcta tcagggcgat ggcccactac gtgaaccatc accctaatca   3000
```

-continued

```
agttttttgg ggtcgaggtg ccgtaaagca ctaaatcgga accctaaagg gagcccccga   3060
tttagagctt gacggggaaa gccggcgaac gtggcgagaa aggaagggaa gaaagcgaaa   3120
ggagcgggcg ctagggcgct ggcaagtgta gcggtcacgc tgcgcgtaac caccacaccc   3180
gccgcgctta atgcgccgct acagggcgcg tggggatacc ccctagagcc ccagctggtt   3240
ctttccgcct cagaagccat agagcccacc gcatccccag catgcctgct attgtcttcc   3300
caatcctccc ccttgctgtc ctgccccacc ccacccccca gaatagaatg acacctactc   3360
agacaatgcg atgcaatttc ctcattttat taggaaagga cagtgggagt ggcaccttcc   3420
agggtcaagg aaggcacggg ggaggggcaa acaacagatg gctggcaact agaaggcaca   3480
gtcgaggctg atcagcgggt ttaaacgggc cctctagact cgaggtcgac ggtatcgggc   3540
cgccactgtg ctggatctag aatatctttg atattaaaat agcaagagtc agtgttctat   3600
ccacagaccc accaccctca gttaaaatga gagacactgg tcaccaggta catagtataa   3660
atggatattt tggcttcaaa aaaataatga ccaggttatc gagtccaccc tacaatccag   3720
atgtctttct taaaaaaatt tttttaataa taataagcaa tttttctggc tgtatcctgg   3780
catttggcac tttacaataa caatatacaa aggggacaac aagagattct taaccaggca   3840
atctgctctg gaaagaagaa tgcagagaaa gtgccaacct tccttcctgg ggagacaatt   3900
ttatagtgta cactggaaac acaaaataaa ggatggcaat ccagctccct gggtctgact   3960
tgccttcagt attttgcaca gtaaagcagt aacacaggtg ggcaagaatg gttcttgtcc   4020
ccagaatctg acaataattg aaactaggat cattaataaa tgaaagaaaa tgagtgaagg   4080
cttatccacc tagttcaggc ctgcttttca tagtcaacac tgcaccaaca caccaaagtg   4140
gtagggagat cttggactga tgggctgaaa aatgggacaa tcagtactgt gtttattaat   4200
aacacagaag ggctttggg tagtcagcat actcagaagc aatgcgaaag gaagtagagg    4260
ggttcatgta taatgggtgg gaccaaggaa agtgcaactg agaattgttt aagtccaaga   4320
gaaagggcct tgtccggtca acattaccca gcaaagaggc aaaaggggca gggcagaggg   4380
aagggaagag ggagacagca caatcttacc taatagctgc aaatatggac acctgagatt   4440
gtgagcaata gtctgtaaaa aggggccaag ggcacacaag ggcagagag agggaagact    4500
tcgtatataa agcatgacac catggctacc tgtgatttta cacactggcg caatgcaaaa   4560
gggttgggag tatggaccac tgtttgatag acaagtgcat ggaatactcc aatgcttata   4620
ctttattatg ccatgggaaa ctaagggtgg ggtggggcgc ttgcttaaca aggtcaggga   4680
gggagaaaac cattgataac tgccattgtg cctattaaca gtcccaggag aagttttgag   4740
tagtcagcag cccctgcagt aatgcaaagg ggatactagg gcataatatc ccactctacc   4800
agaaggagac atatataatt gcaaatattc acattaacag tacaaggggc cttagtgggt   4860
cagtaccccc gatgtaagca acgaggaagc aggagtctta tctaatgatc agtgcccttg   4920
ataattgtta ttaatgctat taattgtcca agagctgaga ttatgagtag ttaacacttc   4980
tcagcagcaa tccaaagggt aatgggagga acatagggtc tttttctcct acacaggtcc   5040
acaaatacaa ttatgacatt aatattaaaa gaaaagggtt cattcataat taacatgccc   5100
ctgatgcaag gggaatatgt ggagatcaac tcttagtcta aaagaagagg tggacaattg   5160
cattaatgca tattaagtcc aaaagaaggg gcacttagtg aatatcatcc ccctgctcta   5220
aagcaaaggt ggtacaggaa catgcttaga gaattgagtt tgtgcacatg aacattccaa   5280
gtgacagtct tgagtagtgg gcactacctg ctaaaaacac taagaaagta ggtaggatcc   5340
```

-continued

```
ttatctagtg cacagatcag gagcaaatgt aattgcacat attaacagtc caaaacaaca   5400
ggactttggt tgatcaggac accctgttgt actacaaagg aaaggtgatg gggtatgacc   5460
ttaatctact gacaaagaca aaagaaaatt tcaattatat gttgatagtc caccagaagg   5520
ggccttggag ggaaacagta taccccacag taatgcaaaa gaggtataat ggtcctagaa   5580
gtgatagggt tgtggacaac tgcaattatt cacattaact gttcaaatgt aaagatcata   5640
aggagtgggc acccactatt gaaaagaggt ggggcatcct tgtctagggc acaagaacca   5700
acataaatgc aattatgcat gtcaacaagc caagaaaagg ggacttaggg ggtcagcaac   5760
cctggtatac tgcaaatgga gggtgagaag gtagaacttt gtttaattag gatgaaccat   5820
gtggtgatta catacattaa tgtccaaggg acattgttgt ggtcaattaa aaccatgtac   5880
tttggacaaa tataagaatc ttaaaaagta gtgggtactc cttgttgaaa agcaaaggga   5940
gtccatgaga aggtgccctt atctagtaca caagaatata gacaagccaa gcaaagaggc   6000
ctcagtgatc agcaccccag ctatactgca aagggggtct gagagtagga ctttattcaa   6060
ataggataag ccatgtgcag ttatgcacat aaatttccaa gatgcatggt tgtggtcact   6120
tacaattgtg caccttgatt gtccaaatgt aagggtctta tggagtgagc actccctgct   6180
gggaggaaaa gaaagattat gcgtagatgg gatggggcag aggaggcttc cttgtctagt   6240
acacagaaac ctggacaaat ataatcacac acataacagg ccaggaaaat gggccttggt   6300
tatcagcacc cctgctgtac tgcaaaaggg gtctgagagt aaggccttat tcagatgaga   6360
taggccgtgt gcagttacac acattattga ccaaggtgca tggctgcggt cacttagaat   6420
tgtgcacctt gactgtccaa atgtaaggtt cttatggagc tggcactccc tgccagaagg   6480
gaaaggaaga ttgagggtgg ggtggggcag gggaggcttc catgtcttat acactggaac   6540
ccagacaaat ataatcacat acgttaacag gccaggaaga ggggccttgg ttatcagcac   6600
acctactgta ctgcaaaagg ggtctgagag taggacctta ttcagatggg atgggccatg   6660
tgcagttaca cacatttatg tccaaggtgc atggttgtgg tcacatacaa ttgtgcacct   6720
tgactgtcca aatgtaaggg tcttatggag cgggtacttc ctgccagaag gaaaggaaga   6780
ttgggggtgg agtgtggcag gggaggcttc catgtctatt acacaggaac tggaacaaat   6840
ataatcacac acataacagg ccaggaaaag gggccttggt gatcagcacc cctgctgtac   6900
tgcaaaaagg gtctgagagt aggaccttat tcagatggga tgggccatgt gcagttatgc   6960
acattcatgt ccaaggtgag tgcctatgct cacttacaat tgtgcacctt gattgtccaa   7020
atgtaagggt atatggagtg gacactccct ggtggaaggg aaaggaagat tggaggtggg   7080
gtgtggcagg ggaggctttc atgtctatta cacagaaact gggataaata taatcacaca   7140
cataacaggc caagaaaaag ggccttggtg attcagtacc cctgctgtac tgcaaaggca   7200
tctgagagta ggtccttatt cagatgggat gggccatgtg cagttacgca cattaatgtc   7260
caataatgtc caaggtgcat ggctgtggtc acttataatt gtgcaccttg attgtccaaa   7320
tgtaatgatc ttatggaggg ggcactccct gctggaaggg aaaggaagac tgggagtggg   7380
ggtgggggcg gggggaaggc ttccttgtct aatacacagg aacccagaca aatataatca   7440
cgcacataac aggccaagaa aaggggcctt ggtgatcagc acccctgctg tactgcaaaa   7500
ggggtctgag agtaggacct tattcagatg gaatgggcaa agtggttatg cacattaatg   7560
tccaaggtgt atgcctgtgg tcacttacaa ctgtgcacct tgattgtcca aacgtaagcg   7620
tcttatggag agggcactcc tgccggaagg gaaaggaaga ttgggggtgg agtgtggcag   7680
gggaggcttc catgtctaat acacaggaac cgggacaaac ataatcacac gcataccagg   7740
```

ccaggaaaaa gggccttggt gatcagcacc cctgctgtac tgcaaaaggg gtctgagagt 7800
aggattttat tcagataggt tgagctgtgt gtagttatgc aaatccatgt ctaaggtgca 7860
tggttgtgtt cacttaacaa ttacgcacct tgactgtcca aatgtgagag tcttatggag 7920
tgggcactcc ctgctggaag ggaaaggtga gactgaggta tgtggagagg accctccttt 7980
tctagtgcat aggatcccag acgattataa tcacacacaa catgccaaga aaaggggact 8040
gcgttatcag caacccttct gtattgcaaa aggggtcgga gagtaggacc ttattcacat 8100
ggaatgagca gtgtgcgatt acgcacataa atgtccaaga tgcatgcttg tggtcactta 8160
caattgtgca cctagactct ccaaataaaa gggtcttatg ggtgggcac ttcctgctgg 8220
aagggaaaag tggggatgag gggagcactt tccttctcta gtgcatagca acctcgacaa 8280
atacaatcac acatattggg aggccaattg gccaacgatc atctgtgatc cattctggtc 8340
cttgccacgg ctcaccacca tgtccacacc aagcaggcct ggagcactgc ccatggcaac 8400
agtgcagtgc agggcagacc agaggggggt agggggtag gggggtaggg gggtggggag 8460
gtgggggtg gggggtgggg gtggggagtt gggggggttg gggggtgggg ggggaggtat 8520
acttagcctt aggtgaggca ccaatacaga ggaatggagg gaggttcaga ccacacagcc 8580
agatatccag cactgcaaga ggcagcactg gacaggaggg gacaaataag aggggacaga 8640
ggtggaaagg ctaaatgtcc ttgaaaagac cttgaaaaca cctggtgtac cgcccactgg 8700
gagacataca cgtggcccct ccacttcttt ctcctgactg gctaaagaca gctgcgaagt 8760
gccatgctaa ttcacccagg tcttcgctga gtagctggac agtgtgtcat cagtctaatt 8820
ccatcttctg ctctaattgg ctgtgatcaa ttccaccccc atttctaatt ggttgggtta 8880
tgcagcaatc cagcactgtc catcccacct tttctcccgc tctgcgtggc actaggcggc 8940
aaaacccgcc atctttaaca atgcggcaag cccgccatga tgtccacgtg acaaaagcca 9000
tgatatacat atgacaacgc ctgccatatt gtccctgcgg caaaacccaa cacgaaaagc 9060
acacagcaaa gacaaagagg cccgccatgt tttacactgc ggcaagacct tcagccgcca 9120
tcttttcctg tgtgaccgca catgtccacc accatgctaa ccacttaaca aagcctcgcc 9180
catcatgatg tggccttccc gccacttgaa cactgcgaca gaactggatc cgccattttg 9240
gacaacctaa caaagcacag cccgccatgc tgagcaatgc cgcaatgtca aaatcgccat 9300
tttaagccct gcaccttagt ctttcctaac cttccatttt taactagtcc cttgtactga 9360
taaaagatga ttcttactgc ctcccgatac aacaatcacg caaagctcct aacaagcccc 9420
aaatcaattc attcagatag gtttagctca tgcaatgcac atgacttcct ctgcctgacc 9480
tgctatcatc catcttgcct ccctagttta acttagcaca aacgactagc cctaagccga 9540
gttatgcggc aagtctaaaa tggcggccac ttttcctcca caatctgaac acgcccttag 9600
cttaactgca gagtcattct ctgccaaagc ggtaggtaca ctcacacacc accaaatgat 9660
cagcagcaaa aaaaagtgta gatattccag agagtgcaac aacccacaaa accaacattt 9720
tttcatccat aaaaagcacc gatgggcgat gaaaaaaaaa aatcaaagca ggtatccgcg 9780
gccccgatgg gcagaaaaac aaaaattaaa gcaggtatcc gaggccccga tgggcaagga 9840
aaataaaaaa aaaaaaagca ggtatccgaa gccccgatgg gccaaaaaaa gaaaattttt 9900
aaaaagcaga tatccgtcac cccgatgggc cagagtgttg ggggttcaga ggggaaggga 9960
atcagcaggt atccgatacc ccgatgggct aaggaaaaaa aaataaaaag caggtatccg 10020
cggccccgat gggcgaataa aaaagaatta aaaggcaggt atccacggcc ccgttgggca 10080
aagaaaaaat aataaaacca ggtatccgca gccccgatgg gcaaaatata gaaaagagag 10140
tggaagagta aaaaactgat ccacaaaaaa cagagatgtc accaaaaatg attccaaaga 10200
aaaattcctt aaatattaaa aattgcctca aaatattcca aatactttct ttaaaaaaat 10260
atggaggacg tgtcaagaag acactaggag aaagtataga atttaaaaaa atattttatg 10320
gaatttaggt gattttttta aagaaatacg ccataaaggg tgttggggga ctagaaaatg 10380
ttctagaatc tgcagaattc caccacactg gactagtgga tccgagctcg gtaccaagct 10440
taagtttaaa cgctagagtc cggaggctgg atcggtcccg gtgtcttcta tggaggtcaa 10500
aacagcgtgg atggcgtctc caggcgatct gacggttcac taaacgagct cgtcgacgat 10560
ctctatcact gatagggaga tctctatcac tgatagggag agctctgctt atatagacct 10620
cccaccgtac acgcctaccg cccatttgcg tcaatggggc ggagttgtta cgacattttg 10680
gaaagtcccg ttgattttgg tgccaaaaca aactcccatt gacgtcaatg gggtggagac 10740
ttggaaatcc ccgtgagtca aaccgctatc cacgcccatt gatgtactgc caaaaccgca 10800
tcaccatggt aatagcgatg actaatacgt agatgtactg ccaagtagga aagtcccata 10860
aggtcatgta ctgggcataa tgccaggcgg gccatttacc gtcattgacg tcaatagggg 10920
gcgtacttgg catatgatac acttgatgta ctgccaagtg ggcagtttac cgtaaatact 10980
ccacccattg acgtcaatgg aaagtcccta ttggcgttac tatgggaaca tacgtcatta 11040
ttgacgtcaa tgggcggggg tcgttgggcg gtcagccagg cgggccattt accgtaagtt 11100
atgtaacgcg gaactccata tatgggctat gaactaatga ccccgtaatt gattactatt 11160
aataactagt caataatcaa tgtcaacgcg tatatctggc ccgtacatcg agctttacta 11220
gggacaggat tggtgacaga aaagccccat ccttaggcct cctccttcct agtctcctga 11280
tattgggtct aacccccacc tcctgttagg cagattcctt atctggtgac acacccccat 11340
ttcctggagc catctctctc cttgccagaa cctctaaggt ttgcttacga tggagccaga 11400
gaggatcctg ggagggagag cttggcaggg ggtgggaggg aagggggggga tgcgtgacct 11460 gcccggttct cagtggccac cctgcgctac cctctcccag aacctgagct gctctgacgc 11520
ggctgtctgg tgcgtttcac tgatcctggt gctgcagctt ccttacactt cccaagagga 11580
gaagcagttt ggaaaaacaa aatcagaata agttggtcct gagttctaac tttggctctt 11640
cacctttcta gtccccaatt tatattgttc ctccgtgcgt cagttttacc tgtgagataa 11700
ggccagtagc cagccccgtc ctggcagggc tgtggtgagg aggggggtgt ccgtgtggaa 11760
aactcccttt gtgagaatgg tgcgtcctag gtgttcacca ggtcgtggcc gcctctactc 11820
cctttctctt tctccatcct tctttcctta aagagtcccc agtgctatct gggacatatt 11880
cctccgccca gagcagggtc ccgcttccct aaggccctgc tctgggcttc tgggtttgag 11940
tccttggcaa gcccaggaga ggcgctcagg cttccctgtc cccctttcctc gtccaccatc 12000 tcatgcccct ggctctcctg cccccttccct acaggggttc ctggctctgc tctaagggca 12060
agggcgaatt cgcggccgct aaattcaatt cgccctatag tgagtcgtat tacaattcac 12120
tggccgtcgt tttacaacgt cgtgactggg aaaaccctgg cgttacccaa cttaatcgcc 12180
ttgcagcaca tccccctttc gccagctggc gtaatagcga agaggcccgc accgatcgcc 12240
cttcccaaca gttgcgcagc ctatacgtac ggcagtttaa ggtttacacc tataaaagag 12300
agagccgtta tcgtctgttt gtggatgtac agagtgatat tattgacacg ccggggcgac 12360
ggatggtgat ccccctggcc agtgcacgtc tgctgtcaga taaagtctcc cgtgaacttt 12420
acccggtggt gcatatcggg gatgaaagct ggcgcatgat gaccaccgat atggccagtg 12480

```
tgccggtctc cgttatcggg gaagaagtgg ctgatctcag ccaccgcgaa aatgacatca  12540
aaaacgccat taacctgatg ttctggggaa tataaatgtc aggcatgaga ttatcaaaaa  12600
ggatcttcac ctagatcctt ttcacgtaga aagccagtcc gcagaaacgg tgctgacccc  12660
ggatgaatgt cagctactgg gctatctgga caagggaaaa cgcaagcgca aagagaaagc  12720
aggtagcttg cagtgggctt acatggcgat agctagactg ggcggtttta tggacagcaa  12780
gcgaaccgga attgccagct ggggcgccct ctggtaaggt tgggaagccc tgcaaagtaa  12840
actggatggc tttcttgccg ccaaggatct gatggcgcag gggatcaagc tctgatcaag  12900
agacaggatg aggatcgttt cgcatgattg aacaagatgg attgcacgca ggttctccgg  12960
ccgcttgggt ggagaggcta ttcggctatg actgggcaca acagacaatc ggctgctctg  13020
atgccgccgt gttccggctg tcagcgcagg ggcgcccggt tctttttgtc aagaccgacc  13080
tgtccggtgc cctgaatgaa ctgcaagacg aggcagcgcg gctatcgtgg ctggccacga  13140
cgggcgttcc ttgcgcagct gtgctcgacg ttgtcactga agcgggaagg gactggctgc  13200
tattgggcga agtgccgggg caggatctcc tgtcatctca ccttgctcct gccgagaaag  13260
tatccatcat ggctgatgca atgcggcggc tgcatacgct tgatccggct acctgcccat  13320
tcgaccacca agcgaaacat cgcatcgagc gagcacgtac tcggatggaa gccggtcttg  13380
tcgatcagga tgatctggac gaagagcatc aggggctcgc gccagccgaa ctgttcgcca  13440
ggctcaaggc gagcatgccc gacggcgagg atctcgtcgt gacccatggc gatgcctgct  13500
tgccgaatat catggtggaa aatggccgct tttctggatt catcgactgt ggccggctgg  13560
gtgtggcgga ccgctatcag gacatagcgt tggctacccg tgatattgct gaagagcttg  13620
gcggcgaatg ggctgaccgc ttcctcgtgc tttacggtat cgccgctccc gattcgcagc  13680
gcatcgcctt ctatcgcctt cttgacgagt tcttctgaat tattaacgct tacaatttcc  13740
tgatgcggta ttttctcctt acgcatctgt gcggtatttc acaccgcatc aggtggcact  13800
tttcggggaa atgtgcgcgg aacccctatt tgtttatttt tctaaataca ttcaaatatg  13860
tatccgctca tgagattatc aaaaaggatc ttcacctaga tccttttaaa ttaaaaatga  13920
agttttaaat caatctaaag tatatatgag taaacttggt ctgacagtta ccaatgctta  13980
atcagtgagg cacctatctc agcgatctgt ctatttcgtt catccatagt tgcctgactc  14040
cccgtcgtgt agataactac gatacgggag ggcttaccat ctggccccag tgctgcaatg  14100
ataccgcgag acccacgctc accggctcca gatttatcag caataaacca gccagccgga  14160
agggccgagc gcagaagtgg tcctgcaact ttatccgcct ccatccagtc tattaattgt  14220
tgccgggaag ctagagtaag tagttcgcca gttaatagtt tgcgcaacgt tgttgccatt  14280
gctacaggca tcgtggtgtc acgctcgtcg tttggtatgg cttcattcag ctccggttcc  14340
caacgatcaa ggcgagttac atgatccccc atgttgtgca aaaaagcggt tagctccttc  14400
ggtcctccga tcgttgtcag aagtaagttg gccgcagtgt tatcactcat ggttatggca  14460
gcactgcata attctcttac tgtcatgcca tccgtaagat gcttttctgt gactggtgag  14520
tactcaacca agtcattctg agaatagtgt atgcggcgac cgagttgctc ttgcccggcg  14580
tcaatacggg ataataccgc gccacatagc agaactttaa aagtgctcat cattggaaaa  14640
cgttcttcgg ggcgaaaact ctcaaggatc ttaccgctgt tgagatccag ttcgatgtaa  14700
cccactcgtg cacccaactg atcttcagca tcttttactt tcaccagcgt ttctgggtga  14760
gcaaaaacag gaaggcaaaa tgccgcaaaa aagggaataa gggcgacacg gaaatgttga  14820
```

```
atactcatac tcttcctttt tcaatattat tgaagcattt atcagggtta ttgtctcatg  14880

accaaaatcc cttaacgtga gttttcgttc cactgagcgt cagaccccgt agaaaagatc  14940

aaaggatctt cttgagatcc tttttttctg cgcgtaatct gctgcttgca aacaaaaaaa  15000

ccaccgctac cagcggtggt ttgtttgccg gatcaagagc taccaactct ttttccgaag  15060

gtaactggct tcagcagagc gcagatacca aatactgttc ttctagtgta gccgtagtta  15120

ggccaccact tcaagaactc tgtagcaccg cctacatacc tcgctctgct aatcctgtta  15180

ccagtggctg ctgccagtgg cgataagtcg tgtcttaccg ggttggactc aagacgatag  15240

ttaccggata aggcgcagcg gtcgggctga acggggggtt cgtgcacaca gcccagcttg  15300

gagcgaacga cctacaccga actgagatac ctacagcgtg agctatgaga aagcgccacg  15360

cttcccgaag ggagaaaggc ggacaggtat ccggtaagcg gcagggtcgg aacaggagag  15420

cgcacgaggg agcttccagg gggaaacgcc tggtatcttt atagtcctgt cgggtttcgc  15480

cacctctgac ttgagcgtcg atttttgtga tgctcgtcag gggggcggag cctatggaaa  15540

aacgccagca acgcggcctt tttacggttc ctggcctttt gctggccttt tgctcacatg  15600

ttctttcctg cgttatcccc tgattctgtg gataaccgta ttaccgcctt tgagtgagct  15660

gataccgctc gccgcagccg aacgaccgag cgcagcgagt cagtgagcga ggaagcggaa  15720

g                                                                  15721
```

<210> SEQ ID NO 21
<211> LENGTH: 20607
<212> TYPE: DNA
<213> ORGANISM: Artificial Sequence
<220> FEATURE:
<223> OTHER INFORMATION: 6.3 kb/mXist/Runx1 construct

<400> SEQUENCE: 21

```
gggcgaattg ggcccgacgt cgcatgctcc cggccgccat ggccgcgggg catctctctc     60

cttcctccag tgtctgcaag cacacacaca cacacacaca cacacacaca cacacacaca    120

cacacacatg cgcgcgagca cctaactaaa aataaaatag ctgtaaatga gaacacgtat    180

tcgaatagag cacttgaatt tgaacatatc taaaaggccc atgtcttttt tattacagag    240

cgtatacaaa gcgagacagg gagggatgga aggagaaggg gaggagggag agagaacctg    300

acctctcgta gaaagacgcc acactatctc agatcttcca catactctgc ccccagcagc    360

tgagactgta acattactcc tgcgcttatg cccatgacaa atcacggact cactcgggat    420

tccggtaacg tggtaccatt accacattac catgtaagaa ctgggacaga ctggcagagc    480

atgttcagac acggctctga aacgtggtga cctctccttc atttttttcc agtggattca    540

cctttttttgt ctcaggacaa atgaagcaag agggataatg ggcagagtca cttgtttgtg    600

tccagtgtat tgcatcagat gacaacaggc cgattgtgtg tgtgcctaat gctctccctc    660

ctgcctcggc ttctccctag actgtataaa tctaactgga aaaaaaaaat ggagtagagc    720

ttcctgttaa ctctcaagca tgtcatggct ctctgtaagc aaaacaagtg acacagagtt    780

tgctcataga ggtccccggt gagggcgcag agatgaaccc tgaggaatga ggtgtggcct    840

gctggctgga ggagaggcta gagggcagcc taccagggca gcctaccaga gccactgttg    900

gtttacagcc tttgcctgcc cacatgtctg acttgctttg aaaagattaa caggagtgtt    960

tgtttgaaag tcagactcct ggtttcctca ttagtagagg gatttgctgc agacttgggc   1020

tgtgcttata aactctaatt acctctctga tgaggagtct atttctctca cattcagccc   1080

aaatgtacac aagagttcct tttgtaaaat cgtgttagag caataaaaga ttattgagag   1140
```

-continued

```
ggggtggagg gggagaggga gaaacaagaa cacaagcccg agctctccgt gctgaaataa   1200
taggcttgga acagaaagaa gttgatcaca gcccatgcct tccaaaaaaa aaaaaagatt   1260
aatccacccg ggtagctttc ctttcaaagg aagcttttcg atcccctcaa gtttctctct   1320
agcaggctca actctgtacc tgaatttgag aatttaacat tttgaacact tagttcgtgc   1380
ctctgccctg tgttgttgct gctgctgagc cgtgctggtg cgaacagtat agtcgcagcc   1440
tgccctcctc tgactgacag acacaagcta cccgaaacac cgtcctaact cactgtggca   1500
gctggtgggc ggatgtgcat cccttcctaa ccattctcag ttatttcgca atgtctggag   1560
attcttttgg atgtcaaagt agcgggcagg gggtcggcag ggaggccact agaggcatct   1620
tgtgggtaaa gaaggaagat gccaccaaac agttatcagt ctccaaacac ccgctagaca   1680
taatacagcc caaagatgcc agcagtggca cttttggcaa gggaaccctc ctgtccctcc   1740
tgtcccctgg tctgcctcaa aggcagcatg cacacgtgcc aagtgcagag ggagccggtg   1800
aagcaagggc agtctgtaga actgtaaatt caaaatgaat cttgtaaaga aagtctgtca   1860
tttctggaca aaacaagttt tgctatccat ttgtgttaga agctagtgag tgacacagca   1920
gctggagcca tgactcagtg gtttagagca tgcactgctc tgggggatgt tggcacccac   1980
ttctagcctc tgggggcact gcacacacac aggctcataa ccacacaagc ataatcacaa   2040
gtaaaattac ctttaagaag aaaacagtga ctcaggtctt agataaagac gagacatgaa   2100
gtcaaatgtc taaggttact atagatggga acaagtcaga aggcagagac agaggcaagt   2160
gatgtgtcaa tcaccgacat tcacgtcgtc cctaccacaa cacgcactgc acctaataat   2220
aggaaattag ccaactttca agggatcaga gtctacaaaa atgacagttt tctattatcc   2280
aacctgacta ctaagtgcaa tgacataata ttgttattat aacatactta acatataata   2340
ttctactatc aacatatcag tggatgcatg acctcagtta ttttaatgtt atgccattgt   2400
atattgttat attaatattg ttatgccaat gtactgatta tattagcaat ataccagtca   2460
gtattgatgc tttcattaga ggataggctt ttttttctcc cccagtaaag gaccaaagag   2520
aagttgttaa gctttggaca ctctgttgtc ctggtcactc aacagcaata ggagctactt   2580
agcgcccatg aaagtgcaca caggtgccaa cttgtgctat aggttgaagc tatgtcgcaa   2640
cagagtagaa atacaatttt tgtgtgtttt tatttttagt cttacaacca tttgaaaagg   2700
taaaattcat tcttaattcc tagaacacat aaaacttctc cccagccaga cttagccaat   2760
gagctacagt ttgccaacct gggatctaac atttatgtgt attggaaact ttacactaca   2820
gtgtgtgtga caggtaccta tatggtacat atgctacggc gtgtcaggat acataccata   2880
tgccgcccac cactccctgc aatgcatctg ccattgctct gtgtcacact gtttgacatc   2940
tgtcatgtca aacatgctgg gggaagccca cttcttgcta gatagtcccc gccacccacc   3000
attccctggc agcagccctc tgcatagaat ctcatcttct taagtgacag tatcttgggt   3060
agttatctgt cctgttgact tctaggtaag tgtacatctc aggcaggaat attctcagtg   3120
gttccctcct ccctgggcag ggagctgtgg gcagtccagt ctgttgggtg ggtgcactct   3180
ccgtgctccc tcctccatgg tcagggccag tctgggcact cttctgtgtc ctgagtagga   3240
gcactccctg tgccaccccc atcccccacc catagtcatt ctgtgcaatc ttgtgtgacc   3300
tggttggaaa cagtcttggt ggtctgggac actctgagca gtcctgtgtc ctgggtggga   3360
gcaattttgc ggtcccccct tccacaggca ggggcagtgt gttgtggggg gagcactctc   3420
tgtgtagccc cctacatggg cagaggcact ctccgtggtc cccccccccc gggcagaagc   3480
```

-continued

```
actctgggta gtcctgtgtg ttagggcagg atcacatgct gtgcccccac tccgtgggca   3540
ggagcactct gggtagtcct gtgtcttagg gcaggtgcac ttgccgtgct cccctccccg   3600
tgggcagggt cactctctgt ggcccccccc tccatgggca ggggtactct gggtagtcca   3660
gtatttgggg caggggtatt ctctatgccc cccccccca tgagcagggc cagtctgggc   3720
aatcctgtgt cctaggtggg agcacttccg gtttcccct ccatggatgg ggcacttttg   3780
gcagtcagtg tgttggggtg ggagcactct ctgggtcgct ccctccatgg gcagaagcac   3840
tctgattagt cctttgtcat agggcaggag cactcgctgt gccccccccc ccgcccccgg   3900
ggcaagggca ctctctgtgg tccctctcca tgggcaggga cactctctgg gcaagtccag   3960
tgtgttggag agggagcact ctttgtgtca gaggcactct ccgtgatcgc ggcctacaga   4020
catgataaga tacattgatg agtttggaca aaccacaact agaatgcagt gaaaaaaatg   4080
ctttatttgt gaaatttgtg atgctattgc tttatttgta accattataa gctgcaataa   4140
acaagttggg gtgggcgaag aactccagca tgagatcccc gcgctggagg atcatccagc   4200
cggcgtcccg gaaaacgatt ccgaagccca acctttcata gaaggcggcg gtggaatcga   4260
aatctcgtag cacgtgctat tcctttgccc tcggacgagt gctggggcgt cggtttccac   4320
tatcggcgag tacttctaca cagccatcgg tccagacggc cgcgcttctg cgggcgattt   4380
gtgtacgccc gacagtcccg gctccggatc ggacgattgc gtcgcatcga ccctgcgccc   4440
aagctgcatc atcgaaattg ccgtcaacca agctctgata gagttggtca agaccaatgc   4500
ggagcatata cgcccggagc cgcggcgatc ctgcaagctc cggatgcctc cgctcgaagt   4560
agcgcgtctg ctgctccata caagccaacc acggcctcca gaagaagatg ttggcgacct   4620
cgtattggga atccccgaac atcgcctcgc tccagtcaat gaccgctgtt atgcggccat   4680
tgtccgtcag gacattgttg gagccgaaat ccgcgtgcac gaggtgccgg acttcggggc   4740
agtcctcggc ccaaagcatc agctcatcga gagcctgcgc gacggacgca ctgacggtgt   4800
cgtccatcac agtttgccag tgatacacat ggggatcagc aatcgcgcat atgaaatcac   4860
gccatgtagt gtattgaccg attccttgcg gtccgaatgg gccgaacccg ctcgtctggc   4920
taagatcggc cgcagcgatc gcatccatgg cctccgcgac cggctgcaga acagcgggca   4980
gttcggtttc aggcaggtct tgcaacgtga caccctgtgc acggcgggag atgcaatagg   5040
tcaggctctc gctgaattcc ccaatgtcaa gcacttccgg aatcgggagc gcggccgatg   5100
caaagtgccg ataaacataa cgatctttgt agaaaccatc ggcgcagcta tttacccgca   5160
ggacatatcc acgccctcct acatcgaagc tgaaagcacg agattcttcg ccctccgaga   5220
gctgcatcag gtcggagacg ctgtcgaact tttcgatcag aaacttctcg acagacgtcg   5280
cggtgagttc aggctttttc atcacgtgct gatcagatcc gaaaatggat atacaagctc   5340
ccgggagctt tttgcaaaag cctaggcctc caaaaaagcc tcctcactac ttctggaata   5400
gctcagaggc agaggcggcc tcggcctctg cataaataaa aaaaattagt cagccatggg   5460
gcggagaatg ggcggaactg ggcggagtta ggggcgggat gggcggagtt aggggcggga   5520
ctatggttgc tgactaattg agatgcatgc tttgcatact tctgcctgct ggggagcctg   5580
gggactttcc acacctggtt gctgactaat tgagatgcat gctttgcata cttctgcctg   5640
ctggggagcc tggggacttt ccacacccta actgacacac attccacaga attaattcgc   5700
gttaaatttt tgttaaatca gctcattttt taaccaatag gccgaaatcg gcaaaatccc   5760
ttataaatca aaagaataga ccgagatagg gttgagtgtt gttccagttt ggaacaagag   5820
tccactatta aagaacgtgg actccaacgt caaagggcga aaaaccgtct atcagggcga   5880
```

-continued

```
tggcccacta cgtgaaccat caccctaatc aagtttttg gggtcgaggt gccgtaaagc   5940
actaaatcgg aaccctaaag ggagcccccg atttagagct tgacggggaa agccggcgaa   6000
cgtggcgaga aaggaaggga agaaagcgaa aggagcgggc gctagggcgc tggcaagtgt   6060
agcggtcacg ctgcgcgtaa ccaccacacc cgccgcgctt aatgcgccgc tacagggcgc   6120
gtggggatac cccctagagc cccagctggt tctttccgcc tcagaagcca tagagcccac   6180
cgcatcccca gcatgcctgc tattgtcttc ccaatcctcc cccttgctgt cctgccccac   6240
cccacccccc agaatagaat gacacctact cagacaatgc gatgcaattt cctcatttta   6300
ttaggaaagg acagtgggag tggcaccttc cagggtcaag gaaggcacgg gggaggggca   6360
aacaacagat ggctggcaac tagaaggcac agtcgaggct gatcagcggg tttaaacggg   6420
ccctctagac tcgagcggcc cgaagtcggc catatccaga gcgccgtagg gggcggagtc   6480
gtgggggta aatcccggac ccggggaatc cccgtccccc aacatgtcca gatcgaaatc   6540
gtctagcgcg tcggcatgcg ccatcgccac gtcctcgccg tctaagtgga gctcgtcccc   6600
caggctgaca tcggtcgggg gggccgtcga cggtatcgcg cgcagcaaca tgcatgtaca   6660
cacacacata catacactca tacacaatag ctcccaaaaa agacctaagt actcggcggc   6720
tacaaagcac ccttcacact agagaaagct cttttcttac taggaaaatc tctctttgaa   6780
gtgtacgttt aaaggaatga ttagatcctg gcagacatat tttaaaatgt aaagtgggga   6840
aacaggttct atcatctcta aaataaattc ccactttagg aattttcaag ctacttcaaa   6900
ttattgccag agtttaatgg tggatagaat gaattaatta aatgtgatgg cctatataat   6960
tttcaaaggc gacttgacat gttctcaaat ttaatccatc cagtcacctt ttaaaaataa   7020
gcaaggactg gtgaccaatg tcagacaaaa tataatgatt agaaggctta ggtcatcttc   7080
caaaaagtta atcatactaa aggccacaca aagattgact ttttcgtttt gttaaacttg   7140
tagtaaagac caagcaaaga tacttgtctt aaacattctg caatagttgc actgatcttt   7200
ccacagactc atcaccctca gtacactgag acactgctta gtcttcagaa acatgacaca   7260
aatggctatt tttacttcac aaaagctaat gatctcacag tcaatccacc ttgcaatcca   7320
aatgcctttc ttaaggaata aaattatcaa taacttttct ggcagttggt cctgtacagt   7380
agcaatatac aaaatcgggc ttaaagtttc ttaagcagac agttggctcc ttcctggagg   7440
aagaatggaa agaaaagtgc taagcttcct tctcaggaag acaattttca gttcatactg   7500
taaaggaaag ccccaagtaa aaggtggcaa tccaactccc tgagctactt gcctgcaata   7560
ttttgcacaa taaagcatta ataaaggtag gcaagaatgg ttcctggccc tagaatgtgc   7620
cagcagttgg aattggaata atttagaagt gcaagttaaa gattgaaggc tcatccacct   7680
agttttggcc tgcttttgct attcagtgta taaatacacc aaaatttatt aatgacacat   7740
agggtgtttg gggtaattaa cattacccag aataatgtaa gaattcgagg tgtctctgtt   7800
cagtgggagc aaggagaagg caactgagac actgtagcca tatgaagtga gtaaactggt   7860
gttgttgact ttaagtcaag agaagggctt tgcccagtca atactgttca aacaaagagg   7920
caaaagggat ggcatgatgg aattgagaaa gggcacaaac tcttccttaa tgatgggttt   7980
gtgagaatta gtgattcaga aaagtggtca atggacaaac tagaggccgg gcaaaaggaa   8040
cactataaag tgtgagattg tgactattta ggattgtata tattaaagca atgcaaaaag   8100
ggtcgaaatc cgggtcattg ttgggtgtac atactgctgt actttattat atcattggga   8160
aactagcagg ggatttgctc aagttggagt agaaaataaa ccatccagaa ctgccattgt   8220
```

gcctattaag agtcccaaaa tcagtttaag gaagagagca ggtcattcgt cagagcccct 8280
gtgctcattg acagtaccgg gtagtttcgg gggctcagca acctctgcaa taatgtaaag 8340
gggacaaaat attccagaca ttcatagtta taaatacgca taacttagca attaattctg 8400
ggactcagta gccttgatgg tatgcaaaga gagcacacag gtccttgaca tttttgcata 8460
gtaatcatcc aaatgctgag gttactaata gttactacca ctcagcagcc ccagtcaaaa 8520
ggtaggcatt tcagaacctt tgctgccgca caggtcatat gtgtaagggt acagattaat 8580
attgacaaga gaagtgctca gaaataatta atatgcctct ggtgtcaaaa gagtacaagg 8640
atgtaaaatc caactccaaa ggtaatgatg gacaactaac tgcattaatg cacttaagtc 8700
caaatgaaga gcacttcgta caaccctctt tctgctttaa agcggagaag agggtacagt 8760
agttcttaga gaagtgctta gacatgtgaa ctttccaaat gaaagtcttg agcttattat 8820
cacttcctgc tgaaggtgct aaggaagtga gtgggatcct ttcaagtgca cagagcaggt 8880
ggcagtgcat acgcatacat ttaatatatg ataacagtcc aaaagaatgc ggccttgttg 8940
atcagcatat cctgatatag tgcaaatgaa aggcgaagga gtatggcctt tgtttactgg 9000
caaagacaaa ggaagattca ctgtatatta atggtccact agcagggacc ttgggagata 9060
aacggtatcc cttgcaggag tgcaagagat acaatggtcc gaaaagtaat aaggttgtgg 9120
ataagtgtaa ttttacacat taactggcca agtattttta ttaaaatgaa tggatcatgt 9180
ccctgttata tacattaatg ttcaagggac atgttatcaa ttaaaaaccc catcctttat 9240
gcaaatatta agtctttaaa gtaatagtcc tggaaattaa agagtggaaa ggaggggaca 9300
gccttatcca gtgtccagga agatgaagaa gccaaaagat tagtgaccct tgctgtactg 9360
caaaagggtt tgagagtagg atcgtatcca aatggaatga gatgtgtgca gtaaatgcat 9420
actaatatgc aaggtacatg tttatggcca ttacagtttt acgctgttca ggtttccttc 9480
tgtagtgaac agaaaaggcc tactacaatc agtcattatt attagcaagc cacaaaatgg 9540
gaccttatag gtcaacacca cttctgtact tcaaagttaa gagtaaaatt gatcctacta 9600
aaattgccag tatgtacata aatagtttga ggaaggggtt tcaagtgcac agcacataca 9660
taattccata aagcaaagag gatatgaatg atcagagaca gaagtcttac cttgaaggac 9720
cattgaccgt attggaatcg tttcaatcta tagtctcatg aaagaagctt tatattagtg 9780
agcctctttg ctttgctaag tacaggagtc ctgatctaaa aggcacaact gtggacatga 9840
gaatatgtac aatagagtta acactgtgca catttactat gttaaggatc ttaaatactg 9900
ctgcaataca aataagtctt caccagatgc agattactac agtgaaatga catatgcaca 9960
ttcacaatat gaaagactgc atgcagggca tagtggtagg aaccagatat gccaacactt 10020
gttaaacgca ggctagatcc tgagctcaag gctagcctgg gttatatgct aagttccagg 10080
ccagcctgga agttaaaaac aggacagatc aaaggtcttc ttgattacca acaaaatgac 10140
ttgacttagt ttggtttctt tatccaatgc ttaggaagag ggacaaatgc agctgtgcac 10200
acaacaggca caaatatgtt tacattacag gtggcaatgc ctgtaagtcc cgcccagccc 10260
aggctacata agaggctgtt ctctcaaacc accacacggt ggggctgtag ctctatgaca 10320
gtgctttact agcgtacaca agactcaagg tttgattccc cagcacagca gaaagaccag 10380
aacagagaag tggtctcatt ggttggcacc cttgattgtc acccattagg gtatgagggt 10440
atgggatctt ggttactaac agaaggggac ttgaacaact gcaattttgc acaattgtgt 10500
aagaggcatt aagtaatcag caccctcttt acataaagca agggtagtat taggaccttg 10560
agaaaagact caattcctag tcaggattat ccacataaaa tgttccagtg cagaggtttt 10620

```
tggctgaaat aagaaagcat gtgagactag tatacaatat catgagcaaa taaatgtatc  10680
tccatcagtt agaaagatgt gacctggggc gatagcaccc atgacagcat gccaacagta  10740
tatagtattc tacccccttt aatggccaat gccttgaaaa ttgggactga gcactttaac  10800
tgtctgataa cagacctgtg tttgcccctt tgctaaatgc acacagggct ggactagcta  10860
aagtctaatc caatggacaa aatatttctg acagaattat tcagtactca aggtaataca  10920
tgagaaaaga cgactgaaca ctgcttagaa acttgggact gtgactacta cagcaatgac  10980
agaatggttt tctttcctta aaggaaagga gacttgagag atgatacctc catggatccg  11040
acatcatcca acacttcagt gttagaattg caagcatgcg ctctcccgac ctgggcaggc  11100
acttcgaaaa aatgatgact aaagacacac gtgaagtacc aagcgaaact cacgtcctta  11160
tgggacagtg actcatcaca gtctaattcc atcctggcca ccaagcaata atgcacattt  11220
ctaactggaa gtcaagcaaa caccaacact ttcacacttg tgcccatttc tgacgagtta  11280
cgtcaagtgg caaccaacac ttccacttag ccttgcctca gcttcgagtg gcacaaggta  11340
ggaccaacca caccctacca taatgcacca agtgtaccct cgggcaaagc ccgccaagta  11400
gctaaagccc gccaaaaaaa aaatcactga aagaaaccac tagagggcag gtcacatgac  11460
ttccgccatc ttagacacat tcaagagcat gtgccacctc tccaggctaa ctcagacatg  11520
aagctgacat gtgacacaca aagccctttg cgttataccg caccaagaac ttgagccgcc  11580
atcttttcct gtacgaccta aatgtcctat aatccattgc tacacaccag aacaaagatt  11640
gggctgtcga gcctcgggtg gagcccccga gccgccattt tatagacttc tgagcagccc  11700
ttaaagccac gggggaccgc gccaggggtc catatgcaca cacaccctgc ccaatcccca  11760
cacccacgct gagccctatc ccctagtcct ctgcggcttc cgcgcaacac cgcacactaa  11820
tacgagcact ccttggcttt ctacttccgg ctagcacaac cccgcaaatg ctaccacaaa  11880
tcaaggcgaa tcccgcaacc ccgcacatat aaagaaagcc tttagctagc gcagcgcaat  11940
tggttgcttt tatccagtcc gctgtgctcc tcggtgtcct aattcttggc gtaactggct  12000
cgagaatagc cgtatcacgc agaagccata atggcggacg cgggctctcc acgccctgaa  12060
cacccactca gtttaagagc aaagtcgttt ttctaagcca taggttcact cacacagcac  12120
caaacgatca gcagcaacag tacacgcaaa taagaggcat agatattcca ggtagtgcaa  12180
taactcacaa aaccatattt ccatccacca agcgccccgt tgggccgtga aaaaaaaaat  12240
ttaaagcagg tatccacagc cccgatgggc aaaagaaaaa gaaaaaaaaa taataacagc  12300
aggtatccga ggccccgttg ggcatgggaa aaaaagacta aacgcaggta tccgaggtcc  12360
cgatggaccg agaaaggttt tttttttttt tttttttttt ttacaaaaag caggtatcca  12420
tggccccgat gggctaagga gaagaaaaaa agaataaaag caggtatcca cagcccagat  12480
gggcaagttt agaaaaaaaa ataataagaa aaaaaaagaa tgaaaaggca ggtaagtatc  12540
caaaaccccg ttgggcatgg aatggcgggg aggacacaca ggtatccgtg gccccgatgg  12600
gcaagaatat ataaacaatg aaagaaaggt aagtccacca tacacacaca agtatcaacc  12660
aaaaggcaca acaaagaaat attccttaaa aatgaaaaat tgactgaaaa tattacaaat  12720
atcaaaaagt atggaggaca tgtcaaaaaa aaaatcttac cagaacatat caaaacgtca  12780
aaaatctcgt ggaattttga tatgttttct taaataagcc ataaggcttg gtggtagggg  12840
aactaaaaat gttcccccaa agctccttag atggagagaa accacggaag aaccgcacat  12900
ccacgggaaa cgagcaaaca tggctggagc aagccgttgc acgcctttaa ctgatccgcg  12960
```

-continued

```
gaggctggat cggtcccggt gtcttctatg gaggtcggat ccgagctcgg taccaagctt  13020
aagtttaaac gctagagtcc ggaggctgga tcggtcccgg tgtcttctat ggaggtcaaa  13080
acagcgtgga tggcgtctcc aggcgatctg acggttcact aaacgagctc gtcgacgatc  13140
tctatcactg atagggagat ctctatcact gatagggaga gctctgctta tatagacctc  13200
ccaccgtaca cgcctaccgc ccatttgcgt caatggggcg gagttgttac gacattttgg  13260
aaagtcccgt tgattttggt gccaaaacaa actcccattg acgtcaatgg ggtggagact  13320
tggaaatccc cgtgagtcaa accgctatcc acgcccattg atgtactgcc aaaaccgcat  13380
caccatggta atagcgatga ctaatacgta gatgtactgc caagtaggaa agtcccataa  13440
ggtcatgtac tgggcataat gccaggcggg ccatttaccg tcattgacgt caatagggggg  13500
cgtacttggc atatgataca cttgatgtac tgccaagtgg gcagtttacc gtaaatactc  13560
cacccattga cgtcaatgga aagtccctat tggcgttact atgggaacat acgtcattat  13620
tgacgtcaat gggcgggggt cgttgggcgg tcagccaggc gggccattta ccgtaagtta  13680
tgtaacgcgg aactccatat atgggctatg aactaatgac ccgtaattg attactatta  13740
ataactagtc aataatcaat gtcaacgcgt atatctggcc cgtacatcgg gccgcgtggg  13800
caggagcact cgctgtgccc cacccaccca cccaccgtgg gcaggggcac cctgggcaat  13860
cctgtgtgtc ctgagccgca gcactctggc agtctaggaa gcctgtgcct ccctgaccac  13920
acactcatgc cttctcttcc tctgcccgcc cacagcggct ccggacctga ccgccttcgg  13980
cgacccacgc cagttcccta ctctgccgtc catctccgac ccgcgcatgc actacccagg  14040
cgccttcacc tactcgccgc ccgtcacgtc gggcatcggc atcggcatgt cagccatgag  14100
ctcggcctct cgctaccaca ccgccctgcc gccgccctac cccggctcat cacaggcgca  14160
ggccgggccc ttccagaccg gctcgccctc ctaccatcta tactacggcg cctcggccgg  14220
ttcctaccag ttctccatgg tgggcggaga gagatcgccc ccgcgcatcc tgccgccctg  14280
caccaacgca tccaccggcg ccgcgctgct caaccccagc ctccccagcc agagcgacgt  14340
ggtggagacc gagggcagcc atagcaactc gcccaccaac atgccccccg cgcgcctgga  14400
ggaggccgtg tggcggccct actgagctga gcgccatcgc catcgaggga ctgggcctgc  14460
cgtccatgca cagaccccgc caggagggcc cttggaggcc accaggaaga atcccggagg  14520
gaaactgtga atgcttctga tttagcaatg ctgtgaataa aagaaagatt ttataccctt  14580
gacttcactt tttaaccacg ttgtttattc caaagagtgt ggaatgtttt cggttcgggg  14640
tggggaagac gcagcccatc ctgtttggca tctatttctt atttcggagt tttcttttcc  14700
gcaccttatc gattgcaaaa atgcctgttt gcatctgggt ggtcatttat ttttaagtgt  14760
gtatagattt gagcttgctt ttttttcttc ctttgaccaa ctcaaagaaa taaaattccc  14820
ttctctgtaa ggtttattta acttttagac tttcatgtag ctgggggttt tatttgtgtt  14880
tggtttttgt ttttattttt aaagagacag ctacagcttt gggtcatttt ttaactactg  14940
tatttccaca aagaaatccc tagatattta tgtatcttga tgtttgaaca tttacatatg  15000
tgttgatact tttttaatta tttaaatgta cttatattaa gaaagatatc aagtactaca  15060
tttttcttta taatagccaa agttaaatat tattgcgttg aagatgtctg gaaaaaaaag  15120
agatcgcttg gttaactaga aatattgttt acattaaact ccctttatgt tattcaaaca  15180
agttggtagg taacgcagca atgtttttaa ttggattgta gacactgagg gtcactccaa  15240
ggtcagaagt acaaaatttt ctgctaggct caacaaatag tctcatacct ggctccttcc  15300
cttcaaaaag agaggcaaac tctgtcctga aagggttcag agaggtgcca aggatttgct  15360
```

```
ctgaagagga tttcattttg gcctggagat atacttgccc caaggcctcc tcattctggc  15420
atgctttatc acagagctca accaagtaag ctgttggtca ggggtttact tacatagtat  15480
ttacatagac ccaaaccact gaatgtgatt tttaaattgc cttccattaa tagtacccgt  15540
tcattgatga aaaccaaaac ttgaggctgt accccaaaga tccaaataga agagttaaga  15600
ccaggtgtct ttgaggccta aaggctgagt tttaagagag tgtaccccaa aagtctgaag  15660
gagccggttt ccttctccca gtcttagtgg aatcagtcat gggaggcaga tgccacgccc  15720
acctgtgcag gatgctcctc agaagctgcc ccttcaccag catcttctcc caccaggccg  15780
agcccctgac ctttggggtg catcagtgtg atagatcctg gtctctgcag tccgccatgg  15840
ctacggttca gatgtgcatc gtgtcactgt aaatgtaatg gtactgttgt tacagtggag  15900
gacttggtca aaatccagtt gttctacaac gtatgaagcc taaccgctgg ttctgacata  15960
catgtgctca aaatgatctg gttgtttgga tttttctttt gttgttttgt tttttaatgt  16020
acctcttaaa ttagttgaag tgatgtcagg tcaactccga agagcgtttg aaagcaggac  16080
ttcagcacag tgtttgattt ttttattatt attaatatta ttttataaat ttaagcattc  16140
agattagatc tttggctgca ggcagcaaaa acggctggac ttatttaaaa aaaatacagc  16200
ttgttttttg agttatctat atctatatct atatgttgat tctttgtctt acatagagca  16260
gcagcacttt ggtaacctgt gataccaggt tgctcttgtc tggagaagag cgctagcagg  16320
attcagagaa actcagaata gatcttcata tcagccatac cttcctcctc catccggtct  16380
ccactcagtt attccacaga acactttgac agctgtgttg tcagaaaaat aaaaaaaaat  16440
ttaatttctc aaaaggagtt tgtttctcca acattagatg ttcctcttac cataggctgc  16500
cgtatctggc ctgagaaaac ggtagggaag gacgaaggaa agagatttct attttttcat  16560
attaattttg atatctaaag atacgctagc cctcagagga gcagataatc tcacacattg  16620
aattttcgcc ctgggcacca tgcatcaaga aggcttgtca ctgtgttaga gccatttagt  16680
gcttcctaaa cttttatcaa cataggcagt atttagtctc agagaaaaaa aaatccatca  16740
ggcacatgta gtcttggaga tagattccac ggggcaggta tttctctacc tgagaaattg  16800
tgttcattgc cttcgggtgc ttccagcggt ctcctcattc gctgtcttca aggaagaccc  16860
ataagccaat tctgagataa tggagctgtt gggaatactg gtccagagaa agaaaaatgg  16920
gataagccat tcttactgct tattcaagcc cctatttata attttaacac actttccatt  16980
ccttctggtt ttctcgccgt ctatatcctc ccaatagccc ttctcacttt tcttttccct  17040
cctgcaaaca cacacacaca cacacacaca cacacacata aggcacacac acacacatcc  17100
tctcccccat accaagtgtc cagaacacag aaagtccagt tcttctccgt ttattaaaga  17160
acagggtgag tcagccattc tcttgctcac gggttttttt ccccaacaga acagaggcgt  17220
tgccagccat tttgggtctg ctttctgtcc agatactgca gcaaaaactc ttgaggatca  17280
caacccgttg gctgagcagc tgtgctgctg cccaaacgtc ctgcgcagac aaacgcacgc  17340
tgggaccgga aggggtgtct ctccttctgc ctcttttctt tcatacgttt ctctcgaaag  17400
gcctcaactg aggactgcaa atttctttct tgaaataact ttcccccagg gacattcggt  17460
cttagggatt ttttggtttt gatgggtttt gttttgtttt ggttttttttg gttcttctca  17520
ttttctttgt aggagaaggc atgagatgtt gagggtcttt catacatgaa aataaatagt  17580
ttgacagcaa tctcagaata tattttttcc ttatttgaac aaagtactgt tttgtttact  17640
ctacagtaca cctttatttg gtgggtttgg ctgttggtcg ggtcgaccat atgggagagc  17700
```

-continued

```
tcccaacgcg ttggatgcat agcttgagta ttctatagtg tcacctaaat agcttggcgt  17760
aatcatggtc atagctgttt cctgtgtgaa attgttatcc gctcacaatt ccacacaaca  17820
tacgagccgg aagcataaag tgtaaagcct ggggtgccta atgagtgagc taactcacat  17880
taattgcgtt gcgctcactg cccgctttcc agtcgggaaa cctgtcgtgc cagctgcatt  17940
aatgaatcgg ccaacgcgcg gggagaggcg gtttgcgtat tgggcgctct tccgcttcct  18000
cgctcactga ctcgctgcgc tcggtcgttc ggctgcggcg agcggtatca gctcactcaa  18060
aggcggtaat acggttatcc acagaatcag gggataacgc aggaaagaac atgtgagcaa  18120
aaggccagca aaaggccagg aaccgtaaaa aggccgcgtt gctggcgttt ttccataggc  18180
tccgcccccc tgacgagcat cacaaaaatc gacgctcaag tcagaggtgg cgaaacccga  18240
caggactata aagataccag gcgtttcccc ctggaagctc cctcgtgcgc tctcctgttc  18300
cgaccctgcc gcttaccgga tacctgtccg cctttctccc ttcgggaagc gtggcgcttt  18360
ctcatagctc acgctgtagg tatctcagtt cggtgtaggt cgttcgctcc aagctgggct  18420
gtgtgcacga accccccgtt cagcccgacc gctgcgcctt atccggtaac tatcgtcttg  18480
agtccaaccc ggtaagacac gacttatcgc cactggcagc agccactggt aacaggatta  18540
gcagagcgag gtatgtaggc ggtgctacag agttcttgaa gtggtggcct aactacggct  18600
acactagaag aacagtattt ggtatctgcg ctctgctgaa gccagttacc ttcggaaaaa  18660
gagttggtag ctcttgatcc ggcaaacaaa ccaccgctgg tagcggtggt ttttttgttt  18720
gcaagcagca gattacgcgc agaaaaaaag gatctcaaga agatcctttg atcttttcta  18780
cggggtctga cgctcagtgg aacgaaaact cacgttaagg gattttggtc atgagattat  18840
caaaaaggat cttcacctag atccttttaa attaaaaatg aagttttaaa tcaatctaaa  18900
gtatatatga gtaaacttgg tctgacagtt accaatgctt aatcagtgag gcacctatct  18960
cagcgatctg tctatttcgt tcatccatag ttgcctgact ccccgtcgtg tagataacta  19020
cgatacggga gggcttacca tctggcccca gtgctgcaat gataccgcga gacccacgct  19080
caccggctcc agatttatca gcaataaacc agccagccgg aagggccgag cgcagaagtg  19140
gtcctgcaac tttatccgcc tccatccagt ctattaattg ttgccgggaa gctagagtaa  19200
gtagttcgcc agttaatagt ttgcgcaacg ttgttgccat tgctacaggc atcgtggtgt  19260
cacgctcgtc gtttggtatg gcttcattca gctccggttc ccaacgatca aggcgagtta  19320
catgatcccc catgttgtgc aaaaaagcgg ttagctcctt cggtcctccg atcgttgtca  19380
gaagtaagtt ggccgcagtg ttatcactca tggttatggc agcactgcat aattctctta  19440
ctgtcatgcc atccgtaaga tgcttttctg tgactggtga gtactcaacc aagtcattct  19500
gagaatagtg tatgcggcga ccgagttgct cttgcccggc gtcaatacgg gataataccg  19560
cgccacatag cagaacttta aaagtgctca tcattggaaa acgttcttcg gggcgaaaac  19620
tctcaaggat cttaccgctg ttgagatcca gttcgatgta acccactcgt gcacccaact  19680
gatcttcagc atcttttact ttcaccagcg tttctgggtg agcaaaaaca ggaaggcaaa  19740
atgccgcaaa aaagggaata agggcgacac ggaaatgttg aatactcata ctcttccttt  19800
ttcaatatta ttgaagcatt tatcagggtt attgtctcat gagcggatac atatttgaat  19860
gtatttagaa aaataaacaa ataggggttc cgcgcacatt tccccgaaaa gtgccacctg  19920
atgcggtgtg aaataccgca cagatgcgta aggagaaaat accgcatcag gaaattgtaa  19980
gcgttaatat tttgttaaaa ttcgcgttaa atttttgtta aatcagctca ttttttaacc  20040
aataggccga aatcggcaaa atcccttata aatcaaaaga atagaccgag atagggttga  20100
```

gtgttgttcc agtttggaac aagagtccac tattaaagaa cgtggactcc aacgtcaaag 20160
ggcgaaaaac cgtctatcag ggcgatggcc cactacgtga accatcaccc taatcaagtt 20220
ttttggggtc gaggtgccgt aaagcactaa atcggaaccc taaagggagc ccccgattta 20280
gagcttgacg gggaaagccg gcgaacgtgg cgagaaagga agggaagaaa gcgaaaggag 20340
cgggcgctag ggcgctggca agtgtagcgg tcacgctgcg cgtaaccacc acacccgccg 20400
cgcttaatgc gccgctacag ggcgcgtcca ttcgccattc aggctgcgca actgttggga 20460
agggcgatcg gtgcgggcct cttcgctatt acgccagctg gcgaaagggg gatgtgctgc 20520
aaggcgatta agttgggtaa cgccagggtt ttcccagtca cgacgttgta aaacgacggc 20580
cagtgaattg taatacgact cactata 20607

<210> SEQ ID NO 22
<211> LENGTH: 20647
<212> TYPE: DNA
<213> ORGANISM: Artificial Sequence
<220> FEATURE:
<223> OTHER INFORMATION: pEF1?/hDYRK1A/FL mXist construct

<400> SEQUENCE: 22
ctcgagtaca tttatattgg ctcatgtcca acattaccgc catgagtaat tcatacaaaa 60
ggactcgccc ctgccttggg gaatcccagg gaccgtcgtt aaactcccac taacgtagaa 120
cccagagatc gctgcgttcc cgccccctca cccgcccgct ctcgtcatca ctgaggtgga 180
gaagagcatg cgtgaggctc cggtgcccgt cagtgggcag agcgcacatc gcccacagtc 240
cccgagaagt tggggggagg ggtcggcaat tgaaccggtg cctagagaag gtggcgcggg 300
gtaaactggg aaagtgatgt cgtgtactgg ctccgccttt ttcccgaggg tgggggagaa 360
ccgtatataa gtgcagtagt cgccgtgaac gttctttttc gcaacgggtt tgccgccaga 420
acacaggtaa gtgccgtgtg tggttcccgc gggcctggcc tctttacggg ttatggccct 480
tgcgtgcctt gaattacttc cacgcccctg gctgcagtac gtgattcttg atcccgagct 540
tcgggttgga agtgggtggg agagttcgag gccttgcgct taaggagccc cttcgcctcg 600
tgcttgagtt gaggcctggc ttgggcgctg gggccgccgc gtgcgaatct ggtggcacct 660
tcgcgcctgt ctcgctgctt tcgataagtc tctagccatt taaaattttt gatgacctgc 720
tgcgacgctt tttttctggc aagatagtct tgtaaatgcg ggccaagatc tgcacactgg 780
tatttcggtt tttggggccg cgggcggcga cggggcccgt gcgtcccagc gcacatgttc 840
ggcgaggcgg ggcctgcgag cgcggccacc gagaatcgga cgggggtagt ctcaagctgg 900
ccggcctgct ctggtgcctg gcctcgcgcc gccgtgtatc gccccgccct gggcggcaag 960
gctggcccgg tcggcaccag ttgcgtgagc ggaaagatgg ccgcttcccg gccctgctgc 1020
agggagctca aaatggagga cgcggcgctc gggagagcgg gcgggtgagt cacccacaca 1080
aaggaaaagg gcctttccgt cctcagccgt cgcttcatgt gactccacgg agtaccgggc 1140
gccgtccagg cacctcgatt agttctcgag cttttggagt acgtcgtctt taggttgggg 1200
ggaggggttt tatgcgatgg agtttcccca cactgagtgg gtggagactg aagttaggcc 1260
agcttggcac ttgatgtaat tctccttgga atttgccctt tttgagtttg gatcttggtt 1320
cattctcaag cctcagacag tggttcaaag tttttttctt ccatttcagg tgtcgtgagc 1380
tcgtttagtg aaccgtcaga tcgcctggag acgccatcca cgctgttttg acctccatag 1440
aagacaccgg gaccgatcca gcctccgcgg ccccgaattt cgacaccggg gcccagatct 1500

-continued

```
ggtaccatcg atcggccgga tgcggatcag ttaaaggcgt gcaacggctt gctccagcca   1560
tgtttgctcg tttcccgtgg atgtgcggtt cttccgtggt ttctctccat ctaaggagct   1620
ttgggggaac atttttagtt cccctaccac caagccttat ggcttattta agaaaacata   1680
tcaaaattcc acgagatttt tgacgttttg atatgttctg gtaagatttt ttttttgaca   1740
tgtcctccat actttttgat atttgtaata ttttcagtca atttttcatt tttaaggaat   1800
atttctttgt tgtgcctttt ggttgatact tgtgtgtgta tggtggactt acctttcttt   1860
cattgtttat atattcttgc ccatcggggc cacggatacc tgtgtgtcct ccccgccatt   1920
ccatgcccaa cggggttttg gatacttacc tgccttttca ttcttttttt ttcttattat   1980
tttttttct aaacttgccc atctgggctg tggatacctg cttttattct tttttcttc    2040
tccttagccc atcggggcca tggatacctg ctttttgtaa aaaaaaaaaa aaaaaaaaaa   2100
aaacctttct cggtccatcg ggacctcgga tacctgcgtt tagtcttttt ttcccatgcc   2160
caacggggcc tcggatacct gctgttatta ttttttttc tttttctttt gcccatcggg    2220
gctgtggata cctgctttaa atttttttt tcacggccca acggggcgct tggtggatgg    2280
aaatatggtt ttgtgagtta ttgcactacc tggaatatct atgcctctta tttgcgtgta   2340
ctgttgctgc tgatcgtttg gtgctgtgtg agtgaaccta tggcttagaa aaacgacttt   2400
gctcttaaac tgagtgggtg ttcagggcgt ggagagcccg cgtccgccat tatggcttct   2460
gcgtgatacg gctattctcg agccagttac gccaagaatt aggacaccga ggagcacagc   2520
ggactggata aaagcaacca attgcgctgc gctagctaaa ggctttcttt atatgtgcgg   2580
ggttgcggga ttcgccttga tttgtggtag catttgcggg gttgtgctag ccggaagtag   2640
aaagccaagg agtgctcgta ttagtgtgcg gtgttgcgcg gaagccgcag aggactaggg   2700
gatagggctc agcgtgggtg tggggattgg gcagggtgtg tgtgcatatg gacccctggc   2760
gcggtccccc gtggctttaa gggctgctca gaagtctata aaatggcggc tcgggggctc   2820
cacccgaggc tcgacagccc aatctttgtt ctggtgtgta gcaatggatt ataggacatt   2880
taggtcgtac aggaaaagat ggcggctcaa gttcttggtg cggtataacg caaagggctt   2940
tgtgtgtcac atgtcagctt catgtctgag ttagcctgga gaggtggcac atgctcttga   3000
atgtgtctaa gatggcggaa gtcatgtgac ctgccctcta gtggtttctt tcagtgattt   3060
tttttttggc gggctttagc tacttggcgg gctttgcccg agggtacact tggtgcatta   3120
tggtagggtg tggttggtcc taccttgtgc cactcgaagc tgaggcaagg ctaagtggaa   3180
gtgttggttg ccacttgacg taactcgtca gaaatgggca caagtgtgaa agtgttggtg   3240
tttgcttgac ttccagttag aaatgtgcat tattgcttgg tggccaggat ggaattagac   3300
tgtgatgagt cactgtccca taaggacgtg agtttcgctt ggtacttcac gtgtgtcttt   3360
agtcatcatt ttttcgaagt gcctgcccag gtcgggagag cgcatgcttg caattctaac   3420
actgaagtgt tggatgatgt cggatccgat tcgagagacc gaggctgcgg gttcttggtc   3480
gatgtaaatc attgaaacct cacctattaa aagaaagaaa agtatctaag gccatttcaa   3540
ggacatttga ctcatccgct tgcgttcata gtctcttaca gtgctctata cgtggcggtg   3600
caaactaaaa ctcagcccgt tccattcctt tgtattgttc agtggctagt ctacttacac   3660
cttggcctct gatttagcca gcactgatct caagcggttc tctaagccta ctgggtataa   3720
gtggtgactt tggccagagt catagtggat cacaaatcac tggtgaagag gtagaatcct   3780
accttcttcc aaaatctacc ccatgactat tgctggggtt gcattttgat ttcaatgaat   3840
attttggatg ccaacgacac gtctgatagt gtgctttgct agtgtttgaa tttaaaaccg   3900
```

-continued

```
aagtgattgt tttcaaaatg tatttacgga tttgcttact tgttgaattc attttaatta   3960
cctttagtga attgttactt tggagtcctt aaagttttca ataatttttt tggcagatga   4020
tactcaaatt acttggcact taaatgtact ttctttcaaa ctcatccacc gagctactct   4080
tcaaattttt aagtcttata acacagatac tgttaatgta aagtgaacat tatgactgga   4140
tgtcaggagt atttgaggtt ctataccagt tcaggctttg cttttgttgc tattgttgat   4200
gctatattga ctaatggttt tacttgtcag caagagcctt gaattgtaat gctctgtgtc   4260
ctctatcaga cttactgtta taatagtaat attaaggcct acatttcaac tttctgtgtg   4320
ttcttgcctt tatggcatct agattctcct caagactcag caaatagtgc tgctgctatt   4380
gctgccccag ccccaggccc agccccagcc cctgccccag ccccagcccc agcccctgcc   4440
ccagccccag cccctgcccc tgccccagcc cctgccccag ccccagcccc agcccctacc   4500
cctgcccctg cccctgcccc acccaaccaa cccaatccag tccagccctg ccccagccca   4560
gtcctagccc caggcccaga tactttcaga cctatcccaa gcccacttct acttagagaa   4620
attcgaatct tcattgattc agtgctaaaa tgcagtgtcc atcactcagc ctataagact   4680
gagacagccc atctataccc cctccatact gacttctaga gtcatggaat ttcacttaat   4740
gcatagaatc gtattgctaa aatgcagtgc ccatcactca gcctataaga ctgagatagc   4800
ccatctatac cccctccata ctgacttaca gagtcatgga gtttcactta atgcatgcag   4860
tcctattgct aaaatgcagt gcccataact cagcctataa gactgagata gcccatttat   4920
accccatacc ccctccatac tgacttctag ggtcatggaa tttcacttaa tacatagaat   4980
cgtattgcta aaatgcagtg tccatcactc agtctataag actgagatat ccctatgtat   5040
accccatact ccctccatac tgacttccag agtcatagaa tttcactttg catacggtcc   5100
tattgctaaa atgcagtgtc catcactcag tctataagac tgagatatcc ctatgtatac   5160
cccatactcc ctccatactg acttccagag tcatagaatt tcactttgca tacggtccta   5220
ttgctaaaat gcagtgccca tcactcagcc tataagactg agatagccca tctatacccc   5280
ctccatactg acttccagag tcatggaatt tcacttaatg catgcagtcc tattgctaaa   5340
atgcagtgcc catcactcag cctataagac tgagatagcc catctatacc ccataccccc   5400
tccatactga cttccagagt catggaattt cacttaatgc atgcagtcct attgctaaaa   5460
tgcagtgccc atcactcagc ctataagact gagatagccc atctataccc actccatact   5520
gacttccaga gtcatggaat ttcacttaat gcatgcagtc ctattgctaa aatgcagtgc   5580
ccatcactca gcctataaga ctgagatagc ccatctatac ccactccata ctgacttcca   5640
gagtcatgga gtttcactta atgcatgcag tcctattgct aaaatgcagt gcccataact   5700
cagcctataa gactgagata gcccatttat accccatacc ccctccatac tgacttctag   5760
ggtcatggaa tttcacttaa tgcatagaat cgtattgcta aaatgcagtg tccattactc   5820
agcctataag actgagatat ccctatgtat accccatacc ccctccatac tgacttccag   5880
agacatagaa tttcactttg catacggtcc tattgctaaa atgcagtgcc catcactcag   5940
cctataagac tgagatatcc ctatctatac cctctacccc ctccatactg acttccagag   6000
tcatggaatt tcacataatg tatagatttc tattgctaaa atgcagtgcc cataactcag   6060
cctataagac tgagatagcc catctatacc ccctccatac tgagttccag agtcatggaa   6120
tttcacttaa tgcatagaat cgtattgcta aaatgcagtg cccatcactc agcctataag   6180
actgagccca tctatacccc ataccccctc catactgact tccagagtca tggaatttca   6240
```

ctttgcatac agtcctactt tacttgtcca tggacaagta aacaaagaac tcttgtcctt 6300
catgttaatc aagatacacc aatcaaacaa gagttttata tcagagactt gccatggagg 6360
tatcatctct caagtctcct ttcctttaag gaaagaaaac cattctgtca ttgctgtagt 6420
agtcacagtc ccaagtttct aagcagtgtt cagtcgtctt ttctcatgta ttaccttgag 6480
tactgaataa ttctgtcaga aatattttgt ccattggatt agactttagc tagtccagcc 6540
ctgtgtgcat ttagcaaagg ggcaaacaca ggtctgttat cagacagtta aagtgctcag 6600
tcccaatttt caaggcattg gccattaaag ggggtagaat actatatact gttggcatgc 6660
tgtcatgggt gctatcgccc caggtcacat ctttctaact gatggagata catttatttg 6720
ctcatgatat tgtatactag tctcacatgc tttcttattt cagccaaaaa cctctgcact 6780
ggaacatttt atgtggataa tcctgactag gaattgagtc ttttctcaag gtcctaatac 6840
tacccttgct ttatgtaaag agggtgctga ttacttaatg cctcttacac aattgtgcaa 6900
aattgcagtt gttcaagtcc ccttctgtta gtaaccaaga tcccataccc tcatacccta 6960
atgggtgaca atcaagggtg ccaaccaatg agaccacttc tctgttctgg tctttctgct 7020
gtgctgggga atcaaacctt gagtcttgtg tacgctagta aagcactgtc atagagctac 7080
agccccaccg tgtggtggtt tgagagaaca gcctcttatg tagcctgggc tgggcgggac 7140
ttacaggcat tgccacctgt aatgtaaaca tatttgtgcc tgttgtgtgc acagctgcat 7200
ttgtccctct tcctaagcat tggataaaga aaccaaacta agtcaagtca ttttgttggt 7260
aatcaagaag acctttgatc tgtcctgttt ttaacttcca ggctggcctg gaacttagca 7320
tataacccag gctagccttg agctcaggat ctagcctgcg tttaacaagt gttggcatat 7380
ctggttccta ccactatgcc ctgcatgcag tctttcatat tgtgaatgtg catatgtcat 7440
ttcactgtag taatctgcat ctggtgaaga cttatttgta ttgcagcagt atttaagatc 7500
cttaacatag taaatgtgca cagtgttaac tctattgtac atattctcat gtccacagtt 7560
gtgcctttta gatcaggact cctgtactta gcaaagcaaa gaggctcact aatataaagc 7620
ttctttcatg agactataga ttgaaacgat tccaatacgg tcaatggtcc ttcaaggtaa 7680
gacttctgtc tctgatcatt catatcctct ttgctttatg gaattatgta tgtgctgtgc 7740
acttgaaacc ccttcctcaa actatttatg tacatactgg caattttagt aggatcaatt 7800
ttactcttaa ctttgaagta cagaagtggt gttgacctat aaggtcccat tttgtggctt 7860
gctaataata atgactgatt gtagtaggcc ttttctgttc actacagaag gaaacctgaa 7920
cagcgtaaaa ctgtaatggc cataaacatg taccttgcat attagtatgc atttactgca 7980
cacatctcat tccatttgga tacgatccta ctctcaaacc cttttgcagt acagcaaggg 8040
tcactaatct tttggcttct tcatcttcct ggacactgga taaggctgtc ccctcctttc 8100
cactctttaa tttccaggac tattacttta aagacttaat atttgcataa aggatggggt 8160
ttttaattga taacatgtcc cttgaacatt aatgtatata acagggacat gatccattca 8220
ttttaataaa aatacttggc cagttaatgt gtaaaattac acttatccac aaccttatta 8280
cttttcggac cattgtatct cttgcactcc tgcaagggat accgtttatc tcccaaggtc 8340
cctgctagtg gaccattaat atacagtgaa tcttcctttg tctttgccag taaacaaagg 8400
ccatactcct tcgcctttca tttgcactat atcaggatat gctgatcaac aaggccgcat 8460
tcttttggac tgttatcata tattaaatgt atgcgtatgc actgccacct gctctgtgca 8520
cttgaaagga tcccactcac ttccttagca ccttcagcag gaagtgataa taagctcaag 8580
actttcattt ggaaagttca catgtctaag cacttctcta agaactactg taccctcttc 8640

```
tccgctttaa agcagaaaga gggttgtacg aagtgctctt catttggact taagtgcatt   8700
aatgcagtta gttgtccatc attacctttg gagttggatt ttacatcctt gtactctttt   8760
gacaccagag gcatattaat tatttctgag cacttctctt gtcaatatta atctgtaccc   8820
ttacacatat gacctgtgcg gcagcaaagg ttctgaaatg cctacctttt gactggggct   8880
gctgagtggt agtaactatt agtaacctca gcatttggat gattactatg caaaaatgtc   8940
aaggacctgt gtgctctctt tgcataccat caaggctact gagtcccaga attaattgct   9000
aagttatgcg tatttataac tatgaatgtc tggaatattt tgtccccttt acattattgc   9060
agaggttgct gagcccccga aactacccgg tactgtcaat gagcacaggg gctctgacga   9120
atgacctgct ctcttcctta aactgatttt gggactctta ataggcacaa tggcagttct   9180
ggatggttta ttttctactc caacttgagc aaatcccctg ctagtttccc aatgatataa   9240
taaagtacag cagtatgtac acccaacaat gacccggatt tcgacccttt ttgcattgct   9300
ttaatatata caatcctaaa tagtcacaat ctcacacttt atagtgttcc ttttgcccgg   9360
cctctagttt gtccattgac cacttttctg aatcactaat tctcacaaac ccatcattaa   9420
ggaagagttt gtgccctttc tcaattccat catgccatcc cttttgcctc tttgtttgaa   9480
cagtattgac tgggcaaagc ccttctcttg acttaaagtc aacaacacca gtttactcac   9540
ttcatatggc tacagtgtct cagttgcctt ctccttgctc ccactgaaca gagacacctc   9600
gaattcttac attattctgg gtaatgttaa ttaccccaaa caccctatgt gtcattaata   9660
aattttggtg tatttataca ctgaatagca aaagcaggcc aaaactaggt ggatgagcct   9720
tcaatcttta acttgcactt ctaaattatt ccaattccaa ctgctggcac attctagggc   9780
caggaaccat tcttgcctac ctttattaat gctttattgt gcaaaatatt gcaggcaagt   9840
agctcaggga gttggattgc caccttttac ttggggcttt cctttacagt atgaactgaa   9900
aattgtcttc ctgagaagga agcttagcac ttttctttcc attcttcctc caggaaggag   9960
ccaactgtct gcttaagaaa ctttaagccc gattttgtat attgctactg tacaggacca  10020
actgccagaa aagttattga taattttatt ccttaagaaa ggcatttgga ttgcaaggtg  10080
gattgactgt gagatcatta gcttttgtga agtaaaaata gccatttgtg tcatgtttct  10140
gaagactaag cagtgtctca gtgtactgag ggtgatgagt ctgtggaaag atcagtgcaa  10200
ctattgcaga atgtttaaga caagtatctt tgcttggtct ttactacaag tttaacaaaa  10260
cgaaaaagtc aatctttgtg tggcctttag tatgattaac tttttggaag atgacctaag  10320
ccttctaatc attatatttt gtctgacatt ggtcaccagt ccttgcttat ttttaaaagg  10380
tgactggatg gattaaattt gagaacatgt caagtcgcct ttgaaaatta tataggccat  10440
cacatttaat taattcattc tatccaccat taaactctgg caataatttg aagtagcttg  10500
aaaattccta aagtgggaat ttattttaga gatgatagaa cctgtttccc cactttacat  10560
tttaaaatat gtctgccagg atctaatcat tcctttaaac gtacacttca aagagagatt  10620
ttcctagtaa gaaaagagct ttctctagtg tgaagggtgc tttgtagccg ccgagtactt  10680
aggtcttttt tgggagctat tgtgtatgag tgtatgtatg tgtgtgtgta catgcatgtt  10740
gctgcgcgca gtcattcatt cacatggtgc tcagacaaca atgggagctg gttcgtctat  10800
cttgtgggtc ctggagatca aagtgagatc atcaggcttg gcagcaagtg cctttaccct  10860
ccgcgtgcca tcttgccatc ccgctgctga gtgtttgata tgacattgct gatgaaaata  10920
atcatcacaa cagcagttct cccagcatta ctgagaaatg atactatttt tctgaggagg  10980
```

-continued

```
atgttcaagt aactcatcca gtgcaggatc ctgcttgaac tactgctcct ccgttacatc  11040
agactctggc tgtttagact acaggatgaa tttggagtct gttttgtgct cctgcctcaa  11100
gaagaaggat tgcctggatt tagaggagtg aagagtgctg gagagagccc aaagggacaa  11160
acaatcccta tgtgagactc aaggactgcc agcagcctat acagctacat tacatctcag  11220
cagaacttct cttcaagtcc tcgctactct gaacaaaaag cttacaggcc acatggagaa  11280
aaaaagatct ccccccagaa ttgtgggctt gctgctttgc agtgctggcg acctattccc  11340
tttgacgatc cctaggtgga gatggggcat gaggatcctc caggggaata gctcaccacc  11400
actgggcaac aggcctagcc cagatttcag tgagacgctt tcctgaaccc agcaaggaag  11460
acaaaggctc aaagaatgcc accctacatc aaagtaggag aaaagctgct gcaatagtgg  11520
cactgacctt cgaggaagcc attctgctct atttggttct ctctccagaa gctaggaaag  11580
ctttgccagc tgtttacata cttcaagatg cactgctacc ctactcatgc catataatac  11640
acaatgccat ctaccaaata ttacccttcc ccaaagcagc acagaaaact gggtcttcag  11700
cgtgatcaag caatgtgaac acacaaaagg aaggcagctt tataaatgac ccgaggatca  11760
acatgcctga ctgcagcatc ttaaaagcaa tagaatgagt gtgtattgtg ggtgtgtcta  11820
tttcttgttt tatgtatcta tttttccctt ggtctgtgtg tctaattctt tgttacatct  11880
atttcttcct tgctttgtgt gtctatttct tccttgcttt gtgtgtctat ttcttccttg  11940
cattatgtct aattctttgt tatatctatt tcttccttgc tttgtgtcta tttcttcctt  12000
gcagttgtgt ctaattcttt gttacatcta tttcttcctt gctttgtgtg tctatttctt  12060
ccttgcattg tgtctaattc tttgttatat ctatttcttc cttgctttgt gtgtctgtct  12120
tccttgcttt gtgtctattt cttccttgca gttgtgtcta attctttgtt acatctattt  12180
cttccttgct tttgtgtgtc tttctttctt gcttttgtgt gtctatttct tccttgcagt  12240
tgtgtctaat tctttgttac atctatttct tccttgcttt tgtgtgtcta tttcttcctt  12300
gcattgtgtc taattctttg gtatatatat ttcttcattg ctttgtgtgt ctatgtctcc  12360
ttgtgttgtc taattcgttg ttgcatctat ttcttccttg ctttgtgtgt ctatttcttc  12420
cttgctttgt gtgtctatgt cttccttgct ttgtgtgtct atgtcttcct tgttttgtgt  12480
atctacttct tccttgtgtg tctaattctt tgttacatct atttcttcct tcctttgcat  12540
gtctccttct ttcctttgtg tgtcttttct gtctgcagtg tgtcttacct attcccatgt  12600
ttctcctgca tgttctttct tgcagagctt tgagctttgt ttcactttct ctggtgcctg  12660
tgtggtctgc tttgtcttca ctagctatgg ctctctgttt tatctatctg gttgctattt  12720
ctcttagctt ttctttcact cctgcctttc gtgactcccc tttgggtcac atgttgcatg  12780
catccctctc tttttcttgt gctcacccca cttgttcttt gttcaagttc tctttgtcag  12840
tccatttcag ttttctttct gctgcttcta tccttagtga attcttgttt acatttcttc  12900
cctgcctttc ttgggccact ttctctgttt tcttttgtat ttgtgtctct ttgctattgg  12960
tggatttctt atctcagcat cattctgttg ctttgtgttt gcttgtgttt ctatcttcta  13020
ctttcctcct ttctgttcac tttgagcatt tcatctcttt acaagtctgt gtctctcttg  13080
tattctaaag taatcctttc ttggatgttt ctttgtatgt acatgtgcgt gtgtgcatgt  13140
gtgttatgtg tgtcatgtgt gagaggagct tcatagcccc ttcccaatag gtccagaatg  13200
tcacccgtgg agccgttcct cacaccagac tgccctgaga aataatctaa gacaaaatac  13260
atcattccgt ccggtcagga ttcaagtggc tctgaagtga acgcccaagt agaagacaga  13320
agttttgcga cttgagattt aaaaggacca aaatacacag atggcccgtc ttgagctggc  13380
```

tggacagaat gctgacaacc caaagaagag gaactgtttc tacaggacac ctgtgacttc 13440
caagagcggg gaactacgta tgtcataaga cacaaaacct gagctaagtc caagcataag 13500
acctaaggac ccaatcctat atggacagaa tatttaagag ataaaggcct atggcccaga 13560
actctggaag gatatttcta tccttctatc cccaagacca agaagggaaa ttcgaagatg 13620
agacctgccc cccaacccca gcatcccttt ccatttctta tatttctatt taagctgtct 13680
tcacttgaga tgtaattttt cattgttgcc attgcccata aaggaatacg tttttagctg 13740
gatagtattg tgcaagggtc tgttttaaac tgggtcttag ccatttgtta aattgttgat 13800
gttttacaac ttccatttct cttcacatct gctccacttg agacggaact aaatccagcc 13860
agtgtatata gcctgactat tgaaacttcc ctaggaataa gcatgcatac agatatgcat 13920
actgccatcc tccctacctc agaagcccta ggctgacaag aaaaggaaag catcaggttg 13980
ttagggggaa aacaatgtca ggctatctag agaaaatata aagagttgtt ccagaccaat 14040
gagaagaatt agacaagcaa tatgcagatg tgccaaccct ctgagaagca ccagccagtg 14100
tcaccttctt tctttgggct taggtgagca gggtatggtt ttctaataat ggtttgggga 14160
caaaatgagg tctgaactcc ctgctcatag tagtggccga gtaatttggt gcatttcacc 14220
aaaggaactc ctgggtctaa tacctacctt taaaattaat gatgagagac tctaaggact 14280
acttaacggg cttaatcttt ttcgtgcctt cctcttcctc tgtaagaggg aagttaaatg 14340
acacaggatg aaaaagtaac atgctcatag cacattggca attatacatg gttattatct 14400
gaaagtgtag agcttttcct ataaggcatc agactaagta cctgaagctt tgtgggttca 14460
tggtcttagt tgcatattcc ttagttgcaa atccttttca aaaggtaaga aaaaggcaca 14520
ctggtctatt gcctgtactt gatcaagccc tgatatgaat gccagggaat gtctgagtaa 14580
cattaatttc cttccctgca tattttttgt gctgaatact aaggctgtga tgcttcactg 14640
tggtcacccc caggtaacaa gatattacca ggtaaccagg aaacgtatga atacgtaaac 14700
catgaagcct actgtaactt ccaagtcagt gctgagtatg tattacatag tagctgaagt 14760
ctacgcctct gtgtgctata ggcacaaaga ttgctctagg aataacatgc tttgtaaaaa 14820
caaatatatg aacataacgg ggcttgaatg aataacagtc catatactta aggccagtgt 14880
gtttcttctg ctttggtgag gctcagtaag ttatattata ccaggtagca gaagagaaaa 14940
cacatggaaa ctgattttaa actacaaact aggtcactaa tgcaggtgat tgattaccct 15000
attctgatca ccttctaatt tctgaatacc catgttcagc actgggaata acaaaggggg 15060
acattaccac agaactagaa tttacaaaag aatgcattaa ataaagcatt atacagctat 15120
caattgttcc atgtgtgcaa atgaatgact actaactacc tctgatgtat ccgatattgt 15180
tttgggtaca tgaaatattc atgagtaact gccatgaaat aagaatgttt gcattccata 15240
ctattcataa ggaatgagcc aatgcttaat ttaatcagtc aaaacttgag tgataagggc 15300
atgttaatac aagaacattt gcccaggtca cattatggtt gtgggtactt tcttaactat 15360
aaagcagttc agtagtataa gacaagacaa attttctata gaaataaagc tgcctataaa 15420
ataggcatag tctctacaaa attttcattg tactttttag cccataatgg gaagagtaca 15480
gttaacaagc tgggtgtggt agcatgtgct ctgagctgaa gcaacaggac cacttgagcc 15540
cagaaattgg aggctagcct gggaagacca taaggtcaat ctcaaacctg gaggctaaat 15600
attgtctccc atgtgtatat tctctttcat gggtactgga gagatacaca gacgtacatt 15660
tcagtgtgtc cacacttgag aataatatgt acgttggcat tttatgaact cggaggtacc 15720

-continued

```
atataaatgt aacaattcat tttcttactt ggtatcaatt tccaggcttt taaaattctg  15780
ccacatttat tatactgtga aaataaagta aataagtaac tgtgaaccac tgaatatatg  15840
aagcattcaa tacttgatga gtacatactg aatggcagtc atttattaca aaacagtgcc  15900
cttgctaggc actgggatgc aaagagcatt ctcattgtcc tgtgtatcta aagaaattat  15960
gcatgagatt aatttataat ttgtaaactg ccatatatat gtgtatatat gcaatatttg  16020
cctggtgtgc aatgactttg cttttatccc aggcatgcac aacagatctg tgtggagctt  16080
tgtgaagtct acagttctat aaagccggga cctaactgtt ggctttatca gtgaacagtg  16140
attactttct aagtttcata atggctgaaa cttaatcata atgcttatca cctaacacca  16200
cctaataata attttaccat gctatgtgtt gagcgaacac atagattgct ttctagcatt  16260
atgtagcact tataggagtg aaatctagac caaaacttca attcacttca atgaggaaat  16320
gaaaacagaa aaaaaaaatg gatttgtgca aggcagtgtg ctaaatgtta cactgagtgg  16380
actatgctgt ctaggatact tcccagatca agcttatcga taccgtcgaa tcacgcgtca  16440
tatggctagc ctgcagggat ccaatgtaac tgtattcagc gatgacgaaa ttcttagcta  16500
ttgtaatact ctagaggatc tttgtgaagg aaccttactt ctgtggtgtg acataattgg  16560
acaaactacc tacagagatt taaagctcta aggtaaatat aaaattttta agtgtataat  16620
gtgttaaact actgattcta attgtttgtg tattttagat tccaacctat ggaactgatg  16680
aatgggagca gtggtggaat gcctttaatg aggaaaacct gttttgctca gaagaaatgc  16740
catctagtga tgatgaggct actgctgact ctcaacattc tactcctcca aaaaagaaga  16800
gaaaggtaga agaccccaag gactttcctt cagaattgct aagtttttg agtcatgctg  16860
tgtttagtaa tagaactctt gcttgctttg ctatttacac cacaaaggaa aaagctgcac  16920
tgctatacaa gaaaattatg gaaaaatatt ctgtaacctt tataagtagg cataacagtt  16980
ataatcataa catactgttt tttcttactc cacacaggca tagagtgtct gctattaata  17040
actatgctca aaaattgtgt acctttagct ttttaatttg taaaggggtt aataaggaat  17100
atttgatgta tagtgccttg actagagatc ataatcagcc ataccacatt tgtagaggtt  17160
ttacttgctt taaaaaacct cccacacctc cccctgaacc tgaaacataa aatgaatgca  17220
attgttgttg ttaacttgtt tattgcagct tataatggtt acaaataaag caatagcatc  17280
acaaatttca caaataaagc atttttttca ctgcattcta gttgtggttt gtccaaactc  17340
atcaatgtat cttatcatgt ctgcggctct agagctgcat taatgaatcg gccaacgcgc  17400
ggggagaggc ggtttgcgta ttgggcgctc ttccgcttcc tcgctcactg actcgctgcg  17460
ctcggtcgtt cggctgcggc gagcggtatc agctcactca aaggcggtaa tacggttatc  17520
cacagaatca ggggataacg caggaaagaa catgtacgta aactggcaaa ggggtggctg  17580
ggccaaaaga cagaggaatt aagtaagaag tccaggaaaa atgaacttca catcaaattt  17640
tagagcacgg tagccatgaa tcttgtgaat agctcccaaa aatgtcctgt ggaagacaac  17700
tagaaagcat tctacaatca ggcacccacc tccacctgca gcctcctgtg ttgttctcat  17760
ggggcacctc tgggctccag ctcctccaag gcacctccac actctctcaa gtacactctt  17820
cactcttccc caaacatgat tcccctactg ctctgcctaa ctcccacttc tctttcaagt  17880
agcagcttaa acgtcacctc atatttggct ggaaaataga atatagacag aggggtaagt  17940
taaggctaga aaggcaggct gggtcaacag aatggcaagc taaaacatgg gatttctaa  18000
aacagcctaa gagggtgaca gataaaagtg tgcaaggagt ggcacaactc cagtttcatc  18060
tttagctata gcaattaaca ccataaggag tctggattca attttgccat ttactagcta  18120
```

```
gctaccaact tctgtgtcgc tttgggcaaa tcaattaaat ccatacctcc ctttccatct  18180
gcagaatggg tttataacag tacttaaacc tcaaggtact aagaacagta aagagttaat  18240
ggtacatgtg agcaaaaggc cagcaaaagg ccaggaaccg taaaaaggcc gcgttgctgg  18300
cgtttttcca taggctccgc ccccctgacg agcatcacaa aaatcgacgc tcaagtcaga  18360
ggtggcgaaa cccgacagga ctataaagat accaggcgtt tccccctgga agctccctcg  18420
tgcgctctcc tgttccgacc ctgccgctta ccggatacct gtccgccttt ctcccttcgg  18480
gaagcgtggc gctttctcat agctcacgct gtaggtatct cagttcggtg taggtcgttc  18540
gctccaagct gggctgtgtg cacgaacccc ccgttcagcc cgaccgctgc gccttatccg  18600
gtaactatcg tcttgagtcc aacccggtaa gacacgactt atcgccactg gcagcagcca  18660
ctggtaacag gattagcaga gcgaggtatg taggcggtgc tacagagttc ttgaagtggt  18720
ggcctaacta cggctacact agaagaacag tatttggtat ctgcgctctg ctgaagccag  18780
ttaccttcgg aaaaagagtt ggtagctctt gatccggcaa acaaaccacc gctggtagcg  18840
gtggtttttt tgtttgcaag cagcagatta cgcgcagaaa aaaaggatct caagaagatc  18900
ctttgatctt ttctacgggg tctgacgctc agtggaacga aaactcacgt taagggattt  18960
tggtcatgag attatcaaaa aggatcttca cctagatcct tttaaattaa aaatgaagtt  19020
ttaaatcaat ctaaagtata tatgagtaaa cttggtctga cagttaccaa tgcttaatca  19080
gtgaggcacc tatctcagcg atctgtctat ttcgttcatc catagttgcc tgactccccg  19140
tcgtgtagat aactacgata cgggagggct taccatctgg ccccagtgct gcaatgatac  19200
cgcgagaccc acgctcaccg gctccagatt tatcagcaat aaaccagcca gccggaaggg  19260
ccgagcgcag aagtggtcct gcaactttat ccgcctccat ccagtctatt aattgttgcc  19320
gggaagctag agtaagtagt tcgccagtta atagtttgcg caacgttgtt gccattgcta  19380
caggcatcgt ggtgtcacgc tcgtcgtttg gtatggcttc attcagctcc ggttcccaac  19440
gatcaaggcg agttacatga tcccccatgt tgtgcaaaaa agcggttagc tccttcggtc  19500
ctccgatcgt tgtcagaagt aagttggccg cagtgttatc actcatggtt atggcagcac  19560
tgcataattc tcttactgtc atgccatccg taagatgctt ttctgtgact ggtgagtact  19620
caaccaagtc attctgagaa tagtgtatgc ggcgaccgag ttgctcttgc ccggcgtcaa  19680
tacgggataa taccgcgcca catagcagaa ctttaaaagt gctcatcatt ggaaaacgtt  19740
cttcggggcg aaaactctca aggatcttac cgctgttgag atccagttcg atgtaaccca  19800
ctcgtgcacc caactgatct tcagcatctt ttactttcac cagcgtttct gggtgagcaa  19860
aaacaggaag gcaaaatgcc gcaaaaaagg gaataagggc gacacggaaa tgttgaatac  19920
tcatactctt cctttttcaa tattattgaa gcatttatca gggttattgt ctcatgagcg  19980
gatacatatt tgaatgtatt tagaaaaata aacaaatagg ggttccgcgc acatttcccc  20040
gaaaagtgcc acctgacgtc taagaaacca ttattatcat gacattaacc tataaaaata  20100
ggcgtatcac gaggcccttt cgtcttcaag aattcgaaaa ccagaaagta ttctcagtaa  20160
tgatagtatg gataaagcag gtttctatga ccctttatta cagaatctgt gagtttttca  20220
caattaaaaa gtaataaaaa gtagtgacaa cattcactga actcttattc tatgccaact  20280
tgttccggta tgcccttaca cccacaaaag ccctatgcat aaggtggcat tattccagca  20340
tgtattgcat tgtacacaca aagaggtcaa gcactccacc acggccctaa gcatggtggc  20400
tgaggtggga aggccagagg taggtgggcc cgcgcccttt tccactctga accatgcctc  20460
```

caagatagga gggtgggaaa gtgctcaaga cacattagaa attccccata aaagacaaga 20520
ttgttgaaca cctgcaagtg aataaagata aactgatctc agaggggaaa aagacgcagg 20580
gttaggaaac agcaccctgc tcgaggacgt tctttccaaa cagcctgctc atcacccgtt 20640
cgaattc 20647

<210> SEQ ID NO 23
<211> LENGTH: 12230
<212> TYPE: DNA
<213> ORGANISM: Artificial Sequence
<220> FEATURE:
<223> OTHER INFORMATION: pEF1?/hDYRK1A/6.3kb mXist construct

<400> SEQUENCE: 23
ctcgagtaca tttatattgg ctcatgtcca acattaccgc catgagtaat tcatacaaaa 60
ggactcgccc ctgccttggg gaatcccagg gaccgtcgtt aaactcccac taacgtagaa 120
cccagagatc gctgcgttcc cgcccctca cccgcccgct ctcgtcatca ctgaggtgga 180
gaagagcatg cgtgaggctc cggtgcccgt cagtgggcag agcgcacatc gcccacagtc 240
cccgagaagt tggggggagg ggtcggcaat tgaaccggtg cctagagaag gtggcgcggg 300
gtaaactggg aaagtgatgt cgtgtactgg ctccgccttt ttcccgaggg tgggggagaa 360
ccgtatataa gtgcagtagt cgccgtgaac gttcttttc gcaacgggtt tgccgccaga 420
acacaggtaa gtgccgtgtg tggttcccgc gggcctggcc tctttacggg ttatggccct 480
tgcgtgcctt gaattacttc cacgcccctg gctgcagtac gtgattcttg atcccgagct 540
tcgggttgga agtgggtggg agagttcgag gccttgcgct taaggagccc cttcgcctcg 600
tgcttgagtt gaggcctggc ttgggcgctg gggccgccgc gtgcgaatct ggtggcacct 660
tcgcgcctgt ctcgctgctt tcgataagtc tctagccatt taaaattttt gatgacctgc 720
tgcgacgctt tttttctggc aagatagtct tgtaaatgcg ggccaagatc tgcacactgg 780
tatttcggtt tttggggccg cgggcggcga cggggcccgt gcgtcccagc gcacatgttc 840
ggcgaggcgg ggcctgcgag cgcggccacc gagaatcgga cgggggtagt ctcaagctgg 900
ccggcctgct ctggtgcctg gcctcgcgcc gccgtgtatc gccccgccct gggcggcaag 960
gctggcccgg tcggcaccag ttgcgtgagc ggaaagatgg ccgcttcccg gccctgctgc 1020
agggagctca aaatggagga cgcggcgctc gggagagcgg gcgggtgagt cacccacaca 1080
aaggaaaagg gcctttccgt cctcagccgt cgcttcatgt gactccacgg agtaccgggc 1140
gccgtccagg cacctcgatt agttctcgag cttttggagt acgtcgtctt taggttgggg 1200
ggaggggttt tatgcgatgg agtttcccca cactgagtgg gtggagactg aagttaggcc 1260
agcttggcac ttgatgtaat tctccttgga atttgccctt tttgagtttg gatcttggtt 1320
cattctcaag cctcagacag tggttcaaag tttttttctt ccatttcagg tgtcgtgagc 1380
tcgtttagtg aaccgtcaga tcgcctggag acgccatcca cgctgttttg acctccatag 1440
aagacaccgg gaccgatcca gcctccgcgg ccccgaattt cgacaccggg gcccagatct 1500
ggtaccgagc tcggatccga cctccataga agacaccggg accgatccag cctccgcgga 1560
tcagttaaag gcgtgcaacg gcttgctcca gccatgtttg ctcgtttccc gtggatgtgc 1620
ggttcttccg tggtttctct ccatctaagg agctttgggg gaacattttt agttccccta 1680
ccaccaagcc ttatggctta tttaagaaaa catatcaaaa ttccacgaga tttttgacgt 1740
tttgatatgt tctggtaaga ttttttttt gacatgtcct ccatactttt tgatatttgt 1800
aatattttca gtcaattttt catttttaag gaatatttct ttgttgtgcc ttttggttga 1860

-continued

```
tacttgtgtg tgtatggtgg acttaccttt ctttcattgt ttatatattc ttgcccatcg   1920
gggccacgga tacctgtgtg tcctccccgc cattccatgc ccaacggggt tttggatact   1980
tacctgcctt ttcattcttt ttttttctta ttattttttt ttctaaactt gcccatctgg   2040
gctgtggata cctgctttta ttcttttttt cttctcctta gcccatcggg gccatggata   2100
cctgcttttt gtaaaaaaaa aaaaaaaaaa aaaaaaacct ttctcggtcc atcgggacct   2160
cggatacctg cgtttagtct ttttttccca tgcccaacgg ggcctcggat acctgctgtt   2220
attatttttt tttctttttc ttttgcccat cggggctgtg gatacctgct ttaaattttt   2280
tttttcacgg cccaacgggg cgcttggtgg atggaaatat ggttttgtga gttattgcac   2340
tacctggaat atctatgcct cttatttgcg tgtactgttg ctgctgatcg tttggtgctg   2400
tgtgagtgaa cctatggctt agaaaaacga ctttgctctt aaactgagtg ggtgttcagg   2460
gcgtggagag cccgcgtccg ccattatggc ttctgcgtga tacggctatt ctcgagccag   2520
ttacgccaag aattaggaca ccgaggagca cagcggactg gataaaagca accaattgcg   2580
ctgcgctagc taaaggcttt ctttatatgt gcggggttgc gggattcgcc ttgatttgtg   2640
gtagcatttg cggggttgtg ctagccggaa gtagaaagcc aaggagtgct cgtattagtg   2700
tgcggtgttg cgcggaagcc gcagaggact aggggatagg gctcagcgtg ggtgtgggga   2760
ttgggcaggg tgtgtgtgca tatggacccc tggcgcggtc cccgtggct ttaagggctg   2820
ctcagaagtc tataaaatgg cggctcgggg gctccacccg aggctcgaca gcccaatctt   2880
tgttctggtg tgtagcaatg gattatagga catttaggtc gtacaggaaa agatggcggc   2940
tcaagttctt ggtgcggtat aacgcaaagg gctttgtgtg tcacatgtca gcttcatgtc   3000
tgagttagcc tggagaggtg gcacatgctc ttgaatgtgt ctaagatggc ggaagtcatg   3060
tgacctgccc tctagtggtt tctttcagtg attttttttt tggcgggctt tagctacttg   3120
gcgggctttg cccgagggta cacttggtgc attatggtag ggtgtggttg gtcctacctt   3180
gtgccactcg aagctgaggc aaggctaagt ggaagtgttg gttgccactt gacgtaactc   3240
gtcagaaatg ggcacaagtg tgaaagtgtt ggtgtttgct tgacttccag ttagaaatgt   3300
gcattattgc ttggtggcca ggatggaatt agactgtgat gagtcactgt cccataagga   3360
cgtgagtttc gcttggtact tcacgtgtgt ctttagtcat catttttttcg aagtgcctgc  3420
ccaggtcggg agagcgcatg cttgcaattc taacactgaa gtgttggatg atgtcggatc   3480
catggaggta tcatctctca agtctccttt cctttaagga aagaaaacca ttctgtcatt   3540
gctgtagtag tcacagtccc aagtttctaa gcagtgttca gtcgtctttt ctcatgtatt   3600
accttgagta ctgaataatt ctgtcagaaa tattttgtcc attggattag actttagcta   3660
gtccagccct gtgtgcattt agcaaagggg caaacacagg tctgttatca gacagttaaa   3720
gtgctcagtc ccaattttca aggcattggc cattaaaggg ggtagaatac tatatactgt   3780
tggcatgctg tcatgggtgc tatcgcccca ggtcacatct ttctaactga tggagataca   3840
tttatttgct catgatattg tatactagtc tcacatgctt tcttatttca gccaaaaacc   3900
tctgcactgg aacattttat gtggataatc ctgactagga attgagtctt ttctcaaggt   3960
cctaatacta cccttgcttt atgtaaagag ggtgctgatt acttaatgcc tcttacacaa   4020
ttgtgcaaaa ttgcagttgt tcaagtcccc ttctgttagt aaccaagatc ccataccctc   4080
ataccctaat gggtgacaat caagggtgcc aaccaatgag accacttctc tgttctggtc   4140
tttctgctgt gctggggaat caaaccttga gtcttgtgta cgctagtaaa gcactgtcat   4200
```

-continued

```
agagctacag ccccaccgtg tggtggtttg agagaacagc ctcttatgta gcctgggctg   4260
ggcgggactt acaggcattg ccacctgtaa tgtaaacata tttgtgcctg ttgtgtgcac   4320
agctgcattt gtccctcttc ctaagcattg gataaagaaa ccaaactaag tcaagtcatt   4380
ttgttggtaa tcaagaagac ctttgatctg tcctgttttt aacttccagg ctggcctgga   4440
acttagcata taacccaggc tagccttgag ctcaggatct agcctgcgtt taacaagtgt   4500
tggcatatct ggttcctacc actatgccct gcatgcagtc tttcatattg tgaatgtgca   4560
tatgtcattt cactgtagta atctgcatct ggtgaagact tatttgtatt gcagcagtat   4620
ttaagatcct taacatagta aatgtgcaca gtgttaactc tattgtacat attctcatgt   4680
ccacagttgt gccttttaga tcaggactcc tgtacttagc aaagcaaaga ggctcactaa   4740
tataaagctt ctttcatgag actatagatt gaaacgattc caatacggtc aatggtcctt   4800
caaggtaaga cttctgtctc tgatcattca tatcctcttt gctttatgga attatgtatg   4860
tgctgtgcac ttgaaacccc ttcctcaaac tatttatgta catactggca attttagtag   4920
gatcaatttt actcttaact ttgaagtaca gaagtggtgt tgacctataa ggtcccattt   4980
tgtggcttgc taataataat gactgattgt agtaggcctt ttctgttcac tacagaagga   5040
aacctgaaca gcgtaaaact gtaatggcca taaacatgta ccttgcatat tagtatgcat   5100
ttactgcaca catctcattc catttggata cgatcctact ctcaaaccct tttgcagtac   5160
agcaagggtc actaatcttt tggcttcttc atcttcctgg acactggata aggctgtccc   5220
ctcctttcca ctctttaatt tccaggacta ttactttaaa gacttaatat ttgcataaag   5280
gatggggttt ttaattgata acatgtccct tgaacattaa tgtatataac agggacatga   5340
tccattcatt ttaataaaaa tacttggcca gttaatgtgt aaaattacac ttatccacaa   5400
ccttattact tttcggacca ttgtatctct tgcactcctg caagggatac cgtttatctc   5460
ccaaggtccc tgctagtgga ccattaatat acagtgaatc ttcctttgtc tttgccagta   5520
aacaaaggcc atactccttc gcctttcatt tgcactatat caggatatgc tgatcaacaa   5580
ggccgcattc ttttggactg ttatcatata ttaaatgtat gcgtatgcac tgccacctgc   5640
tctgtgcact tgaaaggatc ccactcactt ccttagcacc ttcagcagga agtgataata   5700
agctcaagac tttcatttgg aaagttcaca tgtctaagca cttctctaag aactactgta   5760
ccctcttctc cgctttaaag cagaaagagg gttgtacgaa gtgctcttca tttggactta   5820
agtgcattaa tgcagttagt tgtccatcat tacctttgga gttggatttt acatccttgt   5880
actcttttga caccagaggc atattaatta tttctgagca cttctcttgt caatattaat   5940
ctgtaccctt acacatatga cctgtgcggc agcaaaggtt ctgaaatgcc taccttttga   6000
ctggggctgc tgagtggtag taactattag taacctcagc atttggatga ttactatgca   6060
aaaatgtcaa ggacctgtgt gctctctttg cataccatca aggctactga gtcccagaat   6120
taattgctaa gttatgcgta tttataacta tgaatgtctg gaatattttg tccccttttac  6180
attattgcag aggttgctga gcccccgaaa ctacccggta ctgtcaatga gcacaggggc   6240
tctgacgaat gacctgctct cttccttaaa ctgattttgg gactcttaat aggcacaatg   6300
gcagttctgg atggtttatt ttctactcca acttgagcaa atcccctgct agtttcccaa   6360
tgatataata aagtacagca gtatgtacac ccaacaatga cccggatttc gacccttttt   6420
gcattgcttt aatatataca atcctaaata gtcacaatct cacactttat agtgttcctt   6480
ttgcccggcc tctagtttgt ccattgacca cttttctgaa tcactaattc tcacaaaccc   6540
atcattaagg aagagtttgt gccctttctc aattccatca tgccatccct tttgcctctt   6600
```

tgtttgaaca gtattgactg ggcaaagccc ttctcttgac ttaaagtcaa caacaccagt 6660
ttactcactt catatggcta cagtgtctca gttgccttct ccttgctccc actgaacaga 6720
gacacctcga attcttacat tattctgggt aatgttaatt accccaaaca ccctatgtgt 6780
cattaataaa ttttggtgta tttatacact gaatagcaaa agcaggccaa aactaggtgg 6840
atgagccttc aatctttaac ttgcacttct aaattattcc aattccaact gctggcacat 6900
tctagggcca ggaaccattc ttgcctacct ttattaatgc tttattgtgc aaaatattgc 6960
aggcaagtag ctcagggagt tggattgcca ccttttactt ggggctttcc tttacagtat 7020
gaactgaaaa ttgtcttcct gagaaggaag cttagcactt ttctttccat tcttcctcca 7080
ggaaggagcc aactgtctgc ttaagaaact ttaagcccga ttttgtatat tgctactgta 7140
caggaccaac tgccagaaaa gttattgata attttattcc ttaagaaagg catttggatt 7200
gcaaggtgga ttgactgtga gatcattagc ttttgtgaag taaaaatagc catttgtgtc 7260
atgtttctga agactaagca gtgtctcagt gtactgaggg tgatgagtct gtggaaagat 7320
cagtgcaact attgcagaat gtttaagaca agtatctttg cttggtcttt actacaagtt 7380
taacaaaacg aaaaagtcaa tctttgtgtg gcctttagta tgattaactt tttggaagat 7440
gacctaagcc ttctaatcat tatattttgt ctgacattgg tcaccagtcc ttgcttattt 7500
ttaaaaggtg actggatgga ttaaatttga gaacatgtca agtcgccttt gaaaattata 7560
taggccatca catttaatta attcattcta tccaccatta aactctggca ataatttgaa 7620
gtagcttgaa aattcctaaa gtgggaattt attttagaga tgatagaacc tgtttcccca 7680
ctttacattt taaaatatgt ctgccaggat ctaatcattc ctttaaacgt acacttcaaa 7740
gagagatttt cctagtaaga aaagagcttt ctctagtgtg aagggtgctt tgtagccgcc 7800
gagtacttag gtctttttttg ggagctattg tgtatgagtg tatgtatgtg tgtgtgtaca 7860
tgcatgttgc tgcgcgcgat accgtcgacg gcccccccga ccgatgtcag cctgggggac 7920
gagctccact tagacggcga ggacgtggcg atggcgcatg ccgacgcgct agacgatttc 7980
gatctggaca tgttgggggga cggggattcc ccatcacgcg tcatatggct agcctgcagg 8040
gatccaatgt aactgtattc agcgatgacg aaattcttag ctattgtaat actctagagg 8100
atctttgtga aggaacctta cttctgtggt gtgacataat tggacaaact acctacagag 8160
atttaaagct ctaaggtaaa tataaaattt ttaagtgtat aatgtgttaa actactgatt 8220
ctaattgttt gtgtatttta gattccaacc tatggaactg atgaatggga gcagtggtgg 8280
aatgccttta atgaggaaaa cctgttttgc tcagaagaaa tgccatctag tgatgatgag 8340
gctactgctg actctcaaca ttctactcct ccaaaaaaga agagaaaggt agaagacccc 8400
aaggactttc cttcagaatt gctaagtttt ttgagtcatg ctgtgtttag taatagaact 8460
cttgcttgct ttgctattta caccacaaag gaaaaagctg cactgctata caagaaaatt 8520
atggaaaaat attctgtaac ctttataagt aggcataaca gttataatca taacatactg 8580
ttttttctta ctccacacag gcatagagtg tctgctatta ataactatgc tcaaaaattg 8640
tgtaccttta gctttttaat ttgtaaaggg gttaataagg aatatttgat gtatagtgcc 8700
ttgactagag atcataatca gccataccac atttgtagag gttttacttg ctttaaaaaa 8760
cctcccacac ctccccctga acctgaaaca taaaatgaat gcaattgttg ttgttaactt 8820
gtttattgca gcttataatg gttacaaata aagcaatagc atcacaaatt tcacaaataa 8880
agcatttttt tcactgcatt ctagttgtgg tttgtccaaa ctcatcaatg tatcttatca 8940

-continued

```
tgtctgcggc tctagagctg cattaatgaa tcggccaacg cgcggggaga ggcggtttgc   9000
gtattgggcg ctcttccgct tcctcgctca ctgactcgct gcgctcggtc gttcggctgc   9060
ggcgagcggt atcagctcac tcaaaggcgg taatacggtt atccacagaa tcaggggata   9120
acgcaggaaa gaacatgtac gtaaactggc aaaggggtgg ctgggccaaa agacagagga   9180
attaagtaag aagtccagga aaaatgaact tcacatcaaa ttttagagca cggtagccat   9240
gaatcttgtg aatagctccc aaaaatgtcc tgtggaagac aactagaaag cattctacaa   9300
tcaggcaccc acctccacct gcagcctcct gtgttgttct catggggcac ctctgggctc   9360
cagctcctcc aaggcacctc cacactctct caagtacact cttcactctt ccccaaacat   9420
gattccccta ctgctctgcc taactcccac ttctctttca agtagcagct taaacgtcac   9480
ctcatatttg gctggaaaat agaatataga cagaggggta agttaaggct agaaaggcag   9540
gctgggtcaa cagaatggca agctaaaaca tgggattttc taaaacagcc taagagggtg   9600
acagataaaa gtgtgcaagg agtggcacaa ctccagtttc atctttagct atagcaatta   9660
acaccataag gagtctggat tcaattttgc catttactag ctagctacca acttctgtgt   9720
cgctttgggc aaatcaatta aatccatacc tccctttcca tctgcagaat gggtttataa   9780
cagtacttaa acctcaaggt actaagaaca gtaaagagtt aatggtacat gtgagcaaaa   9840
ggccagcaaa aggccaggaa ccgtaaaaag gccgcgttgc tggcgttttt ccataggctc   9900
cgcccccctg acgagcatca caaaaatcga cgctcaagtc agaggtggcg aaacccgaca   9960
ggactataaa gataccaggc gtttccccct ggaagctccc tcgtgcgctc tcctgttccg  10020
accctgccgc ttaccggata cctgtccgcc tttctccctt cgggaagcgt ggcgctttct  10080
catagctcac gctgtaggta tctcagttcg gtgtaggtcg ttcgctccaa gctgggctgt  10140
gtgcacgaac cccccgttca gcccgaccgc tgcgccttat ccggtaacta tcgtcttgag  10200
tccaacccgg taagacacga cttatcgcca ctggcagcag ccactggtaa caggattagc  10260
agagcgaggt atgtaggcgg tgctacagag ttcttgaagt ggtggcctaa ctacggctac  10320
actagaagaa cagtatttgg tatctgcgct ctgctgaagc cagttacctt cggaaaaaga  10380
gttggtagct cttgatccgg caaacaaacc accgctggta gcggtggttt ttttgtttgc  10440
aagcagcaga ttacgcgcag aaaaaaagga tctcaagaag atcctttgat cttttctacg  10500
gggtctgacg ctcagtggaa cgaaaactca cgttaaggga ttttggtcat gagattatca  10560
aaaaggatct tcacctagat ccttttaaat taaaaatgaa gttttaaatc aatctaaagt  10620
atatatgagt aaacttggtc tgacagttac caatgcttaa tcagtgaggc acctatctca  10680
gcgatctgtc tatttcgttc atccatagtt gcctgactcc ccgtcgtgta gataactacg  10740
atacgggagg gcttaccatc tggccccagt gctgcaatga taccgcgaga cccacgctca  10800
ccggctccag atttatcagc aataaaccag ccagccggaa gggccgagcg cagaagtggt  10860
cctgcaactt tatccgcctc catccagtct attaattgtt gccgggaagc tagagtaagt  10920
agttcgccag ttaatagttt gcgcaacgtt gttgccattg ctacaggcat cgtggtgtca  10980
cgctcgtcgt ttggtatggc ttcattcagc tccggttccc aacgatcaag gcgagttaca  11040
tgatccccca tgttgtgcaa aaaagcggtt agctccttcg gtcctccgat cgttgtcaga  11100
agtaagttgg ccgcagtgtt atcactcatg gttatggcag cactgcataa ttctcttact  11160
gtcatgccat ccgtaagatg cttttctgtg actggtgagt actcaaccaa gtcattctga  11220
gaatagtgta tgcggcgacc gagttgctct tgcccggcgt caatacggga taataccgcg  11280
ccacatagca gaactttaaa agtgctcatc attggaaaac gttcttcggg gcgaaaactc  11340
```

-continued tcaaggatct taccgctgtt gagatccagt tcgatgtaac ccactcgtgc acccaactga 11400
tcttcagcat cttttacttt caccagcgtt tctgggtgag caaaaacagg aaggcaaaat 11460
gccgcaaaaa agggaataag ggcgacacgg aaatgttgaa tactcatact cttccttttt 11520
caatattatt gaagcattta tcagggttat tgtctcatga gcggatacat atttgaatgt 11580
atttagaaaa ataaacaaat aggggttccg cgcacatttc cccgaaaagt gccacctgac 11640
gtctaagaaa ccattattat catgacatta acctataaaa ataggcgtat cacgaggccc 11700
tttcgtcttc aagaattcga aaaccagaaa gtattctcag taatgatagt atggataaag 11760
caggtttcta tgaccottta ttacagaatc tgtgagtttt tcacaattaa aaagtaataa 11820
aaagtagtga caacattcac tgaactctta ttctatgcca acttgttccg gtatgccctt 11880
acacccacaa aagccctatg cataaggtgg cattattcca gcatgtattg cattgtacac 11940
acaaagaggt caagcactcc accacggccc taagcatggt ggctgaggtg ggaaggccag 12000
aggtaggtgg gcccgcgccc ttttccactc tgaaccatgc ctccaagata ggagggtggg 12060
aaagtgctca agacacatta gaaattcccc ataaaagaca agattgttga acacctgcaa 12120
gtgaataaag ataaactgat ctcagagggg aaaaagacgc agggttagga aacagcaccc 12180
tgctcgagga cgttctttcc aaacagcctg ctcatcaccc gttcgaattc 12230

<210> SEQ ID NO 24
<211> LENGTH: 10391
<212> TYPE: DNA
<213> ORGANISM: Artificial Sequence
<220> FEATURE:
<223> OTHER INFORMATION: Rosa26/pEF1x-Tet3G/hPGK-PuroR construct

<400> SEQUENCE: 24
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccag 660
ttaacggcag ccggagtgcg cagccgccgg cagcctcgct ctgcccactg ggtggggcgg 720
gaggtaggtg gggtgaggcg agctggacgt gcgggcgcgg tcggcctctg gcggggcggg 780
ggaggggagg gagggtcagc gaaagtagct cgcgcgcgag cggccgccca ccctcccctt 840
cctctggggg agtcgtttta cccgccgccg gccgggcctc gtcgtctgat tggctctcgg 900
ggcccagaaa actggccctt gccattggct cgtgttcgtg caagttgagt ccatccgccg 960
gccagcgggg gcggcgagga ggcgctccca ggttccggcc ctcccctcgg ctccgcgccg 1020
cagagtctgg ccgcgcgccc ctgcgcaacg tggcaggaag cgcgcgctgg gggcggggac 1080
gggcagtagg gctgagcggc tgcggggcgg gtgcaagcac gtttccgact tgagttgcct 1140

```
caagaggggc gtgctgagcc agacctccat cgcgcactcc ggggagtgga gggaaggagc   1200
gagggctcag ttgggctgtt ttggaggcag gaagcacttg ctctcccaaa gtcgctctga   1260
gttgttatca gtaagggagc tgcagtggag taggcgggga gaaggccgca cccttctccg   1320
gaggggggag gggagtgttg caataccttt ctgggagttc tctgctgcct cctggcttct   1380
gaggaccgcc ctgggcctgg gagaatccct tccccctctt ccctcgtgat ctgcaactcc   1440
agtctttcta gagaattctc tagaaatatt ctcgaggttt aaacgaattc gccctttgct   1500
ttctctgacc agcattctct cccctgggcc tgtgccgctt tctgtctgca gcttgtggcc   1560
tgggtcacct ctacggctgg cccagatcct tccctgccgc ctccttcagg ttccgtcttc   1620
ctccactccc tcttcccctt gctctctgct gtgttgctgc ccaaggatgc tctttccgga   1680
gcacttcctt ctcggcgctg caccacgtga tgtcctctga gcggatcctc cccgtgtctg   1740
ggtcctctcc gggcatctct cctccctcac ccaaccccat gccgtcttca ctcgctgggt   1800
tccctttcc ttctccttct ggggcctgtg ccatctctcg tttcttagga tggccttctc   1860
cgacggatgt ctcccttgcg tcccgcctcc ccttcttgta ggcctgcatc atcaccgttt   1920
ttctggacaa ccccaaagta ccccgtctcc ctggctttag ccacctctcc atcctcttgc   1980
tttctttgcc tggacacccc gttctcctgt ggattcgggt cacctctcac tcctttcatt   2040
tgggcagctc ccctaccccc cttacctctc tagtctgtgc tagctcttcc agccccctgt   2100
catggcatct tccaggggtc cgagagctca gctagtcttc ttcctccaac ccgggcccct   2160
atgtccactt caggacagca tgtttgctgc ctccagggat cctgtgtccc cgagctggga   2220
ccaccttata ttcccagggc cggttaatgt ggctctggtt ctgggtactt ttatctgtcc   2280
cctccacccc acagtggggc aagctagctt ggtcgagctg gatacttccc gtccgccagg   2340
gggacatgcc ggcgatgctg aaggtcgcgc gcattcccga tgaagaggcc ggttaccgcc   2400
tgttgacctg gtgggacggg cagggcgccg cccgagtctt cgcctcggcg gcgggcgctc   2460
tgctcatgga gcgcgcgtcc ggggccgggg accttgcaca gatagcgtgg tccggccagg   2520
acgacgaggc ttgcaggatc ataatcagcc ataccacatt tgtagaggtt ttacttgctt   2580
taaaaaacct cccacacctc cccctgaacc tgaaacataa aatgaatgca attgttgttg   2640
ttaacttgtt tattgcagct tataatggtt acaaataaag caatagcatc acaaatttca   2700
caaataaagc atttttttca ctgcattcta gttgtggttt gtccaaactc atcaatgtat   2760
cttatcatgt ctggatcctt acttagttac ccggggagca tgtcaaggtc aaaatcgtca   2820
agagcgtcag caggcagcat atcaaggtca aagtcgtcaa gggcatcggc tgggagcatg   2880
tctaagtcaa aatcgtcaag ggcgtcggtc ggcccgccgc tttcgcactt tagctgtttc   2940
tccaggccac atatgattag ttccaggccg aaaaggaagg caggttcggc tccctgccgg   3000
tcgaacagct caattgcttg tttcagaagt gggggcatag aatcggtggt aggtgtctct   3060
ctttcctctt ttgctacttg atgctcctgt tcctccaata cgcagcccag tgtaaagtgg   3120
cccacggcgg acagagcgta cagtgcgttc tccagggaga agccttgctg acacaggaac   3180
gcgagctgat tttccagggt ttcgtactgt ttctctgttg ggcgggtgcc gagatgcact   3240
ttagccccgt cgcgatgtga gaggagagca cagcggtatg acttggcgtt gttccgcaga   3300
aagtcttgcc atgactcgcc ttccaggggg caggagtggg tatgatgcct gtccagcatc   3360
tcgattggca gggcatcgag cagggcccgc ttgttcttca cgtgccagta cagggtaggc   3420
tgctcaactc ccagcttttg agcgagtttc cttgtcgtca ggccttcgat accgactcca   3480
ttgagtaatt ccagagcaga gtttatgact ttgctcttgt ccagtctaga catggtgaat   3540
```

-continued

```
tcggggccgc ggaggctgga tcggtcccgg tgtcttctat ggaggtcaaa acagcgtgga   3600
tggcgtctcc aggcgatctg acggttcact aaacgagctc acgacacctg aaatggaaga   3660
aaaaaacttt gaaccactgt ctgaggcttg agaatgaacc aagatccaaa ctcaaaaagg   3720
gcaaattcca aggagaatta catcaagtgc caagctggcc taacttcagt ctccacccac   3780
tcagtgtggg gaaactccat cgcataaaac ccctcccccc aacctaaaga cgacgtactc   3840
caaaagctcg agaactaatc gaggtgcctg gacggcgccc ggtactccgt ggagtcacat   3900
gaagcgacgg ctgaggacgg aaaggccctt ttcctttgtg tgggtgactc acccgcccgc   3960
tctcccgagc gccgcgtcct ccattttgag ctccctgcag cagggccggg aagcggccat   4020
ctttccgctc acgcaactgg tgccgaccgg gccagccttg ccgcccaggg cggggcgata   4080
cacggcggcg cgaggccagg caccagagca ggccggccag cttgagacta cccccgtccg   4140
attctcggtg gccgcgctcg caggccccgc ctcgccgaac atgtgcgctg ggacgcacgg   4200
gccccgtcgc cgcccgcggc cccaaaaacc gaaataccag tgtgcagatc ttggcccgca   4260
tttacaagac tatcttgcca gaaaaaaagc gtcgcagcag gtcatcaaaa attttaaatg   4320
gctagagact tatcgaaagc agcgagacag gcgcgaaggt gccaccagat tcgcacgcgg   4380
cggccccagc gcccaagcca ggcctcaact caagcacgag gcgaaggggc tccttaagcg   4440
caaggcctcg aactctccca cccacttcca acccgaagct cgggatcaag aatcacgtac   4500
tgcagccagg ggcgtggaag taattcaagg cacgcaaggg ccataacccg taaagaggcc   4560
aggcccgcgg gaaccacaca cggcacttac ctgtgttctg gcggcaaacc cgttgcgaaa   4620
aagaacgttc acggcgacta ctgcacttat atacggttct cccccaccct cgggaaaaag   4680
gcggagccag tacacgacat cactttccca gtttaccccg cgccaccttc tctaggcacc   4740
ggttcaattg ccgacccctc cccccaactt ctcggggact gtgggcgatg tgcgctctgc   4800
ccactgacgg gcaccggagc ctcacgcatg ctcttctcca cctcagtgat gacgagagcg   4860
ggcgggtgag gggcgggaa cgcagcgatc tctgggttct acgttagtgg gagtttaacg   4920
acggtccctg ggattcccca aggcaggggc gagtcctttt gtatgaatta ctcatggcgg   4980
taatgttgga catgagccaa tataaatgta catattatga tatggataca acgtatgcaa   5040
tgggccaagc tcctcgaggt ggtgcactct cagtacaatc tgctctgatg ccgcatagtt   5100
aagccagtaa gcttttgggg ttgcgccttt tccaaggcag ccctgggttt gcgcagggac   5160
gcggctgctc tgggcgtggt tccgggaaac gcagcggcgc cgaccctggg tctcgcacat   5220
tcttcacgtc cgttcgcagc gtcacccgga tcttcgccgc tacccttgtg ggcccccccgg   5280
cgacgcttcc tgctccgccc ctaagtcggg aaggttcctt gcggttcgcg gcgtgccgga   5340
cgtgacaaac ggaagccgca cgtctcacta gtaccctcgc agacggacag cgccagggag   5400
caatggcagc gcgccgaccg cgatgggctg tggccaatag cggctgctca gcagggcgcg   5460
ccgagagcag cggccgggaa ggggcggtgc gggaggcggg gtgtggggcg gtagtgtggg   5520
ccctgttcct gcccgcgcgg tgttccgcat tctgcaagcc tccggagcgc acgtcggcag   5580
tcggctccct cgttgaccga atcaccgacc tctctcccca gggggatcca ccggagctta   5640
ccatgaccga gtacaagccc acggtgcgcc tcgccacccg cgacgacgtc cccagggccg   5700
tacgcaccct cgccgccgcg ttcgccgact accccgccac gcgccacacc gtcgatccgg   5760
accgccacat cgagcgggtc accgagctgc aagaactctt cctcacgcgc gtcgggctcg   5820
acatcggcaa ggtgtgggtc gcggacgacg gcgccgcggt ggcggtctgg accacgccgg   5880
```

-continued

```
agagcgtcga agcgggggcg gtgttcgccg agatcggccc gcgcatggcc gagttgagcg   5940
gttcccggct ggccgcgcag caacagatgg aaggcctcct ggcgccgcac cggcccaagg   6000
agcccgcgtg gttcctggcc accgtcggcg tctcgcccga ccaccagggc aagggtctgg   6060
gcagcgccgt cgtgctcccc ggagtggagg cggccgagcg cgccggggtg cccgccttcc   6120
tggagacctc cgcgccccgc aacctcccct tctacgagcg gctcggcttc accgtcaccg   6180
ccgacgtcga ggtgcccgaa ggaccgcgca cctggtgcat gacccgcaag cccggtgcct   6240
gaggtaccct gtgccttcta gttgccagcc atctgttgtt tgcccctccc ccgtgccttc   6300
cttgaccctg gaaggtgcca ctcccactgt cctttcctaa taaaatgagg aaattgcatc   6360
gcattgtctg agtaggtgtc attctattct ggggggtggg gtggggcagg acagcaaggg   6420
ggaggattgg gaagacaata gcaggcatgc tggggatgcg gtgggctcta tggggtacca   6480
agctttacta gggacaggat tggtgacaga aaagccccat ccttaggcct cctccttcct   6540
agtctcctga tattgggtct aacccccacc tcctgttagg cagattcctt atctggtgac   6600
acacccccat ttcctggagc catctctctc cttgccagaa cctctaaggt ttgcttacga   6660
tggagccaga gaggatcctg ggagggagag cttggcaggg ggtgggaggg aagggggga   6720
tgcgtgacct gcccggttct cagtggccac cctgcgctac cctctcccag aacctgagct   6780
gctctgacgc ggctgtctgg tgcgtttcac tgatcctggt gctgcagctt ccttacactt   6840
cccaagagga gaagcagttt ggaaaaacaa aatcagaata agttggtcct gagttctaac   6900
tttggctctt cacctttcta gtccccaatt tatattgttc ctccgtgcgt cagttttacc   6960
tgtgagataa ggccagtagc cagccccgtc ctggcagggc tgtggtgagg agggggtgt   7020
ccgtgtggaa aactcccttt gtgagaatgg tgcgtcctag gtgttcacca ggtcgtggcc   7080
gcctctactc cctttctctt tctccatcct tctttcctta aagagtcccc agtgctatct   7140
gggacatatt cctccgccca gagcagggtc ccgcttccct aaggccctgc tctgggcttc   7200
tgggtttgag tccttggcaa gcccaggaga ggcgctcagg cttccctgtc cccctcctc   7260
gtccaccatc tcatgcccct ggctctcctg cccctccct acaggggttc ctggctctgc   7320
tctaagggca agggcgaatt cgcggccaaa cgtcgacgcg gccgcagatg ggcgggagtc   7380
ttctgggcag gcttaaaggc taacctggtg tgtgggcgtt gtcctgcagg ggaattgaac   7440
aggtgtaaaa ttggagggac aagacttccc acagattttc ggttttgtcg ggaagttttt   7500
taataggggc aaataaggaa aatgggagga taggtagtca tctggggttt tatgcagcaa   7560
aactacaggt tattattgct tgtgatccgc ctcggagtat tttccatcga ggtagattaa   7620
agacatgctc acccgagttt tatactctcc tgcttgagat ccttactaca gtatgaaatt   7680
acagtgtcgc gagttagact atgtaagcag aattttaatc atttttaaag agcccagtac   7740
ttcatatcca tttctcccgc tccttctgca gccttatcaa aaggtatttt agaacactca   7800
ttttagcccc attttcattt attatactgg cttatccaac cctagacag agcattggca   7860
ttttcccttt cctgatctta gaagtctgat gactcatgaa accagacaga ttagttacat   7920
acaccacaaa tcgaggctgt agctggggcc tcaacactgc agttctttta taactcctta   7980
gtacactttt tgttgatcct ttgccttgat ccttaatttt cagtgtctat cacctctccc   8040
gtcaggtggt gttccacatt tgggcctatt ctcagtccag ggagttttac aacaatagat   8100
gtattgagaa tccaacctaa agcttaactt tccactccca tgaatgcctc tctccttttt   8160
ctccatttat aaactgccgc ggtggagctc cagcttttgt tccctttagt gagggttaat   8220
tgcgcgcttg gcgtaatcat ggtcatagct gtttcctgtg tgaaattgtt atccgctcac   8280
```

-continued

```
aattccacac aacatacgag ccggaagcat aaagtgtaaa gcctggggtg cctaatgagt   8340
gagctaactc acattaattg cgttgcgctc actgcccgct ttccagtcgg gaaacctgtc   8400
gtgccagctg cattaatgaa tcggccaacg cgcggggaga ggcggtttgc gtattgggcg   8460
ctcttccgct tcctcgctca ctgactcgct gcgctcggtc gttcggctgc ggcgagcggt   8520
atcagctcac tcaaaggcgg taatacggtt atccacagaa tcaggggata acgcaggaaa   8580
gaacatgtga gcaaaaggcc agcaaaaggc caggaaccgt aaaaaggccg cgttgctggc   8640
gtttttccat aggctccgcc cccctgacga gcatcacaaa aatcgacgct caagtcagag   8700
gtggcgaaac ccgacaggac tataaagata ccaggcgttt ccccctggaa gctccctcgt   8760
gcgctctcct gttccgaccc tgccgcttac cggatacctg tccgcctttc tcccttcggg   8820
aagcgtggcg ctttctcata gctcacgctg taggtatctc agttcggtgt aggtcgttcg   8880
ctccaagctg ggctgtgtgc acgaaccccc cgttcagccc gaccgctgcg ccttatccgg   8940
taactatcgt cttgagtcca acccggtaag acacgactta tcgccactgg cagcagccac   9000
tggtaacagg attagcagag cgaggtatgt aggcggtgct acagagttct tgaagtggtg   9060
gcctaactac ggctacacta gaaggacagt atttggtatc tgcgctctgc tgaagccagt   9120
taccttcgga aaaagagttg gtagctcttg atccggcaaa caaaccaccg ctggtagcgg   9180
tggttttttt gtttgcaagc agcagattac gcgcagaaaa aaaggatctc aagaagatcc   9240
tttgatcttt tctacggggt ctgacgctca gtggaacgaa aactcacgtt aagggatttt   9300
ggtcatgaga ttatcaaaaa ggatcttcac ctagatcctt ttaaattaaa aatgaagttt   9360
taaatcaatc taaagtatat atgagtaaac ttggtctgac agttaccaat gcttaatcag   9420
tgaggcacct atctcagcga tctgtctatt tcgttcatcc atagttgcct gactccccgt   9480
cgtgtagata actacgatac gggagggctt accatctggc cccagtgctg caatgatacc   9540
gcgagaccca cgctcaccgg ctccagattt atcagcaata aaccagccag ccggaagggc   9600
cgagcgcaga agtggtcctg caactttatc cgcctccatc cagtctatta attgttgccg   9660
ggaagctaga gtaagtagtt cgccagttaa tagtttgcgc aacgttgttg ccattgctac   9720
aggcatcgtg gtgtcacgct cgtcgtttgg tatggcttca ttcagctccg gttcccaacg   9780
atcaaggcga gttacatgat cccccatgtt gtgcaaaaaa gcggttagct ccttcggtcc   9840
tccgatcgtt gtcagaagta agttggccgc agtgttatca ctcatggtta tggcagcact   9900
gcataattct cttactgtca tgccatccgt aagatgcttt tctgtgactg gtgagtactc   9960
aaccaagtca ttctgagaat agtgtatgcg gcgaccgagt tgctcttgcc cggcgtcaat  10020
acgggataat accgcgccac atagcagaac tttaaaagtg ctcatcattg gaaaacgttc  10080
ttcggggcga aaactctcaa ggatcttacc gctgttgaga tccagttcga tgtaacccac  10140
tcgtgcaccc aactgatctt cagcatcttt tactttcacc agcgtttctg ggtgagcaaa  10200
aacaggaagg caaaatgccg caaaaaaggg aataagggcg acacggaaat gttgaatact  10260
catactcttc ctttttcaat attattgaag catttatcag ggttattgtc tcatgagcgg  10320
atacatattt gaatgtattt agaaaaataa acaaataggg gttccgcgca catttccccg  10380
aaaagtgcca c                                                       10391
```

<210> SEQ ID NO 25
<211> LENGTH: 286
<212> TYPE: PRT
<213> ORGANISM: Escherichia coli

<400> SEQUENCE: 25

Met Ser Ile Gln His Phe Arg Val Ala Leu Ile Pro Phe Phe Ala Ala
1 5 10 15

Phe Cys Leu Pro Val Phe Ala His Pro Glu Thr Leu Val Lys Val Lys
20 25 30

Asp Ala Glu Asp Gln Leu Gly Ala Arg Val Gly Tyr Ile Glu Leu Asp
35 40 45

Leu Asn Ser Gly Lys Ile Leu Glu Ser Phe Arg Pro Glu Glu Arg Phe
50 55 60

Pro Met Met Ser Thr Phe Lys Val Leu Leu Cys Gly Ala Val Leu Ser
65 70 75 80

Arg Ile Asp Ala Gly Gln Glu Gln Leu Gly Arg Arg Ile His Tyr Ser
85 90 95

Gln Asn Asp Leu Val Glu Tyr Ser Pro Val Thr Glu Lys His Leu Thr
100 105 110

Asp Gly Met Thr Val Arg Glu Leu Cys Ser Ala Ala Ile Thr Met Ser
115 120 125

Asp Asn Thr Ala Ala Asn Leu Leu Leu Thr Thr Ile Gly Gly Pro Lys
130 135 140

Glu Leu Thr Ala Phe Leu His Asn Met Gly Asp His Val Thr Arg Leu
145 150 155 160

Asp Arg Trp Glu Pro Glu Leu Asn Glu Ala Ile Pro Asn Asp Glu Arg
165 170 175

Asp Thr Thr Met Pro Val Ala Met Ala Thr Thr Leu Arg Lys Leu Leu
180 185 190

Thr Gly Glu Leu Leu Thr Leu Ala Ser Arg Gln Gln Leu Ile Asp Trp
195 200 205

Met Glu Ala Asp Lys Val Ala Gly Pro Leu Leu Arg Ser Ala Leu Pro
210 215 220

Ala Gly Trp Phe Ile Ala Asp Lys Ser Gly Ala Gly Glu Arg Gly Ser
225 230 235 240

Arg Gly Ile Ile Ala Ala Leu Gly Pro Asp Gly Lys Pro Ser Arg Ile
245 250 255

Val Val Ile Tyr Thr Thr Gly Ser Gln Ala Thr Met Asp Glu Arg Asn
260 265 270

Arg Gln Ile Ala Glu Ile Gly Ala Ser Leu Ile Lys His Trp
275 280 285

<210> SEQ ID NO 26
<211> LENGTH: 248
<212> TYPE: PRT
<213> ORGANISM: tetracycline transactivator

<400> SEQUENCE: 26

Met Ser Arg Leu Asp Lys Ser Lys Val Ile Asn Ser Ala Leu Glu Leu
1 5 10 15

Leu Asn Gly Val Gly Ile Glu Gly Leu Thr Thr Arg Lys Leu Ala Gln
20 25 30

Lys Leu Gly Val Glu Gln Pro Thr Leu Tyr Trp His Val Lys Asn Lys
35 40 45

Arg Ala Leu Leu Asp Ala Leu Pro Ile Glu Met Leu Asp Arg His His
50 55 60

Thr His Ser Cys Pro Leu Glu Gly Glu Ser Trp Gln Asp Phe Leu Arg
65 70 75 80

```
Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245


<210> SEQ ID NO 27
<211> LENGTH: 215
<212> TYPE: PRT
<213> ORGANISM: Artificial Sequence
<220> FEATURE:
<223> OTHER INFORMATION: vector sequence

<400> SEQUENCE: 27

Met Lys Arg Arg Leu Arg Thr Glu Arg Pro Phe Ser Phe Val Trp Val
1               5                   10                  15

Thr His Pro Pro Ala Leu Pro Ser Ala Ala Ser Ser Ile Leu Ser Ser
            20                  25                  30

Leu Gln Gln Gly Arg Glu Ala Ala Ile Phe Pro Leu Thr Gln Leu Val
        35                  40                  45

Pro Thr Gly Pro Ala Leu Pro Pro Arg Ala Gly Arg Tyr Thr Ala Ala
    50                  55                  60

Arg Gly Gln Ala Pro Glu Gln Ala Gly Gln Leu Glu Thr Thr Pro Val
65                  70                  75                  80

Arg Phe Ser Val Ala Ala Leu Ala Gly Pro Ala Ser Pro Asn Met Cys
                85                  90                  95

Ala Gly Thr His Gly Pro Arg Arg Arg Pro Arg Pro Gln Lys Pro Lys
            100                 105                 110

Tyr Gln Cys Ala Asp Leu Gly Pro His Leu Gln Asp Tyr Leu Ala Arg
        115                 120                 125

Lys Lys Ala Ser Gln Gln Val Ile Lys Asn Phe Lys Trp Leu Glu Thr
    130                 135                 140

Tyr Arg Lys Gln Arg Asp Arg Arg Glu Gly Ala Thr Arg Phe Ala Arg
145                 150                 155                 160

Gly Gly Pro Ser Ala Gln Ala Arg Pro Gln Leu Lys His Glu Ala Lys
                165                 170                 175

Gly Leu Leu Lys Arg Lys Ala Ser Asn Ser Pro Thr His Phe Gln Pro
            180                 185                 190
```

```
Glu Ala Arg Asp Gln Glu Ser Arg Thr Ala Ala Arg Gly Val Glu Val
        195                 200                 205

Ile Gln Gly Thr Gln Gly Pro
    210                 215


<210> SEQ ID NO 28
<211> LENGTH: 215
<212> TYPE: PRT
<213> ORGANISM: Artificial Sequence
<220> FEATURE:
<223> OTHER INFORMATION: puromycin resistance protein

<400> SEQUENCE: 28

Met Lys Arg Arg Leu Arg Thr Glu Arg Pro Phe Ser Phe Val Trp Val
1               5                   10                  15

Thr His Pro Pro Ala Leu Pro Ser Ala Ala Ser Ser Ile Leu Ser Ser
            20                  25                  30

Leu Gln Gln Gly Arg Glu Ala Ala Ile Phe Pro Leu Thr Gln Leu Val
        35                  40                  45

Pro Thr Gly Pro Ala Leu Pro Pro Arg Ala Gly Arg Tyr Thr Ala Ala
    50                  55                  60

Arg Gly Gln Ala Pro Glu Gln Ala Gly Gln Leu Glu Thr Thr Pro Val
65                  70                  75                  80

Arg Phe Ser Val Ala Ala Leu Ala Gly Pro Ala Ser Pro Asn Met Cys
                85                  90                  95

Ala Gly Thr His Gly Pro Arg Arg Arg Pro Arg Pro Gln Lys Pro Lys
            100                 105                 110

Tyr Gln Cys Ala Asp Leu Gly Pro His Leu Gln Asp Tyr Leu Ala Arg
        115                 120                 125

Lys Lys Ala Ser Gln Gln Val Ile Lys Asn Phe Lys Trp Leu Glu Thr
    130                 135                 140

Tyr Arg Lys Gln Arg Asp Arg Arg Glu Gly Ala Thr Arg Phe Ala Arg
145                 150                 155                 160

Gly Gly Pro Ser Ala Gln Ala Arg Pro Gln Leu Lys His Glu Ala Lys
                165                 170                 175

Gly Leu Leu Lys Arg Lys Ala Ser Asn Ser Pro Thr His Phe Gln Pro
            180                 185                 190

Glu Ala Arg Asp Gln Glu Ser Arg Thr Ala Ala Arg Gly Val Glu Val
        195                 200                 205

Ile Gln Gly Thr Gln Gly Pro
    210                 215


<210> SEQ ID NO 29
<211> LENGTH: 264
<212> TYPE: PRT
<213> ORGANISM: Artificial Sequence
<220> FEATURE:
<223> OTHER INFORMATION: neomycin resistance protein

<400> SEQUENCE: 29

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60
```

```
Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

```
<210> SEQ ID NO 30
<211> LENGTH: 273
<212> TYPE: PRT
<213> ORGANISM: Artificial Sequence
<220> FEATURE:
<223> OTHER INFORMATION: vector sequence

<400> SEQUENCE: 30

Met Pro Pro Leu Glu Val Ala Arg Leu Leu Leu His Thr Ser Gln Pro
1               5                   10                  15

Arg Pro Pro Glu Glu Asp Val Gly Asp Leu Val Leu Gly Ile Pro Glu
            20                  25                  30

His Arg Leu Ala Pro Val Asn Asp Arg Cys Tyr Ala Ala Ile Val Arg
        35                  40                  45

Gln Asp Ile Val Gly Ala Glu Ile Arg Val His Glu Val Pro Asp Phe
    50                  55                  60

Gly Ala Val Leu Gly Pro Lys His Gln Leu Ile Glu Ser Leu Arg Asp
65                  70                  75                  80

Gly Arg Thr Asp Gly Val Val His His Ser Leu Pro Val Ile His Met
                85                  90                  95

Gly Ile Ser Asn Arg Ala Tyr Glu Ile Thr Pro Cys Ser Val Leu Thr
            100                 105                 110

Asp Ser Leu Arg Ser Glu Trp Ala Glu Pro Ala Arg Leu Ala Lys Ile
        115                 120                 125

Gly Arg Ser Asp Arg Ile His Gly Leu Arg Asp Arg Leu Gln Asn Ser
    130                 135                 140

Gly Gln Phe Gly Phe Arg Gln Val Leu Gln Arg Asp Thr Leu Cys Thr
145                 150                 155                 160
```

```
Ala Gly Asp Ala Ile Gly Gln Ala Leu Ala Glu Phe Pro Asn Val Lys
                165                 170                 175

His Phe Arg Asn Arg Glu Arg Gly Arg Cys Lys Val Pro Ile Asn Ile
            180                 185                 190

Thr Ile Phe Val Glu Thr Ile Gly Ala Ala Ile Tyr Pro Gln Asp Ile
        195                 200                 205

Ser Thr Pro Ser Tyr Ile Glu Ala Glu Ser Thr Arg Phe Phe Ala Leu
    210                 215                 220

Arg Glu Leu His Gln Val Gly Asp Ala Val Glu Leu Phe Asp Gln Lys
225                 230                 235                 240

Leu Leu Asp Arg Arg Arg Gly Glu Phe Arg Leu Phe His His Val Leu
                245                 250                 255

Ile Arg Ser Glu Asn Gly Tyr Thr Ser Ser Arg Glu Leu Phe Ala Lys
            260                 265                 270

Ala


<210> SEQ ID NO 31
<211> LENGTH: 273
<212> TYPE: PRT
<213> ORGANISM: Artificial Sequence
<220> FEATURE:
<223> OTHER INFORMATION: hygromycin B resistance protein

<400> SEQUENCE: 31

Met Pro Pro Leu Glu Val Ala Arg Leu Leu Leu His Thr Ser Gln Pro
1               5                   10                  15

Arg Pro Pro Glu Glu Asp Val Gly Asp Leu Val Leu Gly Ile Pro Glu
            20                  25                  30

His Arg Leu Ala Pro Val Asn Asp Arg Cys Tyr Ala Ala Ile Val Arg
        35                  40                  45

Gln Asp Ile Val Gly Ala Glu Ile Arg Val His Glu Val Pro Asp Phe
    50                  55                  60

Gly Ala Val Leu Gly Pro Lys His Gln Leu Ile Glu Ser Leu Arg Asp
65                  70                  75                  80

Gly Arg Thr Asp Gly Val Val His His Ser Leu Pro Val Ile His Met
                85                  90                  95

Gly Ile Ser Asn Arg Ala Tyr Glu Ile Thr Pro Cys Ser Val Leu Thr
            100                 105                 110

Asp Ser Leu Arg Ser Glu Trp Ala Glu Pro Ala Arg Leu Ala Lys Ile
        115                 120                 125

Gly Arg Ser Asp Arg Ile His Gly Leu Arg Asp Arg Leu Gln Asn Ser
    130                 135                 140

Gly Gln Phe Gly Phe Arg Gln Val Leu Gln Arg Asp Thr Leu Cys Thr
145                 150                 155                 160

Ala Gly Asp Ala Ile Gly Gln Ala Leu Ala Glu Phe Pro Asn Val Lys
                165                 170                 175

His Phe Arg Asn Arg Glu Arg Gly Arg Cys Lys Val Pro Ile Asn Ile
            180                 185                 190

Thr Ile Phe Val Glu Thr Ile Gly Ala Ala Ile Tyr Pro Gln Asp Ile
        195                 200                 205

Ser Thr Pro Ser Tyr Ile Glu Ala Glu Ser Thr Arg Phe Phe Ala Leu
    210                 215                 220

Arg Glu Leu His Gln Val Gly Asp Ala Val Glu Leu Phe Asp Gln Lys
225                 230                 235                 240
```

```
Leu Leu Asp Arg Arg Arg Gly Glu Phe Arg Leu Phe His His Val Leu
                245                 250                 255

Ile Arg Ser Glu Asn Gly Tyr Thr Ser Ser Arg Glu Leu Phe Ala Lys
            260                 265                 270

Ala


<210> SEQ ID NO 32
<211> LENGTH: 201
<212> TYPE: PRT
<213> ORGANISM: Artificial Sequence
<220> FEATURE:
<223> OTHER INFORMATION: vector sequence

<400> SEQUENCE: 32

Met Ser Thr Arg Ile Ser Gly Pro Tyr Ile Gly Pro Arg Gly Gln Glu
1               5                   10                  15

His Ser Leu Cys Pro Thr His Pro Pro Thr Val Gly Arg Gly Thr Leu
            20                  25                  30

Gly Asn Pro Val Cys Pro Glu Pro Gln His Ser Gly Ser Leu Gly Ser
        35                  40                  45

Leu Cys Leu Pro Asp His Thr Leu Met Pro Ser Leu Pro Leu Pro Ala
    50                  55                  60

His Ser Gly Ser Gly Pro Asp Arg Leu Arg Arg Pro Thr Pro Val Pro
65                  70                  75                  80

Tyr Ser Ala Val His Leu Arg Pro Ala His Ala Leu Pro Arg Arg Leu
                85                  90                  95

His Leu Leu Ala Ala Arg His Val Gly His Arg His Arg His Val Ser
            100                 105                 110

His Glu Leu Gly Leu Ser Leu Pro His Arg Pro Ala Ala Ala Leu Pro
        115                 120                 125

Arg Leu Ile Thr Gly Ala Gly Arg Ala Leu Pro Asp Arg Leu Ala Leu
    130                 135                 140

Leu Pro Ser Ile Leu Arg Arg Leu Gly Arg Phe Leu Pro Val Leu His
145                 150                 155                 160

Gly Gly Arg Arg Glu Ile Ala Pro Ala His Pro Ala Ala Leu His Gln
                165                 170                 175

Arg Ile His Arg Arg Arg Ala Ala Gln Pro Gln Pro Pro Gln Pro Glu
            180                 185                 190

Arg Arg Gly Gly Asp Arg Gly Gln Pro
        195                 200


<210> SEQ ID NO 33
<211> LENGTH: 685
<212> TYPE: DNA
<213> ORGANISM: Artificial Sequence
<220> FEATURE:
<223> OTHER INFORMATION: DYRK1A left arm, reverse

<400> SEQUENCE: 33

aaactggcaa aggggtggct gggccaaaag acagaggaat taagtaagaa gtccaggaaa      60

aatgaacttc acatcaaatt ttagagcacg gtagccatga atcttgtgaa tagctcccaa     120

aaatgtcctg tggaagacaa ctagaaagca ttctacaatc aggcacccac ctccacctgc     180

agcctcctgt gttgttctca tggggcacct ctgggctcca gctcctccaa ggcacctcca     240

cactctctca agtacactct tcactcttcc ccaaacatga ttcccctact gctctgccta     300

actcccactt ctctttcaag tagcagctta aacgtcacct catatttggc tggaaaatag     360
```

aatatagaca gaggggtaag ttaaggctag aaaggcaggc tgggtcaaca gaatggcaag 420
ctaaaacatg ggattttcta aaacagccta agagggtgac agataaaagt gtgcaaggag 480
tggcacaact ccagtttcat ctttagctat agcaattaac accataagga gtctggattc 540
aattttgcca tttactagct agctaccaac ttctgtgtcg ctttgggcaa atcaattaaa 600
tccatacctc cctttccatc tgcagaatgg gtttataaca gtacttaaac ctcaaggtac 660
taagaacagt aaagagttaa tggta 685

<210> SEQ ID NO 34
<211> LENGTH: 502
<212> TYPE: DNA
<213> ORGANISM: Artificial Sequence
<220> FEATURE:
<223> OTHER INFORMATION: DYRK1A right arm, reverse

<400> SEQUENCE: 34
cgaaaaccag aaagtattct cagtaatgat agtatggata aagcaggttt ctatgaccct 60
ttattacaga atctgtgagt ttttcacaat taaaaagtaa taaaaagtag tgacaacatt 120
cactgaactc ttattctatg ccaacttgtt ccggtatgcc cttacaccca caaaagccct 180
atgcataagg tggcattatt ccagcatgta ttgcattgta cacacaaaga ggtcaagcac 240
tccaccacgg ccctaagcat ggtggctgag gtgggaaggc cagaggtagg tgggcccgcg 300
cccttttcca ctctgaacca tgcctccaag ataggagggt gggaaagtgc tcaagacaca 360
ttagaaattc cccataaaag acaagattgt tgaacacctg caagtgaata aagataaact 420
gatctcagag gggaaaaaga cgcagggtta ggaaacagca ccctgctcga ggacgttctt 480
tccaaacagc ctgctcatca cc 502

<210> SEQ ID NO 35
<211> LENGTH: 21
<212> TYPE: DNA
<213> ORGANISM: Artificial Sequence
<220> FEATURE:
<223> OTHER INFORMATION: PCR primers

<400> SEQUENCE: 35
tctctgaaac catagcagcc a 21

<210> SEQ ID NO 36
<211> LENGTH: 22
<212> TYPE: DNA
<213> ORGANISM: Artificial Sequence
<220> FEATURE:
<223> OTHER INFORMATION: PCR primers

<400> SEQUENCE: 36
gccttttgca accaggaaca gc 22

<210> SEQ ID NO 37
<211> LENGTH: 20
<212> TYPE: DNA
<213> ORGANISM: Artificial Sequence
<220> FEATURE:
<223> OTHER INFORMATION: PCR primers

<400> SEQUENCE: 37
aactctgctc caaatgccga 20

<210> SEQ ID NO 38
<211> LENGTH: 23

```
<212> TYPE: DNA
<213> ORGANISM: Artificial Sequence
<220> FEATURE:
<223> OTHER INFORMATION: PCR primers

<400> SEQUENCE: 38

tggggtgatt tgctttccag tgc                                               23


<210> SEQ ID NO 39
<211> LENGTH: 20
<212> TYPE: DNA
<213> ORGANISM: Artificial Sequence
<220> FEATURE:
<223> OTHER INFORMATION: PCR primers

<400> SEQUENCE: 39

cttgtgcaga ccatccctgc                                                   20


<210> SEQ ID NO 40
<211> LENGTH: 22
<212> TYPE: DNA
<213> ORGANISM: Artificial Sequence
<220> FEATURE:
<223> OTHER INFORMATION: PCR primers

<400> SEQUENCE: 40

atcacacaga agaacgtgga gc                                                22


<210> SEQ ID NO 41
<211> LENGTH: 23
<212> TYPE: DNA
<213> ORGANISM: Artificial Sequence
<220> FEATURE:
<223> OTHER INFORMATION: PCR primers

<400> SEQUENCE: 41

cctgtacatc attctctgct tgg                                               23


<210> SEQ ID NO 42
<211> LENGTH: 20
<212> TYPE: DNA
<213> ORGANISM: Artificial Sequence
<220> FEATURE:
<223> OTHER INFORMATION: PCR primers

<400> SEQUENCE: 42

gtgcagtgtc tgccccaagc                                                   20


<210> SEQ ID NO 43
<211> LENGTH: 20
<212> TYPE: DNA
<213> ORGANISM: Artificial Sequence
<220> FEATURE:
<223> OTHER INFORMATION: PCR primers

<400> SEQUENCE: 43

tgcgtctaaa cgttgtccct                                                   20


<210> SEQ ID NO 44
<211> LENGTH: 20
<212> TYPE: DNA
<213> ORGANISM: Artificial Sequence
<220> FEATURE:
<223> OTHER INFORMATION: PCR primers

<400> SEQUENCE: 44
```

-continued atcagccaga ccatcgacac 20

<210> SEQ ID NO 45
<211> LENGTH: 20
<212> TYPE: DNA
<213> ORGANISM: Artificial Sequence
<220> FEATURE:
<223> OTHER INFORMATION: PCR primers

<400> SEQUENCE: 45
gttgggtgaa ctttgaggcg 20

<210> SEQ ID NO 46
<211> LENGTH: 21
<212> TYPE: DNA
<213> ORGANISM: Artificial Sequence
<220> FEATURE:
<223> OTHER INFORMATION: PCR primers

<400> SEQUENCE: 46
ccctcactct gcggaacttt t 21

<210> SEQ ID NO 47
<211> LENGTH: 19
<212> TYPE: DNA
<213> ORGANISM: Artificial Sequence
<220> FEATURE:
<223> OTHER INFORMATION: PCR primers

<400> SEQUENCE: 47
cccatgtgag gtgtgctgt 19

<210> SEQ ID NO 48
<211> LENGTH: 20
<212> TYPE: DNA
<213> ORGANISM: Artificial Sequence
<220> FEATURE:
<223> OTHER INFORMATION: PCR primers

<400> SEQUENCE: 48
tcaaaaccga gagccttccc 20

<210> SEQ ID NO 49
<211> LENGTH: 20
<212> TYPE: DNA
<213> ORGANISM: Artificial Sequence
<220> FEATURE:
<223> OTHER INFORMATION: PCR primers

<400> SEQUENCE: 49
agccttcagt ttggctgtgt 20

<210> SEQ ID NO 50
<211> LENGTH: 20
<212> TYPE: DNA
<213> ORGANISM: Artificial Sequence
<220> FEATURE:
<223> OTHER INFORMATION: PCR primers

<400> SEQUENCE: 50
ggagcgctct cgacttttct 20

<210> SEQ ID NO 51
<211> LENGTH: 22
<212> TYPE: DNA
<213> ORGANISM: Artificial Sequence
<220> FEATURE:
<223> OTHER INFORMATION: PCR primers

<400> SEQUENCE: 51
ttgccgacag gatgcagaag ga 22

<210> SEQ ID NO 52
<211> LENGTH: 20
<212> TYPE: DNA
<213> ORGANISM: Artificial Sequence
<220> FEATURE:
<223> OTHER INFORMATION: PCR primers

<400> SEQUENCE: 52
agtggacgta cggctctttg 20

<210> SEQ ID NO 53
<211> LENGTH: 20
<212> TYPE: DNA
<213> ORGANISM: Artificial Sequence
<220> FEATURE:
<223> OTHER INFORMATION: PCR primers

<400> SEQUENCE: 53
gcccttctct cccttgtagc 20

<210> SEQ ID NO 54
<211> LENGTH: 20
<212> TYPE: DNA
<213> ORGANISM: Artificial Sequence
<220> FEATURE:
<223> OTHER INFORMATION: PCR primers

<400> SEQUENCE: 54
gtgctggagc gctttagttg 20

<210> SEQ ID NO 55
<211> LENGTH: 21
<212> TYPE: DNA
<213> ORGANISM: Artificial Sequence
<220> FEATURE:
<223> OTHER INFORMATION: PCR primers

<400> SEQUENCE: 55
attaaggctg gcacactgct t 21

<210> SEQ ID NO 56
<211> LENGTH: 20
<212> TYPE: DNA
<213> ORGANISM: Artificial Sequence
<220> FEATURE:
<223> OTHER INFORMATION: PCR primers

<400> SEQUENCE: 56
agggccctgg taactttcct 20

<210> SEQ ID NO 57
<211> LENGTH: 20
<212> TYPE: DNA
<213> ORGANISM: Artificial Sequence
<220> FEATURE:
<223> OTHER INFORMATION: PCR primers

<400> SEQUENCE: 57
cggagacggc atcagaatca 20

-continued

<210> SEQ ID NO 58
<211> LENGTH: 22
<212> TYPE: DNA
<213> ORGANISM: Artificial Sequence
<220> FEATURE:
<223> OTHER INFORMATION: PCR primers

<400> SEQUENCE: 58
ggctttggag ttgtaatgct gg 22

<210> SEQ ID NO 59
<211> LENGTH: 20
<212> TYPE: DNA
<213> ORGANISM: Artificial Sequence
<220> FEATURE:
<223> OTHER INFORMATION: PCR primers

<400> SEQUENCE: 59
tgtgcatgtt cagtctgcca 20

<210> SEQ ID NO 60
<211> LENGTH: 22
<212> TYPE: DNA
<213> ORGANISM: Artificial Sequence
<220> FEATURE:
<223> OTHER INFORMATION: PCR primers

<400> SEQUENCE: 60
aggtggacag cgaggccagg at 22

<210> SEQ ID NO 61
<211> LENGTH: 6300
<212> TYPE: DNA
<213> ORGANISM: murine

<400> SEQUENCE: 61
cggcttgctc cagccatgtt tgctcgtttc ccgtggatgt gcggttcttc cgtggtttct 60
ctccatctaa ggagctttgg gggaacattt ttagttcccc taccaccaag ccttatggct 120
tatttaagaa aacatatcaa aattccacga gatttttgac gttttgatat gttctggtaa 180
gatttttttt ttgacatgtc ctccatactt tttgatattt gtaatatttt cagtcaattt 240
ttcattttta aggaatattt ctttgttgtg ccttttggtt gatacttgtg tgtgtatggt 300
ggacttacct ttctttcatt gtttatatat tcttgcccat cggggccacg gatacctgtg 360
tgtcctcccc gccattccat gcccaacggg gttttggata cttacctgcc ttttcattct 420 tttttttct tattattttt ttttctaaac ttgcccatct gggctgtgga tacctgcttt 480
tattcttttt ttcttctcct tagcccatcg gggccatgga tacctgcttt ttgtaaaaaa 540
aaaaaaaaaa aaaaaaaaac ctttctcggt ccatcgggac ctcggatacc tgcgtttagt 600 cttttttttcc catgcccaac ggggcctcgg atacctgctg ttattatttt tttttctttt 660
tcttttgccc atcggggctg tggatacctg ctttaaattt tttttttcac ggcccaacgg 720
ggcgcttggt ggatggaaat atggttttgt gagttattgc actacctgga atatctatgc 780
ctcttatttg cgtgtactgt tgctgctgat cgtttggtgc tgtgtgagtg aacctatggc 840
ttagaaaaac gactttgctc ttaaactgag tgggtgttca gggcgtggag agcccgcgtc 900
cgccattatg gcttctgcgt gatacggcta ttctcgagcc agttacgcca agaattagga 960
caccgaggag cacagcggac tggataaaag caaccaattg cgctgcgcta gctaaaggct 1020
ttctttatat gtgcggggtt gcgggattcg ccttgatttg tggtagcatt tgcggggttg 1080

-continued tgctagccgg aagtagaaag ccaaggagtg ctcgtattag tgtgcggtgt tgcgcggaag 1140
ccgcagagga ctaggggata gggctcagcg tgggtgtggg gattgggcag ggtgtgtgtg 1200
catatggacc cctggcgcgg tcccccgtgg ctttaagggc tgctcagaag tctataaaat 1260
ggcggctcgg gggctccacc cgaggctcga cagcccaatc tttgttctgg tgtgtagcaa 1320
tggattatag gacatttagg tcgtacagga aaagatggcg gctcaagttc ttggtgcggt 1380
ataacgcaaa gggctttgtg tgtcacatgt cagcttcatg tctgagttag cctggagagg 1440
tggcacatgc tcttgaatgt gtctaagatg gcggaagtca tgtgacctgc cctctagtgg 1500
tttctttcag tgattttttt tttggcgggc tttagctact tggcgggctt tgcccgaggg 1560
tacacttggt gcattatggt agggtgtggt tggtcctacc ttgtgccact cgaagctgag 1620
gcaaggctaa gtggaagtgt tggttgccac ttgacgtaac tcgtcagaaa tgggcacaag 1680
tgtgaaagtg ttggtgtttg cttgacttcc agttagaaat gtgcattatt gcttggtggc 1740
caggatggaa ttagactgtg atgagtcact gtcccataag gacgtgagtt tcgcttggta 1800
cttcacgtgt gtctttagtc atcatttttt cgaagtgcct gcccaggtcg ggagagcgca 1860
tgcttgcaat tctaacactg aagtgttgga tgatgtcgga tccatggagg tatcatctct 1920
caagtctcct ttcctttaag gaaagaaaac cattctgtca ttgctgtagt agtcacagtc 1980
ccaagtttct aagcagtgtt cagtcgtctt ttctcatgta ttaccttgag tactgaataa 2040
ttctgtcaga aatattttgt ccattggatt agactttagc tagtccagcc ctgtgtgcat 2100
ttagcaaagg ggcaaacaca ggtctgttat cagacagtta aagtgctcag tcccaatttt 2160
caaggcattg gccattaaag gggtagaat actatatact gttggcatgc tgtcatgggt 2220
gctatcgccc caggtcacat ctttctaact gatggagata catttatttg ctcatgatat 2280
tgtatactag tctcacatgc tttcttattt cagccaaaaa cctctgcact ggaacatttt 2340
atgtggataa tcctgactag gaattgagtc ttttctcaag gtcctaatac tacccttgct 2400
ttatgtaaag agggtgctga ttacttaatg cctcttacac aattgtgcaa aattgcagtt 2460
gttcaagtcc ccttctgtta gtaaccaaga tcccataccc tcataccccta atgggtgaca 2520 atcaagggtg ccaaccaatg agaccacttc tctgttctgg tctttctgct gtgctgggga 2580
atcaaacctt gagtcttgtg tacgctagta aagcactgtc atagagctac agccccaccg 2640
tgtggtggtt tgagagaaca gcctcttatg tagcctgggc tgggcgggac ttacaggcat 2700
tgccacctgt aatgtaaaca tatttgtgcc tgttgtgtgc acagctgcat ttgtccctct 2760
tcctaagcat tggataaaga aaccaaacta agtcaagtca ttttgttggt aatcaagaag 2820
acctttgatc tgtcctgttt ttaacttcca ggctggcctg gaacttagca tataacccag 2880
gctagccttg agctcaggat ctagcctgcg tttaacaagt gttggcatat ctggttccta 2940
ccactatgcc ctgcatgcag tctttcatat tgtgaatgtg catatgtcat ttcactgtag 3000
taatctgcat ctggtgaaga cttatttgta ttgcagcagt atttaagatc cttaacatag 3060
taaatgtgca cagtgttaac tctattgtac atattctcat gtccacagtt gtgcctttta 3120
gatcaggact cctgtactta gcaaagcaaa gaggctcact aatataaagc ttctttcatg 3180
agactataga ttgaaacgat tccaatacgg tcaatggtcc ttcaaggtaa gacttctgtc 3240
tctgatcatt catatcctct ttgctttatg gaattatgta tgtgctgtgc acttgaaacc 3300
ccttcctcaa actatttatg tacatactgg caattttagt aggatcaatt ttactcttaa 3360
ctttgaagta cagaagtggt gttgacctat aaggtcccat tttgtggctt gctaataata 3420

-continued

```
atgactgatt gtagtaggcc ttttctgttc actacagaag gaaacctgaa cagcgtaaaa   3480
ctgtaatggc cataaacatg taccttgcat attagtatgc atttactgca cacatctcat   3540
tccatttgga tacgatccta ctctcaaacc cttttgcagt acagcaaggg tcactaatct   3600
tttggcttct tcatcttcct ggacactgga taaggctgtc ccctcctttc cactctttaa   3660
tttccaggac tattacttta aagacttaat atttgcataa aggatggggt ttttaattga   3720
taacatgtcc cttgaacatt aatgtatata acagggacat gatccattca ttttaataaa   3780
aatacttggc cagttaatgt gtaaaattac acttatccac aaccttatta cttttcggac   3840
cattgtatct cttgcactcc tgcaagggat accgtttatc tcccaaggtc cctgctagtg   3900
gaccattaat atacagtgaa tcttcctttg tctttgccag taaacaaagg ccatactcct   3960
tcgcctttca tttgcactat atcaggatat gctgatcaac aaggccgcat tcttttggac   4020
tgttatcata tattaaatgt atgcgtatgc actgccacct gctctgtgca cttgaaagga   4080
tcccactcac ttccttagca ccttcagcag gaagtgataa taagctcaag actttcattt   4140
ggaaagttca catgtctaag cacttctcta agaactactg taccctcttc tccgctttaa   4200
agcagaaaga gggttgtacg aagtgctctt catttggact taagtgcatt aatgcagtta   4260
gttgtccatc attacctttg gagttggatt ttacatcctt gtactctttt gacaccagag   4320
gcatattaat tatttctgag cacttctctt gtcaatatta atctgtaccc ttacacatat   4380
gacctgtgcg gcagcaaagg ttctgaaatg cctacctttt gactggggct gctgagtggt   4440
agtaactatt agtaacctca gcatttggat gattactatg caaaaatgtc aaggacctgt   4500
gtgctctctt tgcataccat caaggctact gagtcccaga attaattgct aagttatgcg   4560
tatttataac tatgaatgtc tggaatattt tgtccccttt acattattgc agaggttgct   4620
gagcccccga aactacccgg tactgtcaat gagcacaggg gctctgacga atgacctgct   4680
ctcttcctta aactgatttt gggactctta ataggcacaa tggcagttct ggatggttta   4740
ttttctactc caacttgagc aaatcccctg ctagtttccc aatgatataa taaagtacag   4800
cagtatgtac acccaacaat gacccggatt tcgacccttt ttgcattgct ttaatatata   4860
caatcctaaa tagtcacaat ctcacacttt atagtgttcc ttttgcccgg cctctagttt   4920
gtccattgac cacttttctg aatcactaat tctcacaaac ccatcattaa ggaagagttt   4980
gtgccctttc tcaattccat catgccatcc cttttgcctc tttgtttgaa cagtattgac   5040
tgggcaaagc ccttctcttg acttaaagtc aacaacacca gtttactcac ttcatatggc   5100
tacagtgtct cagttgcctt ctccttgctc ccactgaaca gagacacctc gaattcttac   5160
attattctgg gtaatgttaa ttaccccaaa caccctatgt gtcattaata aattttggtg   5220
tatttataca ctgaatagca aaagcaggcc aaaactaggt ggatgagcct tcaatcttta   5280
acttgcactt ctaaattatt ccaattccaa ctgctggcac attctagggc caggaaccat   5340
tcttgcctac ctttattaat gctttattgt gcaaaatatt gcaggcaagt agctcaggga   5400
gttggattgc caccttttac ttggggcttt cctttacagt atgaactgaa aattgtcttc   5460
ctgagaagga agcttagcac ttttctttcc attcttcctc caggaaggag ccaactgtct   5520
gcttaagaaa ctttaagccc gattttgtat attgctactg tacaggacca actgccagaa   5580
aagttattga taattttatt ccttaagaaa ggcatttgga ttgcaaggtg gattgactgt   5640
gagatcatta gcttttgtga agtaaaaata gccatttgtg tcatgtttct gaagactaag   5700
cagtgtctca gtgtactgag ggtgatgagt ctgtggaaag atcagtgcaa ctattgcaga   5760
atgtttaaga caagtatctt tgcttggtct ttactacaag tttaacaaaa cgaaaaagtc   5820
```

aatctttgtg tggcctttag tatgattaac tttttggaag atgacctaag ccttctaatc 5880
attatatttt gtctgacatt ggtcaccagt ccttgcttat ttttaaaagg tgactggatg 5940
gattaaattt gagaacatgt caagtcgcct ttgaaaatta tataggccat cacatttaat 6000
taattcattc tatccaccat taaactctgg caataatttg aagtagcttg aaaattccta 6060
aagtgggaat ttattttaga gatgatagaa cctgtttccc cactttacat tttaaaatat 6120
gtctgccagg atctaatcat tcctttaaac gtacacttca aagagagatt ttcctagtaa 6180
gaaaagagct ttctctagtg tgaagggtgc tttgtagccg ccgagtactt aggtcttttt 6240
tgggagctat tgtgtatgag tgtatgtatg tgtgtgtgta catgcatgtt gctgcgcgcg 6300

<210> SEQ ID NO 62
<211> LENGTH: 14862
<212> TYPE: DNA
<213> ORGANISM: murine

<400> SEQUENCE: 62
cggcttgctc cagccatgtt tgctcgtttc ccgtggatgt gcggttcttc cgtggtttct 60
ctccatctaa ggagctttgg gggaacattt ttagttcccc taccaccaag ccttatggct 120
tatttaagaa aacatatcaa aattccacga gatttttgac gttttgatat gttctggtaa 180 gattttttttt ttgacatgtc ctccatactt tttgatattt gtaatatttt cagtcaattt 240
ttcattttta aggaatattt ctttgttgtg ccttttggtt gatacttgtg tgtgtatggt 300
ggacttacct ttctttcatt gtttatatat tcttgcccat cggggccacg gatacctgtg 360
tgtcctcccc gccattccat gcccaacggg gttttggata cttacctgcc ttttcattct 420 tttttttct tattattttt ttttctaaac ttgcccatct gggctgtgga tacctgcttt 480
tattcttttt ttcttctcct tagcccatcg gggccatgga tacctgcttt ttgtaaaaaa 540
aaaaaaaaaa aaaaaaaaac ctttctcggt ccatcgggac ctcggatacc tgcgtttagt 600 cttttttcc catgcccaac ggggcctcgg atacctgctg ttattatttt tttttctttt 660
tcttttgccc atcggggctg tggatacctg ctttaaattt tttttttcac ggcccaacgg 720
ggcgcttggt ggatggaaat atggttttgt gagttattgc actacctgga atatctatgc 780
ctcttatttg cgtgtactgt tgctgctgat cgtttggtgc tgtgtgagtg aacctatggc 840
ttagaaaaac gactttgctc ttaaactgag tgggtgttca gggcgtggag agcccgcgtc 900
cgccattatg gcttctgcgt gatacggcta ttctcgagcc agttacgcca agaattagga 960
caccgaggag cacagcggac tggataaaag caaccaattg cgctgcgcta gctaaaggct 1020
ttctttatat gtgcggggtt gcgggattcg ccttgatttg tggtagcatt tgcggggttg 1080
tgctagccgg aagtagaaag ccaaggagtg ctcgtattag tgtgcggtgt tgcgcggaag 1140
ccgcagagga ctaggggata gggctcagcg tgggtgtggg gattgggcag ggtgtgtgtg 1200
catatggacc cctggcgcgg tccccccgtgg ctttaagggc tgctcagaag tctataaaat 1260
ggcggctcgg gggctccacc cgaggctcga cagcccaatc tttgttctgg tgtgtagcaa 1320
tggattatag gacatttagg tcgtacagga aaagatggcg gctcaagttc ttggtgcggt 1380
ataacgcaaa gggctttgtg tgtcacatgt cagcttcatg tctgagttag cctggagagg 1440
tggcacatgc tcttgaatgt gtctaagatg gcggaagtca tgtgacctgc cctctagtgg 1500
tttctttcag tgattttttt tttggcgggc tttagctact tggcgggctt tgcccgaggg 1560
tacacttggt gcattatggt agggtgtggt tggtcctacc ttgtgccact cgaagctgag 1620

-continued

```
gcaaggctaa gtggaagtgt tggttgccac ttgacgtaac tcgtcagaaa tgggcacaag   1680
tgtgaaagtg ttggtgtttg cttgacttcc agttagaaat gtgcattatt gcttggtggc   1740
caggatggaa ttagactgtg atgagtcact gtcccataag gacgtgagtt tcgcttggta   1800
cttcacgtgt gtctttagtc atcatttttt cgaagtgcct gcccaggtcg ggagagcgca   1860
tgcttgcaat tctaacactg aagtgttgga tgatgtcgga tccgattcga gagaccgagg   1920
ctgcgggttc ttggtcgatg taaatcattg aaacctcacc tattaaaaga aagaaaagta   1980
tctaaggcca tttcaaggac atttgactca tccgcttgcg ttcatagtct cttacagtgc   2040
tctatacgtg gcggtgcaaa ctaaaactca gcccgttcca ttcctttgta ttgttcagtg   2100
gctagtctac ttacaccttg gcctctgatt tagccagcac tgatctcaag cggttctcta   2160
agcctactgg gtataagtgg tgactttggc cagagtcata gtggatcaca aatcactggt   2220
gaagaggtag aatcctacct tcttccaaaa tctaccccat gactattgct ggggttgcat   2280
tttgatttca atgaatattt tggatgccaa cgacacgtct gatagtgtgc tttgctagtg   2340
tttgaattta aaaccgaagt gattgttttc aaaatgtatt tacggatttg cttacttgtt   2400
gaattcattt taattacctt tagtgaattg ttactttgga gtccttaaag ttttcaataa   2460
tttttttggc agatgatact caaattactt ggcacttaaa tgtactttct ttcaaactca   2520
tccaccgagc tactcttcaa atttttaagt cttataacac agatactgtt aatgtaaagt   2580
gaacattatg actggatgtc aggagtattt gaggttctat accagttcag gctttgcttt   2640
tgttgctatt gttgatgcta tattgactaa tggttttact tgtcagcaag agccttgaat   2700
tgtaatgctc tgtgtcctct atcagactta ctgttataat agtaatatta aggcctacat   2760
ttcaactttc tgtgtgttct tgcctttatg gcatctagat tctcctcaag actcagcaaa   2820
tagtgctgct gctattgctg ccccagcccc aggcccagcc ccagcccctg ccccagcccc   2880
agccccagcc cctgccccag ccccagcccc tgcccctgcc ccagcccctg ccccagcccc   2940
agccccagcc cctacccctg cccctgcccc tgccccaccc aaccaaccca atccagtcca   3000
gccctgcccc agcccagtcc tagccccagg cccagatact ttcagaccta tcccaagccc   3060
acttctactt agagaaattc gaatcttcat tgattcagtg ctaaaatgca gtgtccatca   3120
ctcagcctat aagactgaga cagcccatct ataccccctc catactgact tctagagtca   3180
tggaatttca cttaatgcat agaatcgtat tgctaaaatg cagtgcccat cactcagcct   3240
ataagactga gatagcccat ctataccccc tccatactga cttacagagt catggagttt   3300
cacttaatgc atgcagtcct attgctaaaa tgcagtgccc ataactcagc ctataagact   3360
gagatagccc atttataccc catacccccct ccatactgac ttctagggtc atggaatttc   3420
acttaataca tagaatcgta ttgctaaaat gcagtgtcca tcactcagtc tataagactg   3480
agatatccct atgtataccc catactccct ccatactgac ttccagagtc atagaatttc   3540
actttgcata cggtcctatt gctaaaatgc agtgtccatc actcagtcta taagactgag   3600
atatccctat gtatacccca tactccctcc atactgactt ccagagtcat agaatttcac   3660
tttgcatacg gtcctattgc taaaatgcag tgcccatcac tcagcctata agactgagat   3720
agcccatcta tacccctcc atactgactt ccagagtcat ggaatttcac ttaatgcatg   3780
cagtcctatt gctaaaatgc agtgcccatc actcagccta taagactgag atagcccatc   3840
tatacccccat accccctcca tactgacttc cagagtcatg gaatttcact taatgcatgc   3900
agtcctattg ctaaaatgca gtgcccatca ctcagcctat aagactgaga tagcccatct   3960
atacccactc catactgact tccagagtca tggaatttca cttaatgcat gcagtcctat   4020
```

-continued

```
tgctaaaatg cagtgcccat cactcagcct ataagactga gatagcccat ctatacccac   4080

tccatactga cttccagagt catggagttt cacttaatgc atgcagtcct attgctaaaa   4140

tgcagtgccc ataactcagc ctataagact gagatagccc atttataccc catacccccct  4200

ccatactgac ttctagggtc atggaatttc acttaatgca tagaatcgta ttgctaaaat   4260

gcagtgtcca ttactcagcc tataagactg agatatccct atgtataccc catacccccct  4320

ccatactgac ttccagagac atagaatttc actttgcata cggtcctatt gctaaaatgc   4380

agtgcccatc actcagccta taagactgag atatccctat ctataccctc taccccctcc   4440

atactgactt ccagagtcat ggaatttcac ataatgtata gatttctatt gctaaaatgc   4500

agtgcccata actcagccta taagactgag atagcccatc tataccccct ccatactgag   4560

ttccagagtc atggaatttc acttaatgca tagaatcgta ttgctaaaat gcagtgccca   4620

tcactcagcc tataagactg agcccatcta taccccatac cccctccata ctgacttcca   4680

gagtcatgga atttcacttt gcatacagtc ctactttact tgtccatgga caagtaaaca   4740

aagaactctt gtccttcatg ttaatcaaga tacaccaatc aaacaagagt tttatatcag   4800

agacttgcca tggaggtatc atctctcaag tctcctttcc tttaaggaaa gaaaaccatt   4860

ctgtcattgc tgtagtagtc acagtcccaa gtttctaagc agtgttcagt cgtcttttct   4920

catgtattac cttgagtact gaataattct gtcagaaata ttttgtccat tggattagac   4980

tttagctagt ccagccctgt gtgcatttag caaaggggca aacacaggtc tgttatcaga   5040

cagttaaagt gctcagtccc aattttcaag gcattggcca ttaaaggggg tagaatacta   5100

tatactgttg gcatgctgtc atgggtgcta tcgccccagg tcacatcttt ctaactgatg   5160

gagatacatt tatttgctca tgatattgta tactagtctc acatgctttc ttatttcagc   5220

caaaaacctc tgcactggaa cattttatgt ggataatcct gactaggaat tgagtctttt   5280

ctcaaggtcc taatactacc cttgctttat gtaaagaggg tgctgattac ttaatgcctc   5340

ttacacaatt gtgcaaaatt gcagttgttc aagtcccctt ctgttagtaa ccaagatccc   5400

ataccctcat accctaatgg gtgacaatca agggtgccaa ccaatgagac cacttctctg   5460

ttctggtctt tctgctgtgc tggggaatca aaccttgagt cttgtgtacg ctagtaaagc   5520

actgtcatag agctacagcc ccaccgtgtg gtggtttgag agaacagcct cttatgtagc   5580

ctgggctggg cgggacttac aggcattgcc acctgtaatg taaacatatt tgtgcctgtt   5640

gtgtgcacag ctgcatttgt ccctcttcct aagcattgga taaagaaacc aaactaagtc   5700

aagtcatttt gttggtaatc aagaagacct ttgatctgtc ctgtttttaa cttccaggct   5760

ggcctggaac ttagcatata acccaggcta gccttgagct caggatctag cctgcgttta   5820

acaagtgttg gcatatctgg ttcctaccac tatgccctgc atgcagtctt tcatattgtg   5880

aatgtgcata tgtcatttca ctgtagtaat ctgcatctgg tgaagactta tttgtattgc   5940

agcagtattt aagatcctta acatagtaaa tgtgcacagt gttaactcta ttgtacatat   6000

tctcatgtcc acagttgtgc cttttagatc aggactcctg tacttagcaa agcaaagagg   6060

ctcactaata taaagcttct ttcatgagac tatagattga aacgattcca atacggtcaa   6120

tggtccttca aggtaagact tctgtctctg atcattcata tcctctttgc tttatggaat   6180

tatgtatgtg ctgtgcactt gaaacccctt cctcaaacta tttatgtaca tactggcaat   6240

tttagtagga tcaattttac tcttaacttt gaagtacaga agtggtgttg acctataagg   6300

tcccattttg tggcttgcta ataataatga ctgattgtag taggcctttt ctgttcacta   6360
```

```
cagaaggaaa cctgaacagc gtaaaactgt aatggccata aacatgtacc ttgcatatta   6420
gtatgcattt actgcacaca tctcattcca tttggatacg atcctactct caaacccttt   6480
tgcagtacag caagggtcac taatcttttg gcttcttcat cttcctggac actggataag   6540
gctgtcccct cctttccact ctttaatttc caggactatt actttaaaga cttaatattt   6600
gcataaagga tggggttttt aattgataac atgtcccttg aacattaatg tatataacag   6660
ggacatgatc cattcatttt aataaaaata cttggccagt taatgtgtaa aattacactt   6720
atccacaacc ttattacttt tcggaccatt gtatctcttg cactcctgca agggataccg   6780
tttatctccc aaggtccctg ctagtggacc attaatatac agtgaatctt cctttgtctt   6840
tgccagtaaa caaaggccat actccttcgc ctttcatttg cactatatca ggatatgctg   6900
atcaacaagg ccgcattctt ttggactgtt atcatatatt aaatgtatgc gtatgcactg   6960
ccacctgctc tgtgcacttg aaaggatccc actcacttcc ttagcacctt cagcaggaag   7020
tgataataag ctcaagactt tcatttggaa agttcacatg tctaagcact tctctaagaa   7080
ctactgtacc ctcttctccg ctttaaagca gaaagagggt tgtacgaagt gctcttcatt   7140
tggacttaag tgcattaatg cagttagttg tccatcatta cctttggagt tggattttac   7200
atccttgtac tcttttgaca ccagaggcat attaattatt tctgagcact tctcttgtca   7260
atattaatct gtacccttac acatatgacc tgtgcggcag caaaggttct gaaatgccta   7320
ccttttgact ggggctgctg agtggtagta actattagta acctcagcat ttggatgatt   7380
actatgcaaa aatgtcaagg acctgtgtgc tctctttgca taccatcaag gctactgagt   7440
cccagaatta attgctaagt tatgcgtatt tataactatg aatgtctgga atattttgtc   7500
ccctttacat tattgcagag gttgctgagc ccccgaaact acccggtact gtcaatgagc   7560
acaggggctc tgacgaatga cctgctctct tccttaaact gattttggga ctcttaatag   7620
gcacaatggc agttctggat ggtttatttt ctactccaac ttgagcaaat cccctgctag   7680
tttcccaatg atataataaa gtacagcagt atgtacaccc aacaatgacc cggatttcga   7740
cccttttttgc attgctttaa tatatacaat cctaaatagt cacaatctca cactttatag   7800
tgttcctttt gcccggcctc tagtttgtcc attgaccact tttctgaatc actaattctc   7860
acaaacccat cattaaggaa gagtttgtgc cctttctcaa ttccatcatg ccatcccttt   7920
tgcctctttg tttgaacagt attgactggg caaagccctt ctcttgactt aaagtcaaca   7980
acaccagttt actcacttca tatggctaca gtgtctcagt tgccttctcc ttgctcccac   8040
tgaacagaga cacctcgaat tcttacatta ttctgggtaa tgttaattac cccaaacacc   8100
ctatgtgtca ttaataaatt ttggtgtatt tatacactga atagcaaaag caggccaaaa   8160
ctaggtggat gagccttcaa tctttaactt gcacttctaa attattccaa ttccaactgc   8220
tggcacattc tagggccagg aaccattctt gcctaccttt attaatgctt tattgtgcaa   8280
aatattgcag gcaagtagct cagggagttg gattgccacc ttttacttgg ggctttcctt   8340
tacagtatga actgaaaatt gtcttcctga gaaggaagct tagcactttt ctttccattc   8400
ttcctccagg aaggagccaa ctgtctgctt aagaaacttt aagcccgatt ttgtatattg   8460
ctactgtaca ggaccaactg ccagaaaagt tattgataat tttattcctt aagaaaggca   8520
tttggattgc aaggtggatt gactgtgaga tcattagctt ttgtgaagta aaaatagcca   8580
tttgtgtcat gtttctgaag actaagcagt gtctcagtgt actgagggtg atgagtctgt   8640
ggaaagatca gtgcaactat tgcagaatgt ttaagacaag tatctttgct tggtctttac   8700
tacaagttta acaaaacgaa aaagtcaatc tttgtgtggc ctttagtatg attaactttt   8760
```

tggaagatga cctaagcctt ctaatcatta tattttgtct gacattggtc accagtcctt 8820
gcttattttt aaaaggtgac tggatggatt aaatttgaga acatgtcaag tcgcctttga 8880
aaattatata ggccatcaca tttaattaat tcattctatc caccattaaa ctctggcaat 8940
aatttgaagt agcttgaaaa ttcctaaagt gggaatttat tttagagatg atagaacctg 9000
tttccccact ttacatttta aaatatgtct gccaggatct aatcattcct ttaaacgtac 9060
acttcaaaga gagattttcc tagtaagaaa agagctttct ctagtgtgaa gggtgctttg 9120
tagccgccga gtacttaggt cttttttggg agctattgtg tatgagtgta tgtatgtgtg 9180
tgtgtacatg catgttgctg cgcgcagtca ttcattcaca tggtgctcag acaacaatgg 9240
gagctggttc gtctatcttg tgggtcctgg agatcaaagt gagatcatca ggcttggcag 9300
caagtgcctt taccctccgc gtgccatctt gccatcccgc tgctgagtgt ttgatatgac 9360
attgctgatg aaaataatca tcacaacagc agttctccca gcattactga gaaatgatac 9420
tatttttctg aggaggatgt tcaagtaact catccagtgc aggatcctgc ttgaactact 9480
gctcctccgt tacatcagac tctggctgtt tagactacag gatgaatttg gagtctgttt 9540
tgtgctcctg cctcaagaag aaggattgcc tggatttaga ggagtgaaga gtgctggaga 9600
gagcccaaag ggacaaacaa tccctatgtg agactcaagg actgccagca gcctatacag 9660
ctacattaca tctcagcaga acttctcttc aagtcctcgc tactctgaac aaaaagctta 9720
caggccacat ggagaaaaaa agatctcccc ccagaattgt gggcttgctg ctttgcagtg 9780
ctggcgacct attccctttg acgatcccta ggtggagatg gggcatgagg atcctccagg 9840
ggaatagctc accaccactg ggcaacaggc ctagcccaga tttcagtgag acgctttcct 9900
gaacccagca aggaagacaa aggctcaaag aatgccaccc tacatcaaag taggagaaaa 9960
gctgctgcaa tagtggcact gaccttcgag gaagccattc tgctctattt ggttctctct 10020
ccagaagcta ggaaagcttt gccagctgtt tacatacttc aagatgcact gctaccctac 10080
tcatgccata taatacacaa tgccatctac caaatattac ccttccccaa agcagcacag 10140
aaaactgggt cttcagcgtg atcaagcaat gtgaacacac aaaaggaagg cagctttata 10200
aatgacccga ggatcaacat gcctgactgc agcatcttaa aagcaataga atgagtgtgt 10260
attgtgggtg tgtctatttc ttgttttatg tatctatttt ttccttggtc tgtgtgtcta 10320
attctttgtt acatctattt cttccttgct ttgtgtgtct atttcttcct tgctttgtgt 10380
gtctatttct tccttgcatt atgtctaatt ctttgttata tctatttctt ccttgctttg 10440
tgtctatttc ttccttgcag ttgtgtctaa ttctttgtta catctatttc ttccttgctt 10500
tgtgtgtcta tttcttcctt gcattgtgtc taattctttg ttatatctat ttcttccttg 10560
ctttgtgtgt ctgtcttcct tgctttgtgt ctatttcttc cttgcagttg tgtctaattc 10620
tttgttacat ctatttcttc cttgcttttg tgtgtctttc tttcttgctt ttgtgtgtct 10680
atttcttcct tgcagttgtg tctaattctt tgttacatct atttcttcct tgcttttgtg 10740
tgtctatttc ttccttgcat tgtgtctaat tctttggtat atatatttct tcattgcttt 10800
gtgtgtctat gtctccttgt gttgtctaat tcgttgttgc atctatttct tccttgcttt 10860
gtgtgtctat ttcttccttg ctttgtgtgt ctatgtcttc cttgctttgt gtgtctatgt 10920
cttccttgtt ttgtgtatct acttcttcct tgtgtgtcta attctttgtt acatctattt 10980
cttccttcct ttgcatgtct ccttctttcc tttgtgtgtc ttttctgtct gcagtgtgtc 11040
ttacctattc ccatgtttct cctgcatgtt ctttcttgca gagctttgag ctttgtttca 11100
ctttctctgg tgcctgtgtg gtctgctttg tcttcactag ctatggctct ctgttttatc 11160
tatctggttg ctatttctct tagcttttct ttcactcctg cctttcgtga ctcccctttg 11220
ggtcacatgt tgcatgcatc cctctctttt tcttgtgctc accccacttg ttctttgttc 11280
aagttctctt tgtcagtcca tttcagtttt ctttctgctg cttctatcct tagtgaattc 11340
ttgtttacat ttcttccctg cctttcttgg gccactttct ctgttttctt ttgtatttgt 11400
gtctctttgc tattggtgga tttcttatct cagcatcatt ctgttgcttt gtgtttgctt 11460
gtgtttctat cttctacttt cctcctttct gttcactttg agcatttcat ctctttacaa 11520
gtctgtgtct ctcttgtatt ctaaagtaat cctttcttgg atgtttcttt gtatgtacat 11580
gtgcgtgtgt gcatgtgtgt tatgtgtgtc atgtgtgaga ggagcttcat agccccttcc 11640
caataggtcc agaatgtcac ccgtggagcc gttcctcaca ccagactgcc ctgagaaata 11700
atctaagaca aaatacatca ttccgtccgg tcaggattca agtggctctg aagtgaacgc 11760
ccaagtagaa gacagaagtt ttgcgacttg agatttaaaa ggaccaaaat acacagatgg 11820
cccgtcttga gctggctgga cagaatgctg acaacccaaa gaagaggaac tgtttctaca 11880
ggacacctgt gacttccaag agcggggaac tacgtatgtc ataagacaca aaacctgagc 11940
taagtccaag cataagacct aaggacccaa tcctatatgg acagaatatt taagagataa 12000
aggcctatgg cccagaactc tggaaggata tttctatcct tctatcccca agaccaagaa 12060
gggaaattcg aagatgagac ctgcccccca accccagcat ccctttccat ttcttatatt 12120
tctatttaag ctgtcttcac ttgagatgta atttttcatt gttgccattg cccataaagg 12180
aatacgtttt tagctggata gtattgtgca agggtctgtt ttaaactggg tcttagccat 12240
ttgttaaatt gttgatgttt tacaacttcc atttctcttc acatctgctc cacttgagac 12300
ggaactaaat ccagccagtg tatatagcct gactattgaa acttccctag gaataagcat 12360
gcatacagat atgcatactg ccatcctccc tacctcagaa gccctaggct gacaagaaaa 12420
ggaaagcatc aggttgttag ggggaaaaca atgtcaggct atctagagaa aatataaaga 12480
gttgttccag accaatgaga agaattagac aagcaatatg cagatgtgcc aaccctctga 12540
gaagcaccag ccagtgtcac cttctttctt tgggcttagg tgagcagggt atggttttct 12600
aataatggtt tggggacaaa atgaggtctg aactccctgc tcatagtagt ggccgagtaa 12660
tttggtgcat ttcaccaaag gaactcctgg gtctaatacc tacctttaaa attaatgatg 12720
agagactcta aggactactt aacgggctta atctttttcg tgccttcctc ttcctctgta 12780
agagggaagt taaatgacac aggatgaaaa agtaacatgc tcatagcaca ttggcaatta 12840
tacatggtta ttatctgaaa gtgtagagct tttcctataa ggcatcagac taagtacctg 12900
aagctttgtg ggttcatggt cttagttgca tattccttag ttgcaaatcc ttttcaaaag 12960
gtaagaaaaa ggcacactgg tctattgcct gtacttgatc aagccctgat atgaatgcca 13020
gggaatgtct gagtaacatt aatttccttc cctgcatatt ttttgtgctg aatactaagg 13080
ctgtgatgct tcactgtggt cacccccagg taacaagata ttaccaggta accaggaaac 13140
gtatgaatac gtaaaccatg aagcctactg taacttccaa gtcagtgctg agtatgtatt 13200
acatagtagc tgaagtctac gcctctgtgt gctataggca caaagattgc tctaggaata 13260
acatgctttg taaaaacaaa tatatgaaca taacggggct tgaatgaata acagtccata 13320
tacttaaggc cagtgtgttt cttctgcttt ggtgaggctc agtaagttat attataccag 13380
gtagcagaag agaaaacaca tggaaactga ttttaaacta caaactaggt cactaatgca 13440
ggtgattgat taccctattc tgatcacctt ctaatttctg aatacccatg ttcagcactg 13500

-continued

```
ggaataacaa agggggacat taccacagaa ctagaattta caaaagaatg cattaaataa  13560

agcattatac agctatcaat tgttccatgt gtgcaaatga atgactacta actacctctg  13620

atgtatccga tattgttttg ggtacatgaa atattcatga gtaactgcca tgaaataaga  13680

atgtttgcat tccatactat tcataaggaa tgagccaatg cttaatttaa tcagtcaaaa  13740

cttgagtgat aagggcatgt taatacaaga acatttgccc aggtcacatt atggttgtgg  13800

gtactttctt aactataaag cagttcagta gtataagaca agacaaattt tctatagaaa  13860

taaagctgcc tataaaatag gcatagtctc tacaaaattt tcattgtact ttttagccca  13920

taatgggaag agtacagtta acaagctggg tgtggtagca tgtgctctga gctgaagcaa  13980

caggaccact tgagcccaga aattggaggc tagcctggga agaccataag gtcaatctca  14040

aacctggagg ctaaatattg tctcccatgt gtatattctc tttcatgggt actggagaga  14100

tacacagacg tacatttcag tgtgtccaca cttgagaata atatgtacgt tggcatttta  14160

tgaactcgga ggtaccatat aaatgtaaca attcattttc ttacttggta tcaatttcca  14220

ggcttttaaa attctgccac atttattata ctgtgaaaat aaagtaaata agtaactgtg  14280

aaccactgaa tatatgaagc attcaatact tgatgagtac atactgaatg gcagtcattt  14340

attacaaaac agtgcccttg ctaggcactg ggatgcaaag agcattctca ttgtcctgtg  14400

tatctaaaga aattatgcat gagattaatt tataatttgt aaactgccat atatatgtgt  14460

atatatgcaa tatttgcctg gtgtgcaatg actttgcttt tatcccaggc atgcacaaca  14520

gatctgtgtg gagctttgtg aagtctacag ttctataaag ccgggaccta actgttggct  14580

ttatcagtga acagtgatta ctttctaagt ttcataatgg ctgaaactta atcataatgc  14640

ttatcaccta acaccaccta ataataattt taccatgcta tgtgttgagc gaacacatag  14700

attgctttct agcattatgt agcacttata ggagtgaaat ctagaccaaa acttcaattc  14760

acttcaatga ggaaatgaaa acagaaaaaa aaaatggatt tgtgcaaggc agtgtgctaa  14820

atgttacact gagtggacta tgctgtctag gatacttccc ag                     14862
```